(12) United States Patent  
Fevig et al.

(10) Patent No.: US 8,513,265 B2  
(45) Date of Patent: Aug. 20, 2013

(54) [6,6] AND [6,7]-BICYCLIC GPR119 G PROTEIN-COUPLED RECEPTOR AGONISTS

(71) Applicant: Bristol-Myers Squibb Company, Princeton, NJ (US)

(72) Inventors: John M. Fevig, Doylestown, PA (US); Dean A. Wacker, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/648,436

(22) Filed: Oct. 10, 2012

(65) Prior Publication Data

US 2013/0116237 A1    May 9, 2013

Related U.S. Application Data

(62) Division of application No. 13/289,375, filed on Nov. 4, 2011, now Pat. No. 8,314,095.

(51) Int. Cl.
    *C07D 413/04*    (2006.01)
    *A61K 31/538*    (2006.01)

(52) U.S. Cl.
    USPC ............... 514/264.1; 514/264.11; 544/279

(58) Field of Classification Search
    USPC ............... 544/279; 514/264.1, 264.11
    See application file for complete search history.

(56) References Cited

U.S. PATENT DOCUMENTS

| | | | |
|---|---|---|---|
| 3,826,643 | A | 7/1974 | Diehl et al. |
| 5,488,064 | A | 1/1996 | Sher |
| 5,491,134 | A | 2/1996 | Sher et al. |
| 5,541,204 | A | 7/1996 | Sher et al. |
| 5,612,359 | A | 3/1997 | Murugesan |
| 5,770,615 | A | 6/1998 | Cheng et al. |
| 5,776,983 | A | 7/1998 | Washburn et al. |
| 6,043,265 | A | 3/2000 | Murugesan et al. |
| 6,566,384 | B1 | 5/2003 | Owen et al. |
| 7,928,230 | B2 | 4/2011 | Wacker et al. |
| 2003/0181420 | A1 | 9/2003 | Bayne et al. |
| 2005/0080111 | A1 | 4/2005 | Bayne et al. |
| 2005/0245515 | A1 | 11/2005 | Dehmlow et al. |
| 2006/0155128 | A1 | 7/2006 | Jones et al. |
| 2006/0292073 | A1 | 12/2006 | Goodman et al. |
| 2009/0018055 | A1 | 1/2009 | Fevig et al. |
| 2009/0023702 | A1 | 1/2009 | Wacker et al. |

FOREIGN PATENT DOCUMENTS

| | | |
|---|---|---|
| EP | 1 338 651 | 8/2003 |
| WO | WO 96/38144 | 12/1996 |
| WO | WO 97/12613 | 4/1997 |
| WO | WO 97/12615 | 4/1997 |
| WO | WO 99/26659 | 6/1999 |
| WO | WO 00/01389 | 1/2000 |
| WO | WO 00/39102 | 7/2000 |
| WO | WO 02/02519 | 1/2002 |
| WO | WO 2004/065380 | 8/2004 |
| WO | WO 2004/076413 | 9/2004 |
| WO | WO 2004/089885 | 10/2004 |
| WO | WO 2005/007647 | 1/2005 |
| WO | WO 2005/007658 | 1/2005 |
| WO | WO 2005/025504 | 3/2005 |
| WO | WO 2005/089786 | 9/2005 |
| WO | WO 2005/121121 | 12/2005 |
| WO | WO 2006/067532 | 6/2006 |
| WO | WO 2006/083491 | 8/2006 |

OTHER PUBLICATIONS

Chalmers (TIPS vol. 17, pp. 166-172 Apr. 1996).*
Donetti, A. et al., "(Imidazolylphenyl)formamidines. A Structurally Novel Class of Potent Histamine $H_2$ Antagonists", J. Med. Chem., vol. 27, No. 3, pp. 380-386 (1984).
Gomtsyan, A. et al., "Design, Synthesis, and Structure-Activity Relationship of 6-Alkynylpyrimidines as Potent Adenosine Kinase Inhibitors", J. Med. Chem., vol. 45, No. 17, pp. 3639-3648 (2002).
Chalmers, D.T. et al., "Corticotrophin-releasing factor receptors: from molecular biology to drug design", TIPS, vol. 17, pp. 166-172 (1996).
Ahrén, B., "Autonomic regulation of islet hormone secretion—Implications for health and disease", Diabetologia, vol. 43, pp. 393-410 (2000).
Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).
Boger, D.L. et al., "Total Syntheses of Azafluoranthene Alkaloids: Rufescine and Imeluteine", J. Org. Chem., vol. 49, No. 21, pp. 4050-4055 (1984).
Brancati, F.L. et al., "Body Weight Patterns from 20 to 49 Years of Age and Subsequent Risk for Diabetes Mellitus", Arch. Intern. Med., vol. 159, pp. 957-963 (1999).

(Continued)

*Primary Examiner* — Kahsay T. Habte
(74) *Attorney, Agent, or Firm* — Terence J. Bogie

(57) ABSTRACT

Novel compounds are provided which are GPR119 G protein-coupled receptor modulators. GPR119 G protein-coupled receptor modulators are useful in treating, preventing, or slowing the progression of diseases requiring GPR119 G protein-coupled receptor modulator therapy. These novel compounds have the structure:

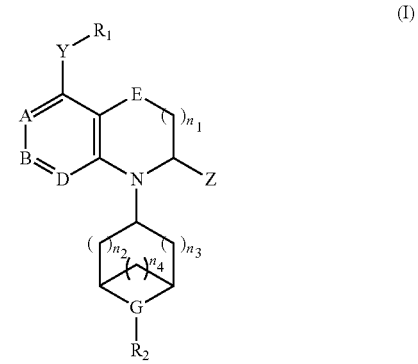

or stereoisomers or prodrugs or pharmaceutically acceptable salts thereof, wherein $n_1$, $n_2$, $n_3$, $n_4$, A, B, D, E, G, Y, Z, $R_1$ and $R_2$ are defined herein.

15 Claims, No Drawings

(56) References Cited

OTHER PUBLICATIONS

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Butler, A.E. et al., "β-Cell Deficit and Increased β-Cell Apoptosis in Humans with Type 2 Diabetes", Diabetes, vol. 52, pp. 102-110 (2003).

Chu, Z.-L. et al., "A Role for β-Cell-Expressed G Protein-Coupled Receptor 119 in Glycemic Control by Enhancing Glucose-Dependent Insulin Release", Endocrinology, vol. 148, No. 6, pp. 2601-2609 (2007).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Deng, H. et al., "Aryllead(IV) Reagents in Synthesis: Formation of the C11 Quaternary Center of N-Methylwelwitindolinone C Isothiocyanate", Organic Letters, vol. 3, No. 19, pp. 3001-3004 (2001).

Ford, E.S. et al., "Prevalence of the Metabolic Syndrome Among US Adults", Journal of the American Medical Association, vol. 287, No. 3, pp. 356-359 (2002).

Fredriksson, R. et al., "Seven evolutionary conserved human rhodopsin G protein-coupled receptors lacking close relatives", FEBS Letters, vol. 554, pp. 381-388 (2003).

Frlan, R. et al., "Recent Progress in Diaryl Ether Synthesis", Synthesis, No. 14, pp. 2271-2285 (2006).

Gennaro, A.R., ed., Remington's Pharmaceutical Sciences, 17$^{th}$ Edition, Mack Publishing Company, publ., p. 1418 (1985).

Greene, T.W. et al., Protective Groups in Organic Synthesis, Second Edition, John Wiley & Sons, Inc., publ., pp. ix-x (table of contents) (1991).

Haning, H. et al., "Novel heterocyclic thyromimetics", Bioorganic & Medicinal Chemistry Letters, vol. 15, pp. 1835-1840 (2005).

Hara, S., "Ileal Na$^+$/bile acid cotransporter inhibitors", Drugs of the Future, vol. 24, No. 4, pp. 425-430 (1999).

Hertzog, D.L., "Recent advances in the cannabinoids", Expert Opin. Ther. Patents, vol. 14, No. 10, pp. 1435-1452 (2004).

Hill, J.O. et al., "Environmental Contributions to the Obesity Epidemic", Science, vol. 280, pp. 1371-1374 (1998).

Hong, C.Y. et al., "Asymmetric Synthesis of Either Enantiomer of Opium Alkaloids and Morphinans. Total Synthesis of (−)- and (+)-Dihydrocodeinone and (−)- and (+)-Morphine", J. Am. Chem. Soc., vol. 115, No. 23, pp. 11028-11029 (1993).

Itoh, T. et al., "A General Palladium-Catalyzed Coupling of Aryl Bromides/Triflates and Thiols", Organic Letters, vol. 6, No. 24, pp. 4587-4590 (2004).

Jiang, G. et al., "Prevention of obesity in mice by antisense oligonucleotide inhibitors of stearoyl-CoA desaturase-1", The Journal of Clinical Investigation, vol. 115, No. 4, pp. 1030-1038 (2005).

Justus, K. et al., "First Synthesis of a Strained 14-Membered Biaryl Ether Lactone by Macrolactonization", Tetrahedron Letters, vol. 32, No. 14, pp. 5781-5784 (1991).

Katritzky, A.R. et al., "Efficient Transformations of Aldehydes and Ketones into One-Carbon Homologated Carboxylic Acids", Synthesis, pp. 1425-1427 (1996).

Ketcha, D.M. et al., "The Reduction of N-(phenylsulfonyl)indoles with Sodium Cyanoborohydride in Trifluoroacetic Acid", Tetrahedron Letters, vol. 30, No. 49, pp. 6833-6836 (1989).

Le Stunff, C. et al., "Early Changes in Postprandial Insulin Secretion, Not in Insulin Sensitivity, Characterize Juvenile Obesity", Diabetes, vol. 43, pp. 696-702 (1994).

Magnus, P. et al., "Studies on the Synthesis of the Antitumor Agent CC-1065. Synthesis of the Unprotected Cyclopropapyrroloindole a Portion Using the 3,3'-Bipyrrole Strategy", J. Am. Chem. Soc., vol. 109, No. 9, pp. 2706-2711 (1987).

NCBI Entrez Accession No. AAP72125 (gi:32165516), Fredriksson, R. et al., Dec. 8, 2003.

NCBI Entrez Accession No. AY288423 (gi:32165529), Fredriksson, R. et al., Dec. 8, 2003.

Nishio, T. et al., "Reduction of Indolin-2-ones and Desulfurization of Indoline-2-thiones to Indoline and Indole Derivatives", Helvetica Chimica Acta, vol. 73, pp. 1719-1723 (1990).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., vol. 43, No. 22, pp. 4288-4312 (2000).

Overton, H.A. et al., "Deorphanization of a G protein-coupled receptor for oleoylethanolamide and its use in the discovery of small-molecule hypophagic agents", Cell Metabolism, vol. 3, pp. 167-175 (2006).

Pedersen, O., "The Impact of Obesity on the Pathogenesis of Non-Insulin-Dependent Diabetes Mellitus: A Review of Current Hypotheses", Diabetes/Metabolism Reviews, vol. 5, No. 6, pp. 495-509 (1989).

Perry, I.J. et al., "Prospective study of risk factors for development of non-insulin dependent diabetes in middle aged British men", BMJ, vol. 310, pp. 560-564 (1995).

Prentki, M. et al., "Islet β cell failure in type 2 diabetes", The Journal of Clinical Investigation, vol. 116, No. 7, pp. 1802-1812 (2006).

Radinov, R. et al., "Lithiation of Polychloropyrimidines and Dichloropyridines", J. Org. Chem., vol. 56, No. 15, pp. 4793-4796 (1991).

Schubert, U., "The Homologation of Hagemann's Ester", Synthesis, pp. 364-365 (1978).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sirowej, H. et al., "Preparation of substituted indoles by reduction of isatin and oxindole derivatives with diborane/tetrahydrofuran", Synthesis, No. 2, p. 84 (1972).

Soga, T. et al., "Lysophosphatidylcholine enhances glucose-dependent insulin secretion via an orphan G-protein-coupled receptor", Biochemical and Biophysical Research Communications, vol. 326, pp. 744-751 (2005).

Takahashi, K. et al., "Efficient Method for a One-Carbon Homologation of Aldehydes and Benzophenone to Carboxylic Acids", J. Org. Chem., vol. 48, No. 20, pp. 3566-3569 (1983).

Testa, B. et al., Hydrolysis in Drug and Prodrug Metabolism: Chemistry, Biochemistry, and Enzymology, Wiley-VCH GmbH & Co., publ., pp. xi-xx (table of contents) (2003).

Urgaonkar, S. et al., "Application of a New Bicyclic Triaminophosphine Ligand in Pd-Catalyzed Buchwald-Hartwig Amination Reactions of Aryl Chlorides, Bromides, and Iodides", J. Org. Chem. vol. 68, No. 22, pp. 8416-8423 (2003).

Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

Yang, B.H. et al., "Palladium-catalyzed amination of aryl halides and sulfonates", Journal of Organometallic Chemistry, vol. 576, pp. 125-146 (1999).

Young, S.D. et al., "L-743,726 (DMP-266): a Novel, Highly Potent Nonnucleoside Inhibitor of the Human Immunodeficiency Virus Type 1 Reverse Transcriptase", Antimicrobial Agents and Chemotherapy, vol. 39, No. 12, pp. 2602-2605 (1995).

Zhang, X. et al., "Dimethyldioxirane Oxidation of Indole Derivatives. Formation of Novel Indole-2,3-epoxides and a Versatile Synthetic Route to Indolinones and Indolines", J. Am. Chem. Soc., vol. 115, No. 19, pp. 8867-8868 (1993).

* cited by examiner

[6,6] AND [6,7]-BICYCLIC GPR119 G PROTEIN-COUPLED RECEPTOR AGONISTS

RELATED APPLICATION

This application is a divisional of U.S. patent application Ser. No. 13/289,375, filed Nov. 4, 2011, now allowed, which claims priority benefit of U.S. patent application Ser. No. 13/022,819, filed Feb. 8, 2011, issued as U.S. Pat. No. 8,076,322 B2, which claims priority benefit of U.S. patent application Ser. No. 12/112,080, filed Apr. 30, 2008, issued as U.S. Pat. No. 7,910,583 B2, which claims priority benefit of U.S. Provisional Application No. 60/915,944, filed on May 4, 2007. The entirety of each of these applications is incorporated herein by reference.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., *Diabetes*, 43:696-702 (1989)). However, over time, β-cell function deteriorates and non-insulin-dependent diabetes develops in about 20% of the obese population (Pederson, P., *Diab. Metab. Rev.*, 5:505-509 (1989) and Brancati, F. L. et al., *Arch. Intern. Med.*, 159:957-963 (1999)). Given its high prevalence in modern societies, obesity has thus become the leading risk factor for NIDDM (Hill, J. O. et al., *Science*, 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., *BMJ*, 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", *J. Clin. Invest.*, 116:1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", *Diabetes*, 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", *Diabetologia*, 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^+$ efflux depolarizes the β-cell leading to an influx of $Ca^{++}$ which promotes the release of insulin.

GPR119 (e.g., human GPR119, GenBank® Accession No. AAP72125 and alleles thereof; e.g., mouse GPR119, GenBank® Accession No. AY288423 and alleles thereof) is a GPCR located at chromosome position Xp26.1 (Fredricksson, R. et al., "Seven evolutionarily conserved human rhodopsin G protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), International Applications WO 04/065380, WO 04/076413, WO 05/007647, WO 05/007658, WO 05/121121, WO 06/083491, and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology*(2007) doi:10.1210/en.2006-1608).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology*(2007) doi:10.1210/en.2006-1608). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), WO 05/007647, WO 05/007658).

SUMMARY OF THE INVENTION

In accordance with the present invention, aryl and heterocyclyl and related compounds are provided that have the general structure of formula I:

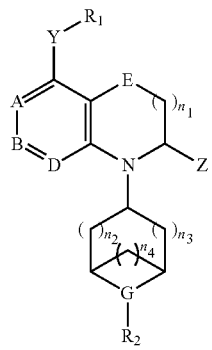

Formula I wherein $n_1$, $n_2$, $n_3$, $n_4$, A, B, D, E, G, Y, Z, $R_1$ and $R_2$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dylsipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma. In general, tested compounds of the instant invention show GPR119 functional activity with an $EC_{50}$ of <10 µM.

The present invention provides compounds of Formula I, pharmaceutical compositions employing such compounds, and methods of using such compounds. In particular, the present invention provides a pharmaceutical composition comprising a therapeutically effective amount of a compound of Formula I, alone or in combination with a pharmaceutically acceptable carrier.

Further, in accordance with the present invention, a method is provided for preventing, modulating, or treating the progression or onset of diseases or disorders associated with the activity of the GPR119 G protein-coupled receptor, such as defined above and hereinafter, wherein a therapeutically effective amount of a compound of Formula I is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I and another compound of Formula I and/or at least one other type of therapeutic agent, is administered to a mammalian, i.e., human, patient in need of treatment.

DESCRIPTION OF THE INVENTION

In accordance with the present invention, compounds of Formula I are provided:

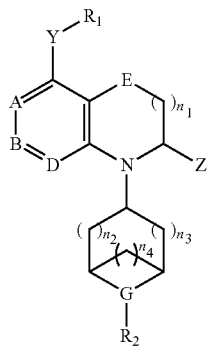

Formula I as well as enantiomers, stereoisomers (such as diastereomers), solvates, and salts (particularly pharmaceutically acceptable salts) thereof wherein:

A, B and D are each independently selected to be $CR_{4b}$ or N;

E is $CH_2$, O or NH, provided that when E is $CH_2$ at least one of A, B or D is N;

G is CH or N;

Y is —$NR_3$, O or S;

Z is absent or =O;

$n_1$ is 1 or 2;

$n_2$ and $n_3$ are each independently selected to be 0-2;

$n_4$ is 0-3;

$R_1$ is aryl or heteroaryl, each of which may optionally be substituted with one or more substituents selected from $R_4$ (more particularly 1-5 of $R_4$);

$R_2$ is selected from the group consisting of cycloalkyl, aryl, heteroaryl, heterocyclyl, —C(=O)$R_5$ and —C(=O)O$R_5$, wherein the cycloalkyl, aryl, heteroaryl and heterocyclyl may each be optionally substituted with one or more $R_6$'s (particularly 1-5) $R_6$'s;

$R_3$ is selected from the group consisting of hydrogen, alkyl, alkoxy, cycloalkyl, aryl, arylalkyl, heteroaryl, heteroarylalkyl, heterocyclyl and heterocyclylalkyl (particularly wherein the heteroaryl, heteroarylalkyl, heterocyclyl and heterocyclylalkyl each contain 1-4 heteroatoms selected from N, O and S);

$R_4$, at each occurrence, is independently selected from the group consisting of alkyl, aryl, alkenyl, alkynyl, cycloalkyl, heteroaryl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3$H$_2$, —C(=O)$NR_9R_9$, —$NR_9R_9$, —S(O)$_2NR_9R_9$, —$NR_9S(O)_2CF_3$, —C(=O) $NR_9S(O)_2R_9$, —S(O)$_2NR_9C$(=O)$OR_9$, —S(O)$_2NR_9C$ (=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —OC (=O)$NR_9R_9$, —C(=$NR_{14}$)$NR_9R_9$, —NHC(=$NR_{14}$) $NR_{14}R_{14}$, —S(=O)$R_{10}$, —S(O)$_2R_{10}$, —$NR_9C$(=O)$OR_8$ and —$NR_9S(O_2)R_8$, wherein the alkyl, aryl, alkenyl, alkynyl, cycloalkyl, heteroaryl and heterocyclyl may each be optionally substituted with one or more $R_6$'s (particularly 1-5 $R_6$'s);

$R_{4b}$, at each occurrence, is independently selected from the group consisting of hydrogen, alkyl, haloalkyl, aryl, alkenyl, alkynyl, cycloalkyl, heteroaryl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3$H$_2$, —C(=O)$NR_9R_9$, —$NR_9R_9$, —S(O)$_2NR_9R_9$, —$NR_9S$ (O)$_2CF_3$, —C(=O)$NR_9S(O)_2R_9$, —S(O)$_2NR_9C$(=O)$OR_9$, —S(O)$_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC (=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —S(O)$_2R_{10}$, —$NR_9C$(=O)$OR_8$ and —$NR_9S(O_2)R_8$, wherein the alkyl, aryl, alkenyl, alkynyl, cycloalkyl, heteroaryl and heterocyclyl may each be optionally substituted with one or more $R_6$'s (particularly 1-5 $R_6$'s);

$R_5$ is selected from the group consisting of alkyl, aryl, cycloalkyl, heteroaryl and heterocyclyl, each of which may optionally be substituted with one or more $R_6$'s (particularly 1-5 $R_6$'s);

$R_6$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3$H$_2$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C$(=O)$OR_9$, —S(O)$_2NR_9C$ (=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —C(=$NR_{14}$)$NR_9R_9$, —NHC(=$NR_{14}$)$NR_{14}R_{14}$, —S(=O) $R_{10}$, —S(O)$_2R_{10}$, —$NR_9C$(=O)$OR_8$ and —$NR_9S(O_2)R_8$;

$R_8$, at each occurrence, is independently selected from the group consisting of alkyl, aryl, cycloalkyl, heteroaryl and heterocyclyl;

$R_9$, at each occurrence, is independently selected from the group consisting of hydrogen, alkyl, alkoxy, cycloalkyl, aryl, arylalkyl, heteroaryl, heteroarylalkyl, heterocyclyl and heterocyclylalkyl, wherein the aryl, arylalkyl, heteroaryl, heteroarylalkyl, heterocyclyl or heterocyclylalkyl may each be optionally substituted with 0-5 $R_{9a}$, and the heteroaryl, heteroarylalkyl, heterocyclyl and heterocyclylalkyl each contain 1-4 heteroatoms selected from N, O and S;

$R_{9a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —S(O)$_3$H, —P(O)$_3$H$_2$, —C(=O)$NR_{14}R_{14}$, —$NR_{14}R_{14}$, —S(O)$_2NR_{14}R_{14}$, —$NR_{14}S(O)_2CF_3$, —C(=O) $NR_{14}S(O)_2R_{10}$, —S(O)$_2NR_{14}C$(=O)$OR_{10}$, —S(O)$_2NR_{14}C$ (=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —S(O)$_2R_{14}$, —$NR_{14}C$(=O)$OR_8$, —$NR_{14}S$ (O$_2$)$R_8$ and arylalkyl;

$R_{10}$, at each occurrence, is independently selected from the group consisting of alkyl, cycloalkyl, alkenyl, alkynyl, aryl, arylalkyl, heteroaryl, heteroarylalkyl, heterocyclyl and heterocyclylalkyl, wherein the aryl, arylalkyl, heterocyclyl and heterocyclylalkyl may each be optionally substituted with 0-5 $R_{10a}$, and the heterocyclyl and heterocyclylalkyl each contain 1-4 heteroatoms selected from N, O and S;

$R_{10a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl; and R$_{14}$, at each occurrence, is independently selected from the group consisting of hydrogen, alkyl, cycloalkyl and aryl.

In a first particular embodiment, compounds of Formula I are provided wherein A and D are each independently CR$_{4b}$ or N, and B is CH.

In a second particular embodiment, compounds of Formula I are provided wherein A and D are each independently CR$_{4b}$ or N, B is CH, and E is O or NH.

In a third particular embodiment, compounds of Formula I are provided wherein A, B and D are each CR$_{4b}$.

In a fourth particular embodiment, compounds of Formula I are provided wherein A, B and D are each CR$_{4b}$, and E is O or NH.

In a fifth particular embodiment, compounds of Formula I are provided wherein A and D are each N, and B is CR$_{4b}$.

In a sixth particular embodiment, compounds of Formula I are provided wherein A and D are each N, B is CR$_{4b}$, and E is O or NH.

In a seventh particular embodiment, compounds of Formula I are provided wherein A is N, and B and D are each CR$_{4b}$.

In an eighth particular embodiment, compounds of formula I are provided wherein A is N, B and D are each CR$_{4b}$, and E is O or NH.

In a ninth particular embodiment, compounds of Formula I are provided wherein R$_{4b}$ is H.

In a tenth particular embodiment, compounds of formula I are provided wherein:

Y is —NR$_3$, O or S;
Z is absent or =O;
n$_1$ is 1 or 2;
n$_2$ and n$_3$ are each independently 1 or 2;
n$_4$ is 0-3;
R$_1$ is aryl or heteroaryl, each of which may be optionally substituted with one or more substituents selected from R$_4$;
R$_2$ is selected from the group consisting of cycloalkyl, aryl, heteroaryl, heterocyclyl, —C(=O)R$_5$ and —C(=O)OR$_5$, wherein the cycloalkyl, aryl, heteroaryl and heterocyclyl may each be optionally substituted with one or more R$_6$'s;
R$_3$ is hydrogen, alkyl, or cycloalkyl;
R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more R$_6$'s;

R$_{4b}$, at each occurrence, is independently selected from the group consisting of hydrogen, alkyl, haloalkyl, cycloalkyl, halo, CN, —OH, —OR$_{10}$, —SR$_{10}$, aryl, heteroaryl and heterocyclyl, wherein the alkyl, cycloalkyl, aryl, heteroaryl and heterocyclyl may each be optionally substituted with one or more R$_6$'s;

R$_5$ is selected from the group consisting of alkyl, aryl, cycloalkyl, heteroaryl and heterocyclyl, each of which may optionally be substituted with one or more R$_6$'s;

R$_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;

R$_8$, at each occurrence, is independently selected from the group consisting of alkyl, aryl, cycloalkyl, heteroaryl and heterocyclyl;

R$_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may optionally be substituted with 0-5 R$_{9a}$, and the heteroaryl and heterocyclyl each contain 1-4 heteroatoms selected from N, O and S;

R$_{9a}$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —C(=O)OH, —C(=O)OR$_{14}$, —OCF$_3$, —OR$_{14}$ and —OH;

R$_{10}$, at each occurrence, is independently selected from the group consisting of alkyl, cycloalkyl, aryl, heteroaryl and heterocyclyl, wherein the aryl, heteroaryl and heterocyclyl may each be optionally substituted with 0-5 R$_{10a}$, and the heteroaryl and heterocyclyl each contains 1-4 heteroatoms selected from N, O and S;

R$_{10a}$, at each occurrence, is independently selected from C1-6 alkyl, C1-4 haloalkyl, C6-10 aryl, C3-6 cycloalkyl, heteroaryl, heterocyclyl, halo, —NH$_2$, —CN, —C(=O)OH, —C(=O)OR$_{14}$, —OCF$_3$, —OR$_{14}$, and —OH; and R$_{14}$, at each occurrence, is independently selected from hydrogen, C1-6 alkyl, C3-6 cycloalkyl or C6-10 aryl.

In an eleventh particular embodiment, compounds of Formula I are provided wherein:

Y is —NR$_3$, O or S;
Z is absent or =O;
n$_1$ is 1 or 2;
n$_2$ and n$_3$ are each independently 1 or 2;
n$_4$ is 0-3;
R$_1$ is aryl or heteroaryl, each of which may be optionally substituted with one or more substituents selected from R$_4$;
R$_2$ is selected from the group consisting of aryl, heteroaryl, heterocyclyl, —C(=O)R$_5$ and —C(=O)OR$_5$, wherein the aryl, heteroaryl and heterocyclyl may each be optionally substituted with one or more R$_6$'s;
R$_3$ is hydrogen or alkyl;
R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)

$NR_{14}R_{14}$, —S(=O)$R_{10}$, —S(O)$_2R_{10}$, —$NR_9$C(=O)$OR_8$ and —$NR_9$S(O$_2$)$R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C1-4 haloalkyl, C6-10 aryl, C3-6 cycloalkyl, halo, CN, —OH, —$OR_{10}$ and —$SR_{10}$, wherein the alkyl, cycloalkyl, and aryl may each be optionally substituted with one or more $R_6$'s;

$R_5$ is selected from the group consisting of C1-6 alkyl, C6-10 aryl, C3-6 cycloalkyl, heteroaryl and heterocyclyl, each of which may optionally be substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —$SR_{10}$, —S(O)$_3$H, —P(O)$_3H_2$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2CF_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, —$NR_9$C(=O)$OR_8$ and —$NR_9$S(O$_2$)$R_8$;

$R_8$, at each occurrence, is independently selected from the group consisting of C1-6 alkyl, C6-10 aryl, C3-6 cycloalkyl, heteroaryl and heterocyclyl;

$R_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may each be optionally substituted with 0-5 $R_{9a}$, and the heteroaryl and heterocyclyl each contain 1-4 heteroatoms selected from N, O and S;

$R_{9a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH;

$R_{10}$, at each occurrence, is independently selected from the group consisting of C1-6 alkyl, C3-6 cycloalkyl, C6-10 aryl, heteroaryl and heterocyclyl, wherein the aryl, heteroaryl and heterocyclyl may each be optionally substituted with 0-5 $R_{10a}$, and the heteroaryl and heterocyclyl each contains 1-4 heteroatoms selected from N, O and S;

$R_{10a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH; and $R_{14}$, at each occurrence, is independently selected from the group consisting of hydrogen, C1-6 alkyl and C6-10 aryl.

In a twelfth particular embodiment, compounds of Formula I are provided wherein:

Y is —$NR_3$, O or S;

Z is absent or =O;

$n_1$ is 1 or 2;

$n_2$ and $n_3$ are each independently 1 or 2;

$n_4$ is 0 or 2;

$R_1$ is C6-10 aryl or heteroaryl, each of which may optionally be substituted with one or more substituents selected from $R_4$;

$R_2$ is selected from the group consisting of C6-10 aryl, heteroaryl, —C(=O)$R_5$ and —C(=O)$OR_5$, wherein the aryl and heteroaryl may each be optionally substituted with one or more $R_6$'s;

$R_3$ is hydrogen or C1-4 alkyl;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —$SR_{10}$, —S(O)$_3$H, —P(O)$_3H_2$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2CF_3$, —C(=O)$R_{10}$, —$NR_9$C(=O)H, —$NR_9$C(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —S(O)$_2R_{10}$, —$NR_9$C(=O)$OR_8$ and —$NR_9$S(O$_2$)$R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl, C1-4 haloalkyl, C6-10 aryl, C3-6 cycloalkyl, halo, CN, —OH, —$OR_{10}$ and —$SR_{10}$, wherein the alkyl, cycloalkyl and aryl may each be optionally substituted with one or more $R_6$'s;

$R_5$ is selected from the group consisting of C1-6 alkyl, C6-10 aryl, C3-6 cycloalkyl and heteroaryl each of which may optionally be substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —$SR_{10}$, —S(O)$_3$H, —P(O)$_3H_2$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2CF_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, —$NR_9$C(=O)$OR_8$ and —$NR_9$S(O$_2$)$R_8$;

$R_8$, at each occurrence, is independently selected from the group consisting of C1-6 alkyl, C6-10 aryl, C3-6 cycloalkyl and heteroaryl;

$R_9$, at each occurrence, is independently selected from the group consisting of hydrogen, C1-6 alkyl, C3-6 cycloalkyl, C6-10 aryl and or heteroaryl, wherein the aryl and heteroaryl may each be optionally substituted with 0-5 $R_{9a}$, and the heteroaryl contains 1-4 heteroatoms selected from N, O and S;

$R_{9a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH;

$R_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 $R_{10a}$, and the heteroaryl contains 1-4 heteroatoms selected from N, O and S;

$R_{10a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH; and $R_{14}$, at each occurrence, is independently selected from the group consisting of hydrogen, C1-6 alkyl and C6-10 aryl In a thirteenth particular embodiment, compounds of Formula I are provided wherein:

Y is —$NR_3$, O or S;

Z is absent or =O;

$n_1$ is 1 or 2;

$n_2$ and $n_3$ are independently 1 or 2;

$n_4$ is 0 or 2;

$R_1$ is C6-10 aryl or heteroaryl, each of which may optionally be substituted with one or more substituents selected from $R_4$;

$R_2$ is heteroaryl, —C(=O)$R_5$ or —C(=O)$OR_5$, wherein the heteroaryl may be optionally substituted with one or more $R_6$'s;

$R_3$ is hydrogen;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more R$_6$'s;

$R_{4b}$, at each occurrence, is independently selected from the group consisting of hydrogen, C1-6 alkyl, C6-10 aryl and C3-6 cycloalkyl, wherein the alkyl, cycloalkyl, and aryl may each be optionally substituted with one or more R$_6$'s;

$R_5$ is selected from the group consisting of C1-6 alkyl, C6-10 aryl and C3-6 cycloalkyl, each of which may optionally be substituted with one or more R$_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ or —NR$_9$S(O$_2$)R$_8$;

$R_8$, at each occurrence, is independently selected from the group consisting of C1-6 alkyl and C6-10 aryl;

$R_9$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 R$_{9a}$, and the heteroaryl contains 1-4 heteroatoms selected from N, O and S;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 R$_{10a}$, and the heteroaryl contains 1-4 heteroatoms selected from N, O and S;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently selected from the group consisting of hydrogen, C1-6 alkyl and C6-10 aryl.

In a fourteenth particular embodiment, compounds of Formula I are provided wherein:

Y is —NR$_3$, O or S;

Z is absent or =O;

$n_1$ is 1 or 2;

$n_2$ and $n_3$ are independently 1 or 2;

$n_4$ is 0;

$R_1$ is C6-10 aryl or heteroaryl, each of which may be optionally substituted with one or more substituents (for example, 1-5) of selected from R$_4$;

$R_2$ is heteroaryl, —C(=O)R$_5$ or —C(=O)OR$_5$, wherein the heteroaryl may be optionally substituted with one or more (for example, 1-5) of R$_6$'s;

$R_3$ is hydrogen;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may be each optionally substituted with one or more R$_6$'s;

$R_{4b}$, at each occurrence, is independently selected from the group consisting of hydrogen, C1-6 alkyl and C3-6 cycloalkyl, wherein the alkyl and cycloalkyl may each be optionally substituted with one or more R$_6$'s;

$R_5$ is C1-6 alkyl, C6-10 aryl or C3-6 cycloalkyl, each of which may be optionally substituted with one or more R$_6$'s;

$R_6$, at each occurrence, is independently selected from the group consisting of C1-6 alkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or C6-10 aryl;

$R_9$, at each occurrence, is independently selected from the group consisting of hydrogen, C1-6 alkyl, C3-6 cycloalkyl and C6-10 aryl, wherein the aryl may be optionally substituted with 0-5 R$_{9a}$;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently hydrogen, C1-6 alkyl, C3-6 cycloalkyl or C6-10 aryl, wherein the aryl may optionally be substituted with 0-5 R$_{10a}$;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently hydrogen, C1-6 alkyl or C6-10 aryl.

In a fifteenth particular embodiment, compounds of Formula I are provided wherein:

A and D are each independently CH or N;

B is CH;

E is O or NH;

G is CH or N;

Y is —NR$_3$ or O;

Z is absent or =O;

$n_1$ is 1 or 2;

$n_2$ and $n_3$ are each 1;

$n_4$ is 0;

$R_1$ is phenyl or heteroaryl, each of which may optionally be substituted with one or more substituents (for example, 1-5) selected from R$_4$;

$R_2$ is heteroaryl, —C(=O)R$_5$ or —C(=O)OR$_5$, wherein the heteroaryl may optionally be substituted with one or more R$_6$'s;

$R_3$ is hydrogen;

$R_4$, at each occurrence, is independently selected from the group consisting of C1-6 alkyl, C1-4 haloalkyl, C3-6 cycloalkyl, phenyl, heteroaryl, halo, —$NH_2$, —CN, —C(=O)OH, —C(=O)$OR_{10}$, —$OCF_3$, —$OR_{10}$, —OH, —$SR_{10}$, —C(=O)$NR_9R_9$, —$NR_9R_9$, —S(O)$_2NR_9R_9$, —C(=O)$NR_9S(O)_2R_9$, —S(O)$_2NR_9C$(=O)$OR_9$, —C(=O)$R_{10}$, —$NR_9C$(=O)H, —$NR_9C$(=O)$R_{10}$, —OC(=O)$NR_9R_9$, —S(=O)$R_{10}$, —S(O)$_2R_{10}$, —$NR_9C$(=O)$OR_8$ and —$NR_9S(O_2)R_8$, wherein the alkyl, phenyl, or heteroaryl may each be optionally substituted with one or more (for example, 1-5) $R_6$'s;

$R_{4b}$, at each occurrence, is independently hydrogen or C1-6 alkyl;

$R_5$ is C1-6 alkyl, C3-6 cycloalkyl or phenyl, each of which may optionally be substituted with one or more (for example, 1-5) $R_6$'s;

$R_6$, at each occurrence, is independently selected from the group consisting of C1-6 alkyl, C1-4 haloalkyl, phenyl, heteroaryl, halo, —$NH_2$, —CN, —C(=O)OH, —C(=O)$OR_{10}$, —$OCF_3$, —$OR_{10}$, —OH, —$SR_{10}$, —C(=O)$NR_9R_9$, —$NR_9R_9$, —S(O)$_2NR_9R_9$, —C(=O)$NR_9S(O)_2R_9$, —S(O)$_2NR_9C$(=O)$OR_9$, —C(=O)$R_{10}$, —$NR_9C$(=O)H, —$NR_9C$(=O)$R_{10}$, —OC(=O)$NR_9R_9$, —S(=O)$R_{10}$, —S(O)$_2R_{10}$,—$NR_9C$(=O)$OR_8$ and —$NR_9S(O_2)R_8$;

$R_8$, at each occurrence, is independently C1-6 alkyl or phenyl;

$R_9$, at each occurrence, is independently hydrogen, C1-6 alkyl, C3-6 cycloalkyl or phenyl, wherein the phenyl may be optionally substituted with 0-5 $R_{9a}$;

$R_{9a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH;

$R_{10}$, at each occurrence, is independently C1-6 alkyl, C3-6 cycloalkyl or phenyl, wherein the phenyl may optionally be substituted with 0-5 $R_{10a}$;

$R_{10a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH; and $R_{14}$, at each occurrence, is independently hydrogen or C1-6 alkyl.

In a sixteenth particular embodiment, compounds of Formula I are provided wherein:

A and D are each independently CH or N;
B is CH;
E is O;
G is N;
Y is —$NR_3$ or O;
Z is absent or =O;
$n_1$ is 1 or 2;
$n_2$ and $n_3$ are 1;
$n_4$ is 0;
$R_1$ is phenyl, pyridyl or pyrimidinyl, each of which may be optionally substituted with one or more substituents (for example, 1-5) selected from $R_4$;
$R_2$ is pyrimidinyl, pyridyl, oxadiazolyl, benzoxazole or —C(=O)$OR_5$, wherein the heteroaryl may be optionally substituted with one or more (for example, 1-5) $R_6$'s;
$R_3$ is hydrogen;
$R_4$, at each occurrence, is independently selected from the group consisting of C1-6 alkyl, C1-4 haloalkyl, C3-6 cycloalkyl, phenyl, heteroaryl, halo, —$NH_2$, —CN, —C(=O)OH, —C(=O)$OR_{10}$, —$OCF_3$, —$OR_{10}$, —OH, —$SR_{10}$, —C(=O)$NR_9R_9$, —$NR_9R_9$, —S(O)$_2NR_9R_9$, —C(=O)$NR_9S(O)_2R_9$, —S(O)$_2NR_9C$(=O)$OR_9$, —C(=O)$R_{10}$, —$NR_9C$(=O)H, —$NR_9C$(=O)$R_{10}$, —OC(=O)$NR_9R_9$, —S(=O)$R_{10}$, —S(O)$_2R_{10}$, —$NR_9C$(=O)$OR_8$ and —$NR_9S(O_2)R_8$, wherein the alkyl, phenyl and heteroaryl may each be optionally substituted with one or more (for example, 1-5) $R_6$'s;

$R_{4b}$, at each occurrence, is hydrogen;

$R_5$ is C1-6 alkyl, C3-6 cycloalkyl or phenyl, each of which may be optionally substituted with one or more (for example, 1-5) $R_6$'s;

$R_6$, at each occurrence, is independently selected from the group consisting of C1-6 alkyl, C1-4 haloalkyl, C3-6 cycloalkyl, phenyl, heteroaryl, halo, —$NH_2$, —CN, —C(=O)OH, —C(=O)$OR_{10}$, —$OCF_3$, —$OR_{10}$, —OH, —$SR_{10}$, —C(=O)$NR_9R_9$, —$NR_9R_9$, —S(O)$_2NR_9R_9$, —C(=O)$NR_9S(O)_2R_9$, —S(O)$_2NR_9C$(=O)$OR_9$, —C(=O)$R_{10}$, —$NR_9C$(=O)H, —$NR_9C$(=O)$R_{10}$, —OC(=O)$NR_9R_9$, —S(=O)$R_{10}$, —S(O)$_2R_{10}$, —$NR_9C$(=O)$OR_8$ and —$NR_9S(O_2)R_8$;

$R_8$, at each occurrence, is independently C1-6 alkyl or phenyl;

$R_9$, at each occurrence, is independently hydrogen, C1-6 alkyl, C3-6 cycloalkyl or phenyl, wherein the phenyl may optionally be substituted with 0-5 $R_{9a}$;

$R_{9a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH;

$R_{10}$, at each occurrence, is independently C1-6 alkyl, C3-6 cycloalkyl or phenyl, wherein the phenyl may optionally be substituted with 0-5 $R_{10a}$;

$R_{10a}$, at each occurrence, is independently selected from the group consisting of C1-6 alkyl, halo, —$NH_2$, —CN, —C(=O)OH, —C(=O)$OR_{14}$, —$OCF_3$, —$OR_{14}$ and —OH; and $R_{14}$, at each occurrence, is independently hydrogen or C1-6 alkyl.

In a seventeenth particular embodiment, compounds of Formula I are provided wherein $n_4$=0 to give a compound of Formula Ia:

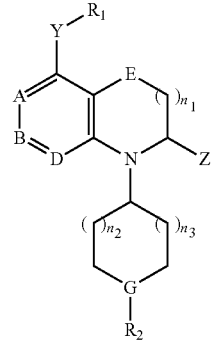

Formula Ia

Further subgroups of Formula Ia comprise a subset of each particular embodiment listed herein (for example, embodiments 1-16 and 18-27, but limited to where $n_4$=0).

For the general description of the invention and as well as for each of the embodiments 1-27 described herein, more particular values are as follows:

"C6-10 aryl" has a more particular value of phenyl.

"Heteroaryl" has a more particular value (especially for $R_4$ and $R_6$) of a single ring with 6 atoms of which 1-4 and, even more particularly 1-3, atoms are each independently selected from O, S and N and the remainder are selected to be carbons. Even more particular values for heteroaryl are oxazole, triazole, imidazole and pyrazole.

"One or more $R_6$'s" has a more particular value of 1-5 of $R_6$'s which are independently selected from the listed definition for $R_6$ for that embodiment.

"Heterocyclyl" has a more particular value of 1-4 atoms selected from N, O and S, with the remaining atoms being carbon; and an even more particular value as a 4- to 6-membered ring with 1-2 members selected from O, S and N and the remaining atoms being carbon.

"One or more substituents selected from $R_4$" has a more particular value of 1-5 of $R_4$.

In an eighteenth particular embodiment, compounds of the present invention are selected from the compounds exemplified in the examples.

In a nineteenth particular embodiment, the present invention relates to pharmaceutical compositions comprised of a therapeutically effective amount of a compound of the present invention (more particularly, a compound according to any of the embodiments described herein), alone or, optionally, in combination with a pharmaceutically acceptable carrier and/or one or more other agent(s), for example, a glucagon-like peptide-1 receptor agonist or fragment thereof.

In a twentieth embodiment, the present invention relates to methods of modulating the activity of the GPR119 G protein-coupled receptor comprising administering to a mammalian patient, for example, a human patient, in need thereof a therapeutically effective amount of a compound of the present invention, alone, or optionally, in combination with another compound of the present invention and/or at least one other type of therapeutic agent.

In a twenty-first embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dylsipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In a twenty-second particular embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-third particular embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-fourth particular embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-fifth embodiment, the present invention relates to a method for preventing, modulating, or treating the progression or onset of obesity comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-sixth particular embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a twenty-seventh particular embodiment, the present invention relates to a method for preventing, modulating, or treating the progression or onset of hypertension comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

This Definition section is listed for convenience, but is subject to the specific and narrower definitions given for the embodiments and Examples listed elsewhere in the specification and the Examples.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as described in Young, S. D. et al., *Antimicrobial Agents and Chemotherapy*, 2602-2605 (1995).

To the extent that compounds of Formula I, and salts thereof, may exist in their tautomeric form, all such tautomeric forms are contemplated herein as part of the present invention.

The term "substituted", as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons and even more preferably 1-6 carbons, in the normal chain. "Lower alkyl" is intended to include alkyls having 1-5 carbons, particularly 1-3 carbons. Examples include methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Alkyl groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, and, even more particularly, 1 ring, including monocyclic alkyl, bicyclic alkyl (or bicycloalkyl) and tricyclic alkyl. Cycloalkyls as defined herein contain a total of 3 to 20 carbons forming the ring, preferably 3 to 15 carbons, more preferably 3 to 10 carbons, forming the ring. A cycloalkyl as defined herein and, even more particularly, 3-6 carbons may be fused to 1 or 2 aromatic rings as described for aryl. Examples of cycloalkyl include cyclopropyl, cyclobutyl, cyclopentyl, cyclohexyl, cycloheptyl, cyclooctyl, cyclodecyl, cyclododecyl, cyclohexenyl,

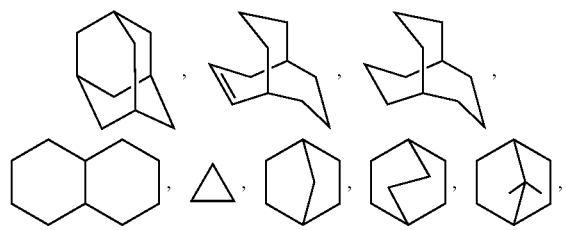

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents defined above for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo (particularly fluoro and chloro); and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings
for example

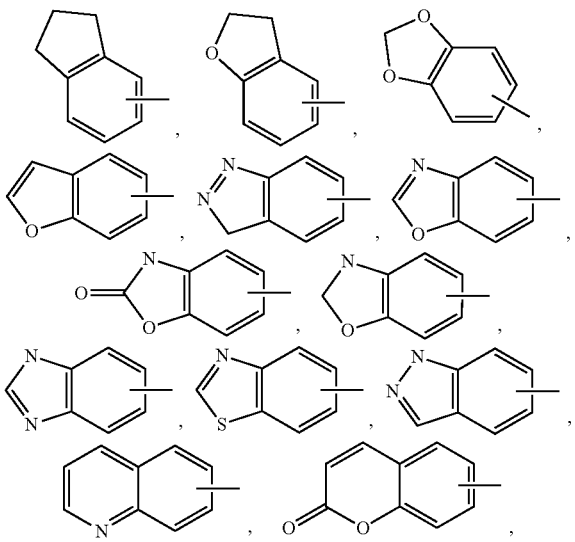

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein. A more particular definition of "aryl" is a monocyclic or bicyclic group containing only carbons in the ring (for example, phenyl) which may be optionally substituted through available carbon atoms with 1, 2 or 3 substituents.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio", "alkylthio", "arylthio" or "aralkylthio" as employed herein alone or as part of another group includes any of the above alkyl, aralkyl, or aryl groups linked to a sulfur atom.

Unless otherwise indicated, the term "lower alkylamino", "alkylamino", "arylamino" or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated, partially unsaturated or unsaturated (aromatic) also called "heteroaryl", and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

As noted above, one particular type of heterocycle is a group known as "heteroaryls". One particular example of "heteroaryl" are those having a single ring of which 1-4 (and, more particularly, 1-3) members are O, S and N and the remainder are carbons. Specific examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.
The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry*, Camille G. Wermuth et al., Ch. 31, (Academic Press, 1996);
b) *Design of Prodrugs*, edited by H. Bundgaard (Elsevier, 1985);

c) *A Textbook of Drug Design and Development*, P. Krogsgaard-Larson and H. Bundgaard, eds., Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of Formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders. As used in this invention, it is believed that a therapeutically effective amount of a compound is in the range of 0.1-100 mg/kg per day.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of formula I falling into a given class may be compatible with some of the reaction conditions required in some of the methods described. Such restrictions to the substituents, which are compatible with the reaction conditions, will be readily apparent to one skilled in the art and alternate methods must be used.

The synthesis routes described in the following schemes are for simplicity shown for compounds of formula I where G is N or CH, $n_2$ and $n_3$ are 1, and $n_4$ is 0, such that the synthesis is described for those compounds of formula I containing a piperidine or cyclohexane ring. It will be recognized by those skilled in the art that the synthesis routes described in the following schemes can also be readily applied to those compounds of formula I where G is N or CH, $n_2$ and $n_3$ are independently 0-2, and $n_4$ is 0-3. It will be further recognized that the appropriate starting materials for those compounds of formula I where G is N or CH, $n_2$ and $n_3$ are independently 0-2, and $n_4$ is 0-3 are either commercially available or can be readily prepared by standard procedures known to those skilled in the art.

Scheme 1 provides a general route to prepare compounds of Formula I where A, B and D are $CR_{4b}$, and E is oxygen. Anilines (1) are either commercially available or are readily prepared by one skilled in the art. For example, treatment of commercially available aniline (1, $R_{4b}$ is H) with a cyclic ketone (2) under reductive amination conditions, such as in the presence of sodium triacetoxyborohydride, affords the substituted aniline (3). Treatment of (3) with a reagent (4), for example 1,2-dibromoethane or 1-bromo-2-chloroethane ($n_1$ is 1, $X^1$ is Br, $X^2$ is Br or Cl, respectively), or 1,3-dibromopropane or 1-bromo-3-chloropropane ($n_1$ is 2, $X^1$ is Br, $X^2$ is Br or Cl, respectively), in the presence of a base such as potassium carbonate or cesium carbonate in a suitable solvent, such as DMF, gives the cyclized product (6) where Z is absent. Likewise, treatment of (3) with a reagent (5), for example chloroacetyl chloride ($n_1$ is 1, $X^3$ and $X^4$ are Cl) or 3-chloropropionyl chloride ($n_1$ is 2, $X^3$ and $X^4$ are Cl), in the presence of a base, such as triethylamine, in a suitable solvent, such as methylene chloride or THF, gives the cyclized product (6) where Z is a carbonyl group. Alternatively, treatment of (3) with a reagent (5) where $X^4$ is OMe, for example methyl bromoacetate ($n_1$ is 1, $X^3$ is Br) in the presence of a base such as sodium hydride in an appropriate solvent, such as THF, gives an O-alkylated ester intermediate, which by heating under various conditions, with or without an acid catalyst such as p-toluenesulfonic acid, can produce the cyclized product (6) where Z is a carbonyl group. Treatment of (6) with an appropriate reagent $R_1$—YH (7), where Y=$NR_3$, O or S, to afford (8) can be accomplished under a wide variety of conditions familiar to those skilled in the art. For example, when Y is $NR_3$, the reaction can be accomplished under palladium-catalyzed coupling conditions, using an appropriate palladium catalyst, such as Pd(dppf)Cl$_2$, Pd$_2$(dba)$_3$, Pd(PPh$_3$)$_4$ or Pd(OAc)$_2$, etc., and a suitable ligand such as BINAP, PPh$_3$, P(tBu)$_3$, o-(biphenyl)P(tBu)$_2$, etc., and a base such as but not limited to NaOtBu or Cs$_2$CO$_3$ in a suitable solvent such as DMF, toluene, THF or DME, at elevated temperatures, to yield (8) (see Yang, B. H. et al., *J. Organomet. Chem.*, 576: 125 (1999) and Urgaonkar, S. et al., *J. Org. Chem.*, 68:8416 (2003), and references cited therein). In a preferred procedure, (6) is treated with an appropriate aniline (7) using Pd(dppf)Cl$_2$ as catalyst, BINAP as the ligand, NaOtBu as the base in toluene at 100° C., with or without microwave irradiation, to afford compounds (8). When Y is O, the reaction can be accomplished by a variety of palladium-catalyzed coupling conditions to afford diaryl ethers (8). For example, treatment of (6) with a phenol (7) in the presence of a palladium catalyst, such as Pd(OAc)$_2$, Pd$_2$(dba)$_3$, etc., a ligand such as DPPF, BINAP, P(tBu)$_3$, o-(biphenyl)P(tBu)$_2$, etc., and a base such as but not limited to K$_2$CO$_3$, or K$_3$PO$_4$ in a suitable solvent such as DMF, toluene, THF or DME, at elevated temperatures, affords ethers (8) (for a recent review of diaryl ether synthesis, see Frlan, R. et al., *Synthesis*, 2271 (2006)). Diaryl ethers (8) can also be prepared by the Ullmann coupling reaction, which involves treatment of (6) with a phenol (7) or its sodium salt in the presence of a copper (I) salt, such as Cu$_2$O, CuI, CuBr, CuPF$_6$(MeCN), etc., a suitable base, such as Cs$_2$CO$_3$ or NaOtBu, with or without an added ligand, such as 1,10-phenanthroline, Chxn-Py-Al, PPh$_3$, etc., in a suitable solvent such as pyridine, toluene, DMF, MeCN, etc, at elevated temperatures, to afford ethers (8) (see Frlan, R. et al., *Synthesis*, 2271 (2006)). When Y is S, the reaction can also be accomplished by palladium-catalyzed coupling of (6) with an aryl thiol (7), for example by using Pd$_2$(dba)$_3$ or Pd(OAc)$_2$ as catalyst, a ligand such as Xantphos or DPEphos, a base such as Hunig's base or potassium carbonate, in dioxane or toluene as solvent at elevated temperature, to afford diaryl thioethers (8) (see Itoh, T. et al., *Org. Lett.*, 6:4587 (2006) and references therein). Alternatively, diaryl thioethers (8) can also be prepared by the Ullman coupling reaction similar to that described for diaryl ethers. For example, treatment of (6) with a thiophenol (7) in the presence of a copper (I) salt, such as Cu$_2$O, CuI, CuBr, CuPF$_6$(MeCN), etc., a suitable base, such as Cs$_2$CO$_3$ or NaOtBu, with or without an added ligand, such as 1,10-phenanthroline, Chxn-Py-Al, PPh$_3$, etc., in a suitable solvent such as pyridine, toluene, DMF, MeCN, etc, at elevated temperatures, affords thioethers (8). Thus, Scheme 1 provides a general route to prepare compounds of Formula I where A, B and D are CR$_{4b}$, and E is oxygen.

Scheme 1

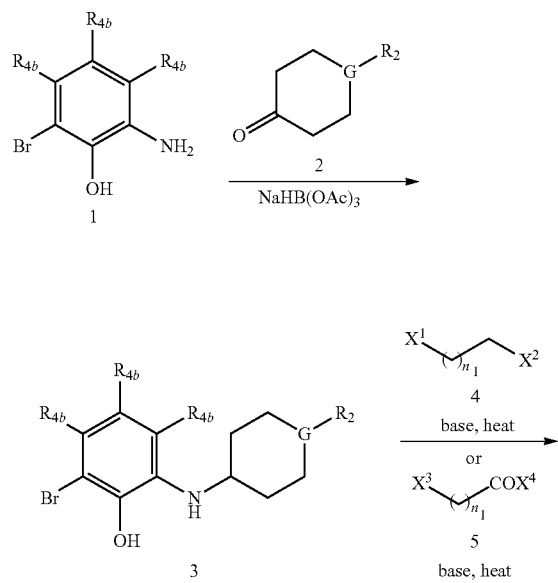

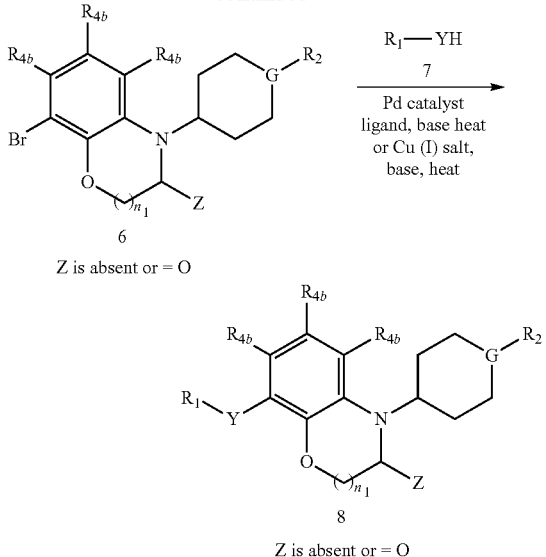

Scheme 2 provides a general route to prepare compounds of Formula I where A is N, B and D are CR$_{4b}$, and E is oxygen. Pyridines (9) are either commercially available or are readily prepared by one skilled in the art. For example, the commercially available 3-hydroxypyridine (9, R$_{4b}$ is H) can be selectively nitrated at the 4-position with nitric acid and sulfuric acid, providing 4-nitropyridine (10, R$_{4b}$ is H) (see US 2006/0155128A1). Protection of the phenol functionality of (10) by, for example, but not limited to, methyl ether (PG=methyl) or any of a variety of trialkylsilyl groups (PG=R$_3$Si), gives (11). The methyl ether can be prepared by treating (10) with methyl iodide in the presence of a base such as sodium hydride or potassium carbonate, in a solvent such as THF or DMF. The trialkylsilyl protecting group can be introduced by treating (10) with a suitable trialkylsilyl chloride or triflate in the presence of a base such as triethylamine, in a solvent such as THF or CH$_2$Cl$_2$. It will be recognized by those skilled in the art that additional protecting groups can be employed for phenol (10). For an excellent reference for alcohol and phenol protecting groups, see Greene, T. et al., *Protecting Groups in Organic Synthesis*, John Wiley & Sons, Inc., New York, N.Y. (1991) and references therein. Conversion of (11) to (13) can be accomplished in two ways. Displacement of the nitro group can be achieved by treatment of (11) with amine (12) in the presence of a base, such as potassium carbonate, in a solvent such as DMF, at elevated temperature with or without microwave irradiation. Alternatively, the nitro group of (11) can be reduced by a variety of reducing agents well known to those skilled in the art, such as by Zn/NH$_4$Cl or SnCl$_2$, to afford a 4-aminopyridine which can then undergo reductive amination with ketone (2) in the presence of a borohydride reducing agent, such as sodium triacetoxyborohydride. Alternatively, the aminopyridine can be treated with ketone (2) in the presence of an acid catalyst, such a p-toluenesulfonic acid, to form the imine upon removal of water, by such methods as toluene at reflux with a Dean-Stark trap. The resulting imine can then be reduced with an appropriate borohydride reducing agent, such as with sodium borohydride, in a solvent such as methanol or THF Deprotection of (13) to liberate the phenol affords (14). When PG is methyl the deprotection can be accomplished using boron tribromide, TMSI, or other methods known to those skilled in the art, to provide the phenol (14). It will be recognized by those skilled in the art that when G is nitrogen and when $R_2$ is an acid labile protecting group, such as BOC, deprotection under acidic conditions may also cause loss of the nitrogen protecting group. In such case (G=N, $R_2$=BOC) the nitrogen can be reprotected using $BOC_2O$ to afford (14). In the case of (13) where PG is trialkylsilyl, the deprotection can be accomplished using tetrabutylammonium fluoride (TBAF) in a solvent such as THF (see Greene, T. et al., *Protecting Groups in Organic Synthesis*, John Wiley & Sons, Inc., New York, N.Y. (1991) and references therein). Cyclization of (14) can be accomplished with the reagents (4) and (5) and a suitable base at elevated temperature, as described in Scheme 1, to afford compound (15), where Z is absent or is a carbonyl group. Coupling of (15) with reagent (7) as described in Scheme 1 affords compounds (16), which represent Formula I where A is N, B and D are $CR_{4b}$, and E is oxygen.

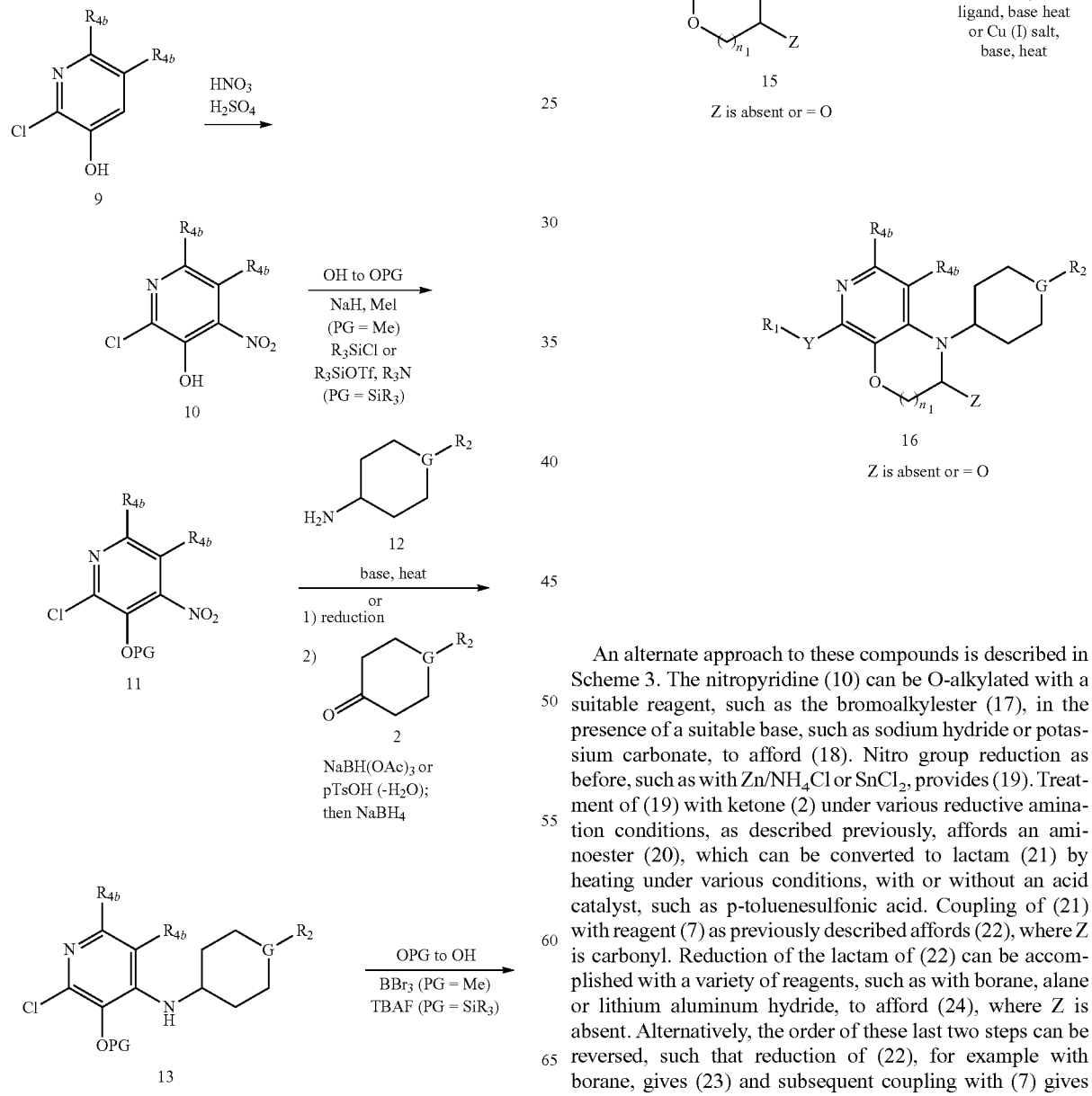

An alternate approach to these compounds is described in Scheme 3. The nitropyridine (10) can be O-alkylated with a suitable reagent, such as the bromoalkylester (17), in the presence of a suitable base, such as sodium hydride or potassium carbonate, to afford (18). Nitro group reduction as before, such as with $Zn/NH_4Cl$ or $SnCl_2$, provides (19). Treatment of (19) with ketone (2) under various reductive amination conditions, as described previously, affords an aminoester (20), which can be converted to lactam (21) by heating under various conditions, with or without an acid catalyst, such as p-toluenesulfonic acid. Coupling of (21) with reagent (7) as previously described affords (22), where Z is carbonyl. Reduction of the lactam of (22) can be accomplished with a variety of reagents, such as with borane, alane or lithium aluminum hydride, to afford (24), where Z is absent. Alternatively, the order of these last two steps can be reversed, such that reduction of (22), for example with borane, gives (23) and subsequent coupling with (7) gives (24).

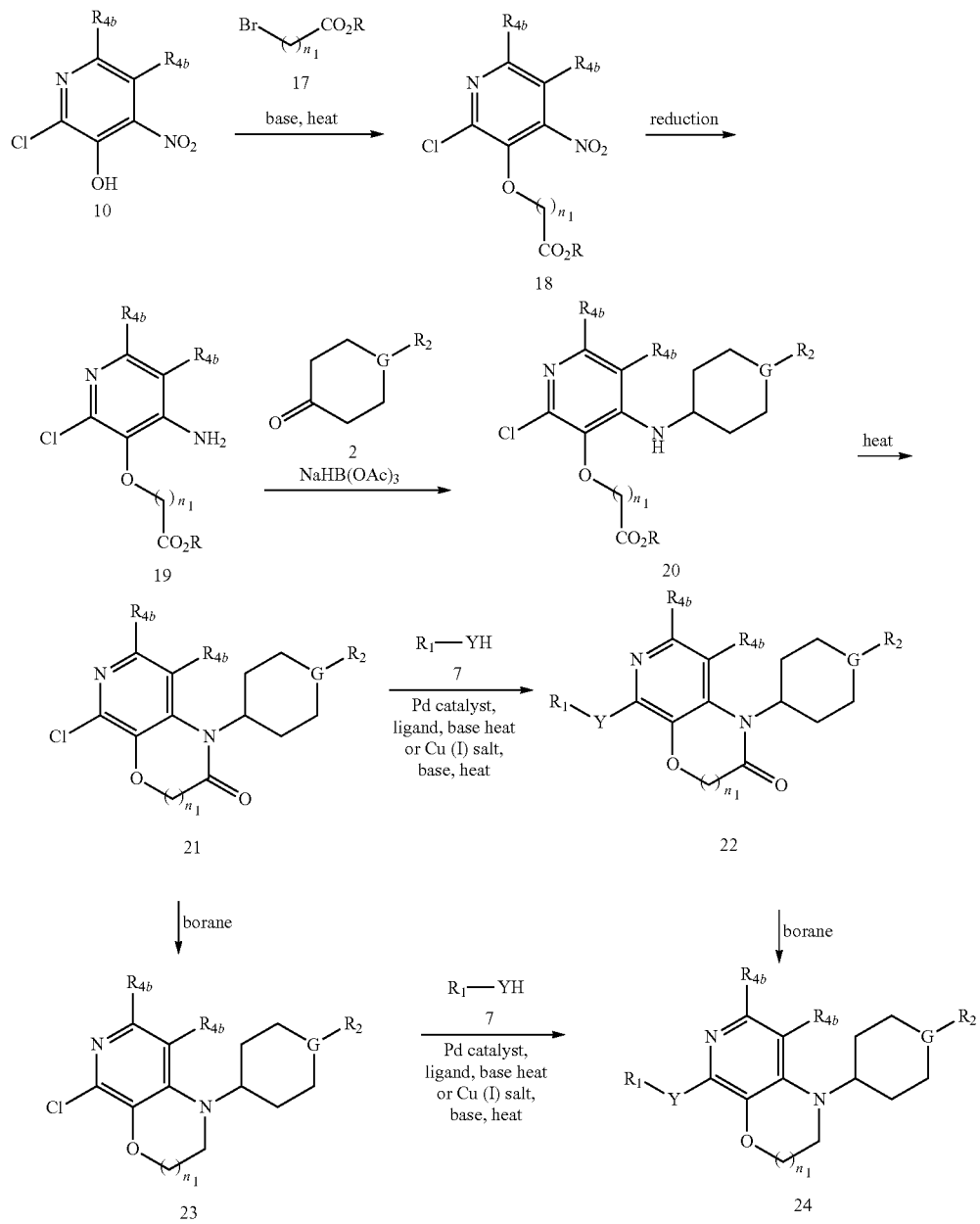

Scheme 3

Scheme 4 provides a general route to prepare compounds of Formula I where B is N, A and D are $CR_{4b}$, and E is oxygen. Pyridines (25) are either commercially available or are readily prepared by one skilled in the art. For example, 5-bromo-3-nitro-pyridinol (25, $R_{4b}$ is H) is readily prepared from 3-nitro-4-hydroxypyridine (see U.S. Pat. No. 3,826, 643). The phenol functionality of (25) can be protected by, for example, but not limited to, methyl ether (PG is methyl) or any of a variety of trialkylsilyl groups (PG is $R_3Si$), to afford (26). The methyl ether can be prepared by treating (25) with methyl iodide in the presence of a base such as sodium hydride or potassium carbonate, in a solvent such as THF or DMF. The trialkylsilyl protecting group can be introduced by treating (25) with a suitable trialkylsilyl chloride or triflate in the presence of a base such as triethylamine, in a solvent such as THF or $CH_2Cl_2$. It will be recognized by those skilled in the art that additional protecting groups can be employed for phenol (25). For an excellent reference for alcohol and phenol protecting groups, see Greene, T. et al., *Protecting Groups in Organic Synthesis*, John Wiley & Sons, Inc., New York, N.Y. (1991) and references therein. The nitro group of (26) can be reduced by a variety of reducing agents well known to those skilled in the art, such as by $Zn/NH_4Cl$ or $SnCl_2$, to afford a 3-aminopyridine which can then undergo reductive amination with ketone (2) in the presence of a borohydride reducing agent, such as sodium triacetoxyborohydride to afford (27). Alternatively, the aminopyridine can be treated with ketone (2) in the presence of an acid catalyst, such a p-toluenesulfonic acid, to form the imine upon removal of water, by such method as toluene at reflux with a Dean-Stark trap. The resulting imine can then be reduced with an appropriate borohydride reducing agent, such as with sodium borohydride, in a solvent such as methanol or THF to afford (27). Deprotection of (27) to liberate the phenol affords (28). When PG is methyl the deprotection can be accomplished using boron tribromide, TMSI, or other methods known to those skilled in the art, to provide the phenol (28). It will be recognized by those skilled in the art that when G is nitrogen and when $R_2$ is an acid labile protecting group, such as BOC, deprotection under acidic conditions may also cause loss of the nitrogen protecting group. In such case (G is N, $R_2$ is BOC) the nitrogen can be reprotected using $BOC_2O$ to afford (28). In the case of (27) where PG is trialkylsilyl, the deprotection can be accomplished using tetrabutylammonium fluoride (TBAF) in a solvent such as THF (see Greene, T. et al., *Protecting Groups in Organic Synthesis*, John Wiley & Sons, Inc., New York, N.Y. (1991) and references therein). Cyclization of (28) can be accomplished with the reagents (4) or (5) and a suitable base at elevated temperature, as described in Scheme 1, to afford compound (29), where Z is absent or is a carbonyl group. Coupling of (29) with reagent (7) under a variety of conditions, as described in Scheme 1, affords compounds (30), which represent Formula I where B is N, A and D are $CR_{4b}$, and E is oxygen.

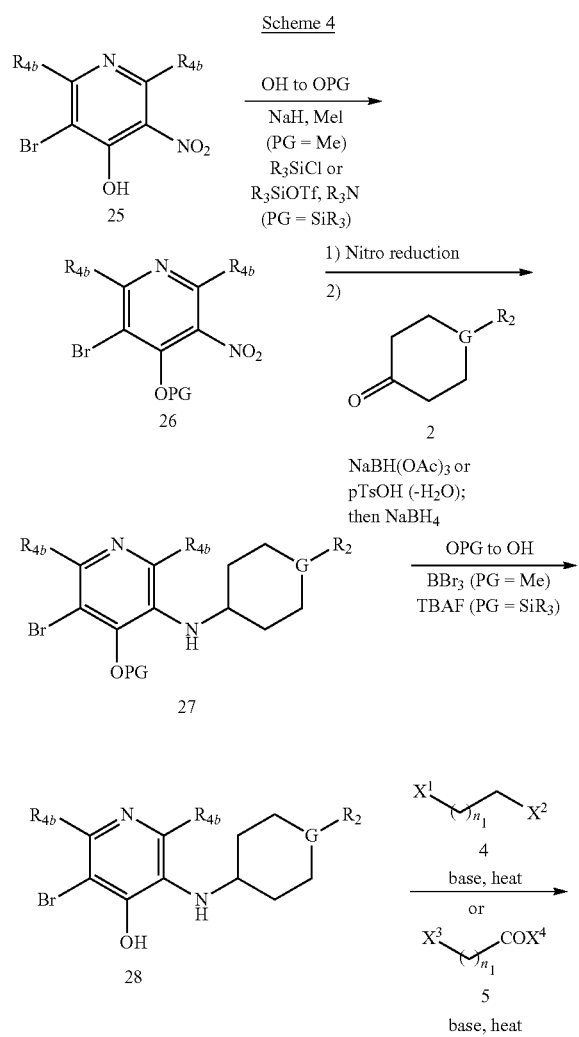

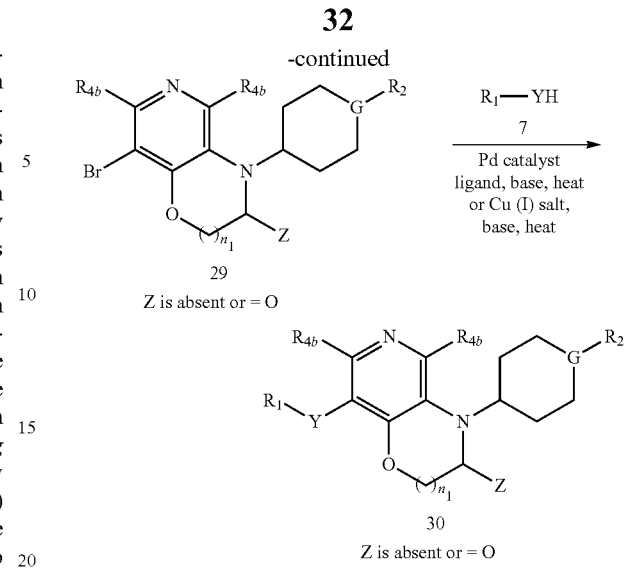

Scheme 5 provides a general route to prepare compounds of Formula I where A and D are N, B is $CR_{4b}$, and E is oxygen. Pyrimidines (31) are either commercially available or are readily prepared by one skilled in the art. For example, treatment of commercially available 4,6-dichloro-5-methoxypyrimidine (31, $R_{4b}$ is H) with 1 equivalent of amine (12) in the presence of a base such as potassium carbonate or cesium carbonate, in a solvent such as DMF, THF or methylene chloride gives (32). Demethylation can be accomplished with $BBr_3$ or TMSI, as described in Scheme 2, to afford the hydroxypyrimidine (33). It will be recognized by those skilled in the art that when G is nitrogen and when $R_2$ is an acid labile protecting group, such as tert-butyloxycarbonyl (BOC), deprotection under acidic conditions may also cause loss of the nitrogen protecting group. In such case (G is N, $R_2$ is BOC) the nitrogen can be reprotected using di-tert-butyl-dicarbonate ($BOC_2O$) to afford (33). Treatment of (33) with a reagent (4), for example 1,2-dibromoethane or 1-bromo-2-chloroethane ($n_1$ is 1, $X^1$ is Br, $X^2$ is Br or Cl, respectively), or 1,3-dibromopropane or 1-bromo-3-chloropropane ($n_1$ is 2, $X^1$ is Br, $X^2$ is Br or Cl, respectively), in the presence of a base such as potassium carbonate or cesium carbonate in a suitable solvent, such as DMF, gives the cyclized product (34) where Z is absent. In a preferred procedure where $n_1$ is 1 in Formula I, (33) is treated with 1-bromo-2-chloroethane and potassium carbonate in DMF at room temperature for several hours to afford an N-chloroethyl intermediate. The temperature of the reaction mixture is then raised to 80-100° C. to afford the cyclized product (34) where Z is absent. Alternatively, treatment of (33) with a reagent (5) where $X^4$ is OMe, for example methyl bromoacetate ($n_1$ is 1, $X^3$ is Br) in the presence of a base such as sodium hydride or cesium carbonate gives an O-alkylated ester intermediate, which by heating under various conditions can produce the cyclized product (34) where Z is a carbonyl group. In a preferred procedure where $n_1$ is 1 in Formula I, (33) is treated with methyl bromoacetate and cesium carbonate in DMF at room temperature for several hours to afford an N-alkylated ester intermediate. The temperature of the reaction mixture is then raised to 60-80° C. to afford the cyclized product (34) where Z is a carbonyl group. Coupling of (34) with reagent (7) under various conditions as described in Scheme 1 affords (35), which represents Formula I where A and D are N, B is $CR_{4b}$, and E is oxygen.

Scheme 5

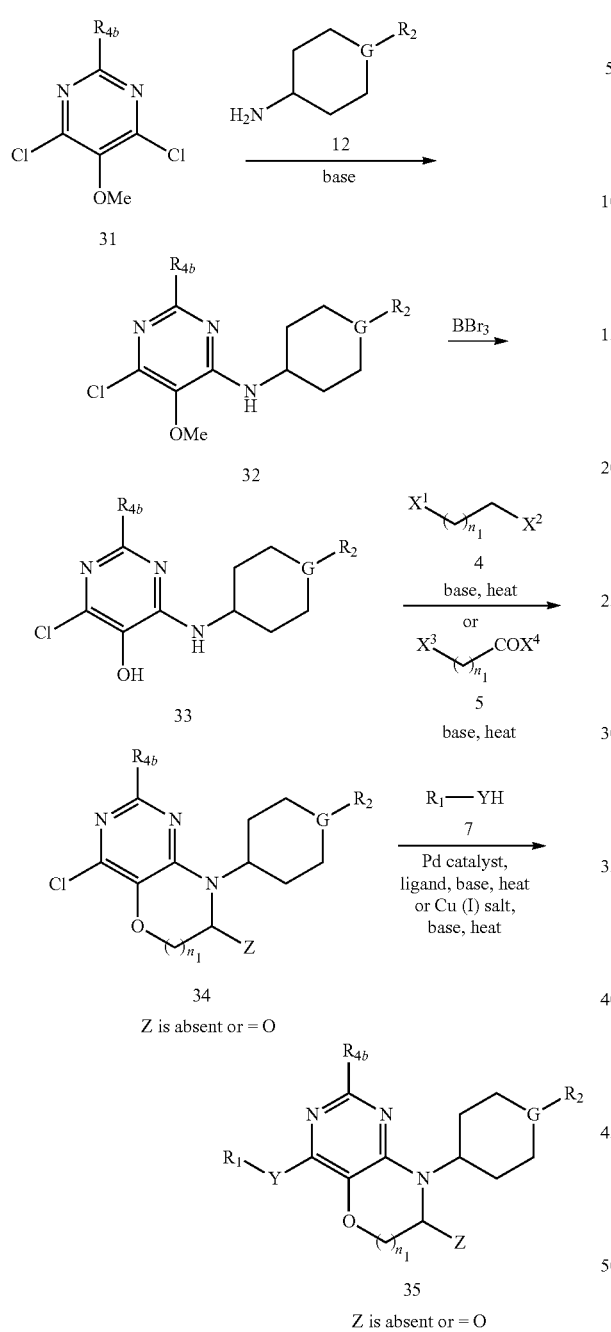

Scheme 6

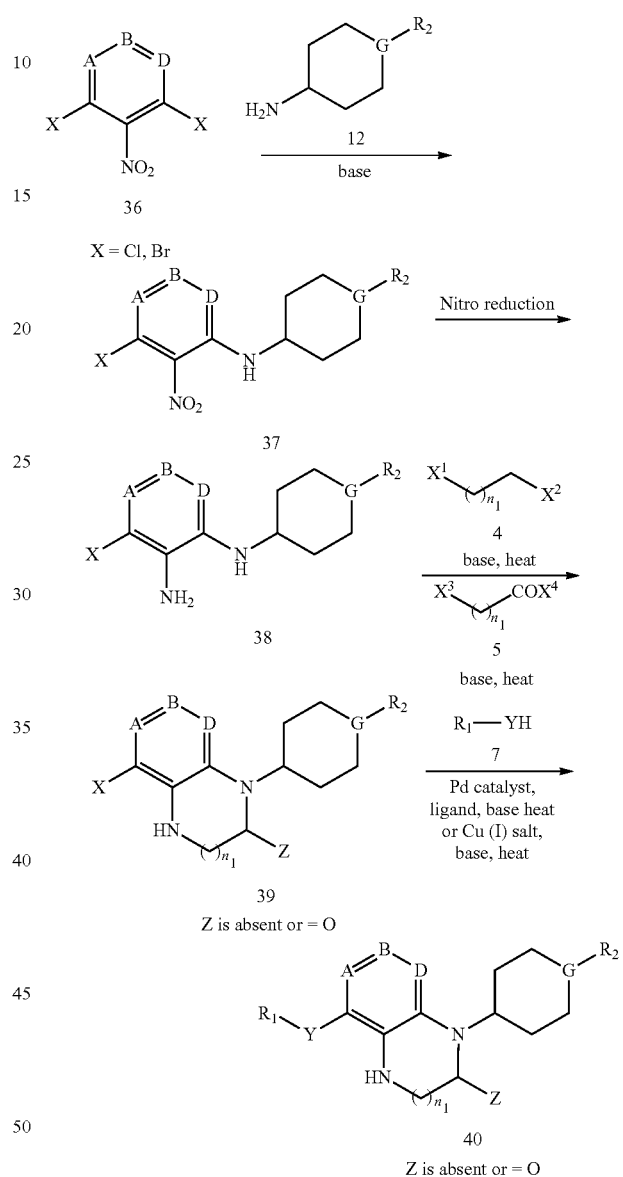

Compounds of Formula I where E is N can be prepared as described in Scheme 6. Dihalo nitro compounds (36) are either commercially available or are readily prepared by methods known to those skilled in the art. For example, 4,6-dichloro-5-nitropyrimidine (36, X is Cl, A and D are N, B is CH) is commercially available, while 2,4-dichloro-3-nitropyridine (36, X is Cl, A is N, B and D are CH) is readily available from 2,4-dihydroxypyridine (see Norman, M. H. et al., *J. Med. Chem.*, 43:4288 (2000)). Treatment of (36) with amine (12) in the presence of a base such as potassium carbonate or cesium carbonate, in a solvent such as DMF, THF or methylene chloride affords (37). Nitro group reduction can be accomplished with a variety of reagents, such as with Zn/NH$_4$Cl or SnCl$_2$, as previously described, to provide diamine (38). Cyclization with reagents (4) or (5) gives compound (39), which can be coupled with reagent (7) as previously described in Scheme 1 to afford (40).

An alternative preparation of these compounds where Y is O or S is shown in Scheme 7. Coupling of (41) with reagent (7) where Y is O or S can precede bicyclic ring formation, giving (42). This reaction can be readily accomplished by treatment of (41) with (7), where Y is O or S, in the presence of a base such as potassium carbonate, cesium carbonate or NaH, in a suitable solvent such as DMF, THF or methylene chloride, at room temperature or elevated temperature, with or without microwave irradiation, to afford (42). Nitro group reduction can then be accomplished as previously described in Scheme 6, using Zn/NH$_4$Cl, SnCl$_2$, catalytic hydrogenation, or other suitable reagent known to those skilled in the art, to afford the diamine (43). As described previously, bicyclic ring formation can be accomplished with reagents (4) or (5) to afford compounds (40), where Z is absent or is a carbonyl, and Y is oxygen or sulfur.

which represents compounds of Formula I where E is $CH_2$, $n_1$ is 1, and Z is C=O. Further reduction of (48), for example by treating with borane or lithium aluminum hydride in a solvent such as THF or ether, or by other known procedures, affords (49), which represents compounds of Formula I where E is $CH_2$, $n_1$ is 1, and Z is absent.

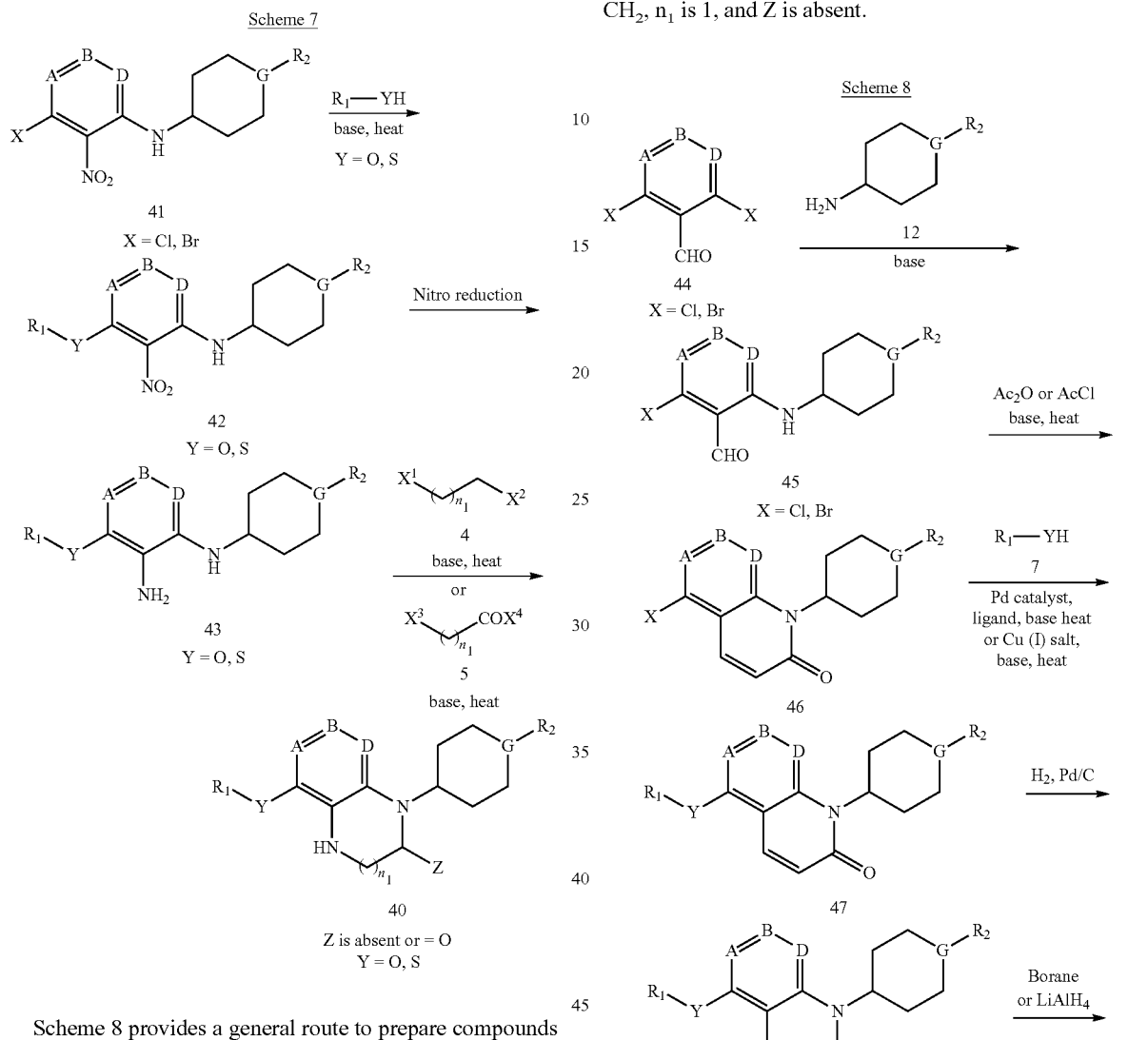

Scheme 8 provides a general route to prepare compounds of Formula I where E is $CH_2$ and $n_1$ is 1. Compounds (44) are either commercially available or readily prepared by methods known to those skilled in the art. For example, 4,6-dichloro-5-formylpyrimidine (44, X is Cl, A and D are N, B is CH) is commercially available, while 2,4-dichloro-3-formylpyridine (44, X is Cl, A is N, B and D are CH) can be readily prepared from 2-4-dichloropyridine (see Radinov, R. et al., *J. Org. Chem.*, 56:4793 (1991)). Treatment of (44) with amine (12) in the presence of a base, such as potassium carbonate, cesium carbonate or triethylamine, in a solvent such as DMF, THF or methylene chloride, affords (45). Treatment of (45) with an acetylating agent such as acetic anhydride or acetyl chloride in the presence of a base such as triethylamine or pyridine, in a solvent such as THF at elevated temperature, with or without microwave irradiation, affords (46) via N-acetylation followed by intramolecular aldol condensation. Coupling of (46) with reagent (7) under various conditions as described in Scheme 1 affords (47). Reduction of the double bond of (47), such as by catalytic hydrogenation over Pd/C catalyst, in a solvent such as methanol or ethanol, or by other methods known to those skilled in the art, affords (48), Scheme 9 provides an alternative route to prepare compounds of Formula I where E is $CH_2$. Treatment of aldehyde (45) with an appropriate Horner-Emmons reagent (50), such as triethylphosphonoacetate (R is Et), in the presence of a suitable base, such as sodium hydride or potassium bis(trimethylsilyl)amide (KHMDS), and in a solvent such as THF affords the olefin (52) where m is 0. Likewise, (45) can be treated with an appropriate homologated Wittig reagent, such as the phosphorane (51), which can be generated in situ from the corresponding triphenylphosphonium salt and a base such as potassium t-butoxide, in a solvent such as THF or toluene, and affords the olefin (52) where m is 1. Coupling of (52) with reagent (7) under a variety of conditions as described in Scheme 1 gives (53). Reduction of the olefin, such as by catalytic hydrogenation over Pd/C catalyst, in a solvent such as methanol or ethanol, or by other methods known to those skilled in the art, affords a saturated ester. Heating this ester in a solvent such as toluene, with or without an appropriate acid catalyst such as p-toluenesulfonic acid, results in ring closure to produce compound (54), which represents Formula I where E is $CH_2$ and Z is carbonyl. Further reduction with a reducing such as, but not limited to, borane, lithium aluminum hydride, or alane, in a solvent such as THF or ether, affords compound (54), which represents Formula I where E is $CH_2$ and Z is absent.

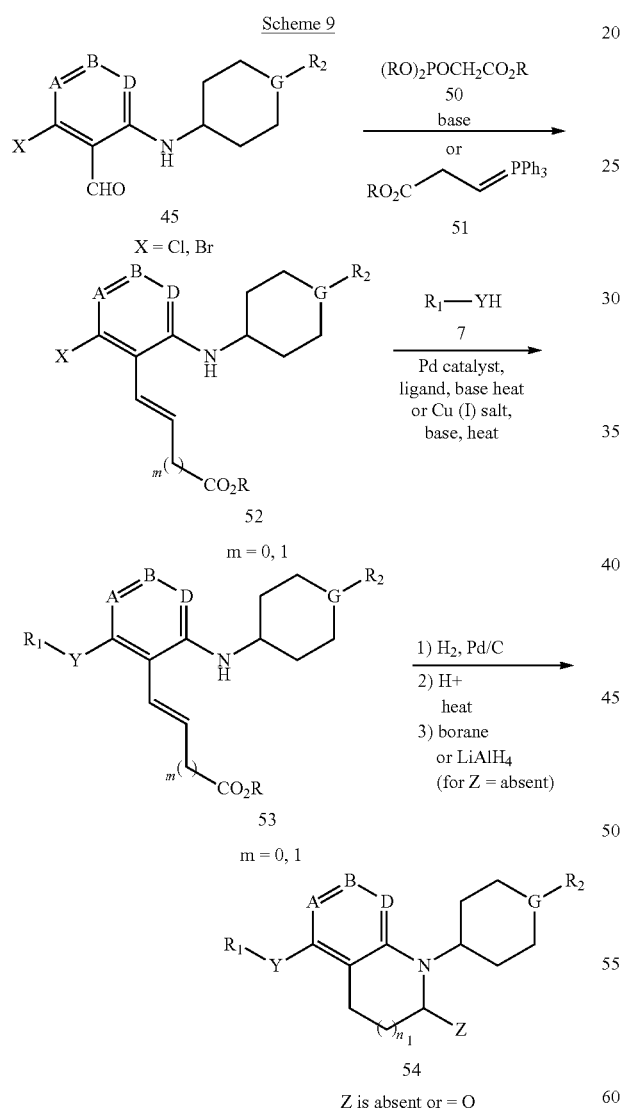

The nature of the $R_2$ group in Formula I can be varied readily by a variety of procedures known to those skilled in the art, for example as shown in Scheme 10 when G is nitrogen. When G is nitrogen, $R_2$ in the previous schemes can represent a nitrogen protecting group, such as but not limited to a tert-butyloxycarbonyl (BOC) or carbobenzyloxy (CBZ) carbamate. Deprotection of (55) when $R_2$ is BOC can be accomplished using HCl or TFA to give (56). When $R_2$ is CBZ, deprotection can be accomplished by catalytic hydrogenation to afford (56). It will be recognized to one skilled in the art that $R_2$ can take the form of a variety of protecting groups (see Greene, T. et al., *Protecting Groups in Organic Synthesis*, John Wiley & Sons, Inc., New York, N.Y. (1991) and references therein). Treatment of (56) with a variety of alkyl or aryl chloroformates, in the presence of a base such as triethylamine, in a solvent such as THF or methylene chloride, affords carbamates (57). Alternatively, treatment of (56) with acid chlorides in the presence of a base such as triethylamine, in a solvent such as THF or methylene chloride, or with carboxylic acids in the presence of a suitable peptide coupling agent, such as but not limited to 1-hydroxybenzotriazole (HOBT) or benzotriazol-1-yloxytris(pyrrolidino)phosphonium hexafluorophosphate (pyBOP), in a solvent such as THF or methylene chloride, affords the amides (58). One skilled in the art of organic synthesis will recognize that a wide variety of procedures are known for carrying out the transformation of (56) to (57) and (58).

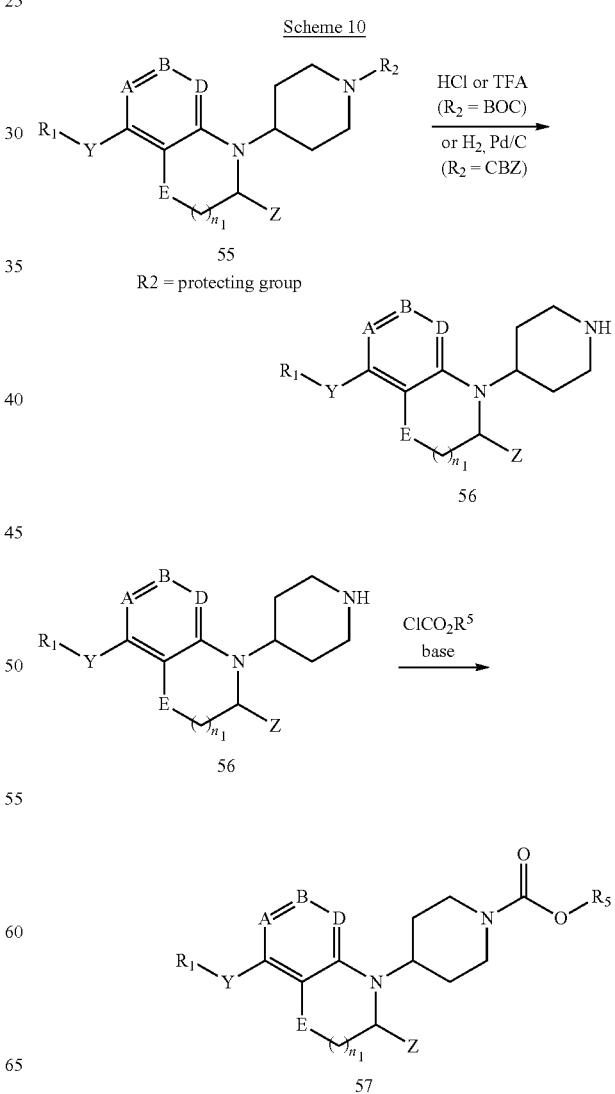

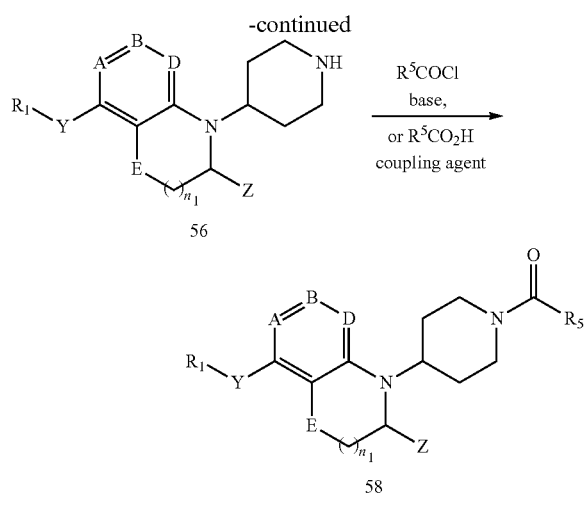

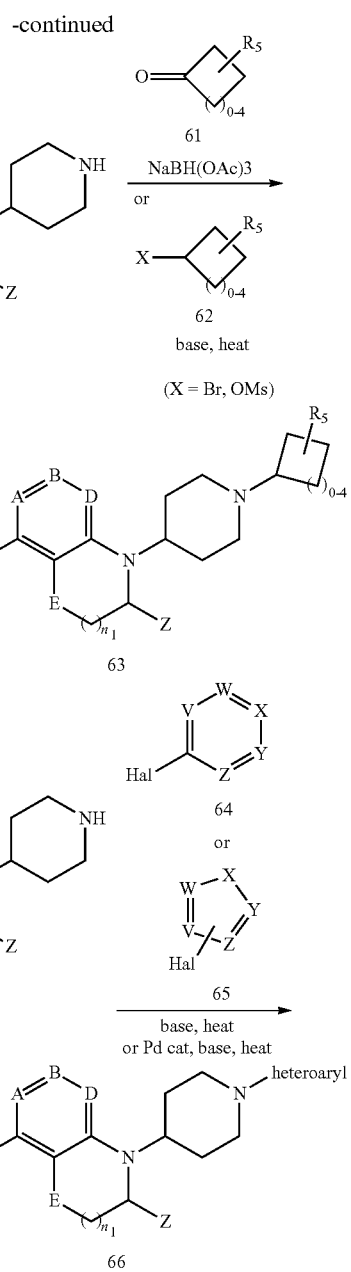

Additional methods for varying the substituent $R_2$ are described in Scheme 11, where G is nitrogen. Treatment of (56) with an optionally substituted aryl halide or aryl triflate (59) in the presence of a suitable palladium catalyst, ligand and base (see Yang, B. H. et al., *J. Organomet. Chem.*, 576: 125 (1999)) affords the aryl substituted compounds (60). Treatment of amine (56) with a cyclic ketone (61) in the presence of a reducing agent, such as sodium triacetoxyborohydride, affords cycloalkyl substituted analogs (63). Alternatively, treatment of (56) with a cyclic bromide or mesylate (62) in the presence of a base such as potassium carbonate, cesium carbonate or triethylamine in a solvent such as THF, DMF or methylene chloride provides the analogs (63). Amine (56) can also be treated with a variety of 5- and 6-membered heterocyclic analogs (64) or (65) in the presence of a suitable base or under a variety of palladium-catalyzed coupling conditions (see Yang, B. H. et al., *J. Organomet. Chem.*, 576:125 (1999)) to afford the heteroaryl substituted analogs (66). For example, treatment of (56) with 2-chloropyrimidine (64, V and Z are N) and potassium carbonate at elevated temperature in DMF gave the pyrimidine substituted analog (66, heteroaryl is 2-pyrimidinyl).

Scheme 11

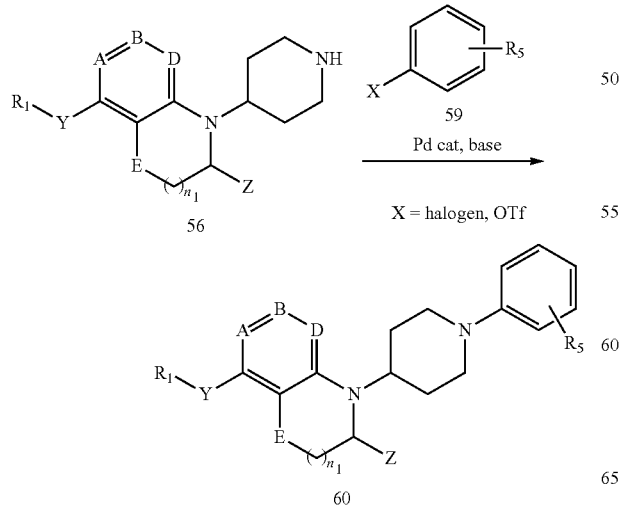

Utilities and Combinations

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodistrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR119 receptor agonists or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar); SGLT2 inhibitors (e.g., 3-(Benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergliflozin (Kissei), AVE 2268 (Sanofi-Aventis)); 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, and denagliptin); glucagon-like peptide-1 (GLP-1) receptor agonists (e.g., Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DACTM); aldose reductase inhibitors (e.g., those disclosed in WO 99/26659); RXR agonists (e.g., reglitizar (JTT-501), 5-[[6-[(2-fluorophenyl)methoxy]-2-naphthalenyl]methyl]-2,4-Thiazolidinedione (MCC-555), 5-[[3-(5,6,7,8-tetrahydro-3,5,5,8,8-pentamethyl-2-naphthalenyl)-4-(trifluoromethoxy)phenyl]methylene]-2,4-Thiazolidinedione (MX-6054), DRF2593, farglitazar, (±)-5-[2,4-dioxothiazolidin-5-yl)methyl]-2-methoxy-N-[[(4-trifluoromethyl)phenyl]methyl]benzamide (KRP-297), 6-[1-(5,6,7,8-tetrahydro-3,5,5,8,8-pentamethyl-2-naphthalenyl)cyclopropyl]-3-Pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., Methyl ester[4-[(2R)-2-[[(2R)-2-(3-chlorophenyl)-2-hydroxyethyl]amino]propyl]phenoxy]-Acetic acid (BRL 35135), 2-[4-[(2S)-2-[[(2S)-2-(3-chlorophenyl)-2-hydroxyethyl]amino]propyl]phenoxy]-Acetic acid (BRL 37344), 4-[(3R)-3-[bis[(2R)-2-hydroxy-2-phenylethyl]amino]butyl]-Benzamide (Ro 16-8714), 2-[4-[2-[[(2S)-2-hydroxy-3-phenoxypropyl]amino]ethoxy]phenoxy]-N-(2-methoxyethyl)-Acetamide (ICI D7114), 5-[(2R)-2-[[(2R)-2-(3-chlorophenyl)-2-hydroxyethyl]amino]propyl]-3-Benzodioxole-2,2-dicarboxylic acid, disodium salt (CL 316, 243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-Cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-Adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyriod receptor agonists (e.g., KB-2115 (Karo Bio)); Glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-Pyridinecarboxylic acid (GKA-50 AstraZeneca)); GPR119 agonists (e.g., 1,1-dimethylethyl ester 4-[[3-(4-pyridinyl)-1,2,4-oxadiazol-5-yl]methoxy]-1-Piperidinecarboxylic acid (PSN-632408 OSI Prosidion)); GDIR agonists (e.g., APD668 (Arena)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole).

Examples of suitable lipid lowering agents and anti-atherosclerotic agents for use in combination with the compounds of the present invention include one or more MTP/ApoB secretion inhibitors (e.g., dirlopatide, N-(2,2,2-Trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyriod receptor agonists (e.g., as set forth above); Ileal Na+/bile acid cotransporter inhibitors (e.g., compounds as disclosed in Drugs of the Future, 24, 425-430 (1999); upregulators of LDL receptor activity (e.g., (3R)-3-[(13R)-β-hydroxy-10-oxotetradecyl]-5,7-dimethoxy-1(3H)-Isobenzofuranone (Taisho Pharmaceutical Co. Ltd) and (3α,4α,5α)-4-(2-propenyl)-Cholestan-3-ol (Eli Lilly); bile acid sequestrants (e.g., WELCHOL®, COLESTID®, LOCHOLEST® AND QUESTRAN®; and fibric acid derivatives, such as ATROMID®, LOPID® AND TRICOT®) cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology,* 120:1199-1206 (1997), and Cornicelli et al., "15-Lipoxygenase and its Inhibition: A Novel Therapeutic Target for Vascular Disease", *Current Pharmaceutical Design,* 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-Pyrazole-1-carboximidamide (SLV 319), CP-945598 (Pfizer), Surinabant (SR-147778, Sanofi-Aventis), N-[(1S,2S)-3-(4-Chlorophenyl)-2-(3-cyanophenyl)-1-methylpropyl]-2-methyl-2-{[5-(trifluoromethyl)pyridin-2-yl] oxy}propanamide (Merck) and those discussed in Hertzog, D. L., *Expert Opin. Ther. Patents,* 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-Benzenesulfonamide (L750355, Merck), or CP331648 (Pfizer) or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-Benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole], with lorcaserin hydrochloride being preferred); 5-HT6 receptor antagonists (SUVEN, BIOVITRUM, EPIX), anti-epileptics topiramate (Johnson & Johnson) and zonisamide, a ciliary neurotrophic factor agonist (eg. axokine (REGENERON); brain-derived neurotrophic factor (BDNF), orexin antagonists, histamine receptor-3(H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer)); acetyl-CoA carboxylase (ACC) inhibitors (e.g., N-(4-(4-(4-isopropoxyphenoxy)phenyebut-3-yn-2-yl)acetamide (A-80040, Abbott), (R)-anthracen-9-yl(3-(morpholine-4-carbonyl)-1,4'-bipiperidin-1'-yl)methanone (CP-640186, Pfizer)), SCD-1 inhibitors as described by Jiang et al, Diabetes 2004, 53, (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)), NPY-Y4 agonists (7™ Pharma WO 2005/089786 (A2,A3)-1), NPY-5 antagonists (e.g., NPYSRA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-Glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, RAZADYNE®, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

Assay(s) for GPR119 G Protein-Coupled Receptor Activity

The in vitro modulation of GPR119 can be determined as follows.
HIT-T15 cAMP Assay A HIT-T15 hamster insulinoma cell line can be purchased from ATCC and grown in the medium recommended by ATCC (i.e., Growth Medium: F12K Medium (Invitrogen 21127-022; 10% D-horse Serum; and 2.5% FBS).

To conduct the cAMP assay, cells are plated on 96 well plates (e.g., BD Falcon: REF 353948, black side, clear bottom, TC surface) at a density of about $4.5 \times 10^4$ cells per well in growth medium and incubated overnight. Following incubation, the growth medium is removed from the wells, followed by a single rinse with the assay buffer from the Hit Hunter cAMP kit (100 µl/well). Following the rinse, 20 µl of assay buffer is added to each well followed by addition of 10 µl of a 3× concentration of compound working solution. The solution is then mixed well. The final concentration range of compound is from about $10^{-5}$M to about $10^{-11}$M. The reaction is incubated at 37° C., in a 5% $CO_2$ for 1 hour. Following incubation, the cAMP concentration is determined using the Hit Hunter cAMP kit according to the manufacturer's protocol.
Human Tet-Inducible cAMP Assay Cell lines using the Flp-In-T-REx 293 tetracycline inducible gene expression system are cultured in culture medium comprising the following components: DMEM#11965, 10% FBS, 2 mM L-glutamine, 200 ug/ml Hygromycin B, and 15 ug/ml blasticidin.

For cAMP assays, cells are plated on 96 well plates (e.g., BD Falcon: REF 353948, black side, clear bottom, TC surface) at a density of about $4.5 \times 10^4$ cells per well in growth medium containing 1.0 ug/ml tetracycline (1.0 mg/ml stock). The cells are then incubated for 48 hours at 37° C.

Following the incubation, the growth medium is removed from the wells and the wells rinsed (once) with the assay buffer included in the Hit Hunter cAMP kit (100 µl/well). Following the wash, 20 µl of assay buffer is added to each well, followed by addition of 10 µl of a 3× concentration compound working solution. The solution is then mixed. The final concentration range of compound is from about $10^{-5}$M to about $10^{-11}$M. The reagents are then incubated at 37° C. at 5% $CO_2$ for 1 hour.

The manufacturer's protocol may be followed for cAMP determination. The Hit Hunter cAMP kit protocol is outlined for the HIT-T15 cAMP assays described above.
Luciferase Assay HEK 293 cells may be plated on poly-D-lysine treated 96-well BD black side/clear bottom plates at a density of about $3 \times 10^4$ cells/well in growth medium. The growth medium may comprise the following: D-MEM (Cat #12430) with high glucose and 10% fetal bovine serum.

Cells may be transfected with vectors comprising native or non-native GPR119 sequences using commercially available vectors (e.g., Stratagene) and transfection reagents. The standard manufacturer's protocols may be followed to transfect the cells. Following transfection, the transfection medium may be removed and assay medium added to the wells of the assay plates.

Once the assay plates are prepared, compound dilution plates may be made. To do so, make a first compound dilution plate using 10 mM of the compound of interest diluted to about 1 mM in DMSO. Then make 12 point half-log dilutions of the compounds (in DMSO) using an automated liquid handler. Next, make a second dilution plate by diluting the wells in the first plate ten fold (10×) using assay medium. Once the plates are complete, the highest dose is about 10 μM and the lowest dose is about 0.03 nM.

Once the dilution plates are complete, one can add about 10 μl of the 10× compound dilution to the assay plate containing the assay medium transiently transfected cells. Tap the plate to mix the reagents and incubate the plate overnight at 37° C., 95% $O_2$, and 5% $CO_2$ in an incubator.

Following incubation, a luciferase assay system may be used (e.g., Stead-Glo Luciferase Assay System from Promega) according to the manufacturer's instructions. Following completion of the reaction, immediately measure the readout of the assay using a top count luminometer.

In general, preferred compounds of the present invention, such as particular compounds disclosed in the following examples, have been identified to modulate the functional activity of GPR119 G protein-coupled receptor at concentrations equivalent to, or more potently than, 10 μM, preferably 5 μM, more preferably 1 μM, and still more preferably 0.1 μM, thereby demonstrating compounds of the present invention as especially effective modulators of GPR119 G protein-coupled receptor. Potencies can be calculated and expressed as $EC_{50}$ values, and refer to activity measured employing the assay system described above.

ABBREVIATIONS

The following abbreviations are employed in the Examples and elsewhere herein:

| | |
|---|---|
| EtOAc = | ethyl acetate |
| DMF = | dimethylformamide |
| THF = | tetrahydrofuran |
| $K_2CO_3$ = | potassiumm carbonate |
| $Na_2CO_3$ = | sodium carbonate |
| $MgSO_4$ = | magnesium sulfate |
| $SiO_2$ = | Silicon Dioxide |
| $CH_2Cl_2$ = | methylene chloride |
| MeOH = | methanol |
| HCl = | hydrochloric acid |
| $Cs_2CO_3$ = | cesium carbonate |
| KOH = | potassium hydroxide |
| DME = | 1,2-dimethoxyethane |
| Pd(dppf)$Cl_2$ = | [1,1'-bis(diphenylphosphino)ferrocene]dichloropalladium (II) |
| t-BuONa = | sodium tert-butoxide |
| $Pd_2(dba)_3$ = | tris(dibenzylideneacetone)dipalladium (0) |
| BINAP = | rac-2,2'-bis(diphenylphosphino)-1,1'-binaphthyl |
| min = | minute(s) |
| h or hr = | hour(s) |
| mL or ml = | milliliter |
| g = | gram(s) |
| mg = | milligram(s) |
| mmol = | millimole(s) |
| μM = | micromolar |
| nM = | nanomolar |
| LRMS = | low resolution mass spectrometry |
| NMR = | nuclear magnetic resonance |

EXAMPLES

The following working Examples serve to better illustrate, but not limit, some of the preferred embodiments of the present invention. Unless otherwise indicated, they have been prepared, isolated and characterized using the methods disclosed herein. The abbreviations and terms used herein are defined above. Chemical symbols have their usual and customary meanings.

Example 1 tert-Butyl 4-(8-(4-(methylsulfonyl)phenylamino)-2H-benzo[b][1,4]oxazin-4(3H)-yl)piperidine-1-carboxylate

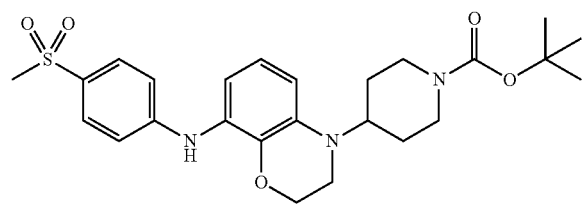 [SMILES: CC(C)(C)OC(=O)N1CCC(N2CCOc3c(Nc4ccc(S(C)(=O)=O)cc4)cccc32)CC1]

Example 1A tert-Butyl 4-(3-bromo-2-hydroxyphenylamino)piperidine-1-carboxylate

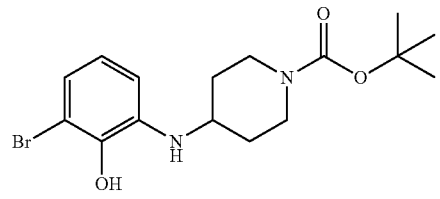 [SMILES: CC(C)(C)OC(=O)N1CCC(Nc2cccc(Br)c2O)CC1]

To a solution of 2-amino-6-bromophenol (4.18 g, 22.35 mmol) and t-butyl-4-oxo-1-piperidinecarboxylate (4.45 g, 22.35 mmol) in 120 mL of methylene chloride was added sodium triacetoxyborohydride (5.19 g, 24.59 mmol) portionwise. Upon completion of addition, the reaction mixture was allowed to stir at ambient temperature for 60 min. After this time, the reaction mixture was filtered through a pad of CELITE® 545 filter aid and concentrated to yield a crude product. The crude product was purified by flash chromatography on silica gel (elution with 0-50% EtOAc/hexane) to afford 5.60 g (68%) of Example 1A as a solid. $^1$H NMR (500 MHz, $CDCl_3$) δ 1.40 (m, 2H), 1.47 (s, 9H), 2.05 (m, 2H), 2.93 (m, 2H), 3.42 (m, 1H), 4.11 (m, 2H), 6.60 (d, J=8.3 Hz, 1H), 6.70 (dd, J=7.7, 8.3 Hz, 1H), 6.81 (d, J=7.7 Hz, 1H). LRMS (ESI): 315.2/317.2 [M+H]$^+$.

Example 1B tert-Butyl 4-(8-bromo-2H-benzo[b][1,4]oxazin-4 (3H)-yl)piperidine-1-carboxylate

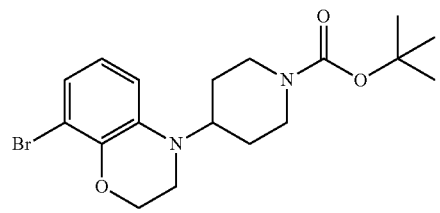 [SMILES: CC(C)(C)OC(=O)N1CCC(N2CCOc3c(Br)cccc32)CC1]

To Example 1A (0.89 g, 2.4 mmol) and K$_2$CO$_3$ (4.6 g, 7.2 mmol) in DMF (25 mL) was added 1,2-dibromoethane (0.31 mL, 3.4 mmol). Upon completion of addition, the reaction mixture was allowed to stir at ambient temperature for 5 h and then at 80° C. for 2 h. At the conclusion of this period, the reaction mixture was diluted with ethyl acetate, washed with water and brine, dried over MgSO$_4$ and concentrated. The resulting residue was purified by flash chromatography on silica gel (elution with 0-25% EtOAc/hexane) to afford 0.67 g (70%) of Example 1B as a solid. LRMS (ESI): 355.0 [M+H]$^+$.

Example 1

A mixture of Example 1B (41 mg, 0.10 mmol), 4-aminophenylmethyl sulfone (51 mg, 0.10 mmol), Pd(dppf)Cl$_2$ (8 mg, 0.009 mmol) and t-BuONa (32 mg, 0.33 mmol) in toluene (2 mL) was degassed and irradiated in a sealed tube in a microwave reactor at 100° C. for 10 h. At the conclusion of this period, the reaction mixture was purified by flash chromatography on silica gel (elution with 0-50% EtOAc/hexane) to afford 8 mg (13%) of Example 1 as a solid. $^1$H NMR (400 MHz, CDCl$_3$): δ 1.46 (s, 9H) 1.58-1.66 (m, 2H) 1.78 (d, J=12.10 Hz, 2H) 2.79 (s, 2H) 3.01 (s, 3H) 3.24-3.29 (m, 2H) 3.71-3.79 (m, 1H) 4.22-4.31 (m, 4H) 6.31 (s, 1H) 6.50 (d, J=8.25 Hz, 1H) 6.72-6.78 (m, 1H) 6.80 (t, J=7.97 Hz, 1H) 7.10 (d, J=8.80 Hz, 2H) 7.73 (d, J=8.80 Hz, 2H). LRMS (ESI): 488.0 [M+H]$^+$.

Example 2 tert-Butyl 4-(8-(4-(methylsulfonyl)phenylamino)-3-oxo-2H-benzo[b][1,4]oxazin-4(3H)-yl)piperidine-1-carboxylate

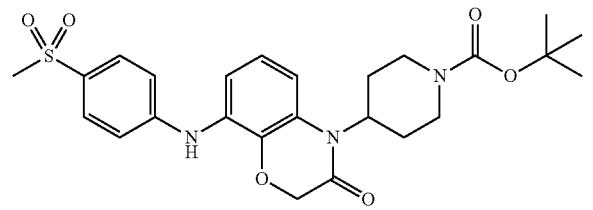 [SMILES: CC(C)(C)OC(=O)N1CCC(N2C(=O)COc3c(Nc4ccc(S(C)(=O)=O)cc4)cccc32)CC1]

Example 2A tert-Butyl 4-(8-bromo-3-oxo-2H-benzo[b][1,4]oxazin-4(3H)-yl)piperidine-1-carboxylate

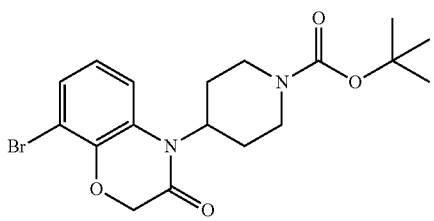 [SMILES: CC(C)(C)OC(=O)N1CCC(N2C(=O)COc3c(Br)cccc32)CC1]

To a mixture of Example 1A (0.65 g, 1.76 mmol) and triethylamine (0.40 mL, 2.63 mmol) in methylene chloride (18 mL) was added bromoacetyl chloride (0.16 mL, 1.93 mmol). Upon completion of addition, the reaction mixture was allowed to stir at ambient temperature for 2 h. After this time, the reaction mixture was concentrated, and the resulting residue was purified by flash chromatography on silica gel (elution with 0-50% EtOAc/hexane) to afford 386 mg (54%) of Example 2A as a solid. LRMS (ESI): 411.0/413.0 [M+H]$^+$.

Example 2

A mixture of Example 2A (41 mg, 0.10 mmol), 4-aminophenylmethyl sulfone (17 mg, 0.10 mmol), Pd$_2$(dba)$_3$ (1.2 mg, 0.002 mmol), BINAP (4.3 mg, 0.006 mmol) and t-BuONa (10 mg, 0.10 mmol) in toluene (2 mL) was degassed and stirred at 110° C. for about 16 h. At the conclusion of this period, the reaction mixture was purified by flash chromatography on silica gel (elution with 0-75% EtOAc/hexane) to afford 48 mg (94%) of Example 2 as a solid. $^1$H NMR (400 MHz, CDCl$_3$): δ 1.59 (s, 9H), 1.66-1.80 (m, 4H), 2.56 (m, 2H), 2.81 (m, 2H), 3.05 (s, 3H), 4.37 (m, 4H), 4.56 (s, 2H), 6.42 (s, 1H), 6.84 (d, 1H, J=7.5 Hz), 7.00 (dd, 1H, J=7.9, 18.4 Hz), 7.15 (m, 4H), 7.80 (m, 2H). LRMS (ESI): 402.0 [M+H−C$_5$H$_8$O$_2$]$^+$.

Example 3 tert-Butyl 4-(4-(2-fluoro-4-(methylsulfonyl)phenylamino)-6H-pyrimido[5,4-b][1,4]oxazin-8(7H)-yl)piperidine-1-carboxylate

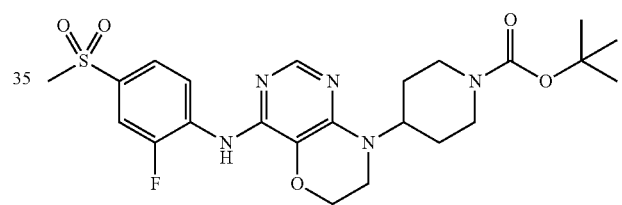

Example 3A tert-Butyl 4-(6-chloro-5-methoxypyrimidin-4-ylamino)piperidine-1-carboxylate

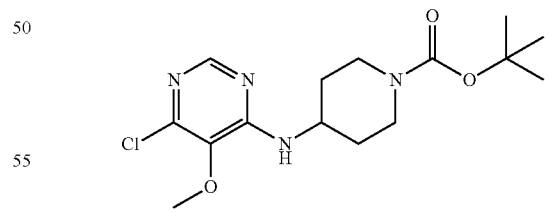

To a mixture of 4,6-dichloro-5-methoxypyrimidine (5.34 g, 30 mmol) and 4-amino-1-BOC-piperidine (6.30 g, 31.5 mmol) in THF (150 mL) was added K$_2$CO$_3$ (6.22 g, 45 mmol). Upon completion of addition, the reaction mixture was allowed to stir at ambient temperature for about 16 h. After this time, the reaction mixture was filtered through a pad of SiO$_2$ gel and concentrated to afford 9.83 g (96%) of Example 3A as an off-white solid. $^1$H NMR (400 MHz, CDCl$_3$): δ 1.40 (m, 2H), 1.47 (s, 9H), 2.04 (m, 2H), 2.92

(broad s, 2H), 3.86 (s, 3H), 4.12 (m, 3H), 5.33 (d, 1H, J=1.7 Hz), 8.13 (s, 1H). LRMS (ESI): 343.1 [M+H]$^+$.

Example 3B tert-Butyl 4-(6-chloro-5-hydroxypyrimidin-4-ylamino)piperidine-1-carboxylate

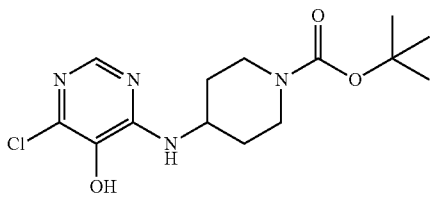 [SMILES: CC(C)(C)OC(=O)N1CCC(Nc2ncnc(Cl)c2O)CC1]

To a solution of Example 3A (16.40 g, 47.8 mmol) in CH$_2$Cl$_2$ (480 mL) was added boron tribromide (22.6 mL, 239.2 mmol) dropwise at ambient temperature. The resulting suspension was refluxed for 2 h. After this time, the reaction mixture was evaporated in vacuo to remove most of the solvent. To the resulting residue was slowly added 200 mL of MeOH, and the resulting mixture was refluxed for 3 h. At the conclusion of this period, the reaction mixture was evaporated thoroughly in vacuo to yield a residue. The residue was dissolved in 200 mL of MeOH and 100 mL of CH$_2$Cl$_2$. The pH of the resulting solution was adjusted to 11-12 by adding triethylamine Once at the prescribed pH, di-tert-butyl-dicarbonate (9.40 g, 43.06 mmol) was added portion-wise. Upon completion of addition, the reaction mixture was allowed to stir at ambient temperature for 30 min. After this time, the reaction mixture was concentrated and separated between CH$_2$Cl$_2$ and water. The organic layer was washed, dried over MgSO$_4$ and concentrated in vacuo to yield a residue. The residue was purified by flash chromatography on silica gel (elution with 0-10% MeOH/CH$_2$Cl$_2$) to afford 11.41 g (67%) of Example 3B as a pale solid. $^1$H NMR (400 MHz, CDCl$_3$): δ 1.24 (m, 2H), 1.27 (s, 9H), 1.82 (m, 2H), 2.75 (broad s, 2H), 3.88 (m, 3H), 4.18 (broad s, 1H), 7.71 (s, 1H). LRMS (ESI): 329.1 [M+H]$^+$.

Example 3C tert-Butyl 4-(4-chloro-6H-pyrimido[5,4-b][1,4]oxazin-8(7H)-yl)piperidine-1-carboxylate

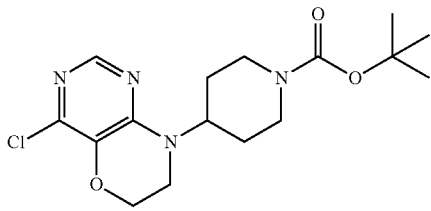 [SMILES: CC(C)(C)OC(=O)N1CCC(N2CCOc3c(Cl)ncnc32)CC1]

To a mixture of Example 3B (2.35 g, 7.0 mmol) and K$_2$CO$_3$ (2.90 g, 21.0 mmol) in DMF (35 mL) was added 1-bromo-2-chloroethane (0.87 mL, 10.5 mmol). Upon completion of addition, the reaction mixture was allowed to stir at ambient temperature for about 16 hours and then at 100° C. for 3 h. At the conclusion of this period, the reaction mixture was diluted with ethyl acetate, washed with water and brine, dried over MgSO$_4$ and concentrated. The resulting residue was purified by flash chromatography on silica gel (elution with 0-50% EtOAc/hexane) to afford 1.78 g (70%) of Example 3C as an off-white solid. $^1$H NMR (400 MHz, CDCl$_3$): δ 1.48 (s, 9H), 1.60-1.72 (m, 4H), 2.88 (broad s, 2H), 3.49 (t, 2H), 4.28 (m, 4H), 4.86 (m, 1H), 8.03 (s, 1H). LRMS (ESI): 355.1 [M+H]$^+$.

Example 3

A mixture of Example 3C (605 mg, 1.71 mmol), 2-fluoro-4-(methylsulfonyl)aniline (323 mg, 1.71 mmol), Pd(dppf)Cl$_2$ (37 mg, 0.051 mmol), BINAP (53 mg, 0.085 mmol) and t-BuONa (164 mg, 1.71 mmol) in toluene (20 mL) was degassed and stirred at 100° C. for 3 h. After this time, the reaction mixture was concentrated, and the resulting residue was purified by flash chromatography on silica gel (elution with 0-75% EtOAc/hexane) to afford 711 mg (82%) of Example 3 as a pale solid. $^1$H NMR (400 MHz, CDCl$_3$): δ 1.48 (s, 9H), 1.60-1.72 (m, 4H), 2.88 (broad s, 2H), 3.05 (s, 3H), 3.47 (t, 2H, J=4.4 Hz), 4.28 (t, 4H, J=4.4 Hz), 4.84 (m, 1H), 7.23 (d, 1H, J=4.4 Hz), 7.65 (dd, 1H, J=2.2, 10.4 Hz), 7.70 (dd, 1H, J=2.2, 8.2 Hz), 8.09 (s, 1H), 8.90 (dd, 1H, J=7.9, 8.6 Hz). LRMS (ESI): 508.1 [M+H]$^+$.

Example 4 tert-Butyl 4-(4-(2-fluoro-4-methylphenylamino)-6H-pyrimido[5,4-b][1,4]oxazin-8(7H)-yl)piperidine-1-carboxylate

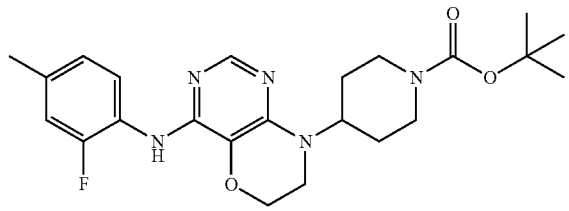 [SMILES: Cc1ccc(Nc2ncnc3c2OCCN3C2CCN(C(=O)OC(C)(C)C)CC2)c(F)c1]

Example 4 was prepared using a similar method as described above for Example 3, with the exception that 2-fluoro-4-(methylsulfonyl)aniline was replaced with 2-fluoro-4-methylaniline. $^1$H NMR (400 MHz, CDCl$_3$): δ 1.47 (s, 9H), 1.60-1.72 (m, 4H), 2.31 (s, 3H), 2.88 (broad s, 2H), 3.44 (dd, 2H, J=4.1, 4.7 Hz), 4.24 (t, 4H, J=4.4 Hz), 4.83 (m, 1H), 6.83-6.94 (m, 3H), 8.05 (s, 1H), 8.21 (t, 1H, J=8.2 Hz). LRMS (ESI): 444.1 [M+H]$^+$.

Example 5 tert-Butyl 4-(4-(2-fluoro-4-methoxyphenylamino)-6H-pyrimido[5,4-b][1,4]oxazin-8(7H)-yl)piperidine-1-carboxylate

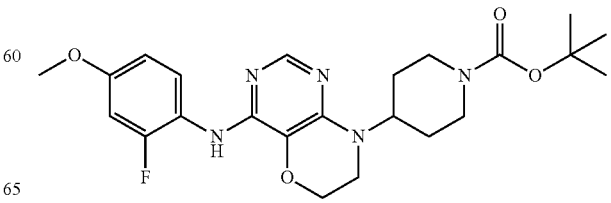

Example 5 was prepared using a similar method as described above for Example 3, with the exception that 2-fluoro-4-(methylsulfonyl)aniline was replaced with 2-fluoro-4-methoxylaniline. $^1$H NMR (400 MHz, CDCl$_3$): δ 1.42-1.49 (m, 9H) 1.60 (d, J=14.30 Hz, 2H) 1.66-1.72 (m, 2H) 2.86 (s, 2H) 3.38-3.44 (m, 2H) 3.77 (s, 3H) 4.14-4.31 (m, 4H) 4.73-4.84 (m, 1H) 6.57 (s, 1H) 6.64-6.71 (m, 2H) 8.00 (s, 1H) 8.12 (t, J=9.35 Hz, 1H). LRMS (ESI): 460.1 [M+H]$^+$.

Example 6 tert-Butyl 4-(4-(4-cyano-2-fluorophenylamino)-6H-pyrimido[5,4-b][1,4]oxazin-8(7H)-yl)piperidine-1-carboxylate

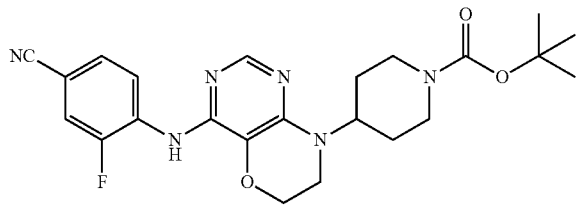 [SMILES: CC(C)(C)OC(=O)N1CCC(N2CCOc3c(Nc4ccc(C#N)cc4F)ncnc32)CC1]

Example 6 was prepared using a similar method as described above for Example 3, with the exception that 2-fluoro-4-(methylsulfonyl)aniline was replaced with 4-amino-3-fluorobenzonitrile. $^1$H NMR (400 MHz, CDCl$_3$): δ 1.47 (s, 9H), 1.60-1.72 (m, 4H), 2.88 (broad s, 2H), 3.47 (dd, 2H, J=8.2, 9.3 Hz), 4.26 (dd, 4H, J=4.4, 4.7 Hz), 4.84 (m, 1H), 7.22 (d, 1H, J=3.3 Hz), 7.35 (dd, 1H, J=1.7, 11.0 Hz), 7.42 (d, 1H, J=8.8 Hz), 8.09 (s, 1H), 8.84 (dd, 1H, J=8.0. 8.5 Hz). LRMS (ESI): 455.1 [M+H]$^+$.

Example 7 tert-Butyl 4-(4-(2-chloro-4-(methylsulfonyl)phenylamino)-6H-pyrimido[5,4-b][1,4]oxazin-8(7H)-yl)piperidine-1-carboxylate

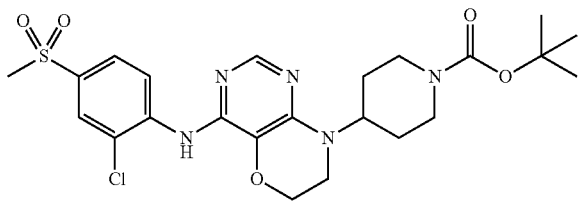

Example 7 was prepared using a similar method as described above for Example 3, with the exception that 2-fluoro-4-(methylsulfonyl)aniline was replaced with 2-chloro-4-(methylsulfonyl)aniline. $^1$H NMR (400 MHz, CDCl$_3$): δ 1.48 (s, 9H), 1.60-1.72 (m, 4H), 2.88 (broad s, 2H), 3.05 (s, 3H), 3.48 (t, 2H, J=4.4 Hz), 4.30 (m, 4H), 4.85 (m, 1H), 7.65 (s, 1H), 7.80 (dd, 1H, J=2.2, 9.3 Hz), 7.85 (d, 1H, J=2.2 Hz), 8.10 (s, 1H), 8.96 (d, 1H, J=9.3 Hz). LRMS (ESI): 524.0 [M+H]$^+$.

Example 8 iso-Propyl 4-(4-(2-fluoro-4-(methylsulfonyl)phenylamino)-6H-pyrimido[5,4-b][1,4]oxazin-8(7H)-yl)piperidine-1-carboxylate

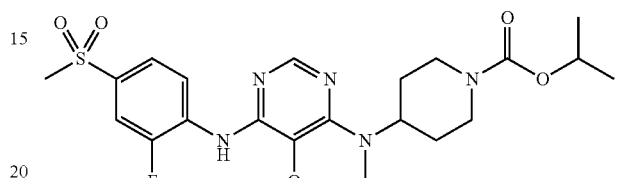

Example 8A

N-(2-Fluoro-4-(methylsulfonyl)phenyl)-8-(piperidin-4-yl)-7,8-dihydro-6H-pyrimido[5,4-b][1,4]oxazin-4-amine, HCl salt

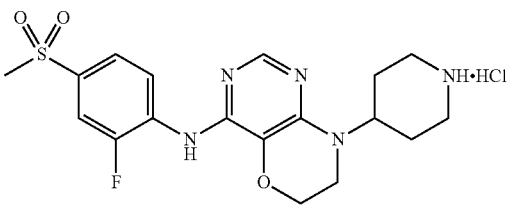

A mixture of Example 3 (95 mg, 0.19 mmol) in 4 mL of 4M HCl in 1,4-dioxane was stirred at ambient temperature for 3 h. After this time, the reaction mixture was evaporated in vacuo to afford Example 8A, which was used without further purification. 408.1 [M+H]$^+$.

Example 8

To a mixture of Example 8A (95 mg, 0.19 mmol) and triethylamine (0.65 mL, 0.47 mmol) in 3 mL of CH$_2$Cl$_2$ was added dropwise isopropylchloroformate (0.19 mL of 1M in toluene, 0.19 mmol). Upon completion of addition, the reaction mixture was stirred at ambient temperature for 0.5 h. At the conclusion of this period, the reaction mixture was evaporated in vacuo, and the resulting residue was purified by flash chromatography on silica gel (elution with 0-100% EtOAc/hexane) to afford 68 mg (70% for 2 steps) of Example 8 as an off-white solid. $^1$H NMR (400 MHz, CDCl$_3$): δ 1.26 (d, 6H, J=6.6 Hz), 1.63-1.76 (m, 4H), 2.91 (broad s, 2H), 3.05 (s, 3H), 3.49 (d, 2H, J=3.3 Hz), 4.29 (s, 4H), 4.93 (m, 2H), 7.65 (broad s, 1H), 7.66 (d, 1H, J=10.4 Hz), 7.71 (d, 1H, J=8.8 Hz), 8.14 (s, 1H), 8.83 (broad s, 1H). LRMS (ESI): 494.1 [M+H]$^+$.

Example 9 p-Tolyl 4-(4-(2-fluoro-4-(methylsulfonyl)phenylamino)-6H-pyrimido[5,4-b][1,4]oxazin-8(7H)-yl)piperidine-1-carboxylate

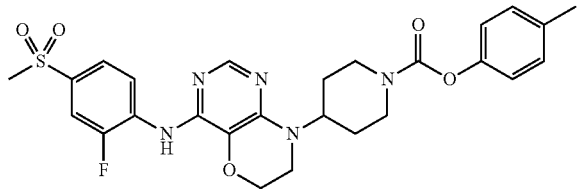

Example 9 was prepared using a similar method as described above for Example 8, with the exception that isopropylchloroformate was replaced with p-tolylchloroformate. $^1$H NMR (400 MHz, CDCl$_3$): δ 1.80 (m, 4H), 2.34 (s, 3H), 3.05 (s, 3H), 3.15 (m, 2H), 3.51 (dd, 2H, J=4.4, 4.8 Hz), 4.30 (t, 2H, J=4.1 Hz), 4.45 (broad s, 2H), 4.92 (m, 1H), 7.00 (d, 2H, J=8.2 Hz), 7.16 (d, 2H, J=8.8 Hz), 7.24 (d, 1H, J=4.4 Hz), 7.65 (d, 1H, J=10.5 Hz), 7.71 (m, 1H), 8.11 (s, 1H), 8.91 (t, 1H, J=8.2 Hz). LRMS (ESI): 542.1 [M+H]$^+$.

Example 10

4-Chlorophenyl 4-(4-(2-fluoro-4-(methylsulfonyl)phenylamino)-6H-pyrimido[5,4-b][1,4]oxazin-8(7H)-yl)piperidine-1-carboxylate

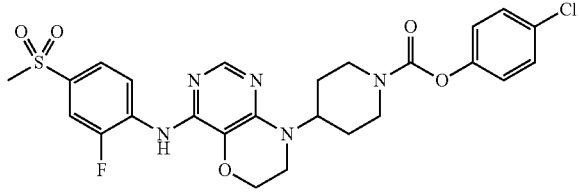 [SMILES: CS(=O)(=O)c1ccc(Nc2ncnc3c2OCCN3C2CCN(C(=O)Oc3ccc(Cl)cc3)CC2)c(F)c1]

Example 10 was prepared using a similar method as described above for Example 8, with the exception that isopropylchloroformate was replaced with 4-chlorophenylchloroformate. $^1$H NMR (400 MHz, CDCl$_3$): δ 1.80 (m, 4H), 3.05 (s, 3H), 3.18 (m, 2H), 3.51 (m, 2H), 4.30 (t, 2H, J=4.4 Hz), 4.32 (m, 2H), 4.93 (m, 1H), 7.07 (m, 2H), 7.24 (d, 1H, J=3.8 Hz), 7.33 (dd, 2H, J=3.2, 6.6 Hz), 7.65 (dd, 1H, J=1.6, 10.5 Hz), 7.71 (d, 1H, J=8.8 Hz), 8.11 (s, 1H), 8.91 (t, 1H, J=8.2 Hz). LRMS (ESI): 562.0 [M+H]$^+$.

Example 11

4-Fluorophenyl 4-(4-(2-fluoro-4-(methylsulfonyl)phenylamino)-6H-pyrimido[5,4-b][1,4]oxazin-8(7H)-yl)piperidine-1-carboxylate

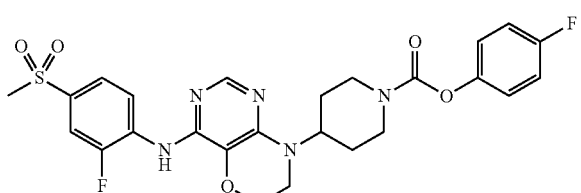

Example 11 was prepared using a similar method as described above for Example 8, with the exception that isopropylchloroformate was replaced with 4-fluorophenylchloroformate. $^1$H NMR (400 MHz, CDCl$_3$): δ 1.80 (m, 4H), 3.05 (s, 3H), 3.17 (m, 2H), 3.51 (t, 2H, J=4.4 Hz), 4.30 (t, 2H, J=4.4 Hz), 4.32 (m, 2H), 4.93 (m, 1H), 7.07 (m, 4H), 7.24 (d, 1H, J=3.8 Hz), 7.65 (dd, 1H, J=1.6, 10.5 Hz), 7.71 (dd, 1H, J=1.6, 7.2 Hz), 8.11 (s, 1H), 8.91 (dd, 1H, J=7.3, 8.2 Hz). LRMS (ESI): 546.0 [M+H]$^+$.

Example 12

4-Methoxyphenyl 4-(4-(2-fluoro-4-(methylsulfonyl)phenylamino)-6H-pyrimido[5,4-b][1,4]oxazin-8(7H)-yl)piperidine-1-carboxylate

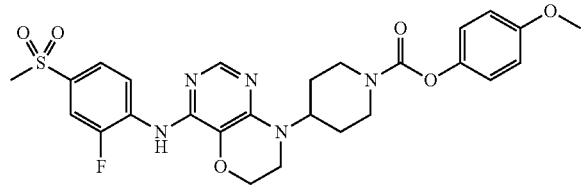

Example 12 was prepared using a similar method as described above for Example 8, with the exception that isopropylchloroformate was replaced with 4-methoxyphenylchloroformate. $^1$H NMR (400 MHz, CDCl$_3$): δ 1.80 (m, 4H), 3.05 (s, 3H), 3.15 (m, 2H), 3.51 (t, 2H, J=4.4 Hz), 3.80 (s, 3H), 4.30 (dd, 2H, J=3.8, 4.4 Hz), 4.44 (broad s, 2H), 4.92 (m, 1H), 6.89 (m, 2H), 7.03 (m, 2H), 7.24 (d, 1H, J=3.8 Hz), 7.65 (dd, 1H, J=2.2, 10.4 Hz), 7.71 (dd, 1H, J=1.6, 8.8 Hz), 8.11 (s, 1H), 8.91 (dd, 1H, J=7.7, 8.2 Hz). LRMS (ESI): 558.1 [M+H]$^+$.

Example 13

2-Chlorophenyl 4-(4-(2-fluoro-4-(methylsulfonyl)phenylamino)-6H-pyrimido[5,4-b][1,4]oxazin-8(7H)-yl)piperidine-1-carboxylate

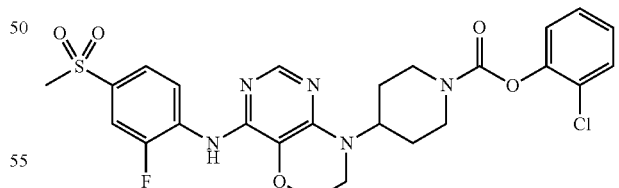

Example 13 was prepared using a similar method as described above for Example 8, with the exception that isopropylchloroformate was replaced with 2-chlorophenylchloroformate. $^1$H NMR (400 MHz, CDCl$_3$): δ 1.83 (broad s, 4H), 3.05 (s, 3H), 3.08-3.20 (m, 2H), 3.50 (dd, 2H, J=4.4, 4.9 Hz), 4.30 (t, 2H, J=4.4 Hz), 4.40-4.60 (m, 2H), 4.96 (m, 1H), 7.20-7.30 (m, 4H), 7.43 (m, 1H), 7.65 (dd, 1H, J=1.6, 10.5 Hz), 7.71 (dd, 1H, J=1.6, 8.8 Hz), 8.11 (s, 1H), 8.92 (dd, 1H, J=8.0, 8.5 Hz). LRMS (ESI): 562.0 [M+H]$^+$.

Example 14

Cyclopentyl 4-(4-(2-fluoro-4-(methylsulfonyl)phenylamino)-6H-pyrimido[5,4-b][1,4]oxazin-8(7H)-yl)piperidine-1-carboxylate

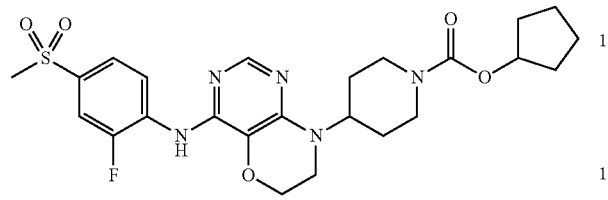

Example 14 was prepared using a similar method as described above for Example 8, with the exception that isopropylchloroformate was replaced with cyclopentylchloroformate. $^1$H NMR (400 MHz, CDCl$_3$): δ 1.56-1.73 (m, 10H), 1.85 (m, 2H), 2.90 (m, 2H), 3.05 (s, 3H), 3.46 (t, 2H, J=8.8 Hz), 4.27 (m, 4H), 4.85 (m, 1H), 5.12 (m, 1H), 7.23 (d, 1H, J=4.4 Hz), 7.65 (dd, 1H, J=2.2, 10.5 Hz), 7.70 (dd, 1H, J=1.7, 8.8 Hz), 8.10 (s, 1H), 8.90 (dd, 1H, J=8.0, 8.5 Hz). LRMS (ESI): 520.1 [M+H]$^+$.

Example 15 iso-Propyl 4-(4-(2-fluoro-4-methoxyphenylamino)-6H-pyrimido[5,4-b][1,4]oxazin-8(7H)-yl)piperidine-1-carboxylate

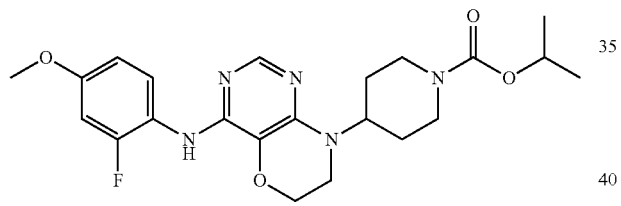

Example 15 was prepared from Example 5 using the methods described in Examples 8A and 8. $^1$H NMR (400 MHz, CDCl$_3$): δ 1.26 (d, 6H, J=6.6 Hz), 1.60-1.72 (m, 4H), 2.88 (m, 2H), 3.43 (t, 2H, J=4.4 Hz), 3.78 (s, 3H), 4.25 (m, 4H), 4.80-4.94 (m, 2H), 6.59 (s, 1H), 6.70 (m, 2H), 8.01 (s, 1H), 8.13 (m, 1H). LRMS (ESI): 446.1 [M+H]$^+$.

Example 16 iso-Propyl 4-(4-(2-chloro-4-(methylsulfonyl)phenylamino)-6H-pyrimido[5,4-b][1,4]oxazin-8(7H)-yl)piperidine-1-carboxylate

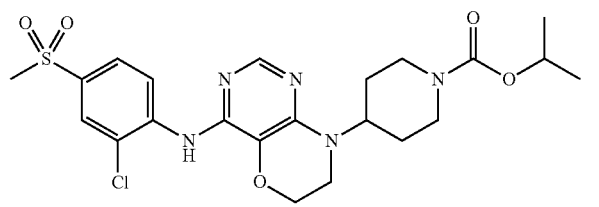

Example 16 was prepared from Example 7 using the methods described in Examples 8A and 8. $^1$H NMR (400 MHz, CDCl$_3$): δ 1.27 (m, 6H), 1.60-1.74 (m, 4H), 2.91 (d, 2H, J=3.3 Hz), 3.05 (s, 3H), 3.30 (t, 4H, J=4.4 Hz), 4.84-4.96 (m, 2H), 7.65 (s, 1H), 7.80 (dd, 1H, J=2.2, 8.8 Hz), 7.94 (d, 1H, J=2.2 Hz), 8.10 (s, 1H), 8.96 (d, 1H, J=9.4 Hz). LRMS (ESI): 510.0 [M+H]$^+$.

Example 17

8-(1-(Benzo[d]oxazol-2-yl)piperidin-4-yl)-N-(2-fluoro-4-(methylsulfonyl)phenyl)-7,8-dihydro-6H-pyrimido[5,4-b][1,4]oxazin-4-amine

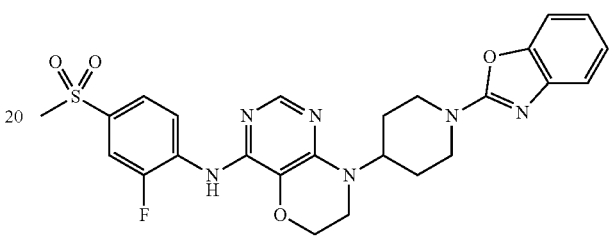

A reaction mixture of Example 8A (30 mg, 0.068 mmol), 2-chlorobenzoxazole (13 mg, 0.082 mmol) and K$_2$CO$_3$ (19 mg, 0.14 mmol) in 1 mL of DMF was heated in a sealed vial in the microwave at 160° C. for 60 min. At the conclusion of this period, the reaction mixture was diluted with ethyl acetate, washed, dried over MgSO$_4$ and concentrated to yield a residue. The residue was purified by flash chromatography on silica gel (elution with 0-100 EtOAc/hexane) to afford 10 mg (28%) of Example 17 as a pale solid. $^1$H NMR (400 MHz, CDCl$_3$): δ 1.85 (m, 4H), 3.05 (s, 3H), 3.24-3.30 (m, 2H), 3.47 (t, 2H, J=4.4 Hz), 4.28 (dd, 2H, J=3.9, 4.9 Hz), 4.49 (m, 2H), 5.00 (m, 1H), 7.05 (m, 1H), 7.18 (dd, 1H, J=6.6, 7.7 Hz), 7.23 (d, 1H, J=3.9 Hz), 7.26 (m, 1H), 7.37 (d, 1H, J=7.2 Hz), 7.65 (dd, 1H, J=2.2, 10.5 Hz), 7.71 (dd, 1H, J=1.6, 8.8 Hz), 8.11 (s, 1H), 8.91 (dd, 1H, J=8.2, 8.8 Hz). LRMS (ESI): 525.0 [M+H]$^+$.

Example 18

8-(1-(Benzo[d]thiazol-2-yl)piperidin-4-yl)-N-(2-fluoro-4-(methylsulfonyl)phenyl)-7,8-dihydro-6H-pyrimido[5,4-b][1,4]oxazin-4-amine

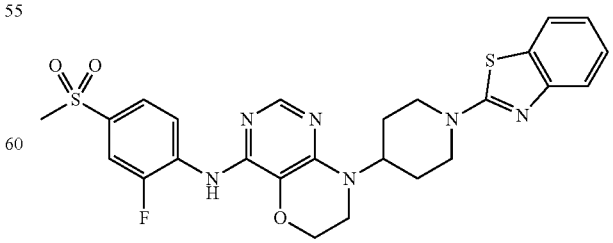

Example 18 was prepared using a similar method as described above for Example 17, with the exception that 2-chlorobenzoxazole was replaced with 2-chlorobenzothiazole. LRMS (ESI): 541.1 [M+H]+.

Example 19

N-(2-Fluoro-4-(methylsulfonyl)phenyl)-8-(1-(pyrimidin-2-yl)piperidin-4-yl)-7,8-dihydro-6H-pyrimido[5,4-b][1,4]oxazin-4-amine

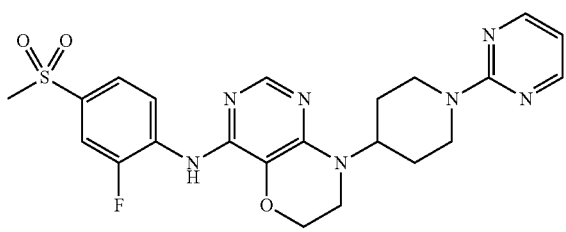 [SMILES: CS(=O)(=O)c1ccc(Nc2ncnc3c2OCCN3C2CCN(c3ncccn3)CC2)c(F)c1]

Example 19 was prepared using a similar method as described above for Example 17, with the exception that 2-chlorobenzoxazole was replaced with 2-chloropyrimidine. LRMS (ESI): 485.1 [M+H]+.

Example 20 iso-Propyl 4-(4-(4-cyano-2-fluorophenylamino)-6H-pyrimido[5,4-b][1,4]oxazin-8 (7H)-yl)piperidine-1-carboxylate

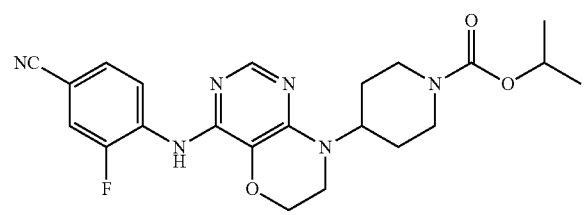 [SMILES: CC(C)OC(=O)N1CCC(N2CCOc3c(Nc4ccc(C#N)cc4F)ncnc32)CC1]

Example 20A iso-Propyl 4-(4-chloro-6H-pyrimido[5,4-b][1,4]oxazin-8(7H)-yl)piperidine-1-carboxylate

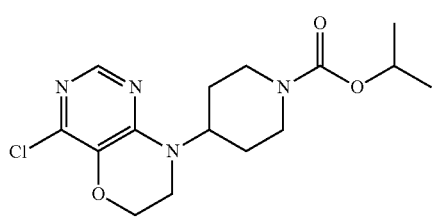 [SMILES: CC(C)OC(=O)N1CCC(N2CCOc3c(Cl)ncnc32)CC1]

A mixture of Example 3C (1.90 g, 5.35 mmol) in 50 mL of 4M HCl in 1,4-dioxane was stirred at ambient temperature for 1 h. After this time, the reaction mixture was evaporated in vacuo to yield a residue. The residue was taken up in 50 mL of methylene chloride and then triethylamine was added to adjust the pH to a pH of 10-11. Once at the prescribed pH, 5.35 mL of isopropylchloroformate (1M in toluene) was added dropwise, and then the reaction was stirred at ambient temperature for 0.5 h. At the conclusion of this period, the reaction mixture was evaporated in vacuo, and the resulting residue was purified by flash chromatography on silica gel (elution with 0-100% EtOAc/hexane) to afford 1.71 g (86%) of Example 20A as a white solid. $^1$H NMR (400 MHz, CDCl$_3$): δ 1.27 (d, 6H, J=6.6 Hz), 1.63 (d, 2H, J=9.4 Hz), 1.72 (d, 2H, J=10.5 Hz), 2.90 (d, 2H, J=6.0 Hz), 3.48 (dd, 2H, J=4.1, 4.7 Hz), 4.28 (m, 4H), 4.92 (m, 2H), 8.03 (s, 1H). LRMS (ESI): 255.1 [M+H]+.

Example 20

A mixture of Example 20A (62 mg, 0.18 mmol), 4-amino-3-fluorobenzonitrile (25 mg, 0.18 mmol), Pd(dppf)Cl$_2$ (5.3 mg, 0.0073 mmol), BINAP (6.7 mg, 0.011 mmol) and t-BuONa (17.5 mg, 0.18 mmol) in toluene (1.5 mL) was degassed and heated in a sealed vial in the microwave at 110° C. for 30 min. After this time, the reaction mixture was purified by flash chromatography on silica gel (elution with 0-100% EtOAc/hexane) to afford 47 mg (59%) of Example 20 as an off-white solid. $^1$H NMR (400 MHz, CDCl$_3$): δ 1.48 (s, 9H), 1.60-1.72 (m, 4H), 2.88 (broad s, 2H), 3.05 (s, 3H), 3.47 (t, 2H, J=4.4 Hz), 4.28 (t, 4H, J=4.4 Hz), 4.84 (m, 1H), 7.23 (d, 1H, J=4.4 Hz), 7.65 (dd, 1H, J=2.2, 10.4 Hz), 7.70 (dd, 1H, J=2.2, 8.2 Hz), 8.09 (s, 1H), 8.90 (dd, 1H, J=7.9, 8.6 Hz). LRMS (ESI): 441.1 [M+H]+.

Example 21 iso-Propyl 4-(4-(4-(methylsulfonyl)phenylamino)-6H-pyrimido[5,4-b][1,4]oxazin-8(7H)-yl)piperidine-1-carboxylate

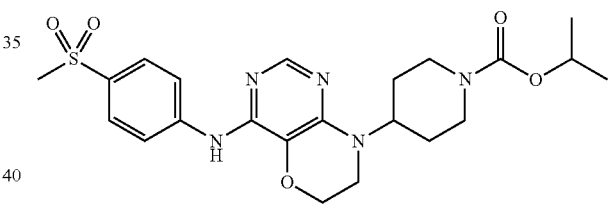

Example 21 was prepared using a similar method as described above for Example 20, with the exception that 4-amino-3-fluorobenzonitrile was replaced with 4-(methylsulfonyl)aniline. $^1$H NMR (400 MHz, CDCl$_3$): δ 1.27 (m, 6H), 1.60-1.80 (m, 4H), 2.90 (d, 2H, J=59.9 Hz), 3.03 (s, 3H), 3.46 (s, 2H), 4.26 (m, 4H), 4.85 (m, 1H), 4.94 (m, 1H), 7.01 (s, 1H), 7.84 (m, 4H), 8.09 (d, 1H, J=2.7 Hz). LRMS (ESI): 476.1 [M+H]+.

Example 22 iso-Propyl 4-(4-(4-cyano-2-chlorophenylamino)-6H-pyrimido[5,4-b][1,4]oxazin-8(7H)-yl)piperidine-1-carboxylate

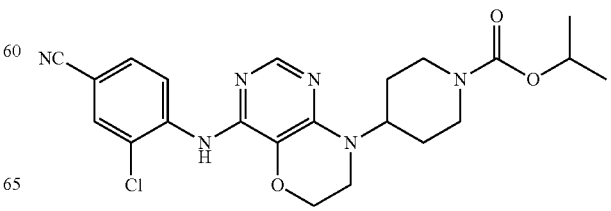

Example 22 was prepared using a similar method as described above for Example 20, with the exception that 4-amino-3-fluorobenzonitrile was replaced with 4-amino-3-chlorobenzonitrile. $^1$H NMR (400 MHz, CDCl$_3$): δ 1.27 (m, 6H), 1.60-1.73 (m, 4H), 2.91 (broad s, 2H), 3.46 (dd, 2H, J=4.1, 4.7 Hz), 4.26 (m, 4H), 4.85 (m, 1H), 4.93 (m, 1H), 7.80 (s, 1H), 7.86 (dd, 1H, J=4.4, 17.6 Hz), 8.09 (s, 1H), 8.49 (s, 1H), 8.65 (d, 1H, J=8.6 Hz). LRMS (ESI): 457.1 [M+H]$^+$.

Example 23 iso-Propyl 4-(4-(2-methylpyridin-3-ylamino)-6H-pyrimido[5,4-b][1,4]oxazin-8(7H)-yl)piperidine-1-carboxylate

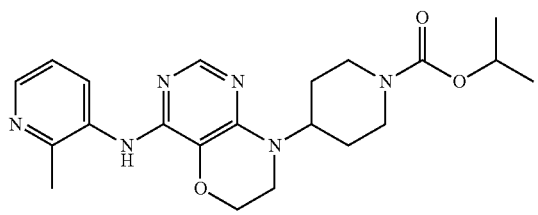 [SMILES: Cc1ncccc1Nc1ncnc2c1OCCN2C1CCN(C(=O)OC(C)C)CC1]

Example 23 was prepared using a similar method as described above for Example 20, with the exception that 4-amino-3-fluorobenzonitrile was replaced with 3-amino-2-methylpyridine. $^1$H NMR (400 MHz, CDCl$_3$): δ 1.26 (d, 6H, J=6.0 Hz), 1.60-1.73 (m, 4H), 2.55 (s, 3H), 2.90 (broad s, 2H), 3.46 (dd, 2H, J=4.1, 4.7 Hz), 4.27 (m, 4H), 4.84 (m, 1H), 4.93 (m, 1H), 6.50 (s, 1H), 7.15 (dd, 2H, J=8.8, 16.5 Hz), 8.02 (s, 1H), 8.18 (dd, 2H, J=1.7, 5.0 Hz), 8.47 (dd, 1H, J=1.7, 8.3 Hz). LRMS (ESI): 413.1 [M+H]$^+$.

Example 24 iso-Propyl 4-(4-(4-(methylsulfonyl)phenoxy)-6H-pyrimido[5,4-b][1,4]oxazin-8(7H)-yl)piperidine-1-carboxylate

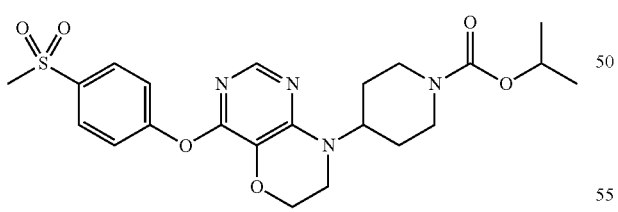

A mixture of Example 20A (34 mg, 0.10 mmol), 4-methylsulfonylphenol (19 mg, 0.10 mmol) and Cs$_2$CO$_3$ (65 mg, 0.20 mmol) in toluene (1 mL) was heated in a sealed vial in the microwave at 150° C. for 7 h. At the conclusion of this period, the reaction mixture was diluted with EtOAc, washed by water and brine, dried over MgSO$_4$, and then concentrated in vacuo to yield a residue. The residue was purified by flash chromatography on silica gel (elution with 0-100% EtOAc/hexane) to afford 19 mg (42%) of Example 24 as a pale solid. $^1$H NMR (400 MHz, CDCl$_3$): δ 1.26 (m, 6H), 1.60-1.76 (m, 4H), 2.90 (broad s, 2H), 3.05 (s, 3H), 3.51 (t, 2H, J=4.4 Hz), 4.28 (m, 4H), 4.94 (m, 2H), 7.31 (m, 2H), 7.95 (m, 3H). LRMS (ESI): 477.0 [M+H]$^+$.

Example 25 iso-Propyl 4-(4-(2-methylpyridin-3-yloxy)-6H-pyrimido[5,4-b][1,4]oxazin-8(7H)-yl)piperidine-1-carboxylate

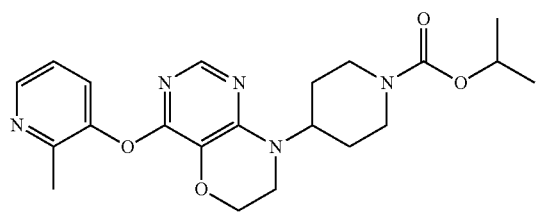 [SMILES: Cc1ncccc1Oc1ncnc2c1OCCN2C1CCN(C(=O)OC(C)C)CC1]

A mixture of Example 20A (52 mg, 0.15 mmol), 3-hydroxyl-2-methylpyridine (25 mg, 0.23 mmol) and KOH powder (17 mg, 0.30 mmol) in DME (1.5 mL) was heated in a sealed vial in the microwave at 150° C. for 1.5 h. After this time, the reaction mixture was purified by flash chromatography (elution with 0-100% EtOAc/hexane) to afford 19 mg (30%) of Example 25 as a pale solid. $^1$H NMR (400 MHz, CDCl$_3$): δ 1.26 (m, 6H), 1.60-1.76 (m, 4H), 2.47 (s, 3H), 2.90 (broad s, 2H), 3.51 (t, 2H, J=4.4 Hz), 4.30 (m, 4H), 4.85-4.95 (m, 2H), 7.18 (dd, 1H, J=4.4, 7.7 Hz), 7.40 (d, 1H, J=8.2 Hz), 7.90 (s, 1H), 8.38 (s, 1H). LRMS (ESI): 414.1 [M+H]$^+$.

Example 26 tert-Butyl 4-(4-(2-fluoro-4-(methylsulfonyl)phenylamino)-7-oxo-6H-pyrimido[5,4-b][1,4]oxazin-8(7H)-yl)piperidine-1-carboxylate

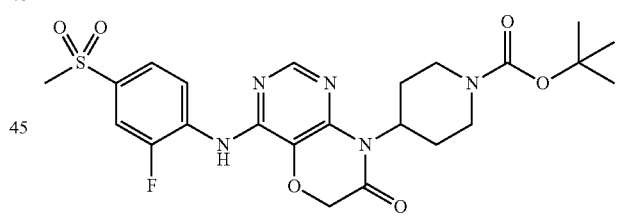

Example 26A tert-Butyl 4-(4-chloro-7-oxo-6H-pyrimido[5,4-b][1,4]oxazin-8(7H)-yl)piperidine-1-carboxylate

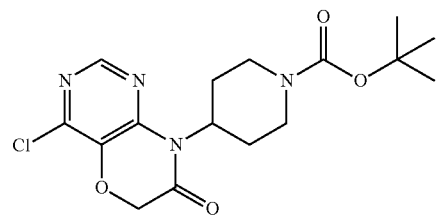 [SMILES: CC(C)(C)OC(=O)N1CCC(N2C(=O)COc3c(Cl)ncnc32)CC1]

To a mixture of Example 3B (1.48 g, 4.50 mmol) and Cs$_2$CO$_3$ (1.76 g, 5.40 mmol) in DMF (25 mL) was added methyl bromoacetate (0.50 mL, 5.40 mmol). Upon completion of addition, the reaction mixture was allowed to stir at ambient temperature for 3 h and then at 65° C. for about 16 h. At the conclusion of this period, the reaction mixture was diluted with ethyl acetate, washed with water and brine, dried over MgSO$_4$ and then concentrated to yield a residue. The residue was purified by flash chromatography on silica gel (elution with 0-100% EtOAc/hexane) to afford 0.44 g (27%) of Example 26A as a pale solid. $^1$H NMR (400 MHz, CDCl$_3$): δ 1.49 (s, 9H), 1.63 (m, 2H), 2.70 (m, 2H), 2.80 (broad s, 2H), 4.25 (broad s, 2H), 4.79 (s, 2H), 5.04 (m, 1H), 8.39 (s, 1H). LRMS (ESI): 369.1/313.1 [M+H]$^+$.

Example 26

Example 26 was prepared from Example 26A using a similar method as described above for Example 3. $^1$H NMR (400 MHz, CDCl$_3$): δ 1.50 (s, 9H), 1.65 (d, 2H, J=11.6 Hz), 2.66-2.90 (m, 4H), 3.05 (s, 3H), 4.29 (m, 1H), 4.76 (s, 2H), 5.03 (m, 1H), 7.40 (d, 1H, J=4.3 Hz), 7.70 (dd, 1H, J=2.2, 10.4 Hz), 7.75 (dd, 1H, J=1.6, 8.8 Hz), 8.34 (s, 1H), 8.97 (dd, 1H, J=8.3, 8.8 Hz). LRMS (ESI): 522.1 [M+H]$^+$.

Example 27 iso-Propyl 4-(4-(2-fluoro-4-(methylsulfonyl)phenylamino)-7-oxo-6H-pyrimido[5,4-b][1,4]oxazin-8(7H)-yl)piperidine-1-carboxylate

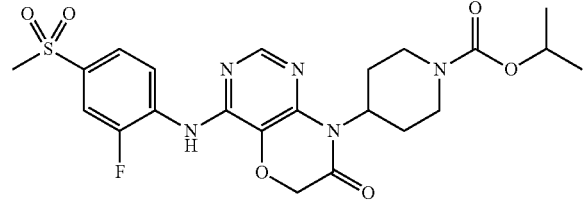 [SMILES: CC(C)OC(=O)N1CCC(N2C(=O)COc3c(Nc4ccc(S(C)(=O)=O)cc4F)ncnc32)CC1]

Example 27 was prepared from Example 26 using the methods described in Examples 8A and 8. $^1$H NMR (400 MHz, CDCl$_3$): δ 1.27 (m, 6H), 1.69 (d, 2H, J=11.5 Hz), 2.70 (m, 2H), 2.85 (broad s, 2H), 3.07 (s, 3H), 4.33 (broad s, 2H), 4.76 (s, 2H), 4.94 (m, 1H), 5.05 (m, 1H), 7.40 (d, 1H, J=3.9 Hz), 7.70 (dd, 1H, J=2.2, 10.4 Hz), 7.75 (dd, 1H, J=1.6, 8.8 Hz), 8.34 (s, 1H), 8.93 (dd, 1H, J=7.9, 8.6 Hz). LRMS (ESI): 508.0 [M+H]$^+$.

Example 28

2-Methoxyphenyl 4-(4-(4-cyano-2-fluorophenylamino)-6H-pyrimido[5,4-b][1,4]oxazin-8(7H)-yl)piperidine-1-carboxylate

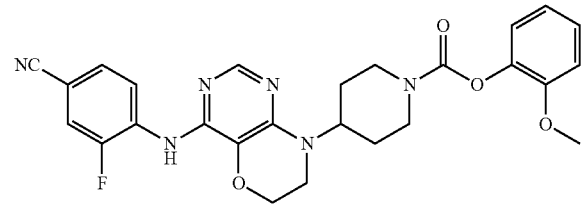 [SMILES: COc1ccccc1OC(=O)N1CCC(N2CCOc3c(Nc4ccc(C#N)cc4F)ncnc32)CC1]

Example 28A

3-Fluoro-4-(8-(piperidin-4-yl)-7,8-dihydro-6H-pyrimido[5,4-b][1,4]oxazin-4-ylamino)benzonitrile, HCl salt

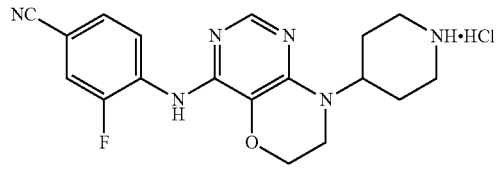

A mixture of Example 6 (540 mg, 1.19 mmol) in 10 mL of 4M HCl in 1,4-dioxane was stirred at ambient temperature for 1 h. After this time, the reaction mixture was evaporated in vacuo to afford Example 28A, which was used without further purification. 355.1 [M+H]$^+$.

Example 28

To a mixture of Example 28A (30 mg, 0.077 mmol) and triethylamine (32 uL, 0.23 mmol) in 2 mL of CH$_2$Cl$_2$ was added 2-methoxyphenylchloroformate (12 uL, 0.077 mmol). Upon completion of addition, the reaction mixture was stirred at ambient temperature for 10 min. At the conclusion of this period, the reaction mixture was purified by flash chromatography (elution with 0-100% EtOAc/hexane) to afford 23 mg (59%) of Example 28 as an off-white solid. $^1$H NMR (400 MHz, CDCl$_3$): δ 1.80 (broad s, 4H), 3.03 (broad s, 1H), 3.18 (broad s, 1H), 3.51 (dd, 2H, J=3.8, 5.0 Hz), 3.85 (s, 3H), 4.30 (dd, 2H, J=3.9, 4.4 Hz), 4.40 (m, 2H), 4.95 (m, 1H), 6.95 (m, 1H), 7.09 (dd, 2H, J=1.6, 8.2 Hz), 7.20 (m, 3H), 7.35 (dd, 1H, J=1.7, 11.0 Hz), 7.44 (d, 1H, J=8.2 Hz), 8.10 (s, 1H), 8.86 (dd, 1H, J=8.2, 8.6 Hz). LRMS (ESI): 505.1 [M+H]$^+$.

Example 29 p-Tolyl 4-(4-(4-cyano-2-fluorophenylamino)-6H-pyrimido[5,4-b][1,4]oxazin-8(7H)-yl)piperidine-1-carboxylate

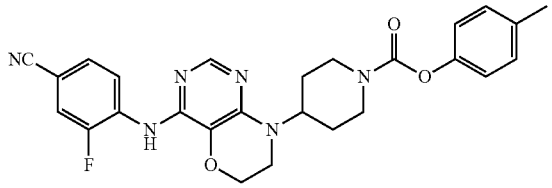 [SMILES: Cc1ccc(OC(=O)N2CCC(N3CCOc4c(Nc5ccc(C#N)cc5F)ncnc43)CC2)cc1]

Example 29 was prepared using a similar method as described above for Example 28, with the exception that 2-methoxyphenylchloroformate was replaced with p-tolylchloroformate. $^1$H NMR (400 MHz, CDCl$_3$): δ 1.78 (m, 4H), 2.34 (s, 3H), 3.00 (broad s, 1H), 3.15 (broad s, 1H), 3.51 (d, 2H, J=4.4 Hz), 4.30 (t, 2H, J=4.4 Hz), 4.45 (broad s, 2H), 4.91 (m, 1H), 6.99 (d, 2H, J=8.2 Hz), 7.16 (d, 2H, J=8.3 Hz), 7.21 (d, 2H, J=8.4 Hz), 7.35 (dd, 1H, J=1.7, 11.0 Hz), 7.44 (d, 1H, J=8.8 Hz), 8.10 (s, 1H), 8.86 (dd, 1H, J=8.3, 8.8 Hz). LRMS (ESI): 489.1 [M+H]$^+$.

Example 30

Cyclopentyl 4-(4-(4-cyano-2-fluorophenylamino)-6H-pyrimido[5,4-b][1,4]oxazin-8(7H)-yl)piperidine-1-carboxylate

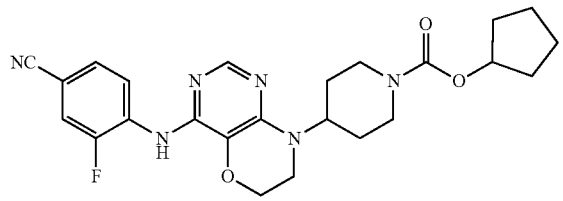 [SMILES: N#Cc1ccc(Nc2ncnc3c2OCCN3C2CCN(C(=O)OC3CCCC3)CC2)c(F)c1]

Example 30 was prepared using a similar method as described above for Example 28, with the exception that 2-methoxyphenylchloroformate was replaced with cyclopentylchloroformate. $^1$H NMR (400 MHz, CDCl$_3$): δ 1.60-1.80 (m, 10 H), 1.90 (m, 2H), 2.90 (m, 2H), 3.46 (m, 2H), 4.27 (m, 4H), 4.85 (m, 1H), 5.12 (m, 1H), 7.20 (d, 1H, J=3.8 Hz), 7.35 (dd, 1H, J=1.6, 11.0 Hz), 7.43 (d, 1H, J=8.8 Hz), 8.08 (s, 1H), 8.85 (t, 1H, J=8.2 Hz). LRMS (ESI): 467.1 [M+H]$^+$.

Example 31

4-Methoxyphenyl 4-(4-(4-cyano-2-fluorophenylamino)-6H-pyrimido[5,4-b][1,4]oxazin-8(7H)-yl)piperidine-1-carboxylate

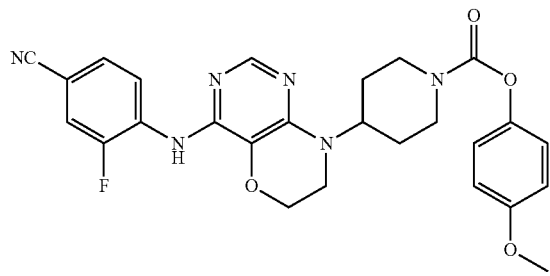 [SMILES: COc1ccc(OC(=O)N2CCC(N3CCOc4c(Nc5ccc(C#N)cc5F)ncnc43)CC2)cc1]

Example 31 was prepared using the same method described above for Example 28, with the exception that 2-methoxyphenylchloroformate was replaced with 4-methoxyphenylchloroformate. $^1$H NMR (500 MHz, CDCl$_3$) d ppm 1.70-1.83 (m, 4 H) 3.00 (s, 1 H) 3.14 (s, 1 H) 3.46-3.52 (m, 2 H) 3.76-3.81 (m, 3 H) 4.25-4.30 (m, 2 H) 4.43 (s, 2 H) 4.86-4.95 (m, 1 H) 6.83-6.91 (m, 2 H) 6.99-7.04 (m, 2 H) 7.21 (d, J=4.40 Hz, 1 H) 7.31-7.37 (m, 1 H) 7.43 (d, J=8.80 Hz, 1 H) 8.09 (s, 1 H) 8.85 (t, J=8.52 Hz, 1 H). LRMS (ESI): 505.5 [M+H]$^+$.

Example 32

3-Fluoro-4-(8-(1-(pyrimidin-2-yl)piperidin-4-yl)-7,8-dihydro-6H-pyrimido[5,4-b][1,4]oxazin-4-ylamino)benzonitrile

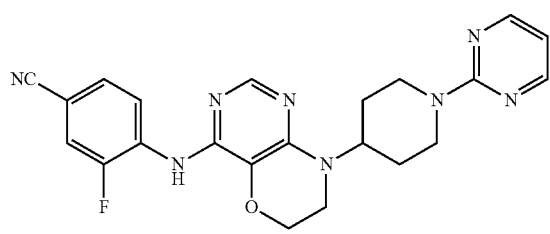 [SMILES: N#Cc1ccc(Nc2ncnc3c2OCCN3C2CCN(c3ncccn3)CC2)c(F)c1]

A reaction mixture of 3-fluoro-4-(8-(piperidin-4-yl)-7,8-dihydro-6H-pyrimido[5,4-b][1,4]oxazin-4-ylamino)benzonitrile, HCl salt from Example 29A (65 mg, 0.167 mmol), 2-chloropyrimidine (23 mg, 0.20 mmol) and K$_2$CO$_3$ (35 mg, 0.25 mmol) in 1 mL of DMF was heated in a sealed vial in the microwave at 160° C. for 30 min. The reaction was purified by flash chromatography on silica gel (elution with 0-100 EtOAc/hexane) to afford 26 mg (36%) of Example 32 as a pale solid. $^1$H NMR (500 MHz, CDCl$_3$) δ ppm 1.68 (dd, J=12.65, 4.40 Hz, 2 H) 1.80 (d, J=9.90 Hz, 2 H) 2.98-3.08 (m, 2 H) 3.40-3.48 (m, 2 H) 4.20-4.28 (m, 2 H) 4.88-5.05 (m, 3 H) 6.48 (t, J=4.67 Hz, 1 H) 7.19 (d, J=3.85 Hz, 1 H) 7.34 (d, J=11.00 Hz, 1 H) 7.42 (d, J=8.80 Hz, 1 H) 8.09 (s, 1 H) 8.31 (d, J=4.95 Hz, 2 H) 8.85 (t, J=8.52 Hz, 1 H). LRMS (ESI): 433.1 [M+H]$^+$.

Example 33

3-Fluoro-4-(8-(1-(4-methylpyrimidin-2-yl)piperidin-4-yl)-7,8-dihydro-6H-pyrimido[5,4-b][1,4]oxazin-4-ylamino)benzonitrile

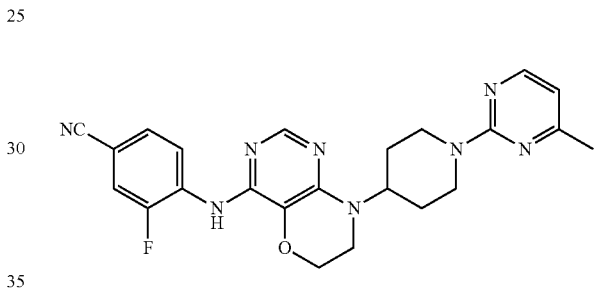

Example 33 was prepared using the same method described above for Example 32, with the exception that 2-chloropyrimidine was replaced with 2-chloro-4-methylpyrimidine. $^1$H NMR (500 MHz, CDCl$_3$) δ ppm 1.68 (dd, J=12.10, 4.40 Hz, 2 H) 1.79 (d, J=9.35 Hz, 2 H) 2.32 (s, 3 H) 2.93-3.05 (m, 2 H) 3.41-3.48 (m, 2 H) 4.21-4.28 (m, 2 H) 4.97 (dd, J=12.65, 3.30 Hz, 3 H) 6.37 (d, J=4.95 Hz, 1 H) 7.19 (d, J=4.40 Hz, 1 H) 7.34 (dd, J=11.00, 2.20 Hz, 1 H) 7.42 (d, J=8.80 Hz, 1 H) 8.10 (s, 1 H) 8.16 (d, J=4.95 Hz, 1 H) 8.85 (t, J=8.25 Hz, 1 H). LRMS (ESI): 447.5 [M+H]$^+$.

Example 34

4-(8-(1-(Benzo[d]oxazol-2-yl)piperidin-4-yl)-7,8-dihydro-6H-pyrimido[5,4-b][1,4]oxazin-4-ylamino)-3-fluorobenzonitrile

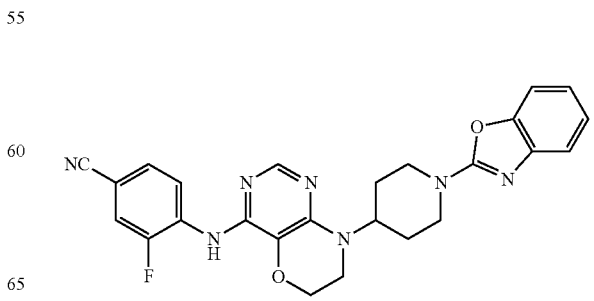

Example 34 was prepared using the same method described above for Example 32, with the exception that 2-chloropyrimidine was replaced with 2-chlorobenzoxazole. ¹H NMR (500 MHz, CDCl₃) δ ppm 1.77-1.89 (m, 4 H) 3.21-3.30 (m, 2 H) 3.41-3.50 (m, 2 H) 4.22-4.30 (m, 2 H) 4.47 (d, J=13.20 Hz, 2 H) 4.91-5.03 (m, 1 H) 7.03 (t, J=7.15 Hz, 1 H) 7.18-7.21 (m, 1 H) 7.25-7.28 (m, 1 H) 7.31-7.37 (m, 2 H) 7.43 (d, J=8.80 Hz, 1 H) 8.06-8.12 (m, 1 H) 8.85 (t, J=8.52 Hz, 1 H). LRMS (ESI): 472.5 [M+H]⁺.

Example 35 iso-Propyl 4-(4-(2-fluoro-4-(1-methyl-1H-imidazol-2-yl)phenylamino)-6H-pyrimido[5,4-b][1,4]oxazin-8 (7H)-yl)piperidine-1-carboxylate

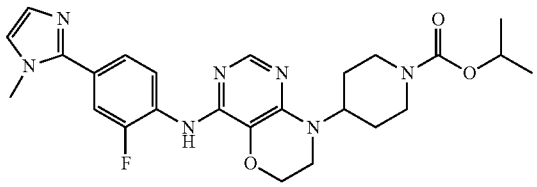 [SMILES: CC(C)OC(=O)N1CCC(N2CCOc3c(Nc4ccc(-c5nccn5C)cc4F)ncnc32)CC1]

Example 35 was prepared using the same method described above for Example 20, with the exception that 4-amino-3-fluorobenzonitrile was replaced with 2-fluoro-4-(1-methyl-1H-imidazol-2-yl)aniline. ¹H NMR (500 MHz, CDCl₃): δ ppm 1.19-1.30 (m, 6 H) 1.58-1.73 (m, 4 H) 2.90 (s, 2 H) 3.40-3.48 (m, 2 H) 3.75 (s, 3H) 4.20-4.35 (m, 4 H) 4.83 (s, 1 H) 4.89-4.96 (m, 1 H) 6.94 (s, 1 H) 7.03 (d, J=3.85 Hz, 1 H) 7.09 (s, 1 H) 7.35 (d, J=8.80 Hz, 1H) 7.41-7.47 (m, 1 H) 8.07 (s, 1 H) 8.64 (t, J=8.52 Hz, 1 H). LRMS (ESI): 496.2 [M+H]⁺.

Example 36

N-(2-Chloro-4-(methylsulfonyl)phenyl)-8-(1-(pyrimidin-2-yl)piperidin-4-yl)-7,8-dihydro-6H-pyrimido[5,4-b][1,4]oxazin-4-amine

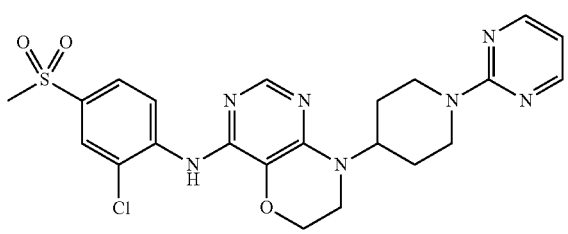 [SMILES: CS(=O)(=O)c1ccc(Nc2ncnc3c2OCCN3C2CCN(c3ncccn3)CC2)c(Cl)c1]

Example 36 was prepared using the same method described above for Example 32, with the exception that 3-fluoro-4-(8-(piperidin-4-yl)-7,8-dihydro-6H-pyrimido[5,4-b][1,4]oxazin-4-ylamino)benzonitrile, HCl salt was replaced with N-(2-fluoro-4-(methylsulfonyl)phenyl)-8-(piperidin-4-yl)-7,8-dihydro-6H-pyrimido[5,4-b][1,4]oxazin-4-amine, HCl salt. ¹H NMR (500 MHz, CDCl₃): δ ppm 1.65-1.72 (m, 2H) 1.81 (d, J=9.35 Hz, 2 H) 3.01-3.08 (m, 5 H) 3.42-3.50 (m, 2 H) 4.23-4.32 (m, 2 H) 4.91-5.01 (m, 3 H) 6.48 (t, J=4.67 Hz, 1 H) 7.63 (s, 1 H) 7.74-7.81 (m, 1 H) 7.93 (d, J=2.20 Hz, 1 H) 8.11 (s, 1 H) 8.30 (d, J=4.40 Hz, 2 H) 8.96 (d, J=8.80 Hz, 1H). LRMS (ESI): 502.1 [M+H]⁺.

Example 37 iso-Propyl 4-(4-(4-cyanophenylamino)-6H-pyrimido [5,4-b][1,4]oxazin-8(7H)-yl)piperidine-1-carboxylate

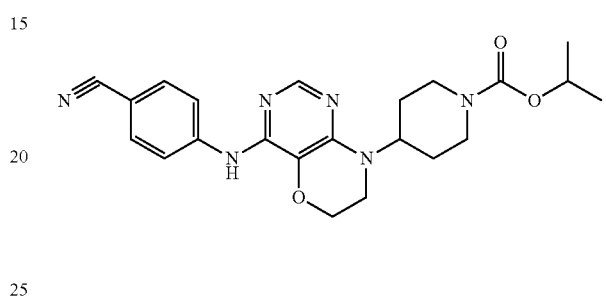

Example 37 was prepared using the same method described above for Example 20, with the exception that 4-amino-3-fluorobenzonitrile was replaced with 4-aminobenzonitrile. ¹H NMR (500 MHz, CDCl₃): δ ppm 1.23 (d, J=6.05 Hz, 6 H) 1.60 (d, J=9.90 Hz, 2 H) 1.65-1.72 (m, 2H) 2.87 (s, 2 H) 3.39-3.47 (m, 2 H) 4.15-4.35 (m, 4 H) 4.81 (t, J=4.12 Hz, 1 H) 4.87-4.95 (m, 1 H) 6.93 (s, 1 H) 7.53 (d, J=8.80 Hz, 2 H) 7.74 (d, J=8.80 Hz, 2 H) 8.03 (s, 1 H). LRMS (ESI): 423.2 [M+H]⁺.

Example 38 iso-Propyl 4-(4-(2-chloro-4-(methoxycarbonyl)phenylamino)-6H-pyrimido[5,4-b][1,4]oxazin-8(7H)-yl) piperidine-1-carboxylate

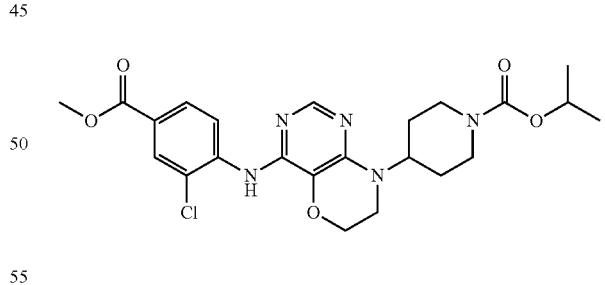

Example 38 was prepared using the same method described above for Example 20, with the exception that 4-amino-3-fluorobenzonitrile was replaced with methyl 4-amino-3-chlorobenzoate. ¹H NMR (500 MHz, CDCl₃): δ ppm 1.24 (d, J=6.05 Hz, 6 H) 1.61 (s, 2 H) 1.67-1.78 (m, 2 H) 2.90 (s, 2 H) 3.41-3.49 (m, 2 H) 3.88 (s, 3 H) 4.19-4.40 (m, 4 H) 4.79-4.87 (m, 1H) 4.89-4.96 (m, 1H) 7.59 (s, 1 H) 7.92 (d, J=8.80 Hz, 1 H) 8.04 (s, 1H) 8.08 (s, 1 H) 8.79 (d, J=8.80 Hz, 1 H). LRMS (ESI): 490.2 [M+H]⁺.

Example 39 tert-Butyl 4-(4-(2-chloro-4-(dimethylcarbamoyl) phenylamino)-6H-pyrimido[5,4-b][1,4]oxazin-8 (7H)-yl)piperidine-1-carboxylate

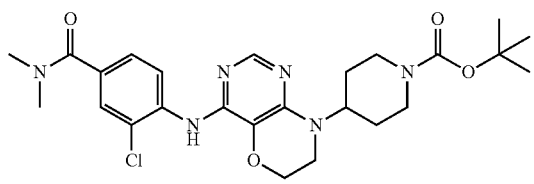 [SMILES: CN(C)C(=O)c1ccc(Nc2ncnc3c2OCCN3C2CCN(C(=O)OC(C)(C)C)CC2)c(Cl)c1]

Example 39 was prepared using the same method described above for Example 3, with the exception that 2-fluoro-4-(methylsulfonyl)aniline was replaced with 4-amino-3-chloro-N,N-dimethylbenzamide. $^1$H NMR (500 MHz, CDCl$_3$): δ ppm 1.46 (s, 9 H) 1.61 (d, J=9.35 Hz, 2 H) 1.65-1.74 (m, 2 H) 2.86 (s, 2 H) 3.05 (s, 6 H) 3.45 (s, 2 H) 4.26 (d, J=3.30 Hz, 4 H) 4.81 (s, 1 H) 7.32 (d, J=8.25 Hz, 1 H) 7.42 (s, 1 H) 7.49 (s, 1 H) 8.06 (s, 1 H) 8.68 (d, J=8.25 Hz, 1H). LRMS (ESI): 517.3 [M+H]$^+$.

Example 40 iso-Propyl 4-(4-(2-chloro-4-(dimethylcarbamoyl) phenylamino)-6H-pyrimido[5,4-b][1,4]oxazin-8 (7H)-yl)piperidine-1-carboxylate

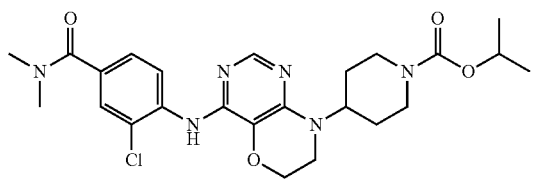 [SMILES: CC(C)OC(=O)N1CCC(N2CCOc3c(Nc4ccc(C(=O)N(C)C)cc4Cl)ncnc32)CC1]

Example 40 was prepared from Example 39 using the methods described in Examples 8A and 8. $^1$H NMR (500 MHz, CDCl$_3$): δ ppm 1.24 (d, J=6.05 Hz, 6 H) 1.59-1.66 (m, 2 H) 1.67-1.74 (m, 2 H) 2.89 (s, 2 H) 3.05 (s, 6 H) 3.39-3.46 (m, 2H) 4.19-4.37 (m, 4 H) 4.83 (s, 1 H) 4.87-4.96 (m, 1 H) 7.32 (d, J=10.45 Hz, 1 H) 7.43 (s, 1 H) 7.49 (s, 1 H) 8.06 (s, 1 H) 8.69 (d, J=8.80 Hz, 1H). LRMS (ESI): 503.2 [M+H]$^+$.

Example 41 iso-Propyl 4-(4-(2,6-difluoro-4-methoxypheny-lamino)-6H-pyrimido[5,4-b][1,4]oxazin-8(7H)-yl) piperidine-1-carboxylate

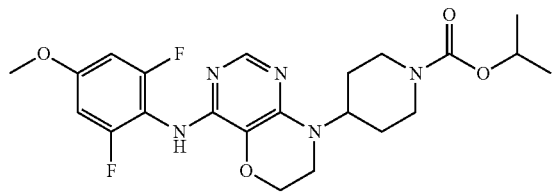 [SMILES: COc1cc(F)c(Nc2ncnc3c2OCCN3C2CCN(C(=O)OC(C)C)CC2)c(F)c1]

Example 41 was prepared using the same method described above for Example 20, with the exception that 4-amino-3-fluorobenzonitrile was replaced with 2,6-difluoro-4-methoxyaniline. NMR (500 MHz, CDCl$_3$): δ ppm 1.24 (t, J=6.32 Hz, 6 H) 1.60 (s, 2 H) 1.65-1.74 (m, 2 H) 2.88 (s, 2 H) 3.36-3.44 (m, 2 H) 3.76 (s, 3 H) 4.17-4.35 (m, 4 H) 4.79 (s, 1 H) 4.86-4.94 (m, 1 H) 5.92 (s, 1 H) 6.52 (d, J=8.80 Hz, 2 H) 7.93 (s, 1 H). LRMS (ESI): 464.2 [M+H]$^+$.

Example 42 iso-Propyl 4-(4-(3-fluoro-4-methoxyphenylamino)-6H-pyrimido[5,4-b][1,4]oxazin-8(7H)-yl)piperidine-1-carboxylate

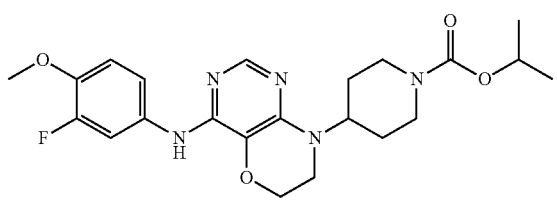 [SMILES: COc1ccc(Nc2ncnc3c2OCCN3C2CCN(C(=O)OC(C)C)CC2)cc1F]

Example 42 was prepared using the same method described above for Example 20, with the exception that 4-amino-3-fluorobenzonitrile was replaced with 3-fluoro-4-methoxyaniline. $^1$H NMR (500 MHz, CDCl$_3$): δ ppm 1.24 (t, J=6.05 Hz, 6 H) 1.60 (s, 2 H) 1.69 (d, J=10.45 Hz, 2 H) 2.88 (s, 2 H) 3.36-3.44 (m, 2 H) 3.84 (s, 3 H) 4.17-4.36 (m, 4 H) 4.80 (s, 1 H) 4.87-4.96 (m, 1 H) 6.55 (s, 1 H) 6.89 (t, J=9.07 Hz, 1 H) 7.13 (d, J=8.80 Hz, 1 H) 7.53 (dd, J=13.20, 2.75 Hz, 1 H) 8.00 (s, 1 H). LRMS (ESI): 446.2 [M+H]$^+$.

Example 43 tert-Butyl 4-(4-(2,6-dichloro-4-(methylsulfonyl)phe-nylamino)-6H-pyrimido[5,4-b][1,4]oxazin-8(7H)-yl) piperidine-1-carboxylate

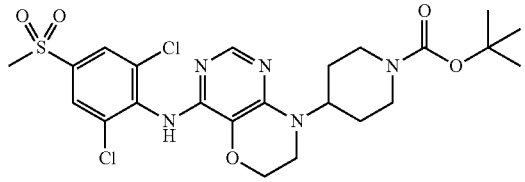 [SMILES: CC(C)(C)OC(=O)N1CCC(N2CCOc3c(Nc4c(Cl)cc(S(C)(=O)=O)cc4Cl)ncnc32)CC1]

Example 43 was prepared using the same method described above for Example 3, with the exception that 2-fluoro-4-(methylsulfonyl)aniline was replaced with 2,6-dichloro-4-(methylsulfonyl)aniline. $^1$H NMR (500 MHz, CDCl$_3$): δ ppm 1.46 (s, 9 H) 1.57-1.65 (m, 2 H) 1.68-1.75 (m, 2 H) 2.85 (s, 2 H) 3.07 (s, 3 H) 3.44-3.53 (m, 2 H) 4.17-4.31 (m, 4 H) 4.74-4.86 (m, 1 H) 6.53 (s, 1 H) 7.88-7.98 (m, 3 H). LRMS (ESI): 558.2 [M+H]$^+$.

Example 44 iso-Propyl 4-(4-(2,6-dichloro-4-(methylsulfonyl) phenylamino)-6H-pyrimido[5,4-b][1,4]oxazin-8 (7H)-yl)piperidine-1-carboxylate

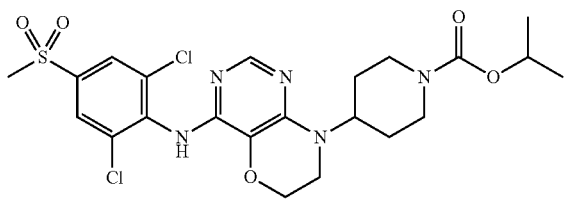 [SMILES: CC(C)OC(=O)N1CCC(N2CCOc3c(Nc4c(Cl)cc(S(C)(=O)=O)cc4Cl)ncnc32)CC1]

Example 44 was prepared from Example 43 using the methods described in Examples 8A and 8. ¹H NMR (500 MHz, CDCl₃): δ ppm 1.21-1.29 (m, 6 H) 1.64 (s, 2 H) 1.69-1.78 (m, 2 H) 2.89 (s, 2 H) 3.08 (s, 3 H) 3.42-3.50 (m, 2 H) 4.23-4.37 (m, 4 H) 4.79-4.86 (m, 1 H) 4.89-4.96 (m, 1 H) 6.55 (s, 1 H) 7.89-7.96 (m, 3 H). LRMS (ESI): 544.2 [M+H]⁺.

Example 45 tert-Butyl 4-(4-(2-chloro-4-(methoxycarbonyl)phenylamino)-6H-pyrimido[5,4-b][1,4]oxazin-8(7H)-yl) piperidine-1-carboxylate

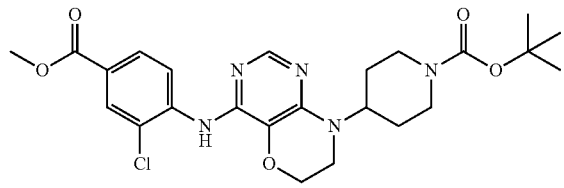 [SMILES: COC(=O)c1ccc(Nc2ncnc3c2OCCN3C2CCN(C(=O)OC(C)(C)C)CC2)c(Cl)c1]

Example 45 was prepared using the same method described above for Example 3, with the exception that 2-fluoro-4-(methylsulfonyl)aniline was replaced with methyl 4-amino-3-chlorobenzoate. ¹H NMR (500 MHz, CDCl₃): δ ppm 1.42 (s, 9 H) 1.53-1.61 (m, 2 H) 1.63-1.69 (m, 2 H) 2.82 (s, 2 H) 3.36-3.41 (m, 2 H) 3.82 (s, 3 H) 4.14-4.26 (m, 4 H) 4.70-4.82 (m, 1 H) 7.53 (s, 1 H) 7.85 (dd, J=8.80, 2.20 Hz, 1 H) 7.97 (s, 1 H) 8.02 (s, 1 H) 8.75 (d, J=8.80 Hz, 1H). LRMS (ESI): 504.3 [M+H]⁺.

Example 46

4-(8-(1-(tert-Butoxycarbonyl)piperidin-4-yl)-7,8-dihydro-6H-pyrimido[5,4-b][1,4]oxazin-4-ylamino)-3-chlorobenzoic acid

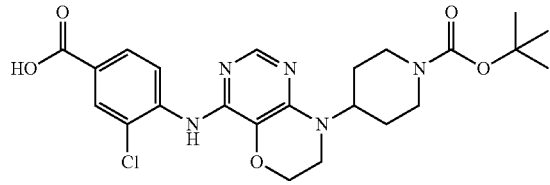 [SMILES: CC(C)(C)OC(=O)N1CCC(N2CCOc3c(Nc4ccc(C(=O)O)cc4Cl)ncnc32)CC1]

To tert-butyl 4-(4-(2-chloro-4-(methoxycarbonyl)phenylamino)-6H-pyrimido[5,4-b][1,4]oxazin-8(7H)-yl)piperidine-1-carboxylate (315 mg, 0.625 mmol) from Example 45 in THF (5 ml) and Water (5 ml) was added LiOH (29.9 mg, 1.250 mmol). The reaction was stirred at room temperature overnight. The reaction was diluted with 1M aq NaOH, washed with EtOAc. The aqueous layer was adjusted to pH=5~6 with 1M HCl aq solution and then extracted with EtOAc, the organic layer was evaporated and dried in vacuo overnight to yield 302 mg (99%) of crude Example 46 as an off-white solid. ¹H NMR (500 MHz, CDCl₃): δ ppm 1.48 (s, 9 H) 1.66 (dd, J=12.37, 8.52 Hz, 2 H) 2.91 (s, 2 H) 3.44-3.60 (m, 2 H) 4.00-4.16 (m, 2 H) 4.18-4.42 (m, 4 H) 4.71-4.90 (m, 1 H) 7.90-8.00 (m, 1 H) 8.02-8.23 (m, 2 H) 8.67-8.87 (m, 1 H). LRMS (ESI): 490.3 [M+H]⁺.

Example 47 tert-Butyl 4-(4-(4-carbamoyl-2-chlorophenylamino)-6H-pyrimido[5,4-b][1,4]oxazin-8(7H)-yl)piperidine-1-carboxylate

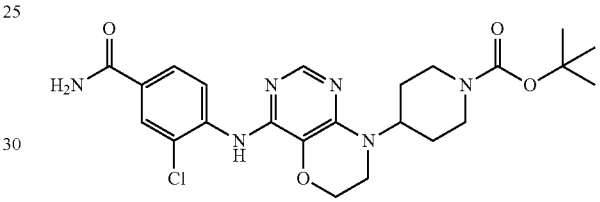

To 4-(8-(1-(tert-butoxycarbonyl)piperidin-4-yl)-7,8-dihydro-6H-pyrimido[5,4-b][1,4]oxazin-4-ylamino)-3-chlorobenzoic acid from Example 46 (34 mg, 0.069 mmol) and TEA (0.029 ml, 0.208 mmol) in DCM (2 ml) was added isopropyl chloroformate (1M in toluene, 0.15 mL, 0.15 mmol), the mixture was stirred at r.t. for 15 minutes, 2M NH₃ in methanol (0.22 ml, 0.44 mmol) was added, the resulting suspension was stirred at room temperature for 30 minutes, the reaction was evaporated in vacuo and the residue was purified by flash column (eluted by 0-100% EtOAc/Hexane) to yield 13 mg (38%) of Example 47 as a white solid. ¹H NMR (500 MHz, CDCl₃): δ ppm 1.46 (s, 9 H) 1.58-1.66 (m, 2 H) 1.66-1.74 (m, 2 H) 2.86 (s, 2 H) 3.41-3.50 (m, 2 H) 4.15-4.32 (m, 4 H) 4.77-4.89 (m, 1 H) 7.55 (s, 1 H) 7.64 (dd, J=8.80, 2.20 Hz, 1 H) 7.91 (d, J=2.20 Hz, 1 H) 8.08 (s, 1 H) 8.78 (d, J=8.80 Hz, 1H). LRMS (ESI): 489.2 [M+H]⁺.

Example 48 tert-Butyl 4-(4-(2-chloro-4-(methylcarbamoyl)phenylamino)-6H-pyrimido[5,4-b][1,4]oxazin-8(7H)-yl) piperidine-1-carboxylate

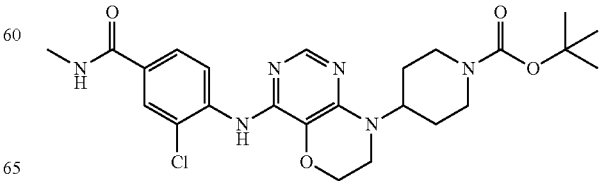

To 4-(8-(1-(tert-butoxycarbonyl)piperidin-4-yl)-7,8-dihydro-6H-pyrimido[5,4-b][1,4]oxazin-4-ylamino)-3-chlorobenzoic acid from Example 46 (33 mg, 0.067 mmol) and TEA (0.028 ml, 0.202 mmol) in DCM (2 ml) was added isopropyl chloroformate (1M in toluene, 0.15 mL, 0.15 mmol) the mixture was stirred at rt for 30 minutes, methanamine 40% in water (15.69 mg, 0.202 mmol) was added, the resulting suspension was stirred at room temperature for 30 minutes, the reaction was loaded onto a flash column and eluted by 0-100% EtOAc/Hexane to yield 12 mg (35%) of Example 48 as an off-white solid. $^1$H NMR (500 MHz, CDCl$_3$): δ ppm 1.46 (s, 9 H) 1.59-1.64 (m, 2 H) 1.66-1.73 (m, 2 H) 2.81-2.93 (m, 2 H) 2.99 (d, J=4.95 Hz, 3 H) 3.41-3.48 (m, 2 H) 4.18-4.32 (m, 4 H) 4.75-4.88 (m, 1 H) 6.08 (d, J=4.95 Hz, 1 H) 7.50 (s, 1 H) 7.58 (dd, J=8.80, 2.20 Hz, 1 H) 7.86 (d, J=2.20 Hz, 1 H) 8.07 (s, 1 H) 8.74 (d, J=8.80 Hz, 1 H). LRMS (ESI): 503.3 [M+H]$^+$.

Example 49 iso-Propyl 4-(4-(4-carbamoyl-2-chlorophenylamino)-6H-pyrimido[5,4-b][1,4]oxazin-8(7H)-yl)piperidine-1-carboxylate

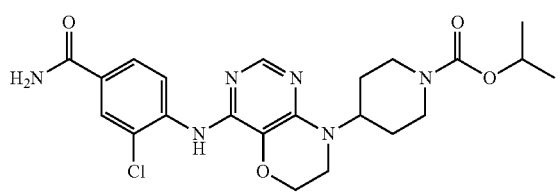 [SMILES: CC(C)OC(=O)N1CCC(N2CCOc3c(Nc4ccc(C(N)=O)cc4Cl)ncnc32)CC1]

Example 49 was prepared from Example 47 using the methods described in Examples 8A and 8. $^1$H NMR (500 MHz, CDCl$_3$): δ ppm 1.25 (d, J=6.05 Hz, 6 H) 1.62 (s, 2 H) 1.66-1.76 (m, 2 H) 2.90 (t, J=12.10 Hz, 2 H) 3.40-3.50 (m, 2 H) 4.22-4.36 (m, 4 H) 4.80-4.87 (m, 1 H) 4.89-4.97 (m, 1 H) 7.55 (s, 1 H) 7.61-7.68 (m, 1 H) 7.91 (d, J=2.20 Hz, 1 H) 8.08 (s, 1 H) 8.78 (d, J=8.80 Hz, 1 H). LRMS (ESI): 475.3 [M+H]$^+$.

Example 50 iso-Propyl 4-(4-(2-chloro-4-(methylcarbamoyl)phenylamino)-6H-pyrimido[5,4-b][1,4]oxazin-8(7H)-yl)piperidine-1-carboxylate

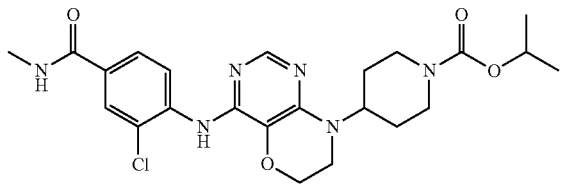 [SMILES: CNC(=O)c1ccc(Nc2ncnc3c2OCCN3C2CCN(C(=O)OC(C)C)CC2)c(Cl)c1]

Example 50 was prepared from Example 48 using the methods described in Examples 8A and 8. $^1$H NMR (500 MHz, CDCl$_3$): δ ppm 1.19-1.29 (m, 6 H) 1.57-1.67 (m, 2 H) 1.67-1.76 (m, 2 H) 2.89 (t, J=11.27 Hz, 2 H) 2.99 (d, J=4.95 Hz, 3 H) 3.40-3.50 (m, 2 H) 4.23-4.36 (m, 4 H) 4.80-4.85 (m, 1 H) 4.88-4.95 (m, 1 H) 6.09 (d, J=4.95 Hz, 1 H) 7.50 (s, 1 H) 7.54-7.62 (m, 1 H) 7.86 (d, J=2.20 Hz, 1 H) 8.07 (s, 1 H) 8.74 (d, J=8.80 Hz, 1 H). LRMS (ESI): 489.3 [M+H]$^+$.

Example 51 tert-Butyl 4-(4-(2-chloro-4-(2-morpholinoethylcarbamoyl)phenylamino)-6H-pyrimido[5,4-b][1,4]oxazin-8(7H)-yl)piperidine-1-carboxylate

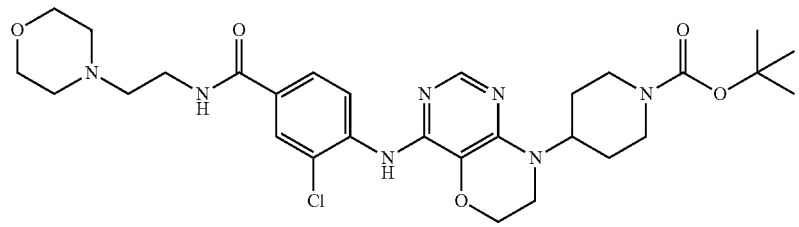 [SMILES: CC(C)(C)OC(=O)N1CCC(N2CCOc3c(Nc4ccc(C(=O)NCCN5CCOCC5)cc4Cl)ncnc32)CC1]

Example 51 was prepared using the same method described above for Example 48, with the exception that methanamine was replaced with 2-morpholinoethanamine. $^1$H NMR (500 MHz, CDCl$_3$): δ ppm 1.46 (s, 9H) 1.64-1.70 (m, 2 H) 1.75 (s, 2 H) 2.50 (s, 4 H) 2.59 (t, J=6.05 Hz, 2 H) 2.86 (s, 2 H) 3.43-3.48 (m, 2 H) 3.53 (q, J=5.50 Hz, 2 H) 3.69-3.76 (m, 4 H) 4.18-4.32 (m, 4 H) 4.76-4.87 (m, 1 H) 6.71 (t, J=4.67 Hz, 1 H) 7.59 (dd, J=8.80, 2.20 Hz, 1 H) 7.88 (d, J=2.20 Hz, 1 H) 8.07 (s, 1 H) 8.75 (d, J=8.80 Hz, 1 H). LRMS (ESI): 602.4 [M+H]$^+$.

Example 52 tert-Butyl 4-(4-(2-chloro-4-(3-(pyrrolidin-1-yl)propylcarbamoyl)phenylamino)-6H-pyrimido[5,4-b][1,4]oxazin-8(7H)-yl)piperidine-1-carboxylate

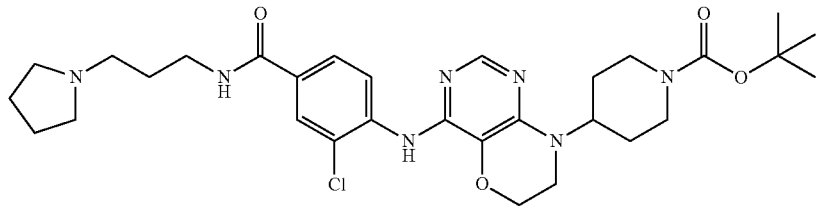 [SMILES: CC(C)(C)OC(=O)N1CCC(N2CCOc3c(Nc4ccc(C(=O)NCCCN5CCCC5)cc4Cl)ncnc32)CC1]

Example 52 was prepared using the same method described above for Example 48, with the exception that methanamine was replaced with 3-(pyrrolidin-1-yl)propan-1-amine. $^1$H NMR (500 MHz, CDCl$_3$): δ ppm 1.34-1.43 (m, 9 H) 1.54-1.63 (m, 2 H) 1.68 (d, J=9.90 Hz, 2 H) 1.98-2.10 (m, 2 H) 2.11-2.19 (m, 2 H) 3.05-3.13 (m, 8 H) 3.15 (t, J=6.60 Hz, 2 H) 3.32 (q, J=6.23 Hz, 2 H) 3.41-3.49 (m, 2 H) 3.62 (q, J=6.05 Hz, 2 H) 4.23-4.32 (m, 2 H) 4.75-4.88 (m, 1 H) 7.50 (s, 1 H) 7.93 (d, J=8.80 Hz, 1 H) 8.02-8.11 (m, 1 H) 8.31 (t, J=5.77 Hz, 1 H) 8.76 (d, J=8.80 Hz, 1 H). LRMS (ESI): 600.4 [M+H]$^+$.

Example 53 tert-Butyl 4-(4-(2-chloro-4-(2-(pyrrolidin-1-yl)ethylcarbamoyl)phenylamino)-6H-pyrimido[5,4-b][1,4]oxazin-8(7H)-yl)piperidine-1-carboxylate

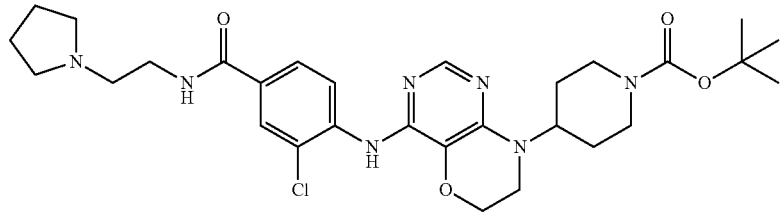 [SMILES: CC(C)(C)OC(=O)N1CCC(N2CCOc3c(Nc4ccc(C(=O)NCCN5CCCC5)cc4Cl)ncnc32)CC1]

Example 53 was prepared using the same method described above for Example 48, with the exception that methanamine was replaced with 2-(pyrrolidin-1-yl)ethanamine. $^1$H NMR (500 MHz, CDCl$_3$): δ ppm 1.45 (s, 9 H) 1.55-1.63 (m, 2 H) 1.65-1.72 (m, 2 H) 2.07-2.19 (m, 4 H) 3.09 (q, J=7.33 Hz, 8 H) 3.35 (s, 2 H) 3.41-3.48 (m, 2 H) 3.61 (d, J=4.95 Hz, 1 H) 3.87 (s, 1 H) 4.22-4.29 (m, 2 H) 4.77-4.91 (m, 1 H) 7.51 (s, 1 H) 8.00 (d, J=8.25 Hz, 1 H) 8.05 (s, 1 H) 8.13 (s, 1 H) 8.57 (s, 1H) 8.79 (d, J=8.25 Hz, 1 H). LRMS (ESI): 586.4 [M+H]$^+$.

Example 54 iso-Propyl 4-(4-(2-chloro-4-(2-morpholinoethylcarbamoyl)phenylamino)-6H-pyrimido[5,4-b][1,4]oxazin-8(7H)-yl)piperidine-1-carboxylate

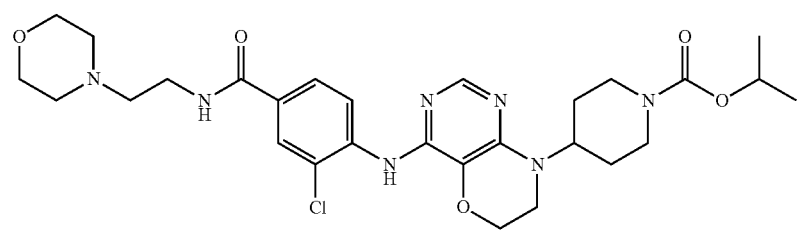 [SMILES: CC(C)OC(=O)N1CCC(N2CCOc3c(Nc4ccc(C(=O)NCCN5CCOCC5)cc4Cl)ncnc32)CC1]

Example 54 was prepared from Example 51 using the methods described in Examples 8A and 8. $^1$H NMR (500 MHz, CDCl$_3$): δ ppm 1.21-1.31 (m, 6 H) 1.67-1.74 (m, 2 H) 1.79 (s, 2 H) 2.51 (s, 4 H) 2.60 (t, J=6.05 Hz, 2 H) 2.90 (s, 2 H) 3.41-3.49 (m, 2 H) 3.53 (q, J=5.50 Hz, 2 H) 3.73 (t, J=4.40 Hz, 4 H) 4.20-4.39 (m, 4 H) 4.79-4.87 (m, 1 H) 4.88-4.98 (m, 1 H) 6.73 (s, 1 H) 7.51 (s, 1 H) 7.60 (d, J=8.80 Hz, 1 H) 7.88 (s, 1 H) 8.07 (s, 1 H) 8.75 (d, J=8.80 Hz, 1 H). LRMS (ESI): 588.3 [M+H]$^+$.

Example 55 tert-Butyl 4-(4-(3,5-dichloropyridin-4-ylamino)-6H-pyrimido[5,4-b][1,4]oxazin-8(7H)-yl)piperidine-1-carboxylate

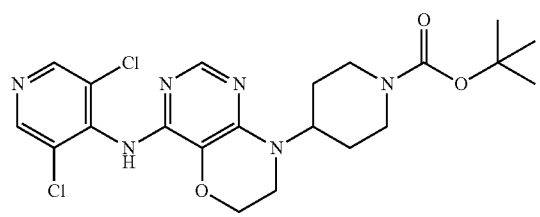 [SMILES: CC(C)(C)OC(=O)N1CCC(N2CCOc3c(Nc4c(Cl)cncc4Cl)ncnc32)CC1]

Example 55 was prepared using the same method described above for Example 3, with the exception that 2-fluoro-4-(methylsulfonyl)aniline was replaced with 3,5-dichloropyridin-4-amine. $^1$H NMR (500 MHz, CDCl$_3$): δ ppm 1.46 (s, 9 H) 1.56-1.67 (m, 2 H) 1.70 (s, 2 H) 2.85 (s, 2 H) 3.44-3.51 (m, 2 H) 4.15-4.29 (m, 4H) 4.75-4.88 (m, 1 H) 6.53 (s, 1 H) 7.95 (s, 1 H) 8.46 (s, 2 H). LRMS (ESI): 481.2 [M+H]$^+$.

Example 56 iso-Propyl 4-(4-(3,5-dichloropyridin-4-ylamino)-6H-pyrimido[5,4-b][1,4]oxazin-8(7H)-yl)piperidine-1-carboxylate

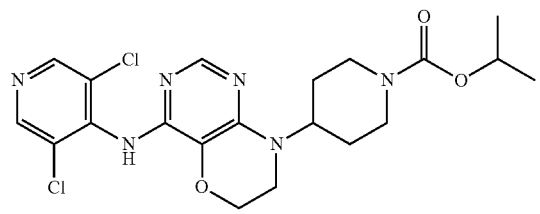 [SMILES: CC(C)OC(=O)N1CCC(N2CCOc3c(Nc4c(Cl)cncc4Cl)ncnc32)CC1]

Example 56 was prepared from Example 55 using the methods described in Examples 8A and 8. $^1$H NMR (500 MHz, CDCl$_3$): δ ppm 1.19-1.30 (m, 6 H) 1.59-1.67 (m, 2 H) 1.69-1.75 (m, 2 H) 2.89 (t, J=11.55 Hz, 2 H) 3.42-3.51 (m, 2H) 4.19-4.38 (m, 4 H) 4.80-4.87 (m, 1 H) 4.89-4.95 (m, 1 H) 6.52 (s, 1 H) 7.96 (s, 1 H) 8.46 (s, 2 H). LRMS (ESI): 467.2 [M+H]$^+$.

Example 57 tert-Butyl 4-(4-(4-(methylthio)phenylamino)-6H-pyrimido[5,4-b][1,4]oxazin-8(7H)-yl)piperidine-1-carboxylate

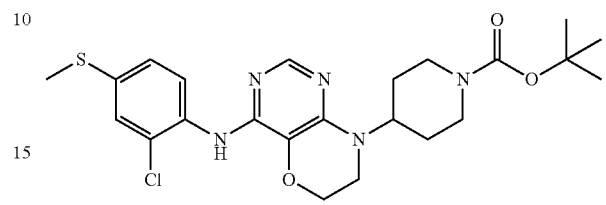

Example 57 was prepared using the same method described above for Example 3, with the exception that 2-fluoro-4-(methylsulfonyl)aniline was replaced with 4-(methylthio)aniline. $^1$H NMR (500 MHz, CDCl$_3$): δ ppm 1.40-1.48 (m, 9 H) 1.54-1.62 (m, 2 H) 1.65-1.71 (m, 2 H) 2.43 (s, 3 H) 2.84 (s, 2 H) 3.35-3.43 (m, 2H) 4.14-4.30 (m, 4 H) 4.74-4.82 (m, 1 H) 6.63 (s, 1 H) 7.21-7.26 (m, 2 H) 7.51 (d, J=8.80 Hz, 2 H) 8.01 (s, 1 H). LRMS (ESI): 458.3 [M+H]$^+$.

Example 58 tert-Butyl 4-(4-(2-chloro-4-(methylsulfinyl)phenylamino)-6H-pyrimido[5,4-b][1,4]oxazin-8(7H)-yl)piperidine-1-carboxylate

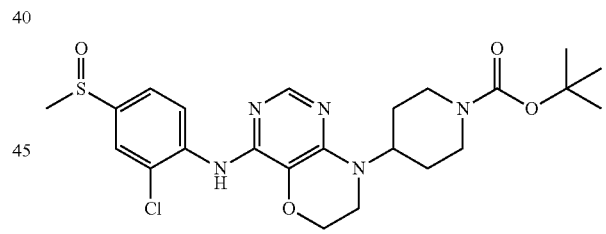

To tert-butyl 4-(4-(4-(methylthio)phenylamino)-6H-pyrimido[5,4-b][1,4]oxazin-8(7H)-yl)piperidine-1-carboxylate from Example 57 (112 mg, 0.245 mmol) in THF (2 mL) at room temperature, NCS (39.2 mg, 0.294 mmol) was added, the reaction mixture was stirred at room temperature for 15 min. The reaction was concentrated in vacuo, and the residue was purified by silica gel flash column, eluted by 20-100% EtOAc/Hexane to afford 33 mg (26.5%) of Example 58 as an off-white solid. $^1$H NMR (500 MHz, CDCl$_3$): δ ppm 1.46 (s, 9 H) 1.54-1.65 (m, 2 H) 1.67-1.74 (m, 2 H) 2.71 (s, 3 H) 2.86 (d, J=9.35 Hz, 2 H) 3.40-3.51 (m, 2 H) 4.17-4.33 (m, 4 H) 4.76-4.87 (m, 1 H) 7.45 (dd, J=8.80, 2.20 Hz, 1 H) 7.49 (s, 1 H) 7.72 (d, J=2.20 Hz, 1 H) 8.04-8.10 (m, 1 H) 8.84 (d, J=8.25 Hz, 1 H). LRMS (ESI): 508.3 [M+H]$^+$.

Example 59 tert-Butyl 4-(4-(2-methylpyridin-3-ylamino)-6H-pyrimido[5,4-b][1,4]oxazin-8(7H)-yl)piperidine-1-carboxylate

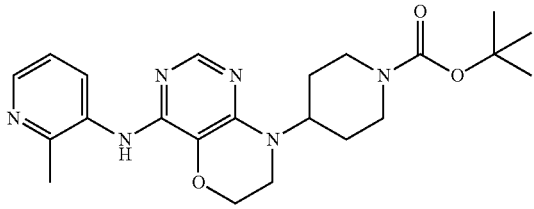 [SMILES: Cc1ncccc1Nc1ncnc2c1OCCN2C1CCN(C(=O)OC(C)(C)C)CC1]

Example 59 was prepared using the same method described above for Example 3, with the exception that 2-fluoro-4-(methylsulfonyl)aniline was replaced with 2-methylpyridin-3-amine. $^1$H NMR (500 MHz, CDCl$_3$): δ ppm 1.45 (s, 9 H) 1.58-1.65 (m, 2 H) 1.66-1.72 (m, 2 H) 2.53 (s, 3 H) 2.86 (d, J=2.20 Hz, 2 H) 3.43 (d, J=3.30 Hz, 2 H) 4.14-4.29 (m, 4 H) 4.72-4.86 (m, 1 H) 6.47 (s, 1 H) 7.13 (dd, J=7.97, 4.67 Hz, 1 H) 8.00 (s, 1 H) 8.16 (d, J=4.40 Hz, 1 H) 8.45 (d, J=8.25 Hz, 1 H). LRMS (ESI): 427.2 [M+H]$^+$.

Example 60 tert-Butyl 4-(4-(4-methylpyridin-3-ylamino)-6H-pyrimido[5,4-b][1,4]oxazin-8(7H)-yl)piperidine-1-carboxylate

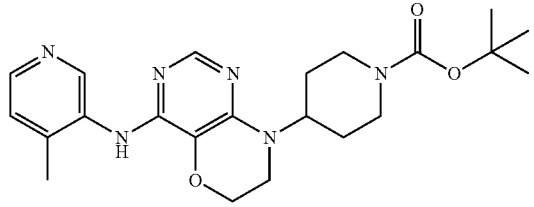 [SMILES: Cc1ccncc1Nc1ncnc2c1OCCN2C1CCN(C(=O)OC(C)(C)C)CC1]

Example 60 was prepared using the same method described above for Example 3, with the exception that 2-fluoro-4-(methylsulfonyl)aniline was replaced with 4-methylpyridin-3-amine. $^1$H NMR (500 MHz, CDCl$_3$): δ ppm 1.45 (s, 9 H) 1.55-1.73 (m, 4 H) 2.27 (s, 3 H) 2.85 (s, 2 H) 3.38-3.48 (m, 2 H) 4.16-4.30 (m, 4H) 4.73-4.86 (m, 1 H) 6.33 (s, 1 H) 7.10 (d, J=4.95 Hz, 1 H) 7.96 (s, 1 H) 8.21 (d, J=4.95 Hz, 1 H) 9.02 (s, 1 H). LRMS (ESI): 427.3 [M+H]$^+$.

Example 61

(S)-sec-butyl 4-(4-(2-fluoro-4-(methylsulfonyl)phenylamino)-6H-pyrimido[5,4-b][1,4]oxazin-8(7H)-yl)piperidine-1-carboxylate

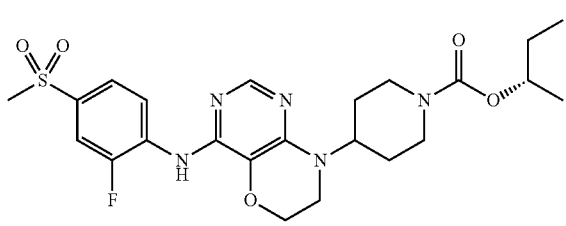 [SMILES: CC[C@H](C)OC(=O)N1CCC(N2CCOc3c(Nc4ccc(S(C)(=O)=O)cc4F)ncnc32)CC1]

To (S)-butan-2-ol (9.02 mg, 0.122 mmol) and phosgene (60.2 mg, 0.122 mmol) in THF (1.5 mL), TEA (0.034 mL, 0.243 mmol) was added dropwise at room temperature, the reaction was stirred for 15 minutes, and then N-(2-fluoro-4-(methylsulfonyl)phenyl)-8-(piperidin-4-yl)-7,8-dihydro-6H-pyrimido[5,4-b][1,4]oxazin-4-amine, HCl from Example 8A (45 mg, 0.101 mmol) was added, the resulting reaction mixture was stirred at room temperature for 15 minutes. The reaction was diluted by EtOAc, washed by water and brine, dried over MgSO4, evaporated in vacuo. The residue was purified by a silica gel flash column, eluted by 0-50% EtOAc/Hexane to yield 44 mg (82%) of Example 61 as a pale solid. $^1$H NMR (500 MHz, CDCl$_3$): δ ppm 0.90 (t, J=7.42 Hz, 3 H) 1.18-1.24 (m, 3 H) 1.51-1.64 (m, 4 H) 1.67-1.75 (m, 2 H) 2.90 (s, 2 H) 3.02 (s, 3 H) 3.39-3.49 (m, 2 H) 4.22-4.35 (m, 4 H) 4.68-4.78 (m, 1 H) 4.84 (s, 1 H) 7.20 (d, J=4.40 Hz, 1 H) 7.63 (d, J=11.00 Hz, 1 H) 7.68 (d, J=8.80 Hz, 1 H) 8.07 (s, 1 H) 8.88 (t, J=8.25 Hz, 1 H). LRMS (ESI): 508.2 [M+H]$^+$.

Example 62

(R)-sec-butyl 4-(4-(2-fluoro-4-(methylsulfonyl)phenylamino)-6H-pyrimido[5,4-b][1,4]oxazin-8(7H)-yl) piperidine-1-carboxylate

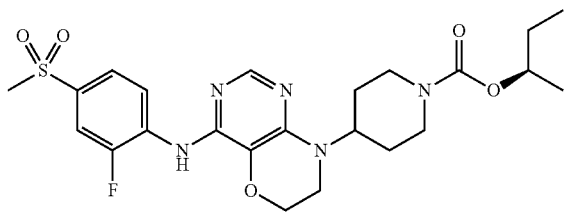 [SMILES: CC[C@@H](C)OC(=O)N1CCC(N2CCOc3c(Nc4ccc(S(C)(=O)=O)cc4F)ncnc32)CC1]

Example 62 was prepared using the same method described above for Example 61, with the exception that (S)-butan-2-ol was replaced with (R)-butan-2-ol. $^1$H NMR (500 MHz, CDCl$_3$): δ ppm 0.90 (t, J=7.42 Hz, 3H) 1.17-1.26 (m, 3 H) 1.49-1.64 (m, 4 H) 1.70 (d, J=13.20 Hz, 2 H) 2.86-2.91 (m, 2 H) 3.02 (s, 3 H) 3.40-3.48 (m, 2 H) 4.20-4.37 (m, 4 H) 4.69-4.77 (m, 1 H) 4.83 (t, J=4.12 Hz, 1 H) 7.20 (d, J=3.85 Hz, 1 H) 7.63 (d, J=10.45 Hz, 1 H) 7.68 (d, J=8.80 Hz, 1 H) 8.07 (s, 1 H) 8.88 (t, J=8.25 Hz, 1 H). LRMS (ESI): 508.2 [M+H]$^+$.

Example 63 tert-Butyl 4-(4-(2-methylpyridin-3-ylamino)-7-oxo-6H-pyrimido[5,4-b][1,4]oxazin-8(7H)-yl)piperidine-1-carboxylate

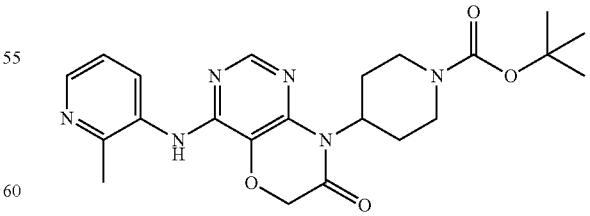

Example 63 was prepared using the same method described above for Example 26, with the exception that 2-fluoro-4-(methylsulfonyl)aniline was replaced with 2-methylpyridin-3-amine. $^1$H NMR (500 MHz, CDCl$_3$): δ ppm 1.42-1.53 (m, 9H) 1.59-1.70 (m, 2 H) 2.55 (s, 3 H) 2.64-2.86

(m, 4 H) 4.25 (d, J=3.85 Hz, 2 H) 4.72 (s, 2 H) 4.96-5.04 (m, 1 H) 6.69 (s, 1 H) 7.19 (dd, J=8.25, 4.95 Hz, 1 H) 8.20 (s, 1 H) 8.27 (d, J=4.40 Hz, 1 H) 8.39 (d, J=8.25 Hz, 1 H). LRMS (ESI): 441.1 [M+H]⁺.

Example 64 iso-Propyl 4-(4-(2-methylpyridin-3-ylamino)-7-oxo-6H-pyrimido[5,4-b][1,4]oxazin-8(7H)-yl)piperidine-1-carboxylate

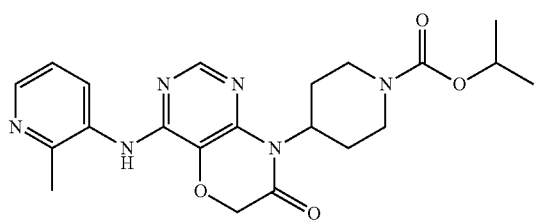 [SMILES: Cc1ncccc1Nc1ncnc2c1OCC(=O)N2C1CCN(C(=O)OC(C)C)CC1]

Example 64 was prepared from Example 63 using the methods described in Examples 8A and 8. ¹H NMR (500 MHz, CDCl₃): δ ppm 1.20-1.32 (m, 6 H) 1.65 (d, J=11.55 Hz, 2 H) 2.56 (s, 3 H) 2.65-2.77 (m, 2 H) 2.82 (s, 2 H) 4.32 (s, 2 H) 4.72 (s, 2 H) 4.88-4.97 (m, 1 H) 4.97-5.06 (m, 1 H) 6.69 (s, 1 H) 7.20 (dd, J=7.97, 4.67 Hz, 1 H) 8.20 (s, 1 H) 8.27 (d, J=3.30 Hz, 1 H) 8.41 (d, J=8.25 Hz, 1 H). LRMS (ESI): 427.2 [M+H]⁺.

Example 65 tert-Butyl 4-(4-(2-methylpyridin-3-yloxy)-7-oxo-6H-pyrimido[5,4-b][1,4]oxazin-8(7H)-yl)piperidine-1-carboxylate

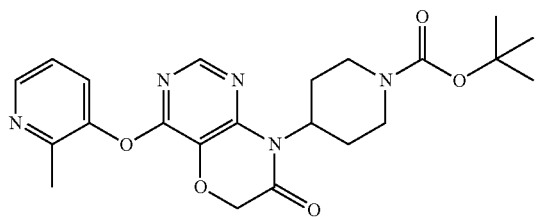 [SMILES: Cc1ncccc1Oc1ncnc2c1OCC(=O)N2C1CCN(C(=O)OC(C)(C)C)CC1]

A reaction mixture of Example 26A (74 mg, 0.2 mmol), 3-hydroxyl-2-methylpyrimidine (26 mg, 0.24 mmol) and K₂CO₃ (33 mg, 0.24 mmol) in 1.5 mL of DMF was heated in a sealed vial in the microwave at 140° C. for 10 min. The reaction was purified by flash chromatography on silica gel (elution with 0-100 EtOAc/hexane) to afford 25 mg (28%) of Example 65 as a pale foam. ¹H NMR (500 MHz, CDCl₃): δ ppm 1.42-1.52 (m, 9 H) 1.65 (d, J=11.55 Hz, 2 H) 2.39-2.45 (m, 3 H) 2.64-2.88 (m, 4 H) 4.22 (s, 2 H) 4.76 (s, 2 H) 4.97-5.05 (m, 1 H) 7.20 (s, 1 H) 7.40 (d, J=6.60 Hz, 1 H) 8.12 (s, 1 H) 8.42 (d, J=3.30 Hz, 1 H). LRMS (ESI): 442.1 [M+H]⁺.

Example 66 tert-Butyl 4-(4-(2-chloro-4-(methylsulfonyl)phenylamino)-7-oxo-6H-pyrimido[5,4-b][1,4]oxazin-8(7H)-yl)piperidine-1-carboxylate

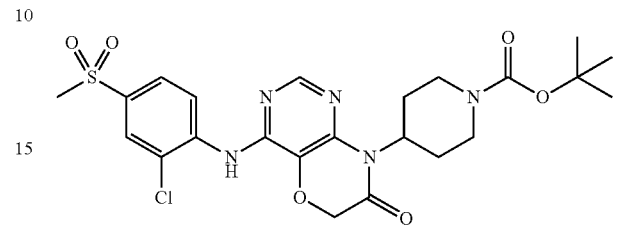

Example 66 was prepared using the same method described above for Example 26, with the exception that 2-fluoro-4-(methylsulfonyl)aniline was replaced with 2-chloro-4-(methylsulfonyl)aniline. ¹H NMR (500 MHz, CDCl₃): δ ppm 1.38-1.45 (m, 9 H) 1.60 (d, J=11.00 Hz, 2 H) 2.55-2.69 (m, 2 H) 2.75 (s, 2 H) 2.98-3.06 (m, 3 H) 3.22 (s, 2 H) 4.17 (s, 2 H) 4.68-4.78 (m, 2 H) 4.90-5.01 (m, 1 H) 7.74-7.81 (m, 1 H) 7.91 (d, J=2.20 Hz, 1 H) 8.26 (s, 1 H) 8.92 (d, J=8.80 Hz, 1 H). LRMS (ESI): 538.1 [M+H]⁺.

Example 67 iso-Propyl 4-(4-(2-chloro-4-(methylsulfonyl)phenylamino)-7-oxo-6H-pyrimido[5,4-b][1,4]oxazin-8(7H)-yl)piperidine-1-carboxylate

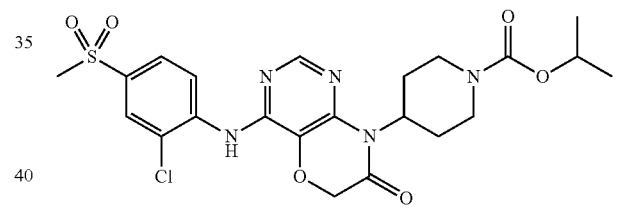

Example 67 was prepared from Example 66 using the methods described in Examples 8A and 8. ¹H NMR (500 MHz, CDCl₃): δ ppm 1.26 (d, J=5.50 Hz, 6 H) 1.66 (d, J=11.55 Hz, 2 H) 2.64-2.76 (m, 2 H) 2.83 (s, 2 H) 3.06 (s, 3 H) 4.34 (s, 2 H) 4.77 (s, 2 H) 4.89-4.97 (m, 1 H) 4.98-5.09 (m, 1 H) 7.78-7.89 (m, 2 H) 7.98 (d, J=2.20 Hz, 1 H) 8.33 (s, 1 H) 8.99 (d, J=8.80 Hz, 1 H). LRMS (ESI): 524.1 [M+H]⁺.

Example 68

4-(2-Chloro-4-(methylsulfonyl)phenylamino)-8-(1-(pyrimidin-2-yl)piperidin-4-yl)-6H-pyrimido[5,4-b][1,4]oxazin-7(8H)-one

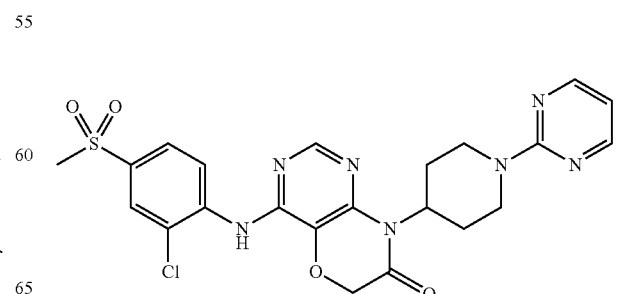

Example 68 was prepared using the same method described above for Example 32, with the exception that 3-Fluoro-4-(8-(piperidin-4-yl)-7,8-dihydro-6H-pyrimido[5,4-b][1,4]oxazin-4-ylamino)benzonitrile, HCl salt was replaced with 4-(2-chloro-4-(methylsulfonyl)phenylamino)-8-(piperidin-4-yl)-6H-pyrimido[5,4-b][1,4]oxazin-7(8H)-one, HCl salt. $^1$H NMR (500 MHz, CDCl$_3$): δ ppm 1.64-1.75 (m, 2 H) 1.81 (d, J=9.35 Hz, 2 H) 3.00-3.07 (m, 3 H) 3.41-3.50 (m, 2 H) 4.24-4.33 (m, 2 H) 4.89-5.04 (m, 3 H) 6.48 (t, J=4.95 Hz, 1 H) 7.63 (s, 1 H) 7.75-7.82 (m, 1H) 7.93 (d, J=2.20 Hz, 1 H) 8.11 (s, 1 H) 8.30 (d, J=4.40 Hz, 2 H) 8.96 (d, J=9.35 Hz, 1 H). LRMS (ESI): 516.1 [M+H]$^+$.

Example 69 tert-Butyl 4-(4-(6-methylpyridin-3-ylamino)-7-oxo-6H-pyrimido[5,4-b][1,4]oxazin-8(7H)-yl)piperidine-1-carboxylate

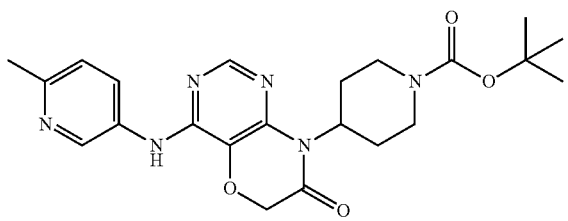 [SMILES: Cc1ccc(Nc2ncnc3c2OCC(=O)N3C2CCN(C(=O)OC(C)(C)C)CC2)cn1]

Example 69 was prepared using the same method described above for Example 26, with the exception that 2-fluoro-4-(methylsulfonyl)aniline was replaced with 6-methylpyridin-3-amine. $^1$H NMR (500 MHz, CDCl$_3$): δ ppm 1.47 (s, 9 H) 1.56-1.67 (m, 2 H) 2.51 (s, 3 H) 2.62-2.71 (m, 2 H) 2.72-2.90 (m, 2 H) 4.28 (s, 2H) 4.68 (s, 2 H) 4.91-5.04 (m, 1 H) 6.88 (s, 1 H) 7.14 (d, J=8.25 Hz, 1 H) 8.13 (dd, J=8.52, 2.47 Hz, 1 H) 8.20 (s, 1 H) 8.53 (d, J=2.75 Hz, 1 H). LRMS (ESI): 441.3 [M+H]$^+$.

Example 70 tert-Butyl 4-(4-(5-methylpyridin-3-ylamino)-7-oxo-6H-pyrimido[5,4-b][1,4]oxazin-8(7H)-yl)piperidine-1-carboxylate

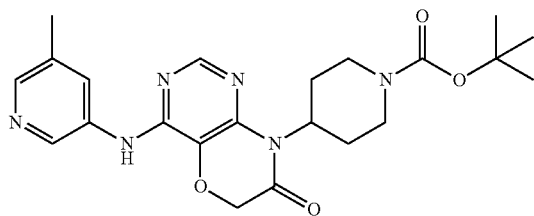 [SMILES: Cc1cncc(Nc2ncnc3c2OCC(=O)N3C2CCN(C(=O)OC(C)(C)C)CC2)c1]

Example 70 was prepared using the same method described above for Example 26, with the exception that 2-fluoro-4-(methylsulfonyl)aniline was replaced with 5-methylpyridin-3-amine. $^1$H NMR (500 MHz, CDCl$_3$): δ ppm 1.47 (s, 9 H) 1.59-1.67 (m, 2 H) 2.36 (s, 3 H) 2.63-2.73 (m, 2 H) 2.82 (d, 2 H) 4.27 (d, J=17.05 Hz, 2 H) 4.69 (s, 2 H) 4.94-5.04 (m, 1 H) 6.89 (s, 1 H) 8.10 (s, 1 H) 8.15 (s, 1 H) 8.24 (s, 1 H) 8.49 (d, J=2.75 Hz, 1 H). LRMS (ESI): 441.3 [M+H]$^+$.

Example 71 tert-Butyl 4-(4-(2,6-dimethylpyridin-3-ylamino)-7-oxo-6H-pyrimido[5,4-b][1,4]oxazin-8(7H)-yl)piperidine-1-carboxylate

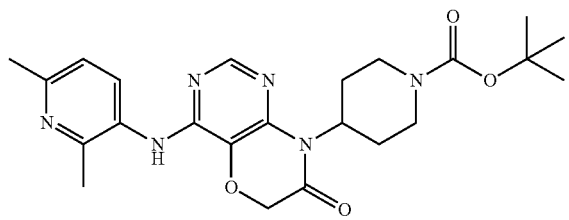 [SMILES: Cc1ccc(Nc2ncnc3c2OCC(=O)N3C2CCN(C(=O)OC(C)(C)C)CC2)c(C)n1]

Example 71 was prepared using the same method described above for Example 26, with the exception that 2-fluoro-4-(methylsulfonyl)aniline was replaced with 2,6-dimethylpyridin-3-amine. $^1$H NMR (500 MHz, CDCl$_3$): δ ppm 1.43-1.50 (m, 9 H) 1.59-1.67 (m, 2 H) 2.50 (s, 6 H) 2.62-2.74 (m, 2 H) 2.75-2.89 (m, 2 H) 4.29 (s, 2 H) 4.71 (s, 2 H) 4.92-5.04 (m, 1 H) 6.57 (s, 1 H) 7.04 (d, J=8.25 Hz, 1 H) 8.09 (d, J=7.70 Hz, 1 H) 8.16 (s, 1 H). LRMS (ESI): 455.3 [M+H]$^+$.

Example 72 iso-Propyl 4-(4-(6-methylpyridin-3-ylamino)-7-oxo-6H-pyrimido[5,4-b][1,4]oxazin-8(7H)-yl)piperidine-1-carboxylate

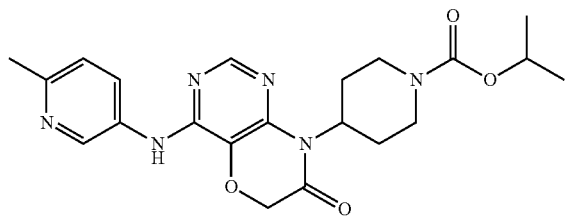 [SMILES: Cc1ccc(Nc2ncnc3c2OCC(=O)N3C2CCN(C(=O)OC(C)C)CC2)cn1]

Example 72 was prepared from Example 69 using the methods described in Examples 8A and 8. $^1$H NMR (500 MHz, CDCl$_3$): δ ppm 1.24 (t, J=7.15 Hz, 6 H) 1.66 (s, 2 H) 2.72 (d, J=20.89 Hz, 3 H) 2.82 (s, 2 H) 4.26 (s, 2 H) 4.61-4.89 (m, 2 H) 4.88-5.07 (m, 4 H) 7.29-7.57 (m, 2 H) 8.23 (s, 2 H) 8.78 (s, 1 H). LRMS (ESI): 427.2 [M+H]$^+$.

Example 73 iso-Propyl 4-(4-(2,6-dimethylpyridin-3-ylamino)-7-oxo-6H-pyrimido[5,4-b][1,4]oxazin-8(7H)-yl)piperidine-1-carboxylate

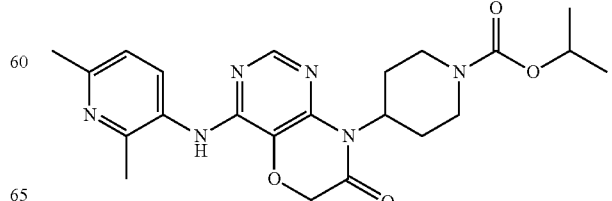

Example 73 was prepared from Example 71 using the methods described in Examples 8A and 8. $^1$H NMR (500 MHz, CDCl3): δ ppm 1.20-1.29 (m, 6 H) 1.66 (d, J=9.90 Hz, 2 H) 2.45-2.55 (m, 6 H) 2.63-2.77 (m, 2 H) 2.83 (s, 2 H) 4.27 (dd, J=12.10, 4.40 Hz, 2 H) 4.71 (s, 2 H) 4.87-4.96 (m, 1 H) 4.96-5.05 (m, 1 H) 6.58 (s, 1 H) 7.05 (d, J=8.25 Hz, 1 H) 8.09 (d, J=8.25 Hz, 1 H) 8.17 (s, 1 H). LRMS (ESI): 441.2 [M+H]+.

Example 74 tert-Butyl 4-(8-(2-chloro-4-(methylsulfonyl)phenylamino)-2H-benzo[b][1,4]oxazin-4 (3H)-yl)piperidine-1-carboxylate

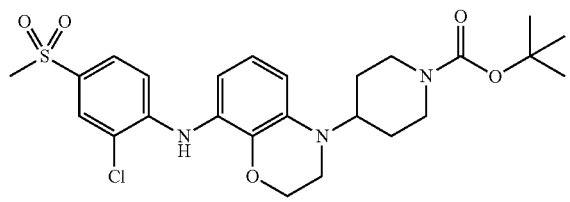 [SMILES: CC(C)(C)OC(=O)N1CCC(N2CCOc3c(Nc4ccc(S(C)(=O)=O)cc4Cl)cccc32)CC1]

Example 74 was prepared using the same method described above for Example 1, with the exception that 4-aminophenylmethyl sulfone was replaced with 2-chloro-4-(methylsulfonyl)aniline. $^1$H NMR (500 MHz, CDCl3): δ ppm 1.45-1.52 (m, 9 H) 1.60-1.67 (m, 2 H) 1.80 (d, J=12.65 Hz, 2 H) 2.81 (s, 2 H) 2.99-3.07 (m, 3H) 3.25-3.32 (m, 2 H) 3.71-3.82 (m, 1 H) 4.21-4.37 (m, 4 H) 6.59 (d, J=8.25 Hz, 1H) 6.66-6.75 (m, 2 H) 6.84 (t, J=8.25 Hz, 1 H) 7.30 (d, J=8.80 Hz, 1 H) 7.59-7.66 (m, 1 H) 7.89 (d, J=2.20 Hz, 1 H). LRMS (ESI): 538.1 [M+H]+.

Example 75 iso-Propyl 4-(8-(2-chloro-4-(methylsulfonyl)phenylamino)-2H-benzo[b][1,4]oxazin-4 (3H)-yl)piperidine-1-carboxylate

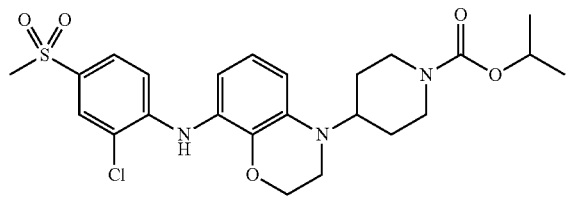

Example 75 was prepared from Example 74 using the methods described in Examples 8A and 8. $^1$H NMR (500 MHz, CDCl3): δ ppm 1.20-1.28 (m, 6 H) 1.61 (d, J=8.80 Hz, 2 H) 1.79 (d, J=12.10 Hz, 2 H) 2.83 (t, J=12.37 Hz, 2 H) 3.01 (s, 3 H) 3.22-3.30 (m, 2 H) 3.72-3.81 (m, 1 H) 4.19-4.40 (m, 4 H) 4.85-4.97 (m, 1H) 6.57 (d, J=7.70 Hz, 1 H) 6.65-6.72 (m, 2 H) 6.82 (t, J=7.97 Hz, 1 H) 7.28 (d, J=8.80 Hz, 1 H) 7.60 (dd, J=8.80, 2.20 Hz, 1 H) 7.87 (d, J=2.20 Hz, 1 H). LRMS (ESI): 524.1 [M+H]+.

Example 76 tert-Butyl 4-(8-(2-methylpyridin-3-ylamino)-2H-benzo[b][1,4]oxazin-4 (3H)-yl)piperidine-1-carboxylate

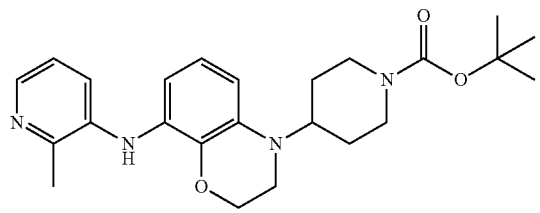 [SMILES: Cc1ncccc1Nc1cccc2c1OCCN2C1CCN(C(=O)OC(C)(C)C)CC1]

Example 76 was prepared using the same method described above for Example 1, with the exception that 4-aminophenylmethyl sulfone was replaced with 2-methylpyridin-3-amine. $^1$H NMR (500 MHz, CDCl3): δ ppm 1.48 (s, 9 H) 1.63-1.70 (m, 2 H) 1.80 (d, J=12.10 Hz, 2 H) 2.53 (s, 3 H) 2.80 (s, 2 H) 3.25-3.34 (m, 2H) 3.76 (t, J=3.30 Hz, 1 H) 4.18-4.34 (m, 4 H) 5.75 (s, 1 H) 6.40 (d, J=8.25 Hz, 1 H) 6.48 (d, J=7.70 Hz, 1 H) 6.75 (t, J=7.97 Hz, 1 H) 7.05 (dd, J=8.25, 4.40 Hz, 1 H) 7.58 (d, J=7.15 Hz, 1 H) 8.10 (d, J=3.30 Hz, 1 H). LRMS (ESI): 425.2 [M+H]+.

Example 77 iso-Propyl 4-(8-(2-methylpyridin-3-ylamino)-2H-benzo[b][1,4]oxazin-4 (3H)-yl)piperidine-1-carboxylate

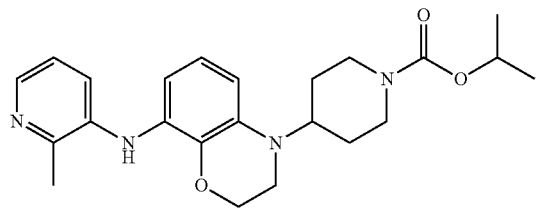 [SMILES: Cc1ncccc1Nc1cccc2c1OCCN2C1CCN(C(=O)OC(C)C)CC1]

Example 77 was prepared from Example 76 using the methods described in Examples 8A and 8. $^1$H NMR (500 MHz, CDCl3): δ ppm 1.25 (d, J=6.60 Hz, 6 H) 1.58-1.69 (m, 2 H) 1.79 (d, J=12.10 Hz, 2 H) 2.51 (s, 3 H) 2.82 (t, J=12.37 Hz, 2 H) 3.22-3.31 (m, 2 H) 3.72-3.81 (m, 1 H) 4.22-4.39 (m, 4 H) 4.86-4.97 (m, 1 H) 5.74 (s, 1 H) 6.39 (d, J=8.25 Hz, 1 H) 6.46 (d, J=8.25 Hz, 1 H) 6.73 (t, J=8.25 Hz, 1H) 7.04 (dd, J=7.97, 4.67 Hz, 1 H) 7.56 (d, J=7.15 Hz, 1 H) 8.08 (d, J=3.30 Hz, 1 H). LRMS (ESI): 411.3 [M+H]⁺.

Example 78

N-(2-methylpyridin-3-yl)-4-(1-(pyrimidin-2-yl)piperidin-4-yl)-3,4-dihydro-2H-benzo[b][1,4]oxazin-8-amine

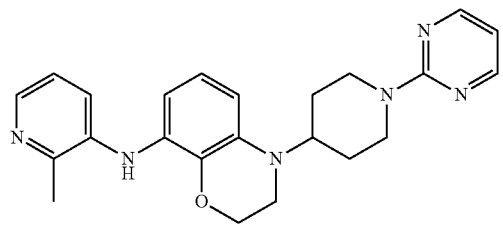 [SMILES: Cc1ncccc1Nc1cccc2c1OCCN2C1CCN(c2ncccn2)CC1]

Example 78 was prepared using the same method described above for Example 32, with the exception that 3-Fluoro-4-(8-(piperidin-4-yl)-7,8-dihydro-6H-pyrimido[5,4-b][1,4]oxazin-4-ylamino)benzonitrile, HCl salt was replaced with N-(2-methylpyridin-3-yl)-4-(piperidin-4-yl)-3,4-dihydro-2H-benzo[b][1,4]oxazin-8-amine, HCl salt. ¹H NMR (500 MHz, CDCl₃): δ ppm 1.65-1.75 (m, 2 H) 1.91 (d, J=12.10 Hz, 2 H) 2.53 (s, 3 H) 2.90-3.01 (m, 2 H) 3.26-3.34 (m, 2 H) 3.93 (t, J=3.57 Hz, 1H) 4.24-4.32 (m, 2 H) 4.97 (d, J=13.75 Hz, 2 H) 5.75 (s, 1 H) 6.43-6.54 (m, 3 H) 6.77 (t, J=7.97 Hz, 1 H) 7.05 (dd, J=8.25, 4.95 Hz, 1 H) 7.59 (d, J=8.25 Hz, 1 H) 8.10 (d, J=3.30 Hz, 1 H) 8.32 (d, J=4.95 Hz, 2 H). LRMS (ESI): 403.3 [M+H]⁺.

Example 79 tert-Butyl 4-(8-(3,5-dichloropyridin-4-ylamino)-2H-benzo[b][1,4]oxazin-4(3H)-yl)piperidine-1-carboxylate

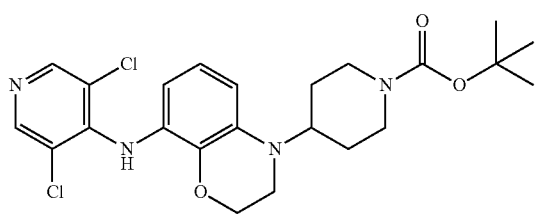 [SMILES: CC(C)(C)OC(=O)N1CCC(N2CCOc3c(Nc4c(Cl)cncc4Cl)cccc32)CC1]

Example 79 was prepared using the same method described above for Example 1, with the exception that 4-aminophenylmethyl sulfone was replaced with 3,5-dichloropyridin-4-amine. ¹H NMR (500 MHz, CDCl₃): δ ppm 1.46 (s, 9 H) 1.55-1.64 (m, 2 H) 1.78 (d, J=12.10 Hz, 2 H) 2.79 (s, 2 H) 3.22-3.30 (m, 2 H) 3.68-3.80 (m, 1 H) 4.17-4.35 (m, 4 H) 6.15 (d, J=7.70 Hz, 1 H) 6.34 (s, 1 H) 6.52 (d, J=7.70 Hz, 1 H) 6.72 (t, J=7.97 Hz, 1 H) 8.32 (s, 2 H). LRMS (ESI): 479.2 [M+H]⁺.

Example 80 iso-Propyl 4-(8-(3,5-dichloropyridin-4-ylamino)-2H-benzo[b][1,4]oxazin-4(3H)-yl)piperidine-1-carboxylate

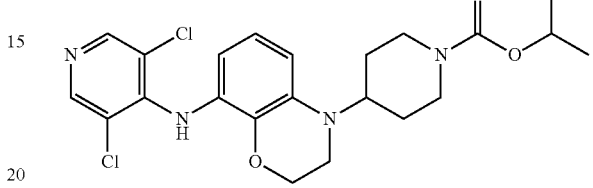

Example 80 was prepared from Example 79 using the methods described in Examples 8A and 8. ¹H NMR (500 MHz, CDCl₃): δ ppm 1.25 (d, J=6.60 Hz, 6H) 1.61 (d, J=9.90 Hz, 2 H) 1.79 (d, J=12.10 Hz, 2 H) 2.75-2.88 (m, 2 H) 3.20-3.32 (m, 2 H) 3.69-3.82 (m, 1 H) 4.21-4.39 (m, 4 H) 4.86-4.97 (m, 1 H) 6.15 (d, J=7.70 Hz, 1 H) 6.34 (s, 1 H) 6.52 (d, J=8.25 Hz, 1 H) 6.72 (t, J=7.97 Hz, 1 H) 8.32 (s, 2 H). LRMS (ESI): 465.2 [M+H]⁺.

Example 81 tert-Butyl 4-(8-(2-methylpyridin-3-ylamino)-3-oxo-2H-benzo[b][1,4]oxazin-4(3H)-yl)piperidine-1-carboxylate

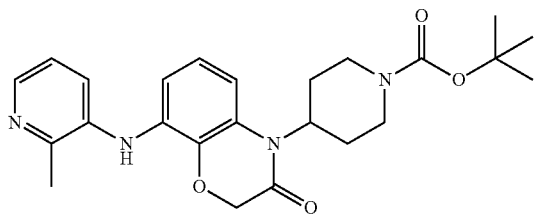 [SMILES: Cc1ncccc1Nc1cccc2c1OCC(=O)N2C1CCN(C(=O)OC(C)(C)C)CC1]

Example 81 was prepared using the same method described above for Example 2, with the exception that 4-aminophenylmethyl sulfone was replaced with 2-methylpyridin-3-amine. ¹H NMR (500 MHz, CDCl₃): δ ppm 1.48 (s, 9 H) 1.76 (d, J=11.42 Hz, 2 H) 2.47-2.54 (m, 3 H) 2.53-2.63 (m, 2 H) 2.78 (d, J=7.91 Hz, 2 H) 3.46 (t, J=7.03 Hz, 1 H) 4.20-4.42 (m, 2 H) 4.57 (s, 2 H) 5.76 (s, 1 H) 6.69 (t, J=9.45 Hz, 2 H) 6.89 (t, J=8.35 Hz, 1 H) 7.10 (dd, J=7.91, 4.83 Hz, 1 H) 7.55 (d, J=7.91 Hz, 1 H) 8.20 (d, J=4.39 Hz, 1 H). LRMS (ESI): 439.3 [M+H]⁺.

Example 82 iso-Propyl 4-(8-(2-methylpyridin-3-ylamino)-3-oxo-2H-benzo[b][1,4]oxazin-4(3H)-yl)piperidine-1-carboxylate

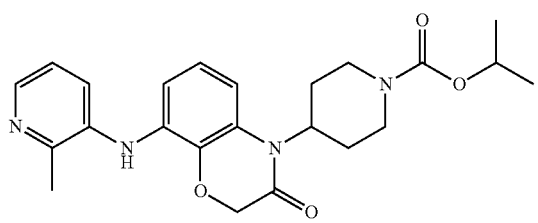 [SMILES: Cc1ncccc1Nc1cccc2c1OCC(=O)N2C1CCN(C(=O)OC(C)C)CC1]

Example 82 was prepared from Example 81 using the methods described in Examples 8A and 8. $^1$H NMR (500 MHz, CDCl$_3$): δ ppm 1.21-1.31 (m, 6 H) 1.78 (d, J=12.10 Hz, 2 H) 2.52 (s, 3 H) 2.56 (dd, J=12.65, 4.40 Hz, 2 H) 2.82 (s, 2 H) 4.21-4.44 (m, 3 H) 4.57 (s, 2 H) 4.86-4.99 (m, 1 H) 5.77 (s, 1 H) 6.69 (dd, J=14.30, 8.25 Hz, 2 H) 6.89 (t, J=8.25 Hz, 1 H) 7.10 (dd, J=7.97, 4.67 Hz, 1 H) 7.55 (d, J=6.60 Hz, 1 H) 8.20 (d, J=4.95 Hz, 1 H). LRMS (ESI): 425.3 [M+H]$^+$.

Example 83 tert-Butyl 4-(4-(2-fluoro-4-(methylsulfonyl)phenylamino)-7,8-dihydropyrimido[5,4-b][1,4]oxazepin-9(6H)-yl)piperidine-1-carboxylate

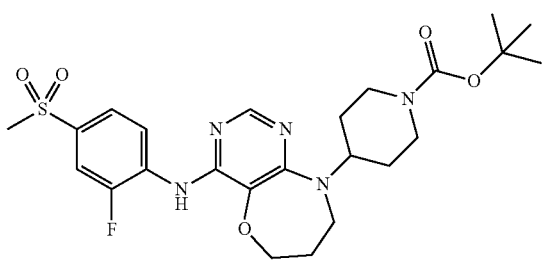 [SMILES: CC(C)(C)OC(=O)N1CCC(N2CCCOc3c(Nc4ccc(S(C)(=O)=O)cc4F)ncnc32)CC1]

Example 83A tert-butyl 4-(4-chloro-7,8-dihydropyrimido[5,4-b][1,4]oxazepin-9(6H)-yl)piperidine-1-carboxylate

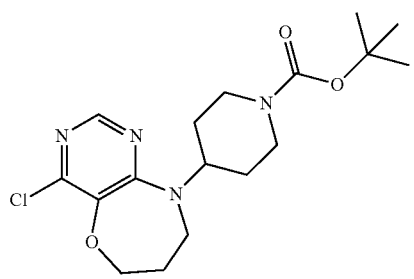 [SMILES: CC(C)(C)OC(=O)N1CCC(N2CCCOc3c(Cl)ncnc32)CC1]

To Example 3B (440 mg, 1.34 mmol) and K2CO3 (555 mg, 4.01 mmol) in DMF (13 ml), 1-bromo-3-chloropropane (421 mg, 2.68 mmol) was added. The reaction mixture was stirred at room temperature for 60 minutes, and then at 50° C. overnight, and then at 100° C. till completion. The reaction was diluted with EtOAc, washed by water and brine, dried over MgSO4, concentrated in vacuo. The residue was purified by Flash Column Chromatography (eluted with 0-25% EtOAc/Hexane) to afford 208 mg (42%) of Example 83A as a pale solid. $^1$H NMR (500 MHz, CDCl$_3$): δ1.46 (s, 9 H) 1.58 (d, J=8.25 Hz, 2 H) 1.72 (d, J=10.45 Hz, 2 H) 2.02-2.11 (m, 2H) 2.82 (s, 2 H) 3.51-3.59 (m, 2 H) 4.20 (t, 2 H) 4.31 (t, J=6.60 Hz, 2 H) 4.59-4.70 (m, 1 H) 8.05 (s, 1 H). LRMS (ESI): 369.2 [M+H]$^+$.

Example 83B iso-propyl 4-(4-chloro-7,8-dihydropyrimido[5,4-b][1,4]oxazepin-9(6H)-yl)piperidine-1-carboxylate

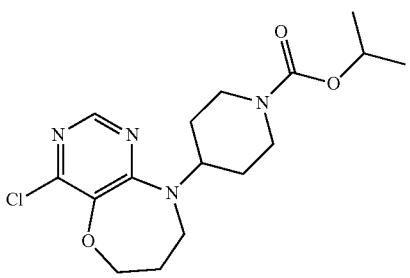 [SMILES: CC(C)OC(=O)N1CCC(N2CCCOc3c(Cl)ncnc32)CC1]

Example 83B was prepared using the same method described above for Example 20A, with the exception that Example 3C was replaced with Example 83A. ES$^+$: found 355.2

Example 83 tert-Butyl 4-(4-(2-fluoro-4-(methylsulfonyl)phenylamino)-7,8-dihydropyrimido[5,4-b][1,4]oxazepin-9(6H)-yl)piperidine-1-carboxylate

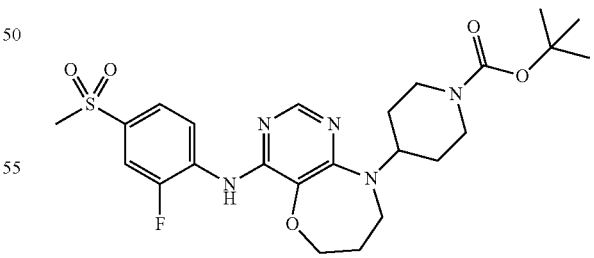

Example 83 was prepared using the same method described above for Example 3, with the exception that Example 3C was replaced with Example 83B. $^1$H NMR (500 MHz, CDCl$_3$): δ ppm 1.46 (s, 9 H) 1.58 (d, J=7.15 Hz, 2 H) 1.74 (d, J=10.45 Hz, 2 H) 2.03-2.12 (m, 2 H) 2.77-2.93 (m, 2 H) 3.03 (s, 3 H) 3.54 (t, J=5.77 Hz, 2 H) 4.21 (s, 2 H) 4.36 (t, J=6.60 Hz, 2 H) 4.56-4.68 (m, J=12.03, 12.03, 3.99, 3.85 Hz, 1 H) 7.53 (d, J=3.85 Hz, 1 H) 7.64 (dd, J=10.45, 2.20 Hz, 1 H) 7.69 (d, J=8.80 Hz, 1 H) 8.08 (s, 1 H) 8.90 (t, J=8.25 Hz, 1 H). LRMS (ESI): 522.2 [M+H]$^+$.

Example 84 iso-Propyl 4-(4-(2-fluoro-4-(methylsulfonyl)phenylamino)-7,8-dihydropyrimido[5,4-b][1,4]oxazepin-9(6H)-yl)piperidine-1-carboxylate

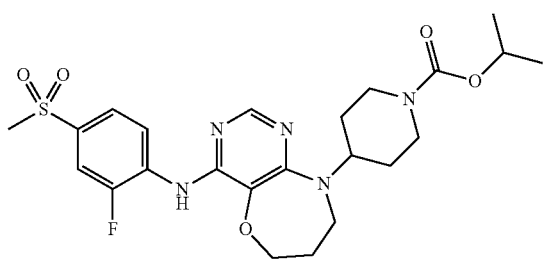 [SMILES: CC(C)OC(=O)N1CCC(N2CCCOc3c(Nc4ccc(S(C)(=O)=O)cc4F)ncnc32)CC1]

Example 84 was prepared from Example 83 using the methods described in Examples 8A and 8. $^1$H NMR (500 MHz, CDCl$_3$): δ ppm 1.24 (t, J=6.32 Hz, 6H) 1.59 (d, J=9.90 Hz, 2 H) 1.76 (d, J=10.45 Hz, 2 H) 2.03-2.10 (m, 2 H) 2.80-2.94 (m, 2 H) 2.99-3.06 (m, 3 H) 3.53 (t, J=5.77 Hz, 2 H) 4.31 (s, 2 H) 4.36 (t, J=6.60 Hz, 2 H) 4.61-4.69 (m, 1 H) 4.86-4.96 (m, 1 H) 7.52 (t, J=4.40 Hz, 1 H) 7.63 (dd, J=10.45, 2.20 Hz, 1 H) 7.68 (d, J=8.80 Hz, 1 H) 8.08 (s, 1 H) 8.90 (t, J=8.52 Hz, 1H). LRMS (ESI): 508.2 [M+H]$^+$.

Example 85 tert-Butyl 4-(4-(2-methylpyridin-3-ylamino)-7,8-dihydropyrimido[5,4-b][1,4]oxazepin-9(6H)-yl)piperidine-1-carboxylate

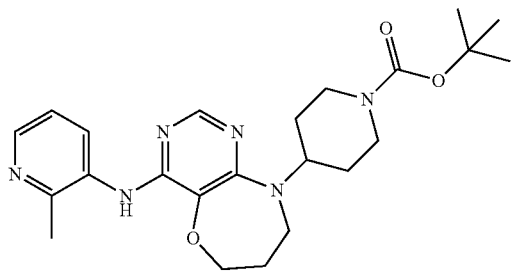 [SMILES: Cc1ncccc1Nc1ncnc2c1OCCCN2C1CCN(C(=O)OC(C)(C)C)CC1]

Example 85 was prepared using the same method described above for Example 83, with the exception that 2-fluoro-4-(methylsulfonyl)aniline was replaced with 2-methylpyridin-3-amine. $^1$H NMR (500 MHz, CDCl$_3$): δ ppm 1.42-1.49 (m, 9 H) 1.58 (d, J=9.35 Hz, 2 H) 1.75 (d, J=12.10 Hz, 2 H) 2.01-2.11 (m, 2 H) 2.53 (s, 3 H) 2.83 (s, 2 H) 3.53 (t, J=6.05 Hz, 2 H) 4.21 (s, 2 H) 4.36 (t, J=6.32 Hz, 2 H) 4.56-4.65 (m, 1 H) 6.82 (s, 1 H) 7.15 (dd, J=8.25, 4.95 Hz, 1 H) 8.01 (s, 1 H) 8.17 (d, J=3.30 Hz, 1 H) 8.46 (d, J=8.25 Hz, 1 H). LRMS (ESI): 441.2 [M+H]$^+$.

Example 86 iso-Propyl 4-(4-(2-methylpyridin-3-ylamino)-7,8-dihydropyrimido[5,4-b][1,4]oxazepin-9(6H)-yl)piperidine-1-carboxylate

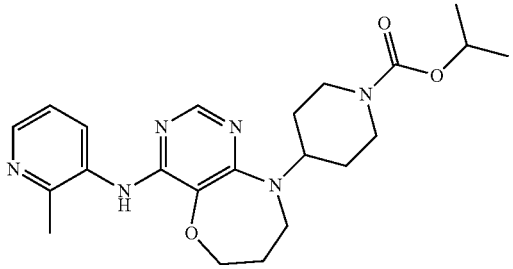 [SMILES: Cc1ncccc1Nc1ncnc2c1OCCCN2C1CCN(C(=O)OC(C)C)CC1]

Example 86 was prepared from Example 85 using the methods described in Examples 8A and 8. $^1$H NMR (500 MHz, CDCl$_3$): δ ppm 1.25 (t, J=6.87 Hz, 6 H) 1.59 (s, 2 H) 1.76 (d, J=11.55 Hz, 2 H) 2.00-2.10 (m, 2 H) 2.53 (s, 3 H) 2.87 (s, 2 H) 3.53 (t, J=6.05 Hz, 2 H) 4.27 (d, J=18.15 Hz, 2 H) 4.35 (t, J=6.32 Hz, 2 H) 4.56-4.67 (m, 1 H) 4.84-4.96 (m, 1 H) 6.82 (s, 1 H) 7.14 (dd, J=7.97, 4.67 Hz, 1 H) 8.00 (s, 1 H) 8.16 (d, J=3.30 Hz, 1 H) 8.46 (d, J=8.25 Hz, 1 H). LRMS (ESI): 427.3 [M+H]$^+$.

Example 87 tert-Butyl 4-(4-(2,6-dimethylpyridin-3-ylamino)-7,8-dihydropyrimido[5,4-b][1,4]oxazepin-9(6H)-yl)piperidine-1-carboxylate

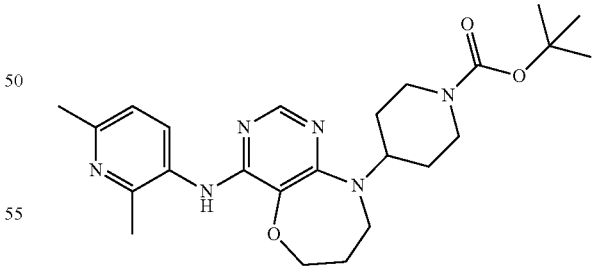

Example 87 was prepared using the same method described above for Example 83, with the exception that 2-fluoro-4-(methylsulfonyl)aniline was replaced with 2,6-dimethylpyridin-3-amine. $^1$H NMR (500 MHz, CDCl$_3$): δ ppm 1.47 (s, 9 H) 1.58 (d, J=8.80 Hz, 2 H) 1.68 (s, 2 H) 1.99-2.14 (m, 2 H) 2.48 (d, J=6.60 Hz, 6 H) 2.84 (s, 2 H) 3.53 (t, J=5.77 Hz, 2 H) 4.21 (t, 2 H) 4.35 (t, J=6.32 Hz, 2 H)

4.52-4.69 (m, 1 H) 6.68 (s, 1 H) 7.00 (d, J=8.25 Hz, 1 H) 7.98 (s, 1 H) 8.17 (d, J=8.25 Hz, 1 H). LRMS (ESI): 455.3 [M+H]+.

Example 88 iso-Propyl 4-(4-(2,6-dimethylpyridin-3-ylamino)-7,8-dihydropyrimido[5,4-b][1,4]oxazepin-9(6H)-yl)piperidine-1-carboxylate

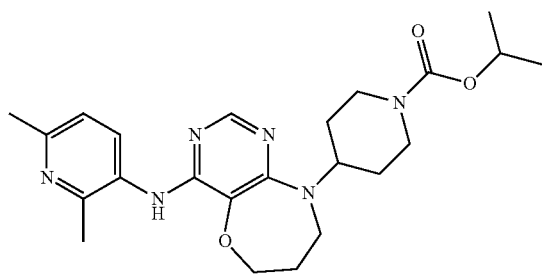 [SMILES: Cc1ccc(Nc2ncnc3c2OCCCN3C2CCN(C(=O)OC(C)C)CC2)c(C)n1]

Example 88 was prepared from Example 87 using the methods described in Examples 8A and 8. $^1$H NMR (500 MHz, CDCl$_3$): δ ppm 1.25 (d, J=6.05 Hz, 6 H) 1.59 (d, J=8.80 Hz, 2 H) 1.76 (d, J=10.45 Hz, 2 H) 2.00-2.14 (m, 2 H) 2.53 (d, J=8.25 Hz, 6 H) 2.87 (s, 2 H) 3.53 (t, J=5.77 Hz, 2 H) 4.15-4.41 (m, 4 H) 4.56-4.70 (m, 1 H) 4.85-4.99 (m, 1 H) 6.72 (s, 1 H) 7.04 (d, J=8.25 Hz, 1 H) 7.98 (s, 1 H) 8.27 (d, J=7.70 Hz, 1 H). LRMS (ESI): 441.3 [M+H]+.

Example 89 tert-Butyl 4-(4-(3,5-dichloropyridin-4-ylamino)-7,8-dihydropyrimido[5,4-b][1,4]oxazepin-9(6H)-yl)piperidine-1-carboxylate

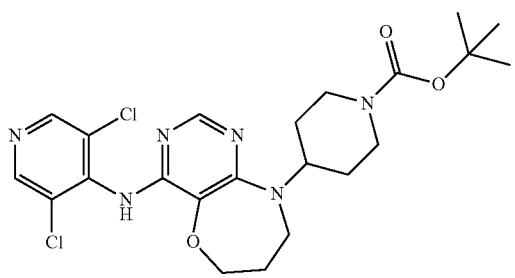

Example 89 was prepared using the same method described above for Example 83, with the exception that 2-fluoro-4-(methylsulfonyl)aniline was replaced with 3,5-dichloropyridin-4-amine. $^1$H NMR (500 MHz, CDCl$_3$): δ ppm 1.47 (s, 9 H) 1.60 (s, 4 H) 2.04-2.18 (m, 2 H) 2.83 (s, 2 H) 3.50-3.64 (m, 2 H) 4.21 (s, 2 H) 4.36 (t, J=6.60 Hz, 2 H) 4.55-4.70 (m, 1 H) 6.77 (s, 1 H) 7.96 (s, 1 H) 8.48 (s, 2 H). LRMS (ESI): 495.2 [M+H]+.

Example 90 iso-Propyl 4-(4-(3,5-dichloropyridin-4-ylamino)-7,8-dihydropyrimido[5,4-b][1,4]oxazepin-9(6H)-yl)piperidine-1-carboxylate

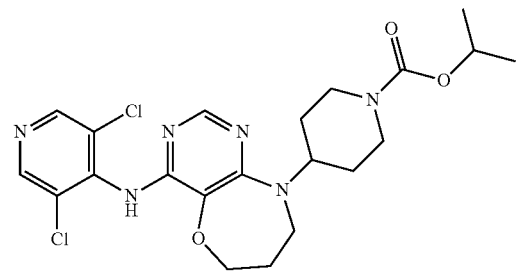 [SMILES: CC(C)OC(=O)N1CCC(N2CCCOc3c(Nc4c(Cl)cncc4Cl)ncnc32)CC1]

Example 90A

N-(3,5-Dichloropyridin-4-yl)-9-(piperidin-4-yl)-6,7,8,9-tetrahydropyrimido[5,4-b][1,4]oxazepin-4-amine, HCl salt

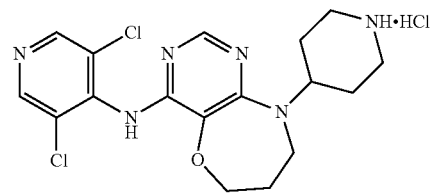

Example 90A was prepared from Example 89 using the same method described above for Example 8A. LRMS (ESI): 395.1 [M+H]+.

Example 90 iso-Propyl 4-(4-(3,5-dichloropyridin-4-ylamino)-7,8-dihydropyrimido[5,4-b][1,4]oxazepin-9(6H)-yl)piperidine-1-carboxylate

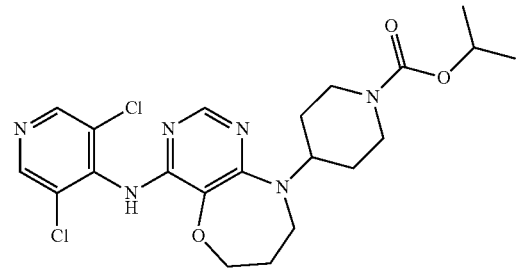 [SMILES: CC(C)OC(=O)N1CCC(N2CCCOc3c(Nc4c(Cl)cncc4Cl)ncnc32)CC1]

Example 90 was prepared from Example 90A using the same method described above for Example 8. $^1$H NMR (500

MHz, CDCl₃): δ ppm 1.25 (d, J=6.60 Hz, 6 H) 1.63 (s, 2 H) 1.76 (d, J=11.00 Hz, 2 H) 2.04-2.18 (m, 2 H) 2.87 (s, 2 H) 3.52-3.60 (m, 2 H) 4.24 (t, 2 H) 4.36 (t, J=6.60 Hz, 2 H) 4.58-4.71 (m, 1 H) 4.86-4.99 (m, 1 H) 6.77 (s, 1 H) 7.96 (s, 1 H) 8.48 (s, 2 H). LRMS (ESI): 481.2 [M+H]⁺.

Example 91

4-Methoxyphenyl 4-(4-(3,5-dichloropyridin-4-ylamino)-7,8-dihydropyrimido[5,4-b][1,4]oxazepin-9(6H)-yl)piperidine-1-carboxylate

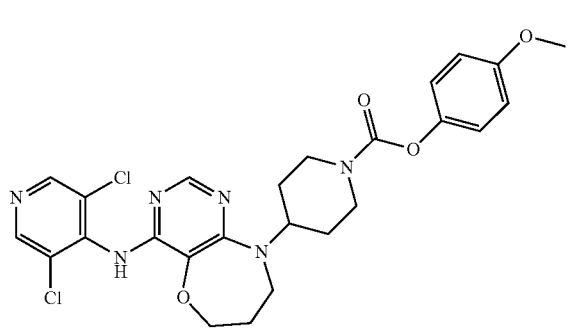 [SMILES: COc1ccc(OC(=O)N2CCC(N3CCCOc4c(Nc5c(Cl)cncc5Cl)ncnc43)CC2)cc1]

Example 91 was prepared from Example 90A using the same method described above for Example 31. ¹H NMR (500 MHz, CDCl₃): δ ppm 1.73 (d, J=8.80 Hz, 2 H) 1.85 (s, 2 H) 2.11 (s, 2 H) 2.97 (d, 1 H) 3.12 (d, 2 H) 3.62 (d, J=3.30 Hz, 2H) 3.79 (s, 3 H) 4.30-4.51 (m, 4 H) 4.73 (s, 1 H) 6.87 (d, J=9.35 Hz, 2 H) 7.02 (d, J=9.35 Hz, 2 H) 8.00 (s, 1 H) 8.49 (s, 2 H). LRMS (ESI): 545.2 [M+H]⁺.

Example 92

4-(4-(3,5-Dichloropyridin-4-ylamino)-7,8-dihydropyrimido[5,4-b][1,4]oxazepin-9(6H)-yl)-N,N-diethylpiperidine-1-carboxamide

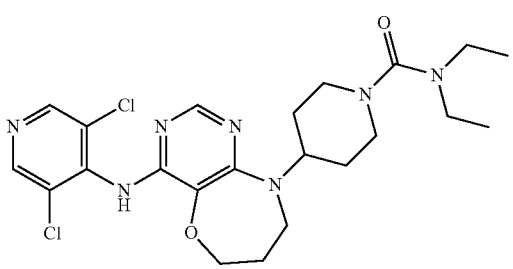 [SMILES: CCN(CC)C(=O)N1CCC(N2CCCOc3c(Nc4c(Cl)cncc4Cl)ncnc32)CC1]

To triphosgene (20.78 mg, 0.070 mmol) and TEA (0.039 mL, 0.280 mmol) in DCM (0.5 mL) was added 2,2,2-trifluoroethanol (21.02 mg, 0.210 mmol), the reaction mixture was stirred at room temperature for 30 min, then Example 90A (21 mg, 72% purity, 0.035 mmol) was added. The resulting solution was stirred at room temperature for 30 minutes. The solvent was removed in vacuo. The residue was purified by PREP-HPLC. The fraction was neutralized with K2CO3, diluted with water and extracted with AcOEt, and the organic layer was dried over MgSO4 and evaporated to yield 14 mg (81%) of Example 92 as a white solid. ¹H NMR (500 MHz, CDCl₃): δ ppm 1.12 (t, J=6.87 Hz, 6 H) 1.60-1.79 (m, 4 H) 2.04-2.14 (m, 2H) 2.83-2.94 (m, 2 H) 3.20 (q, J=7.15 Hz, 4 H) 3.52-3.62 (m, 2 H) 3.73 (d, J=13.20 Hz, 2 H) 4.35 (t, J=6.60 Hz, 2 H) 4.61 (s, 1 H) 6.78 (s, 1 H) 7.96 (s, 1 H) 8.47 (s, 2H). LRMS (ESI): 494.2 [M+H]⁺.

Example 93

N-(3,5-Dichloropyridin-4-yl)-9-(1-(5-propylpyrimidin-2-yl)piperidin-4-yl)-6,7,8,9-tetrahydropyrimido[5,4-b][1,4]oxazepin-4-amine

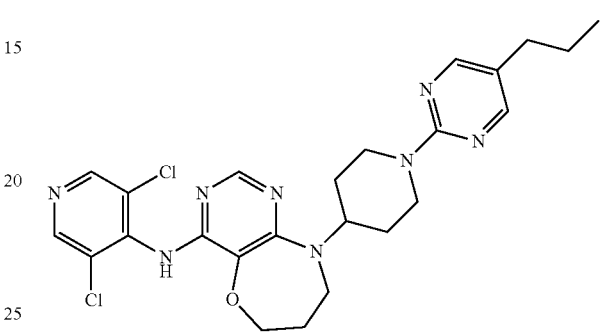

Example 93 was prepared using the same method described above for Example 32, with the exception that Example 29A was replaced Example 90A, and 2-chloropyrimidine was replaced with 2-chloro-5-propylpyrimidine. ¹H NMR (500 MHz, CDCl₃): δ ppm 0.93 (t, J=7.15 Hz, 3 H) 1.50-1.61 (m, 2 H) 1.61-1.77 (m, 2H) 1.85 (d, J=9.90 Hz, 2 H) 1.99-2.08 (m, 2 H) 2.39 (t, J=7.42 Hz, 2 H) 2.99 (t, J=11.82 Hz, 2 H) 3.49-3.61 (m, 2 H) 4.36 (t, J=6.32 Hz, 2 H) 4.77 (s, 1 H) 4.86 (d, J=13.75 Hz, 2 H) 6.78 (s, 1 H) 7.99 (s, 1 H) 8.15 (s, 2 H) 8.48 (s, 2 H). LRMS (ESI): 515.2 [M+H]⁺.

Example 94 tert-Butyl 4-(4-(2-oxo-1,2-dihydropyridin-3-ylamino)-7,8-dihydropyrimido[5,4-b][1,4]oxazepin-9(6H)-yl)piperidine-1-carboxylate

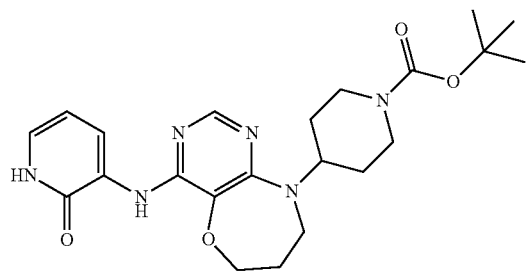 [SMILES: CC(C)(C)OC(=O)N1CCC(N2CCCOc3c(Nc4ccc[nH]c4=O)ncnc32)CC1]

Example 94 was prepared using the same method described above for Example 83, with the exception that 2-fluoro-4-(methylsulfonyl)aniline was replaced with 3-aminopyridin-2(1 H)-one. ¹H NMR (500 MHz, CDCl₃): δ ppm 1.48 (s, 9 H) 1.68 (s, 2 H) 1.76 (d, J=11.00 Hz, 2 H) 2.02-2.08 (m, 2 H) 2.86 (s, 2 H) 3.53 (t, J=5.77 Hz, 2 H) 4.24 (s, 2 H) 4.38 (t, J=6.60 Hz, 2 H) 4.54-4.72 (m, 1 H) 6.30-6.42 (m, 1 H)

6.98 (d, J=5.50 Hz, 1 H) 8.08 (s, 1 H) 8.23 (s, 1 H) 8.66 (d, J=7.70 Hz, 1 H). LRMS (ESI): 443.3 [M+H]⁺.

Example 95 iso-Propyl 4-(4-(2-oxo-1,2-dihydropyridin-3-ylamino)-7,8-dihydropyrimido[5,4-b][1,4]oxazepin-9(6H)-yl)piperidine-1-carboxylate

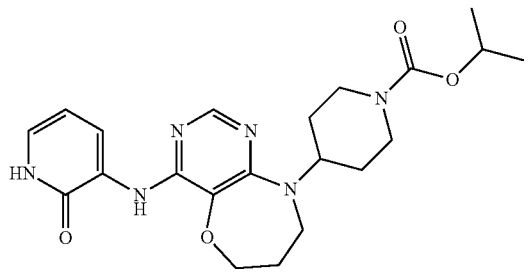

Example 95 was prepared from Example 94 using the methods described in Examples 8A and 8. ¹H NMR (500 MHz, CDCl₃): δ ppm 1.21-1.27 (m, 6 H) 1.61 (s, 2 H) 1.76 (d, J=11.00 Hz, 2 H) 2.00-2.09 (m, 2 H) 2.88 (s, 2 H) 3.52 (t, J=5.77 Hz, 2 H) 4.25 (t, 2 H) 4.36 (t, J=6.32 Hz, 2 H) 4.56-4.66 (m, 1 H) 4.86-4.96 (m, 1 H) 6.29-6.38 (m, 1 H) 6.94 (d, J=4.95 Hz, 1 H) 8.06 (s, 1 H) 8.22 (s, 1 H) 8.64 (d, J=5.50 Hz, 1 H). LRMS (ESI): 429.3 [M+H]⁺.

Example 96 tert-Butyl 4-(4-(6-cyano-2-methylpyridin-3-ylamino)-7,8-dihydropyrimido[5,4-b][1,4]oxazepin-9(6H)-yl)piperidine-1-carboxylate

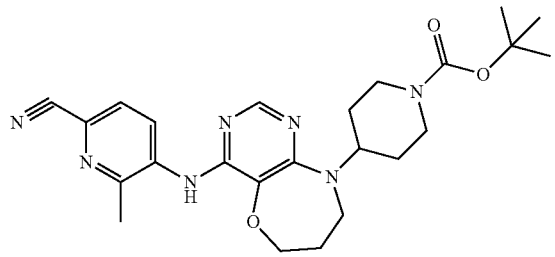 [SMILES: Cc1nc(C#N)ccc1Nc1ncnc2c1OCCCN2C1CCN(C(=O)OC(C)(C)C)CC1]

Example 96 was prepared using the same method described above for Example 83, with the exception that 2-fluoro-4-(methylsulfonyl)aniline was replaced with 5-amino-6-methylpicolinonitrile. ¹H NMR (500 MHz, CDCl₃): δ ppm 1.42-1.51 (m, 9 H) 1.60 (s, 2 H) 1.75 (d, J=11.00 Hz, 2 H) 2.04-2.20 (m, 2 H) 2.57 (s, 3H) 2.84 (s, 2 H) 3.55 (t, J=6.05 Hz, 2 H) 4.23 (s, 2 H) 4.38 (t, J=6.60 Hz, 2 H) 4.56-4.73 (m, 1 H) 7.19 (s, 1 H) 7.53 (d, J=8.80 Hz, 1 H) 8.06 (s, 1 H) 8.97 (d, J=8.25 Hz, 1 H). LRMS (ESI): 466.4 [M+H]⁺.

Example 97 iso-Propyl 4-(4-(6-cyano-2-methylpyridin-3-ylamino)-7,8-dihydropyrimido[5,4-b][1,4]oxazepin-9(6H)-yl)piperidine-1-carboxylate

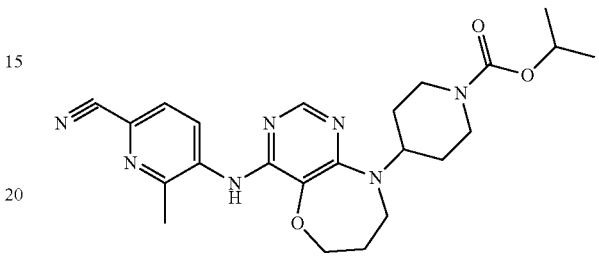

Example 97 was prepared from Example 96 using the methods described in Examples 8A and 8. ¹H NMR (500 MHz, CDCl₃): δ ppm 1.21-1.30 (m, 6 H) 1.55-1.66 (m, 2 H) 1.76 (d, J=10.45 Hz, 2 H) 2.04-2.14 (m, 2 H) 2.57 (s, 3 H) 2.87 (s, 2 H) 3.55 (t, J=5.77 Hz, 2 H) 4.26 (t, 2 H) 4.38 (t, J=6.60 Hz, 2 H) 4.58-4.70 (m, 1 H) 4.85-4.99 (m, 1 H) 7.20 (s, 1 H) 7.53 (d, J=8.80 Hz, 1 H) 8.06 (s, 1 H) 8.96 (d, J=8.80 Hz, 1 H). LRMS (ESI): 452.3 [M+H]⁺.

Example 98 tert-Butyl 4-(4-(4-methylpyridin-3-ylamino)-7,8-dihydropyrimido[5,4-b][1,4]oxazepin-9(6H)-yl)piperidine-1-carboxylate Example 98 was prepared using the same method described above for Example 83, with the exception that 2-fluoro-4-(methylsulfonyl)aniline was replaced with 4-methylpyridin-3-amine. ¹H NMR (500 MHz, CDCl₃): δ ppm 1.44-1.52 (m, 9H) 1.58-1.66 (m, 2 H) 1.77 (d, J=10.45 Hz, 2 H) 2.01-2.12 (m, 2 H) 2.29 (s, 3 H) 2.86 (s, 2 H) 3.50-3.58 (m, 2 H) 4.23 (t, 2 H) 4.36 (t, J=6.32 Hz, 2 H) 4.56-4.71 (m, 1 H 6.65 (s, 1 H) 7.13 (d, J=4.95 Hz, 1 H) 7.99 (s, 1 H) 8.24 (d, J=4.95 Hz, 1 H) 9.04 (s, 1 H). LRMS (ESI): 441.4 [M+H]⁺.

Example 99 tert-Butyl 4-(4-(2-methoxypyridin-3-ylamino)-7,8-dihydropyrimido[5,4-b][1,4]oxazepin-9(6H)-yl)piperidine-1-carboxylate

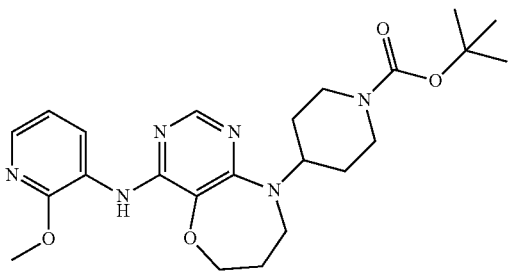 [SMILES: COc1ncccc1Nc1ncnc2c1OCCCN2C1CCN(C(=O)OC(C)(C)C)CC1]

Example 99 was prepared using the same method described above for Example 83, with the exception that 2-fluoro-4-(methylsulfonyl)aniline was replaced with 2-methoxypyridin-3-amine. ¹H NMR (500 MHz, CDCl₃): δ ppm 1.46 (s, 9 H) 1.58 (d, J=10.45 Hz, 2 H) 1.74 (d, J=10.45 Hz, 2 H) 1.99-2.13 (m, 2 H) 2.84 (s, 2 H) 3.52 (t, J=5.77 Hz, 2 H) 4.03 (s, 3 H) 4.13-4.30 (m, 2 H) 4.35 (t, J=6.32 Hz, 2 H) 4.53-4.68 (m, 1 H) 6.88 (dd, J=7.70, 4.95 Hz, 1 H) 7.54 (s, 1 H) 7.72 (d, J=3.30 Hz, 1 H) 8.05 (s, 1 H) 8.78 (d, J=8.25 Hz, 1 H). LRMS (ESI): 457.4 [M+H]⁺.

Example 100 tert-Butyl 4-(4-(pyridin-4-ylamino)-7,8-dihydropyrimido[5,4-b][1,4]oxazepin-9(6H)-yl)piperidine-1-carboxylate

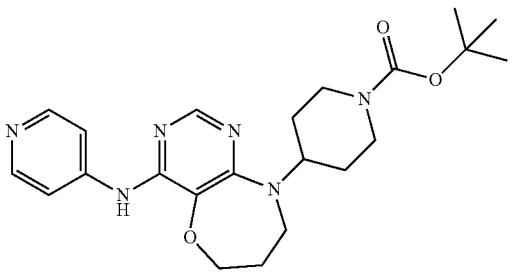 [SMILES: CC(C)(C)OC(=O)N1CCC(N2CCCOc3c(Nc4ccncc4)ncnc32)CC1]

Example 100 was prepared using the same method described above for Example 83, with the exception that 2-fluoro-4-(methylsulfonyl)aniline was replaced with pyridin-4-amine. ¹H NMR (500 MHz, CDCl₃): δ ppm 1.46 (s, 9 H) 1.57 (d, J=12.10 Hz, 2 H) 1.70-1.78 (m, 2 H) 1.98-2.14 (m, 2 H) 2.84 (s, 2 H) 3.52 (t, J=5.77 Hz, 2 H) 4.20 (t, 2 H) 4.33 (t, J=6.60 Hz, 2 H) 4.56-4.69 (m, 1 H) 7.16 (s, 1H) 7.59 (d, J=6.60 Hz, 2 H) 8.08 (s, 1 H) 8.40 (d, J=6.60 Hz, 2 H). LRMS (ESI): 427.3 [M+H]⁺.

Example 101 tert-Butyl 4-(4-(3-fluoropyridin-4-ylamino)-7,8-dihydropyrimido[5,4-b][1,4]oxazepin-9(6H)-yl)piperidine-1-carboxylate

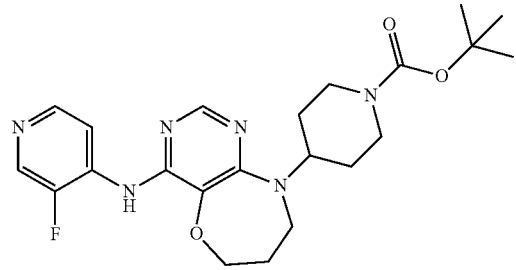 [SMILES: CC(C)(C)OC(=O)N1CCC(N2CCCOc3c(Nc4ccncc4F)ncnc32)CC1]

Example 101 was prepared using the same method described above for Example 83, with the exception that 2-fluoro-4-(methylsulfonyl)aniline was replaced with 3-fluoropyridin-4-amine. ¹H NMR (500 MHz, CDCl₃): δ ppm 1.47 (s, 9 H) 1.58 (d, J=9.90 Hz, 2 H) 1.74 (d, J=11.00 Hz, 2 H) 1.99-2.14 (m, 2 H) 2.84 (s, 2 H) 3.53 (t, J=5.77 Hz, 2 H) 4.22 (s, 2 H) 4.35 (t, J=6.32 Hz, 2 H) 4.56-4.70 (m, 1 H) 7.47 (d, J=3.30 Hz, 1 H) 8.09 (s, 1 H) 8.26 (d, J=5.50 Hz, 1 H) 8.33 (d, J=2.75 Hz, 1H) 8.63-8.72 (m, 1 H). LRMS (ESI): 445.3 [M+H]⁺.

Example 102 iso-Propyl 4-(4-(3-fluoropyridin-4-ylamino)-7,8-dihydropyrimido[5,4-b][1,4]oxazepin-9(6H)-yl)piperidine-1-carboxylate

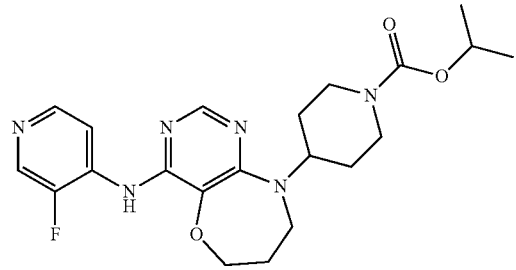 [SMILES: CC(C)OC(=O)N1CCC(N2CCCOc3c(Nc4ccncc4F)ncnc32)CC1]

Example 102 was prepared from Example 101 using the methods described in Examples 8A and 8. ¹H NMR (500 MHz, CDCl₃): δ ppm 1.24 (t, J=6.05 Hz, 6 H) 1.60 (s, 2 H) 1.76 (dd, J=11.55 Hz, 2 H) 1.99-2.11 (m, 2 H) 2.88 (s, 2 H) 3.54 (t, J=5.77 Hz, 2 H) 4.24 (t, 2 H) 4.36 (t, J=6.60 Hz, 2 H) 4.59-4.70 (m, 1H) 4.85-4.97 (m, 1 H) 7.48 (d, J=3.30 Hz, 1 H)

8.10 (s, 1 H) 8.26 (d, J=5.50 Hz, 1H) 8.34 (d, J=2.75 Hz, 1 H) 8.62-8.74 (m, 1 H). LRMS (ESI): 431.3 [M+H]+.

Example 103 tert-Butyl 4-(4-(3-chloropyridin-4-ylamino)-7,8-dihydropyrimido[5,4-b][1,4]oxazepin-9(6H)-yl)piperidine-1-carboxylate

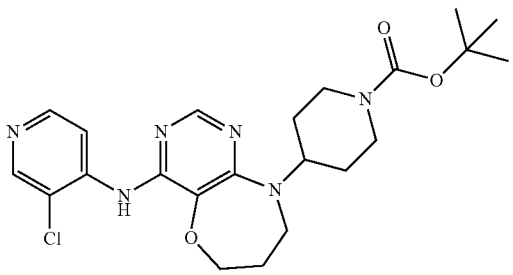 [SMILES: CC(C)(C)OC(=O)N1CCC(N2CCCOc3c(Nc4ccncc4Cl)ncnc32)CC1]

Example 103 was prepared using the same method described above for Example 83, with the exception that 2-fluoro-4-(methylsulfonyl)aniline was replaced with 3-chloropyridin-4-amine. $^1$H NMR (500 MHz, CDCl$_3$): δ ppm 1.43-1.50 (m, 9H) 1.58 (d, J=7.70 Hz, 2 H) 1.75 (d, J=10.45 Hz, 2 H) 2.04-2.16 (m, 2 H) 2.85 (d, J=13.20 Hz, 2 H) 3.55 (t, J=5.77 Hz, 2 H) 4.23 (t, 2 H) 4.37 (t, J=6.60 Hz, 2 H) 4.58-4.70 (m, 1 H) 7.89 (s, 1 H) 8.10 (s, 1 H) 8.32 (d, J=5.50 Hz, 1 H) 8.43 (s, 1 H) 8.70 (d, J=5.50 Hz, 1 H). LRMS (ESI): 461.3 [M+H]+.

Example 104 iso-Propyl 4-(4-(3-chloropyridin-4-ylamino)-7,8-dihydropyrimido[5,4-b][1,4]oxazepin-9(6H)-yl)piperidine-1-carboxylate

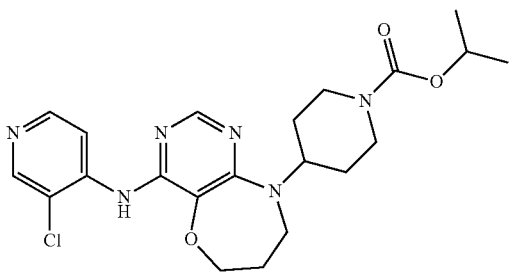 [SMILES: CC(C)OC(=O)N1CCC(N2CCCOc3c(Nc4ccncc4Cl)ncnc32)CC1]

Example 104 was prepared from Example 103 using the methods described in Examples 8A and 8. $^1$H NMR (500 MHz, CDCl$_3$): δ ppm 1.24 (t, J=6.05 Hz, 6 H) 1.60 (s, 2 H) 1.70-1.81 (m, 2 H) 2.04-2.17 (m, 2 H) 2.87 (s, 2 H) 3.54 (t, J=5.77 Hz, 2 H) 4.24 (t, 2 H) 4.37 (t, J=6.60 Hz, 2 H) 4.58-

4.72 (m, 1 H) 4.84-5.02 (m, 1 H) 7.89 (s, 1 H) 8.10 (s, 1 H) 8.32 (d, J=5.50 Hz, 1 H) 8.43 (s, 1 H) 8.70 (d, J=5.50 Hz, 1 H). LRMS (ESI): 447.2 [M+H]+.

Example 105 tert-Butyl 4-(4-(3,5-difluoropyridin-4-ylamino)-7,8-dihydropyrimido[5,4-b][1,4]oxazepin-9(6H)-yl)piperidine-1-carboxylate

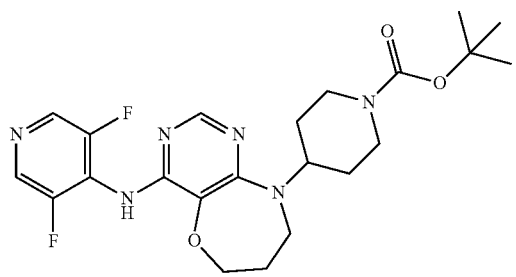 [SMILES: CC(C)(C)OC(=O)N1CCC(N2CCCOc3c(Nc4c(F)cncc4F)ncnc32)CC1]

Example 105 was prepared using the same method described above for Example 83, with the exception that 2-fluoro-4-(methylsulfonyl)aniline was replaced with 3,5-difluoropyridin-4-amine. $^1$H NMR (500 MHz, CDCl$_3$): δ ppm 1.46 (s, 9 H) 1.58 (d, J=8.25 Hz, 2 H) 1.74 (d, J=10.45 Hz, 2 H) 1.99-2.14 (m, 2 H) 2.83 (s, 2 H) 3.54 (t, J=6.05 Hz, 2 H) 4.21 (s, 2 H) 4.35 (t, J=6.32 Hz, 2 H) 4.57-4.69 (m, 1 H) 6.60 (s, 1 H) 7.99 (s, 1 H) 8.32 (s, 2 H). LRMS (ESI): 463.3 [M+H]+.

Example 106

N-(3,5-difluoropyridin-4-yl)-9-(1-(5-propylpyrimidin-2-yl)piperidin-4-yl)-6,7,8,9-tetrahydropyrimido[5,4-b][1,4]oxazepin-4-amine

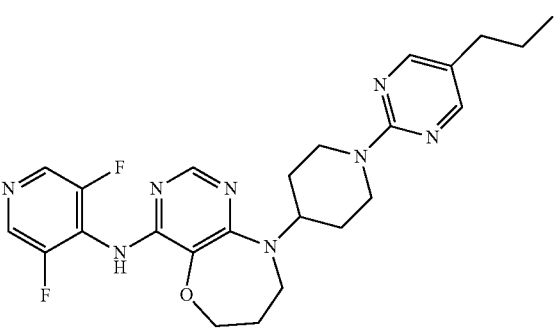

Example 106 was prepared from Example 105 using the methods described in Examples 8A and 32. $^1$H NMR (500 MHz, CDCl$_3$): δ ppm 0.93 (t, J=7.42 Hz, 3 H) 1.57-1.69 (m, 4 H) 1.84 (d, J=9.35 Hz, 2 H) 1.99-2.10 (m, 2 H) 2.34-2.45 (m, 2 H) 2.90-3.08 (m, 2 H) 3.50-3.58 (m, 2 H) 4.36 (t, J=6.60 Hz, 2 H) 4.76 (s, 1 H) 4.86 (d, J=13.75 Hz, 2 H) 6.61 (s, 1 H) 8.02 (s, 1 H) 8.15 (s, 2 H) 8.32 (s, 2 H). LRMS (ESI): 483.3 [M+H]⁺.

Example 107 tert-Butyl 4-(4-(3-methylpyridin-4-ylamino)-7,8-dihydropyrimido[5,4-b][1,4]oxazepin-9(6H)-yl)piperidine-1-carboxylate

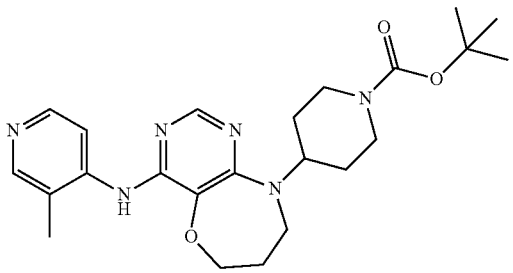 [SMILES: Cc1cnccc1Nc1ncnc2c1OCCCN2C1CCN(C(=O)OC(C)(C)C)CC1]

Example 107 was prepared using the same method described above for Example 83, with the exception that 2-fluoro-4-(methylsulfonyl)aniline was replaced with 3-methylpyridin-4-amine. ¹H NMR (500 MHz, CDCl₃): δ ppm 1.47 (s, 9 H) 1.59 (s, 2 H) 1.75 (d, J=11.00 Hz, 2 H) 1.99-2.13 (m, 2 H) 2.25 (s, 3 H) 2.84 (s, 2 H) 3.54 (t, J=6.05 Hz, 2 H) 4.22 (s, 2 H) 4.36 (t, J=6.60 Hz, 2 H) 4.56-4.70 (m, 1 H) 7.12 (s, 1 H) 8.09 (s, 1 H) 8.27 (s, 1 H) 8.34 (d, J=5.50 Hz, 1 H) 8.45 (d, J=6.05 Hz, 1H). LRMS (ESI): 441.3 [M+H]⁺.

Example 108 tert-Butyl 4-(4-(2-methyl-6-(methylsulfonyl)pyridin-3-ylamino)-7,8-dihydropyrimido[5,4-b][1,4]oxazepin-9(6H)-yl)piperidine-1-carboxylate

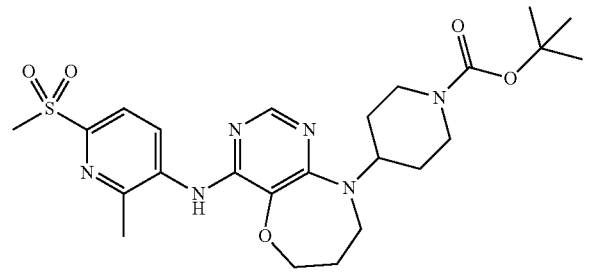

Example 108 was prepared using the same method described above for Example 83, with the exception that 2-fluoro-4-(methylsulfonyl)aniline was replaced with 2-methyl-6-(methylsulfonyl)pyridin-3-amine. ¹H NMR (500 MHz, CDCl₃): δ ppm 1.46 (s, 9 H) 1.74 (d, J=10.45 Hz, 2 H) 2.05-2.18 (m, 2 H) 2.60 (s, 3 H) 2.84 (s, 2 H) 3.15 (s, 3 H) 3.55 (t, J=5.77 Hz, 2 H) 4.10 (q, J=7.15 Hz, 2 H) 4.23 (t, 2 H) 4.38 (t, J=6.60 Hz, 2 H) 4.57-4.69 (m, 1 H) 7.18 (s, 1 H) 7.92 (d, J=8.25 Hz, 1 H) 8.06 (s, 1 H) 9.01 (d, J=8.80 Hz, 1 H). LRMS (ESI): 519.3 [M+H]⁺.

Example 109 iso-Propyl 4-(4-(2-methyl-6-(methylsulfonyl)pyridin-3-ylamino)-7,8-dihydropyrimido[5,4-b][1,4]oxazepin-9(6H)-yl)piperidine-1-carboxylate

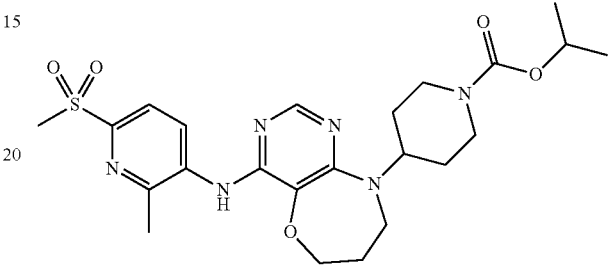

Example 109 was prepared from Example 108 using the methods described in Examples 8A and 8. ¹H NMR (500 MHz, CDCl₃): δ ppm 1.25 (d, J=6.15 Hz, 6 H) 1.60 (s, 2 H) 1.76 (d, J=10.11 Hz, 2 H) 2.02-2.13 (m, 2 H) 2.61 (s, 3H) 2.79-2.94 (m, 2 H) 3.11-3.19 (m, 3 H) 3.55 (t, J=5.71 Hz, 2 H) 4.38 (t, J=6.37 Hz, 4 H) 4.58-4.70 (m, 1 H) 4.85-5.00 (m, 1 H) 7.18 (s, 1 H) 7.92 (d, J=8.79 Hz, 1H) 8.07 (s, 1 H) 9.02 (d, J=8.79 Hz, 1 H). LRMS (ESI): 505.3 [M+H]⁺.

Example 110 iso-Propyl 4-(4-(2-chloropyridin-3-ylamino)-7,8-dihydropyrimido[5,4-b][1,4]oxazepin-9(6H)-yl)piperidine-1-carboxylate

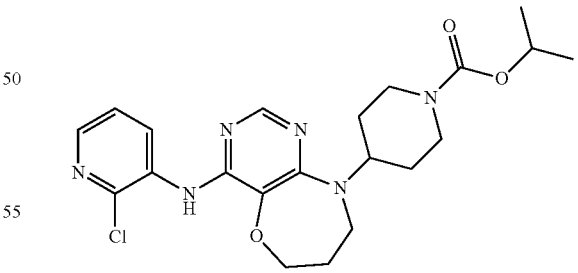

Example 110 was prepared from Example 83A using the same methods described above for Examples 83 and Example 8, with the exception that 2-fluoro-4-(methylsulfonyl)aniline was replaced with 2-chloropyridin-3-amine ¹H NMR (500 MHz, CDCl₃): δ ppm 1.25 (d, J=6.05 Hz, 6 H) 1.63 (s, 2 H) 1.76 (d, J=11.55 Hz, 2H) 2.01-2.12 (m, 2 H) 2.80-2.95 (m, 2 H) 3.54 (t, J=5.50 Hz, 2 H) 4.25 (t, 2 H) 4.37 (t, J=6.32 Hz, 2 H) 4.58-4.69 (m, 1 H) 4.85-4.97 (m, 1 H) 7.22 (dd, J=7.97, 4.67 Hz, 1 H) 7.66 (s, 1 H) 7.96 (d, J=4.95 Hz, 1 H) 8.05 (s, 1 H) 9.00 (d, J=8.25 Hz, 1 H). LRMS (ESI): 447.1 [M+H]+.

Example 111 iso-Propyl 4-(4-(2-chloro-4-methylpyridin-3-ylamino)-7,8-dihydropyrimido[5,4-b][1,4]oxazepin-9(6H)-yl)piperidine-1-carboxylate

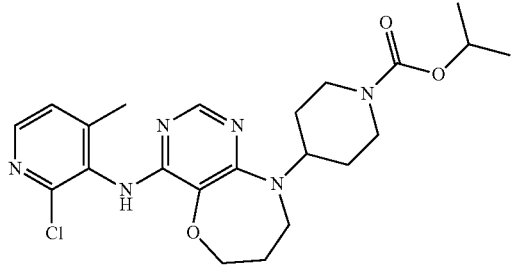 [SMILES: Cc1ccnc(Cl)c1Nc1ncnc2c1OCCCN2C1CCN(C(=O)OC(C)C)CC1]

Example 111 was prepared from Example 83A using the same methods described above for Examples 83 and Example 8, with the exception that 2-fluoro-4-(methylsulfonyl)aniline was replaced with 2-chloro-4-methylpyridin-3-amine 1H NMR (500 MHz, CDCl3): δ ppm 1.25 (d, J=6.60 Hz, 6 H) 1.59 (d, J=7.15 Hz, 2 H) 1.76 (d, J=12.10 Hz, 2 H) 2.05-2.14 (m, 2 H) 2.33 (s, 3 H) 2.86 (s, 2 H) 3.50-3.60 (m, 2 H) 4.24 (t, 2 H) 4.36 (t, J=6.60 Hz, 2 H) 4.57-4.68 (m, 1 H) 4.87-4.98 (m, 1H) 6.59 (s, 1 H) 7.15 (d, J=4.40 Hz, 1 H) 7.90 (s, 1 H) 8.12 (d, J=4.95 Hz, 1 H). LRMS (ESI): 461.1 [M+H]+.

Example 112 tert-Butyl 4-(4-(2-methyl-6-(1H-1,2,4-triazol-1-yl)pyridin-3-ylamino)-7,8-dihydropyrimido[5,4-b][1,4]oxazepin-9(6H)-yl)piperidine-1-carboxylate

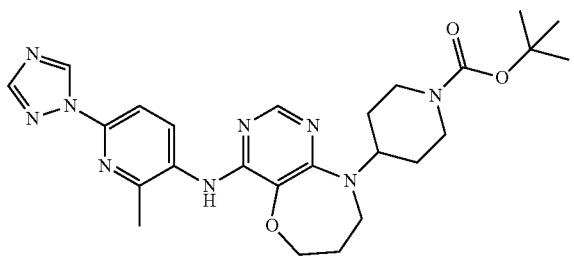 [SMILES: Cc1nc(-n2cncn2)ccc1Nc1ncnc2c1OCCCN2C1CCN(C(=O)OC(C)(C)C)CC1]

Example 112 was prepared using the same method described above for Example 83, with the exception that 2-fluoro-4-(methylsulfonyl)aniline was replaced with 2-methyl-6-(1H-1,2,4-triazol-1-yl)pyridin-3-amine. 1H NMR (500 MHz, CDCl3): δ ppm 1.46 (s, 9 H) 1.58 (d, J=6.60 Hz, 2 H) 1.69-1.80 (m, 2 H) 2.03-2.12 (m, 2 H) 2.55 (s, 3 H) 2.84 (s, 2 H) 3.54 (t, J=5.77 Hz, 2 H) 4.14-4.28 (m, 2 H) 4.37 (t, J=6.60 Hz, 2 H) 4.56-4.69 (m, 1 H) 6.88 (s, 1 H) 7.71 (d, J=8.80 Hz, 1 H) 8.02 (s, 1 H) 8.05 (s, 1 H) 8.68 (d, J=8.80 Hz, 1 H) 9.07 (s, 1 H). LRMS (ESI): 508.3 [M+H]+.

Example 113 iso-Propyl 4-(4-(2-methyl-6-(1H-1,2,4-triazol-1-yl)pyridin-3-ylamino)-7,8-dihydropyrimido[5,4-b][1,4]oxazepin-9(6H)-yl)piperidine-1-carboxylate

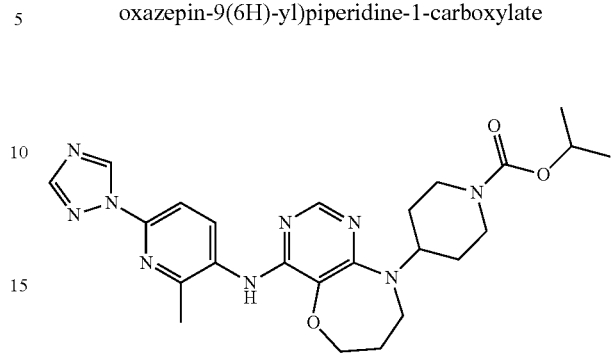

Example 113 was prepared from Example 112 using the methods described in Examples 8A and 8. 1H NMR (500 MHz, CDCl3): δ ppm 1.25 (d, J=6.60 Hz, 6 H) 1.61 (s, 2 H) 1.77 (d, J=11.00 Hz, 2 H) 2.04-2.12 (m, 2 H) 2.55 (s, 3H) 2.88 (s, 2 H) 3.54 (t, J=5.77 Hz, 2 H) 4.26 (t, 2 H) 4.37 (t, J=6.60 Hz, 2 H) 4.64 (s, 1 H) 4.86-4.97 (m, 1 H) 6.88 (s, 1 H) 7.71 (d, J=8.80 Hz, 1 H) 8.03 (s, 1 H) 8.05 (s, 1 H) 8.69 (d, J=8.80 Hz, 1 H) 9.08 (s, 1 H). LRMS (ESI): 494.2 [M+H]+.

Example 114 tert-Butyl 4-(4-(2-methyl-6-(trifluoromethyl)pyridin-3-ylamino)-7,8-dihydropyrimido[5,4-b][1,4]oxazepin-9(6H)-yl)piperidine-1-carboxylate

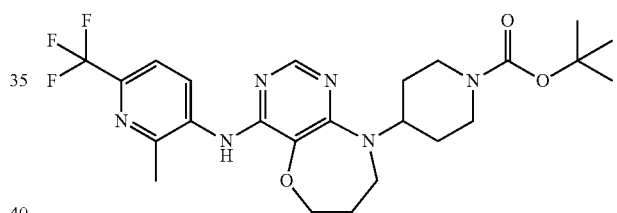

Example 114 was prepared using the same method described above for Example 83, with the exception that 2-fluoro-4-(methylsulfonyl)aniline was replaced with 2-methyl-6-(trifluoromethyl)pyridin-3-amine. 1H NMR (500 MHz, CDCl3): δ ppm 1.47 (s, 9 H) 1.58 (d, J=7.15 Hz, 2 H) 1.75 (d, J=11.00 Hz, 2 H) 2.03-2.12 (m, 2 H) 2.59 (s, 3 H) 2.84 (s, 2 H) 3.54 (t, J=5.77 Hz, 2 H) 4.13-4.29 (m, 2 H) 4.37 (t, J=6.32 Hz, 2 H) 4.56-4.68 (m, 1 H) 7.07 (s, 1 H) 7.51 (d, J=8.80 Hz, 1 H) 8.04 (s, 1H) 8.86 (d, J=8.80 Hz, 1 H). LRMS (ESI): 509.1 [M+H]+.

Example 115 tert-Butyl 4-(4-(2-methylpyridin-3-yloxy)-7,8-dihydropyrimido[5,4-b][1,4]oxazepin-9(6H)-yl)piperidine-1-carboxylate

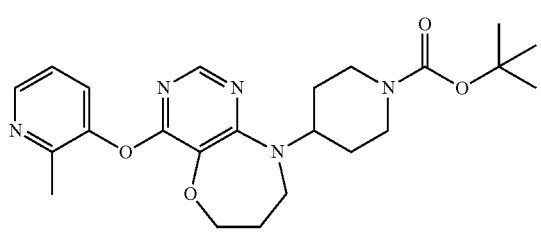 [SMILES: Cc1ncccc1Oc1ncnc2c1OCCCN2C1CCN(C(=O)OC(C)(C)C)CC1]

Example 115 was prepared using the same method described above for Example 65, with the exception that Example 26A was replaced with Example 83A. ¹H NMR (500 MHz, CDCl₃): δ ppm 1.47 (s, 9 H) 1.57-1.66 (m, 2 H) 1.76 (d, J=10.45 Hz, 2 H) 2.04-2.15 (m, 2 H) 2.43 (s, 3 H) 2.76-2.86 (m, 2 H) 3.56-3.67 (m, 2 H) 4.23 (t, 2 H) 4.37 (t, J=6.60 Hz, 2 H) 4.64 (s, 1 H) 7.18 (dd, J=8.25, 4.95 Hz, 1 H) 7.37 (d, J=9.35 Hz, 1 H) 7.90 (s, 1 H) 8.36 (d, J=3.30 Hz, 1 H). LRMS (ESI): 442.3 [M+H]⁺.

Example 116

Isopropyl 4-(4-(2-methylpyridin-3-yloxy)-7-oxopyrido[2,3-d]pyrimidin-8(7H)-yl)piperidine-1-carboxylate

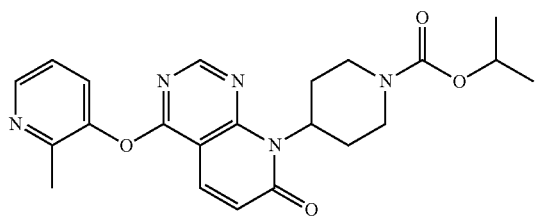 [SMILES: Cc1ncccc1Oc1ncnc2c1ccc(=O)n2C1CCN(C(=O)OC(C)C)CC1]

Example 116A (Z)-Methyl 3-(4,6-dichloropyrimidin-5-yl)acrylate

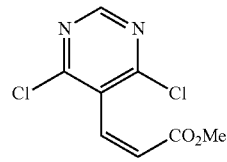 [SMILES: COC(=O)/C=C\c1c(Cl)ncnc1Cl]

To a solution of methyl 2-(bis(2,2,2-trifluoroethoxy)phosphoryl)acetate (2.460 mL, 11.63 mmol) in 70 mL of THF at −78° C. was added 18-CROWN-6 (9.14 g, 34.6 mmol). Added KHMDS (23.05 mL, 11.53 mmol) dropwise over 15 min and allowed the resulting mixture to stir at −78° C. for 30 min. Then 4,6-dichloropyrimidine-5-carbaldehyde (1.7 g, 9.61 mmol) was added in 20 mL of THF and the resulting mixture was allowed to stir at −78° C. for 1.5 h. The reaction was quenched with about 25 mL sat'd NH4Cl, allowed to warm to RT and then most of the THF was removed by rotary evaporator. The resulting mixture was diluted with 1:1 hexane/ethyl acetate, washed with 1N HCl, sat'd aq sodium bicarbonate and brine, dried (MgSO4), filtered through a pad of silica gel and concentrated in vacuo to afford an oil (2.8 g). The residue was purified by silica gel chromatography (80 g ISCO cartridge, 0-80% ethyl acetate/hexane) to afford Example 116A (1.55 g, 69%) as an oil, which was contaminated with ~10% of the (E)-olefin isomer. The material was used without further purification. LRMS (ESI): 233.1 [M+H]⁺.

Example 116B tert-Butyl 4-(4-chloro-7-oxopyrido[2,3-d]pyrimidin-8(7H)-yl)piperidine-1-carboxylate

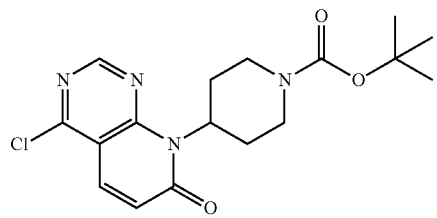 [SMILES: CC(C)(C)OC(=O)N1CCC(n2c(=O)ccc3c(Cl)ncnc32)CC1]

To a solution of (Z)-Methyl 3-(4,6-dichloropyrimidin-5-yl)acrylate from Example 116A (1.2 g, 5.15 mmol) in 40 mL of THF was added tert-butyl 4-aminopiperidine-1-carboxylate (1.08 g, 5.41 mmol) and triethylamine (1.08 mL, 7.72 mmol). The resulting mixture was allowed to stir at 65° C. for 18 h. The reaction was cooled, diluted with 1:1 hexane/ethyl acetate, washed with 1N HCl, sat'd aq sodium bicarbonate and brine, dried (MgSO4), filtered through a pad of silica gel and concentrated in vacuo to afford an oil (1.5 g). The residue was taken up in 15 mL of DMF and then there was added potassium carbonate (1.42 g, 10.3 mmol), and the reaction mixture was stirred at 100° C. for 1.5 h. The reaction was cooled, diluted with 1:2 hexane/ethyl acetate, washed with water and brine, dried (MgSO4), filtered through a pad of silica gel and concentrated in vacuo to afford an oil. The residue was purified by silica gel chromatography (80 g ISCO cartridge, 0-100% ethyl acetate/CH₂Cl₂) to afford Example 116B (0.30 g, 16%) as an off-white solid. 1H NMR (500 MHz, CDCl₃) δ ppm 1.48 (s, 9 H) 1.57 (m, 2 H) 2.78-2.96 (m, 4 H) 4.12-4.39 (m, 2 H) 5.51-5.63 (m, 1 H) 6.77 (d, J=9.90 Hz, 1 H) 7.95 (d, J=9.35 Hz, 1 H) 8.76 (s, 1 H). LRMS (ESI): 309.2 [M+H-C4H8]⁺, 265.2 [M+H-BOC]⁺.

Example 116C tert-Butyl 4-(4-(2-methylpyridin-3-yloxy)-7-oxopyrido[2,3-d]pyrimidin-8(7H)-yl)piperidine-1-carboxylate

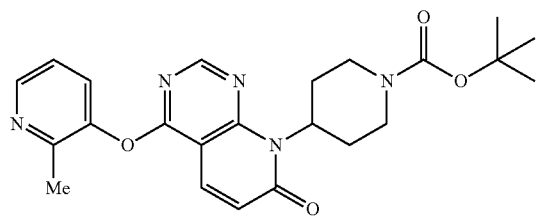 [SMILES: Cc1ncccc1Oc1ncnc2c1ccc(=O)n2C1CCN(C(=O)OC(C)(C)C)CC1]

To a solution of tert-butyl 4-(4-chloro-7-oxopyrido[2,3-d] pyrimidin-8(7H)-yl)piperidine-1-carboxylate from Example 116B (76 mg, 0.21 mmol) in 2 mL of DMF was added 2-methylpyridin-3-ol (23 mg, 0.21 mmol) and potassium carbonate (58 mg, 0.42 mol). The resulting mixture was allowed to stir at 100° C. in a sealed vial for 1 h. The reaction mixture was cooled, diluted with ethyl acetate, washed with water and brine, dried (MgSO₄), filtered through a pad of silica gel and concentrated. The residue was triturated with ether to afford 20 mg (21%) of Example 116C as a pale yellow solid. 1H NMR (500 MHz, CDCl₃) δ 1.47 (s, 9 H) 1.57-1.64 (m, 2 H) 2.42 (s, 3 H) 2.74-2.99 (m, 4 H) 4.10-4.38 (m, 2 H) 5.54-5.67 (m, 1 H) 6.74 (d, J=9.90 Hz, 1 H) 7.26 (dd, J=8.25, 4.95 Hz, 1 H) 7.45 (d, J=8.25 Hz, 1 H) 8.07 (d, J=9.90 Hz, 1 H) 8.47 (d, J=3.30 Hz, 1 H) 8.50 (s, 1 H). LRMS (ESI): 438.3 [M+H]⁺.

Example 116

Isopropyl 4-(4-(2-methylpyridin-3-yloxy)-7-oxopyrido[2,3-d]pyrimidin-8(7H)-yl)piperidine-1-carboxylate

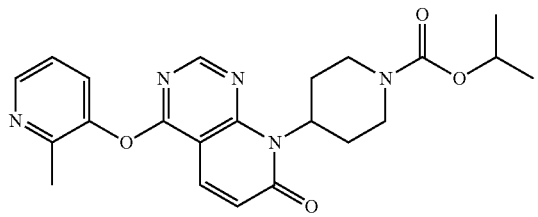 [SMILES: Cc1ncccc1Oc1ncnc2c1ccc(=O)n2C1CCN(C(=O)OC(C)C)CC1]

To a solution of tert-butyl 4-(4-(2-methylpyridin-3-yloxy)-7-oxopyrido[2,3-d]pyrimidin-8(7H)-yl)piperidine-1-carboxylate from Example 116C (56 mg, 0.13 mmol) in 4 mL methylene chloride was added 4 mL of trifluoroacetic acid. The resulting mixture was stirred at room temperature for 1 h and then was concentrated in vacuo. The residue was taken up in 4 mL of methylene chloride and then there was added triethylamine (0.054 mL, 0.38 mmol) and isopropylchloroformate (0.13 mL of a 1M solution in toluene, 0.13 mmol). The resulting mixture was allowed to stir at room temperature for 18 h. The reaction was diluted with ethyl acetate, washed with sat'd aq sodium bicarbonate and brine, dried (MgSO4), filtered through a pad of silica gel and concentrated. The residue was purified by silica gel chromatography (12 g ISCO cartridge, 0-100% ethyl acetate/hexane) to afford 28 mg (49%) of Example 116 as an off-white solid. 1H NMR (500 MHz, CDCl₃) δ ppm 1.21 (d, J=6.05 Hz, 6 H) 1.55-1.61 (m, 2 H) 2.37 (s, 3 H) 2.80-2.93 (m, 4 H) 4.20-4.36 (m, 2 H) 4.85-4.92 (m, 1 H) 5.57 (s, 1 H) 6.70 (d, J=9.35 Hz, 1 H) 7.21 (dd, J=7.97, 4.67 Hz, 1 H) 7.40 (d, J=6.60 Hz, 1 H) 8.02 (d, J=9.35 Hz, 1 H) 8.42 (d, J=4.95 Hz, 1 H) 8.46 (s, 1 H). LRMS (ESI): 424.3 [M+H]⁺.

Example 117

Isopropyl 4-(4-(2-fluoro-4-(methylsulfonyl)phenylamino)-7-oxopyrido[2,3-d]pyrimidin-8(7H)-yl)piperidine-1-carboxylate

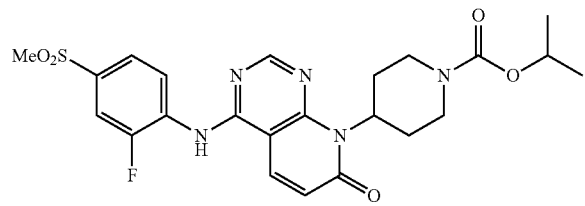 [SMILES: CC(C)OC(=O)N1CCC(n2c(=O)ccc3c(Nc4ccc(S(C)(=O)=O)cc4F)ncnc32)CC1]

By the procedures described in Example 3 and Example 116, tert-butyl 4-(4-chloro-7-oxopyrido[2,3-d]pyrimidin-8(7H)-yl)piperidine-1-carboxylate from Example 116B was converted in Example 117. 1H NMR (500 MHz, CDCl₃) δ ppm 1.21 (d, J=5.50 Hz, 6 H) 1.53-1.59 (m, 2 H) 2.79-2.95 (m, 4 H) 3.02 (s, 3 H) 4.20-4.36 (m, 2 H) 4.86-4.92 (m, 1 H) 5.54-5.69 (m, 1 H) 6.68 (d, J=9.35 Hz, 1 H) 7.45 (d, J=3.30 Hz, 1 H) 7.66-7.70 (m, 2 H) 7.73 (d, J=8.80 Hz, 1 H) 8.61 (s, 1 H) 8.71-8.76 (m, 1 H). LRMS (ESI): 504.2 [M+H]⁺.

Example 118

Isopropyl 4-(4-(2-fluoro-4-(methylsulfonyl)phenylamino)-7-oxo-6,7-dihydropyrido[2,3-d]pyrimidin-8 (5H)-yl)piperidine-1-carboxylate

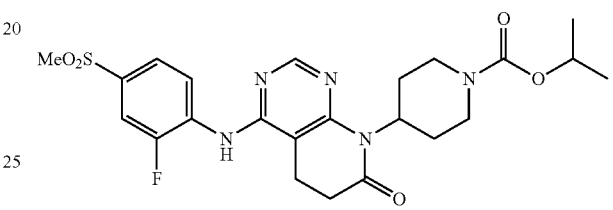

To a solution of isopropyl 4-(4-(2-fluoro-4-(methylsulfonyl)phenylamino)-7-oxopyrido[2,3-d]pyrimidin-8(7H)-yl)piperidine-1-carboxylate from Example 117 (53 mg, 0.105 mmol) in ethanol (10 mL) was added 20% Pd(OH)₂/C (20 mg, 0.057 mmol). Using a three-way stopcock, the reaction mixture was alternately evacuated and purged with hydrogen from a balloon several times. The reaction mixture was then allowed to stir under 1 atm of H₂ at ambient temperature for 18 h. The mixture was filtered through pad of CELITE® 545 filter aid and concentrated to an oil. The residue was purified by flash chromatography (12 g ISCO column, elution with 0-100% ethyl acetate/hexane) to afford 5 mg (9%) of Example 118 as an off white solid. 1H NMR (500 MHz, CDCl₃) δ ppm 1.25 (d, J=5.50 Hz, 6 H) 1.54-1.61 (m, 4H) 2.65-2.81 (m, 6 H) 3.05 (s, 3 H) 4.18-4.32 (m, 2 H), 4.87-4.95 (m, 1 H) 5.02-5.09 (m, 1 H) 6.83 (s, 1 H) 7.69 (d, J=10.45 Hz, 1 H) 7.74 (d, J=8.80 Hz, 1 H) 8.53 (s, 1 H) 8.76-8.81 (m, 1 H). LRMS (ESI): 506.2 [M+H]⁺.

Example 119

Isopropyl 4-(4-(2-chloro-4-(oxazol-5-yl)phenylamino)-6H-pyrimido[5,4-b][1,4]oxazin-8(7H)-yl)piperidine-1-carboxylate

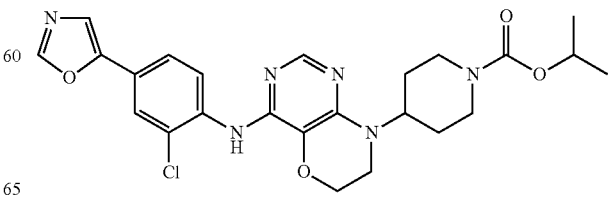

Example 119A

2-Chloro-4-(oxazol-5-yl)aniline

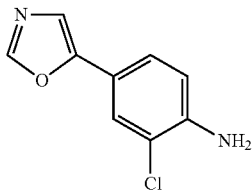 [SMILES: Nc1ccc(-c2cnco2)cc1Cl]

To a solution of 4-(oxazol-5-yl)aniline (1.2 g, 7.49 mmol) in 25 mL of acetonitrile was added N-chlorosuccinimide (1.25 g, 9.36 mmol) as a solution in 15 mL of acetonitrile. The resulting mixture was stirred at reflux for 4 h. The mixture was cooled, diluted with ethyl acetate, washed with water, sat'd aq sodium bicarbonate (2×) and brine, dried (MgSO4), filtered through a pad of silica gel and concentrated. The residue was purified by silica gel chromatography (40 g ISCO cartridge, 0-100% ethyl acetate/hexane) to afford 0.53 g (36%) of Example 119A as a yellow solid. LRMS (ESI): 195.1/197.1 [M+H]$^+$.

Example 119

Isopropyl 4-(4-(2-chloro-4-(oxazol-5-yl)phenylamino)-6H-pyrimido[5,4-b][1,4]oxazin-8(7H)-yl)piperidine-1-carboxylate

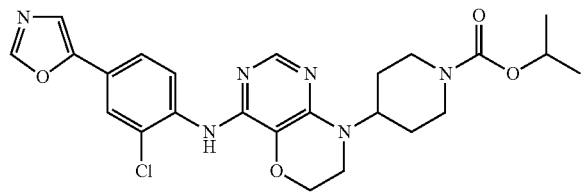 [SMILES: CC(C)OC(=O)N1CCC(N2CCOc3c(Nc4ccc(-c5cnco5)cc4Cl)ncnc32)CC1]

By the procedure described in Example 3, with the exception that Example 119A was used instead of 2-fluoro-4-(methylsulfonyl)aniline, isopropyl 4-(4-chloro-6H-pyrimido[5,4-b][1,4]oxazin-8(7H)-yl)piperidine-1-carboxylate from Example 20A was converted into Example 119. 1H NMR (500 MHz, CDCl$_3$) δ ppm 1.27 (d, J=6.05 Hz, 6 H) 1.59-1.76 (m, 4 H) 2.88-2.98 (m, 2 H) 3.46-3.49 (m, 2 H) 4.28-4.31 (m, 4 H) 4.83-4.90 (m, 1 H) 4.90-4.97 (m, 1 H) 7.29 (s, 1 H) 7.44 (s, 1 H) 7.55 (dd, J=8.80, 2.20 Hz, 1 H) 7.68 (d, J=2.20 Hz, 1 H) 7.90 (s, 1 H) 8.10 (s, 1 H) 8.73 (d, J=8.80 Hz, 1 H). LRMS (ESI): 499.2/501.2 [M+H]$^+$.

Example 120

Isopropyl 4-(4-(3-chloropyridin-4-ylamino)-6H-pyrimido[5,4-b][1,4]oxazin-8(7H)-yl)piperidine-1-carboxylate

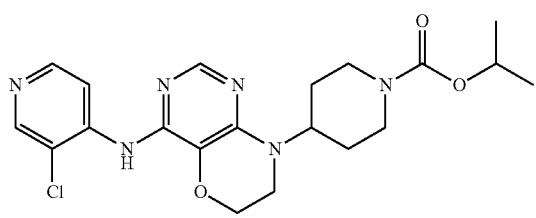

By the procedure described in Example 3, with the exception that 3-chloro-4-aminopyridine was used instead of 2-fluoro-4-(methylsulfonyl)aniline, isopropyl 4-(4-chloro-6H-pyrimido[5,4-b][1,4]oxazin-8(7H)-yl)piperidine-1-carboxylate from Example 20A was converted into Example 120. 1H NMR (500 MHz, CDCl$_3$) δ ppm 1.24 (d, J=6.60 Hz, 6 H) 1.59-1.64 (m, 2 H) 1.66-1.74 (m, 2H) 2.85-2.93 (m, 2 H) 3.44-3.47 (m, 2 H) 4.25-4.29 (m, 4 H) 4.80-4.87 (m, 1 H) 4.87-4.94 (m, 1 H) 7.60 (s, 1 H) 8.09 (s, 1 H) 8.31 (d, J=6.05 Hz, 1 H) 8.44 (s, 1 H) 8.75 (d, J=5.50 Hz, 1 H). LRMS (ESI): 433.3/435.2 [M+H]$^+$.

Example 121

Isopropyl 4-(4-(3-fluoropyridin-4-ylamino)-6H-pyrimido[5,4-b][1,4]oxazin-8(7H)-yl)piperidine-1-carboxylate

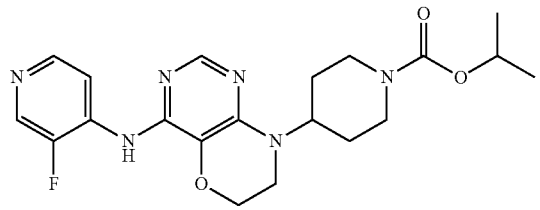 [SMILES: CC(C)OC(=O)N1CCC(N2CCOc3c(Nc4ccncc4F)ncnc32)CC1]

By the procedure described in Example 3, with the exception that 3-fluoro-4-aminopyridine was used instead of 2-fluoro-4-(methylsulfonyl)aniline, isopropyl 4-(4-chloro-6H-pyrimido[5,4-b][1,4]oxazin-8(7H)-yl)piperidine-1-carboxylate from Example 20A was converted into Example 121. 1H NMR (500 MHz, CDCl$_3$) δ ppm 1.23 (d, J=6.60 Hz, 6 H) 1.62 (s, 2 H) 1.66-1.73 (m, 2 H) 2.84-2.93 (m, 2 H) 3.43-3.46 (m, 2 H) 4.23-4.31 (m, 4 H) 4.79-4.87 (m, 1 H) 4.87-4.94 (m, 1 H) 7.19 (d, J=3.30 Hz, 1 H) 8.08 (s, 1 H) 8.25 (d, J=6.05 Hz, 1 H) 8.33 (d, J=2.20 Hz, 1 H) 8.65-8.70 (m, 1 H). LRMS (ESI): 417.2 [M+H]$^+$.

Example 122

Isopropyl 4-(4-(3-(trifluoromethyl)pyridin-4-ylamino)-6H-pyrimido[5][1,4]oxazin-8(7H)-yl)piperidine-1-carboxylate

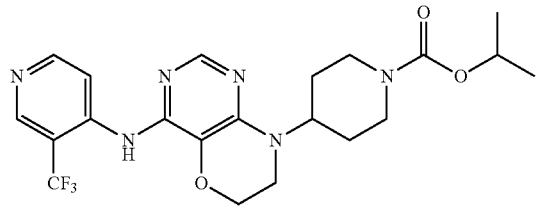 [SMILES: CC(C)OC(=O)N1CCC(N2CCOc3c(Nc4ccncc4C(F)(F)F)ncnc32)CC1]

By the procedure described in Example 3, with the exception that 3-trifluoromethyl-4-aminopyridine was used instead of 2-fluoro-4-(methylsulfonyl)aniline, isopropyl 4-(4-chloro-6H-pyrimido[5,4-b][1,4]oxazin-8(7H)-yl)piperidine-1-carboxylate from Example 20A was converted into Example 122. 1H NMR (500 MHz, CDCl$_3$) δ ppm 1.19 (d, J=6.60 Hz, 6 H) 1.53-1.61 (m, 2 H) 1.62-1.69 (m, 2 H) 2.79-2.89 (m, 2 H) 3.40-3.43 (m, 2 H) 4.21-4.25 (m, 4 H) 4.76-4.82 (m, 1 H) 4.82-4.89 (m, 1 H) 7.57 (broad s, 1 H) 8.05 (s, 1 H) 8.47-8.51 (m, 1H) 8.62 (broad s, 1 H) 8.86 (d, J=5.50 Hz, 1 H). LRMS (ESI): 467.3 [M+H]$^+$.

Example 123 tert-Butyl 4-(4-(2-methyl-6-(methylsulfonyl)pyridin-3-ylamino)-6H-pyrimido[5,4-b][1,4]oxazin-8(7H)-yl)piperidine-1-carboxylate

By the procedure described in Example 3, with the exception that 2-methyl-6-(methylsulfonyl)pyridin-3-amine was used instead of 2-fluoro-4-(methylsulfonyl)-aniline, tert-butyl 4-(4-chloro-6H-pyrimido[5,4-b][1,4]oxazin-8(7H)-yl)piperidine-1-carboxylate from Example 3C was converted into Example 123. 1H NMR (500 MHz, CDCl$_3$) δ ppm 1.45 (s, 9 H) 1.55-1.65 (m, 2 H) 1.66-1.72 (m, 2 H) 2.61 (s, 3 H) 2.82-2.90 (m, 2 H) 3.15 (s, 3 H) 3.45-3.48 (m, 2 H) 4.25-4.28 (m, 4 H) 4.79-4.88 (m, 1 H) 6.86-7.00 (m, 1 H) 7.91 (d, J=8.25 Hz, 1 H) 8.06 (s, 1 H) 8.91 (m, 1 H). LRMS (ESI): 505.3 [M+H]$^+$.

Example 124

Isopropyl 4-(4-(2-methyl-6-(methylsulfonyl)pyridin-3-ylamino)-6H-pyrimido[5,4-b][1,4]oxazin-8(7H)-yl)piperidine-1-carboxylate

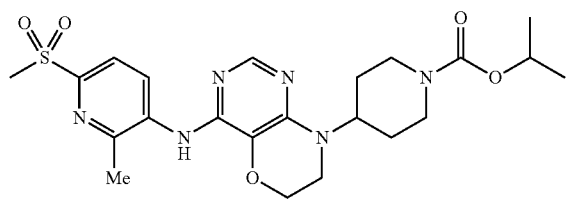

Example 124 was prepared from Example 123 using the methods described in Examples 8A and 8. $^1$H NMR (500 MHz, CD3OD) δ ppm 1.26 (d, J=6.60 Hz, 6 H) 1.69-1.76 (m, 4 H) 2.59 (s, 3 H) 2.86-2.99 (m, 2 H) 3.19 (s, 3 H) 3.54-3.57 (m, 2H) 4.23-4.31 (m, 4 H) 4.84-4.87 (m, 2 H) 7.88-7.91 (m, 2 H) 8.54 (d, J=8.25 Hz, 1H). LRMS (ESI): 491.2 [M+H]$^+$.

Example 125

Isopropyl 4-(4-(2-methyl-6-(methylsulfonyl)pyridin-3-ylamino)-7-oxo-6H-pyrimido[5,4-b][1,4]oxazin-8(7H)-yl)piperidine-1-carboxylate

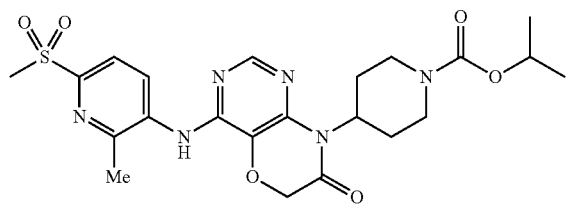 [SMILES: Cc1nc(S(C)(=O)=O)ccc1Nc1ncnc2c1OCC(=O)N2C1CCN(C(=O)OC(C)C)CC1]

Example 125A

Isopropyl 4-(4-chloro-7-oxo-6H-pyrimido[5,4-b][1,4]oxazin-8(7H)-yl)piperidine-1-carboxylate

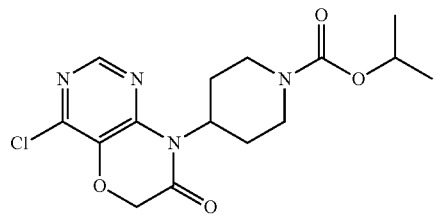 [SMILES: CC(C)OC(=O)N1CCC(N2C(=O)COc3c(Cl)ncnc32)CC1]

Example 125A was prepared from Example 26A following the procedures described in Example 116. LRMS (ESI): 355.1 [M+H]$^+$.

Example 125

Isopropyl 4-(4-(2-methyl-6-(methylsulfonyl)pyridin-3-ylamino)-7-oxo-6H-pyrimido[5,4-b][1,4]oxazin-8(7H)-yl)piperidine-1-carboxylate

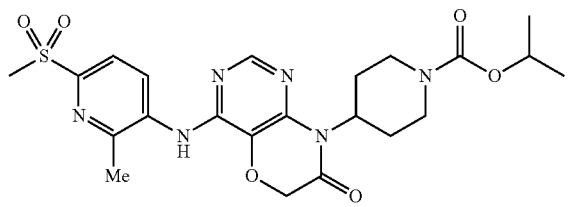

To a solution of isopropyl 4-(4-chloro-7-oxo-6H-pyrimido[5,4-b][1,4]oxazin-8(7H)-yl)piperidine-1-carboxylate from Example 125A (33 mg, 0.093 mmol) in degassed toluene (2 mL) was added 2-methyl-6-(methylsulfonyl)pyridin-3-amine (17.32 mg, 0.093 mmol), Cs$_2$CO$_3$ (42.4 mg, 0.130 mmol), Xantphos (8.07 mg, 0.014 mmol) and Pd$_2$(dba)$_3$ (8.52 mg, 9.30 mmol). Purged for 2 min with stream of argon, stirred in sealed vial at 110° C. for 18 h. The reaction was cooled, diluted with ethyl acetate, washed with brine, dried (MgSO4), filtered through a pad of silica gel and concentrated in vacuo to afford an oil. The residue was purified by silica gel chromatography (12 g ISCO cartridge, 0-80% ethyl acetate/hexane) to afford 8 mg (17%) of Example 125 as a pale yellow solid. $^1$H NMR (400 MHz, CHLOROFORM-d) δ ppm 9.00 (1H, d, J=8.35 Hz), 8.29 (1H, s), 7.96 (1H, d, J=8.35 Hz), 6.97 (1H, s), 4.96-5.06 (1H, m), 4.93 (1H, quin, J=6.15 Hz), 4.76 (2H, s), 4.19-4.41 (2H, m), 3.18 (3H, s), 2.75-2.89 (2H, m), 2.65-2.75 (2H, m), 2.64 (3H, s), 1.61-1.69 (2H, m), 1.25 (6H, d, J=5.71 Hz). LRMS (ESI): 505.1 [M+H]⁺.

Example 126

Isopropyl 4-(4-(2-methyl-6-(1H-1,2,4-triazol-1-yl)pyridin-3-ylamino)-7-oxo-6H-pyrimido[5,4-b][1,4]oxazin-8(7H)-yl)piperidine-1-carboxylate

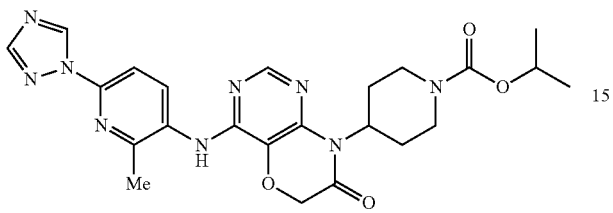

Example 126 was prepared from Example 125A following the procedure described in Example 125, with the exception that 2-methyl-6-(1H-1,2,4-triazol-1-yl)pyridin-3-amine was used instead of 2-methyl-6-(methylsulfonyl)pyridin-3-amine. 1H NMR (500 MHz, CHLOROFORM-d) δ ppm 9.10 (1H, s), 8.60 (1H, d, J=8.25 Hz), 8.22 (1H, s), 8.06 (1H, s), 7.76 (1H, d, J=8.80 Hz), 6.71 (1H, s), 4.96-5.04 (1H, m), 4.89-4.96 (1H, m), 4.73 (2H, s), 4.20-4.40 (2H, m), 2.76-2.88 (2H, m), 2.69 (2H, qd, J=12.28, 4.40 Hz), 2.57 (3H, s), 1.62-1.69 (2H, m), 1.25 (6H, d, J=6.05 Hz). LRMS (ESI): 494.1 [M+H]⁺.

Example 127

Isopropyl 4-(4-(2-chloropyridin-3-ylamino)-7-oxo-6H-pyrimido[5,4-b][1,4]oxazin-8(7H)-yl)piperidine-1-carboxylate

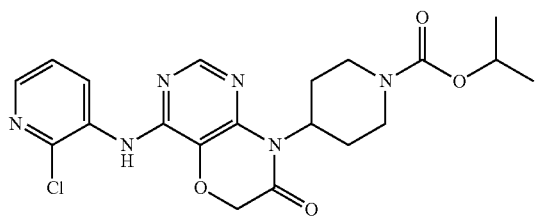

Example 126 was prepared from Example 125A following the procedure described in Example 125, with the exception that 2-chloropyridin-3-amine was used instead of 2-methyl-6-(methylsulfonyl)pyridin-3-amine 1H NMR (400 MHz, CHLOROFORM-d) δ ppm 9.00 (1H, dd, J=8.13, 1.54 Hz), 8.26 (1H, s), 8.05 (1H, dd, J=4.61, 1.54 Hz), 7.50 (1H, s), 7.27 (1H, dd, J=8.13, 4.61 Hz), 4.95-5.04 (1H, m), 4.89-4.95 (1H, m), 4.75 (2H, s), 4.21-4.40 (2H, m), 2.75-2.88 (2H, m), 2.62-2.75 (2H, m), 1.60-1.69 (2H, m), 1.25 (6H, d, J=6.15 Hz). LRMS (ESI): 447.2/449.2 [M+H]⁺.

EXAMPLES 128 to 138

Examples 128 to 138 were prepared from isopropyl 4-(4-chloro-6H-pyrimido[5,4-b][1,4]oxazin-8(7H)-yl)piperidine-1-carboxylate from Example 20A in library format by the following procedure. The required aniline reagents (1.0 eq) were weighed directly into 0.5-2 mL BIOTAGE microwave vials. Isopropyl 4-(4-chloro-6H-pyrimido[5,4-b][1,4]oxazin-8(7H)-yl)piperidine-1-carboxylate from Example 20A (688 mg, 2.02 mmol, 1 eq) was dissolved in 20.2 mL of toluene and agitated. To this core solution was added BINAP (59 mg, 0.06 eq) and NaOt-Bu (192 mg, 1.0 eq). To each reagent vial was added 1.0 mL core solution. Pd₂(dba)₂ (approx. 4 mg, 0.04 eq) was added to each vial. Reactions were heated to 130° C. for 15 minutes in the microwave. The reactions were concentrated, the residues redissolved in 1 mL DMF, and filtered through a 0.45 micron syringe filter. They were purified using preparative LCMS.

Example 128

Isopropyl 4-(4-(4-methoxyphenylamino)-6H-pyrimido[5,4-b][1,4]oxazin-8(7H)-yl)piperidine-1-carboxylate

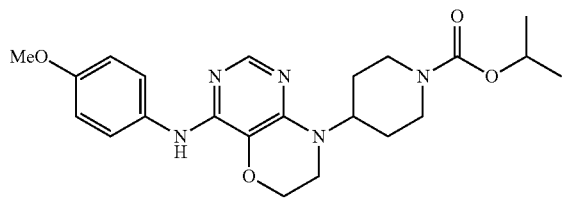 [SMILES: COc1ccc(Nc2ncnc3c2OCCN3C2CCN(C(=O)OC(C)C)CC2)cc1]

LRMS (ESI): 428.1 [M+H]⁺.

Example 129

Isopropyl 4-(4-(4-(oxazol-5-yl)phenylamino)-6H-pyrimido[5,4-b][1,4]oxazin-8(7H)-yl)piperidine-1-carboxylate

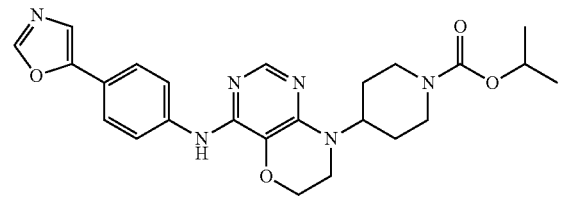 [SMILES: CC(C)OC(=O)N1CCC(N2CCOc3c(Nc4ccc(-c5cnco5)cc4)ncnc32)CC1]

LRMS (ESI): 465.1 [M+H]⁺.

Example 130

Isopropyl 4-(4-(4-(pyrrolidine-1-carbonyl)phenylamino)-6H-pyrimido[5,4-b][1,4]oxazin-8(7H)-yl)piperidine-1-carboxylate

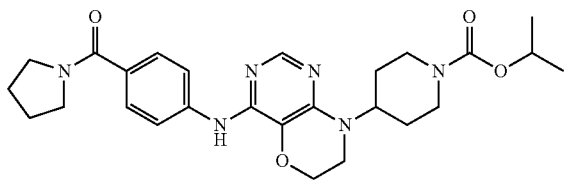 [SMILES: CC(C)OC(=O)N1CCC(N2CCOc3c(Nc4ccc(C(=O)N5CCCC5)cc4)ncnc32)CC1]

LRMS (ESI): 495.3 [M+H]⁺.

Example 131

Isopropyl 4-(4-(4-(1H-pyrazol-1-yl)phenylamino)-6H-pyrimido[5,4-b][1,4]oxazin-8(7H)-yl)piperidine-1-carboxylate

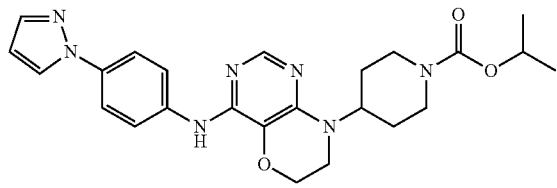 [SMILES: CC(C)OC(=O)N1CCC(N2CCOc3c(Nc4ccc(-n5cccn5)cc4)ncnc32)CC1]

LRMS (ESI): 464.2 [M+H]+.

Example 132

Isopropyl 4-(4-(benzo[d][1,3]dioxol-5-ylamino)-6H-pyrimido[5,4-b][1,4]oxazin-8(7H)-yl)piperidine-1-carboxylate

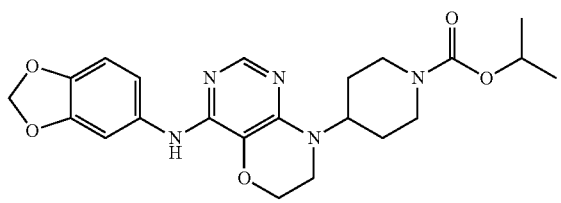 [SMILES: CC(C)OC(=O)N1CCC(N2CCOc3c(Nc4ccc5c(c4)OCO5)ncnc32)CC1]

LRMS (ESI): 442.2 [M+H]+.

Example 133

Isopropyl 4-(4-(4-(methoxycarbonyl)-2-methylphenylamino)-6H-pyrimido[5,4-b][1,4]oxazin-8(7H)-yl)piperidine-1-carboxylate

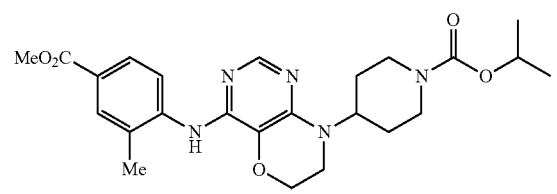 [SMILES: COC(=O)c1ccc(Nc2ncnc3c2OCCN3C2CCN(C(=O)OC(C)C)CC2)c(C)c1]

LRMS (ESI): 470.2 [M+H]+.

Example 134

Isopropyl 4-(4-(4-cyano-2-methylphenylamino)-6H-pyrimido[5,4-b][1,4]oxazin-8(7H)-yl)piperidine-1-carboxylate

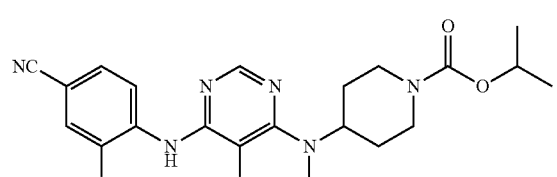

LRMS (ESI): 437.2 [M+H]+.

Example 135

Isopropyl 4-(4-(4-methoxy-2-methylphenylamino)-6H-pyrimido[5,4-b][1,4]oxazin-8(7H)-yl)piperidine-1-carboxylate

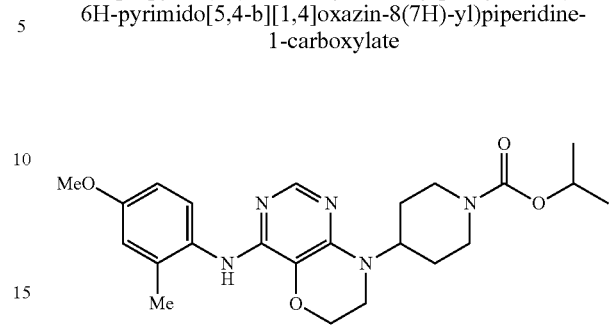

LRMS (ESI): 442.2 [M+H]+.

Example 136

Isopropyl 4-(4-(2,6-difluorophenylamino)-6H-pyrimido[5,4-b][1,4]oxazin-8(7H)-yl)piperidine-1-carboxylate

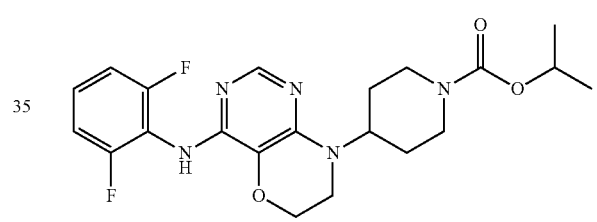

LRMS (ESI): 434.1 [M+H]+.

Example 137

Isopropyl 4-(4-(2-chloro-5-cyanophenylamino)-6H-pyrimido[5,4-b][1,4]oxazin-8(7H)-yl)piperidine-1-carboxylate

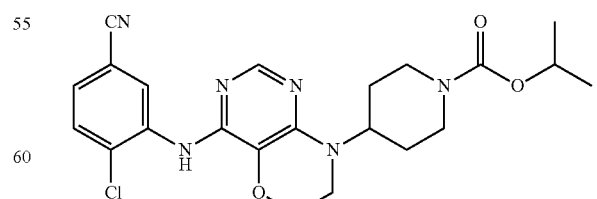

LRMS (ESI): 457/459 [M+H]+.

Example 138

Isopropyl 4-(4-(3-(methoxycarbonyl)-2-methylphenylamino)-6H-pyrimido[5,4-b][1,4]oxazin-8(7H)-yl)piperidine-1-carboxylate

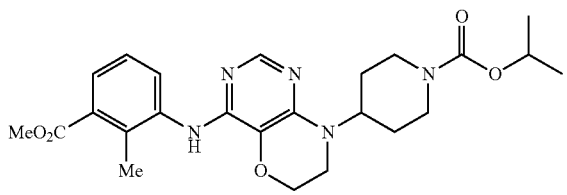 [SMILES: COC(=O)c1cccc(Nc2ncnc3c2OCCN3C2CCN(C(=O)OC(C)C)CC2)c1C]

LRMS (ESI): 470.2 [M+H]⁺.

Example 139

N-(2-Fluoro-4-(methylsulfonyl)phenyl)-8-(1-(5-methylbenzo[d]oxazol-2-yl)piperidin-4-yl)-7,8-dihydro-6H-pyrimido[5,4-b][1,4]oxazin-4-amine

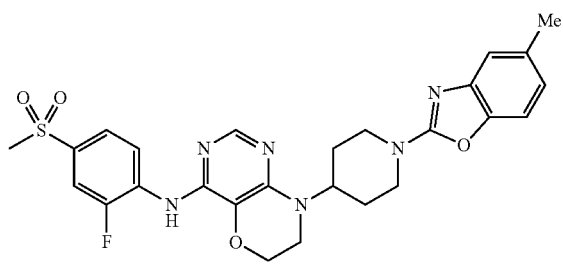 [SMILES: Cc1ccc2oc(N3CCC(N4CCOc5c(Nc6ccc(S(C)(=O)=O)cc6F)ncnc54)CC3)nc2c1]

Example 139 was prepared from Example 8A following the procedure described in Example 17, except that 2-chlorobenzo[d]oxazole was replaced with 2-chloro-5-methylbenzo[d]oxazole. 1H NMR (400 MHz, CDCl₃) δ ppm 8.89 (t, J=8.1 Hz, 1 H) 8.10 (s, 1 H) 7.67-7.75 (m, 1 H) 7.64 (dd, J=10.3, 2.0 Hz, 1 H) 7.25 (s, 1 H) 7.19-7.24 (m, 1 H) 7.14 (d, J=8.4 Hz, 1 H) 6.86 (d, J=7.5 Hz, 2 H) 4.91-5.03 (m, 1H) 4.51 (d, J=12.7 Hz, 2 H) 4.22-4.31 (m, 2 H) 3.42-3.50 (m, 2 H) 3.23-3.36 (m, 2H) 3.03 (s, 3 H) 2.39 (s, 3 H) 1.83-1.93 (m, 3 H)

Example 140

N-(2-fluoro-4-(methylsulfonyl)phenyl)-8-(1-(4-methylpyrimidin-2-yl)piperidin-4-yl)-7,8-dihydro-6H-pyrimido[5,4-b][1,4]oxazin-4-amine

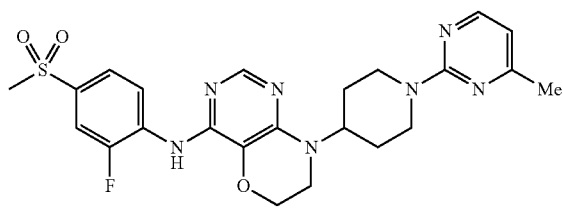 [SMILES: Cc1ccnc(N2CCC(N3CCOc4c(Nc5ccc(S(C)(=O)=O)cc5F)ncnc43)CC2)n1]

Example 140 was prepared from Example 8A following a procedure similar to that described in Example 17, except that 2-chlorobenzo[d]oxazole was replaced with 2-chloro-4-methylpyrimidine. 1H NMR (400 MHz, CDCl₃) δ ppm 8.90 (t, J=8.1 Hz, 1 H) 8.20 (d, J=5.3 Hz, 1 H) 8.11 (s, 1 H) 7.70 (d, J=8.8 Hz, 1 H) 7.62-7.68 (m, 1 H) 7.24 (d, J=4.0 Hz, 1 H) 6.46 (d, J=4.8 Hz, 1 H) 4.93-5.13 (m, 3 H) 4.21-4.30 (m, 2 H) 3.42-3.48 (m, 2 H) 3.05-3.16 (m, 2 H) 3.04 (s, 3 H) 2.38-2.49 (m, 3 H) 1.86 (d, J=11.0 Hz, 2 H) 1.65-1.80 (m, 2 H).

Example 141

8-(1-(5-Ethylpyrimidin-2-yl)piperidin-4-yl)-N-(2-fluoro-4-(methylsulfonyl)phenyl)-7,8-dihydro-6H-pyrimido[5,4-b][1,4]oxazin-4-amine

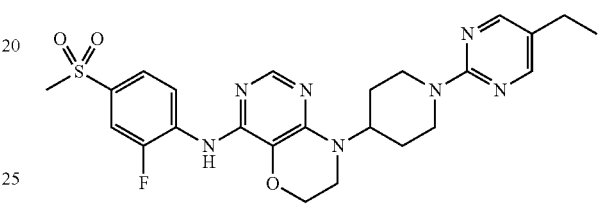

Example 141 was prepared from Example 8A following a procedure similar to that described in Example 17, except that 2-chlorobenzo[d]oxazole was replaced with 2-chloro-5-ethylpyrimidine. 1H NMR (400 MHz, CDCl₃) δ ppm 8.88 (t, J=8.4 Hz, 1 H) 8.22 (s, 2 H) 8.10 (s, 1 H) 7.69 (d, J=8.8 Hz, 1 H) 7.63 (dd, J=10.6, 1.8 Hz, 1 H) 7.22 (d, J=4.4 Hz, 1 H) 4.86-5.02 (m, 3 H) 4.21-4.27 (m, 2 H) 3.40-3.48 (m, 2 H) 3.03-3.15 (m, 2 H) 3.03 (s, 3 H) 2.49 (q, J=7.8 Hz, 2 H) 1.78-1.87 (m, 2 H) 1.62-1.77 (m, 2 H) 1.20 (t, J=7.8 Hz, 3 H).

Example 142

1,1,1-Trifluoropropan-2-yl 4-(4-(4-(methylsulfonyl)phenylamino)-6H-pyrimido[5,4-b][1,4]oxazin-8(7H)-yl)piperidine-1-carboxylate, TFA salt

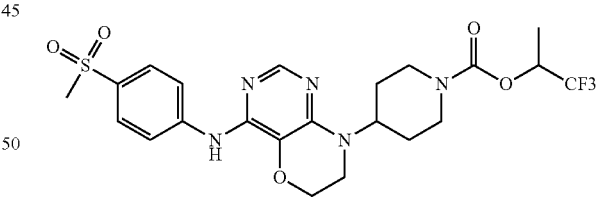

Example 142A 1,1,1-Trifluoropropan-2-yl chloroformate

To a mixture of 1,1,1-trifluoro-2-propanol (114.1 mg, 1.0 mmol, Matrix Scientific) and triphosgene (98 mg, 0.33 mmol, Aldrich) in ethyl ether (10 mL) at −40° C. was added pyridine (80 μL, 1.0 mmol, EMD) in ethyl ether (1.0 mL) dropwise. The reaction mixture was warmed to 0° C. and stirred for 6 h. The flask containing the above reaction mixture was put into a refrigerator overnight and then filtered. The filtrate was concentrated in vacuo in ice both to give a colorless oil which was used directly in the next step.

Example 142

1,1,1-Trifluoropropan-2-yl 4-(4-(4-(methylsulfonyl)phenylamino)-6H-pyrimido[5,4-b][1,4]oxazin-8(7H)-yl)piperidine-1-carboxylate To a suspension of N-(2-fluoro-4-(methylsulfonyl)phenyl)-8-(piperidin-4-yl)-7,8-dihydro-6H-pyrimido[5,4-b][1,4]oxazin-4-amine hydrochloric acid salt from Example 8A (35.5 mg, 0.08 mmol) in CH$_2$Cl$_2$ (1.5 mL) was added DIEP (70 µL, 0.40 mmol, Aldrich) followed by addition of 1,1,1-trifluoropropan-2-ylchloroformate (⅓ of the material from Step A, 0.33 mmol) in CH$_2$Cl$_2$ (0.5 mL). The reaction mixture was stirred for 30 min and then evaporated under the reduced pressure to yield the crude product which was purified by preparative HPLC (C$_{18}$ column; 10-100% acetonitrile in water containing 0.05% trifluoroacetic acid) to give the desired product (33.9 mg, off-white solid, 51%) upon lyophilization. $^1$H NMR (500 MHz, CDCl$_3$, 50° C.). δ 8.42 (t, J=8.25 Hz, 1 H), 8.31 (brs, 1 H), 8.14 (s, 1 H), 7.59-7.78 (m, 2 H), 5.18-5.34 (m, 1 H), 4.78-4.93 (m, 1 H), 4.22-4.41 (m, 4 H), 3.47-3.55 (m, 2 H), 3.04 (s, 3 H), 2.88-3.07 (m, 2 H), 1.79 (m, 2 H), 1.60-1.75 (m, 2 H), 1.42 (d, J=6.60 Hz, 3 H). LRMS (ESI) 548 (M+H)+.

Example 143

1,1,1-Trifluoro-2-methylpropan-2-yl 4-(4-(4-(methylsulfonyl)phenylamino)-6H-pyrimido[5,4-b][1,4]oxazin-8(7H)-yl)piperidine-1-carboxylate

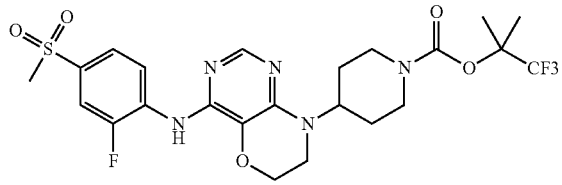 [SMILES: CC(C)(OC(=O)N1CCC(N2CCOc3c(Nc4ccc(S(C)(=O)=O)cc4F)ncnc32)CC1)C(F)(F)F]

Example 143 was prepared according to procedures described in Example 142 with substitution of 2-(trifluoromethyl)propan-2-ol for 1,1,1-trifluoro-2-propanol. The title compound was purified by flash chromatography on silica gel (0-100% EtOAc/hexane). $^1$H NMR (500 MHz, CDCl$_3$). δ 8.87-8.94 (m, 1 H), 8.10 (s, 1 H), 7.71 (d, J=8.80 Hz, 1 H), 7.66 (dd, J=10.45, 2.20 Hz, 1 H), 7.23 (d, J=4.40 Hz, 1 H), 4.79-4.94 (m, 1 H), 4.22-4.37 (m, 3 H), 4.09-4.22 (m, 1 H), 3.43-3.52 (m, 2 H), 3.05 (s, 3 H), 2.83-3.04 (m, 2 H), 1.61-1.81 (m, 10 H). LRMS (ESI) 562 (M+H)+.

Example 144

1,3-Difluoro-2-methylpropan-2-yl 4-(4-(2-fluoro-4-(methylsulfonyl)phenylamino)-6H-pyrimido[5,4-b][1,4]oxazin-8(7H)-yl)piperidine-1-carboxylate

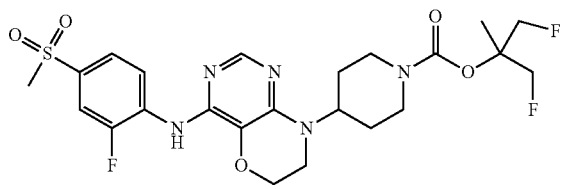 [SMILES: CC(CF)(CF)OC(=O)N1CCC(N2CCOc3c(Nc4ccc(S(C)(=O)=O)cc4F)ncnc32)CC1]

Example 144 was prepared according to procedures described in Example 142 with substitution of 1,3-difluoro-2-methylpropan-2-ol for 1,1,1-trifluoro-2-propanol. The title compound was purified by flash chromatography on silica gel (0-100% EtOAc/hexane). $^1$H NMR (500 MHz, CDCl$_3$). δ 8.90 (t, J=8.52 Hz, 1 H), 8.09 (s, 1 H), 7.71 (d, J=8.80 Hz, 1 H), 7.66 (dd, J=10.45, 2.20 Hz, 1 H), 7.23 (d, J=3.85 Hz, 1 H), 4.78-4.92 (m, 1 H), 4.67-4.79 (m, 1 H), 4.63 (d, J=7.70 Hz, 1 H), 4.54 (d, J=7.70 Hz, 1 H), 4.14-4.33 (m, 4 H), 2.83-3.08 (m, 2 H), 1.60-1.80 (m, 4 H), 1.55 (d, J=15.40 Hz, 3 H). LRMS (ESI) 544 (M+H)+.

Example 145

2,2,2-Trifluoroethyl 4-(4-(2-fluoro-4-(methylsulfonyl)phenylamino)-6H-pyrimido[5,4-b][1,4]oxazin-8(7H)-yl)piperidine-1-carboxylate, TFA salt

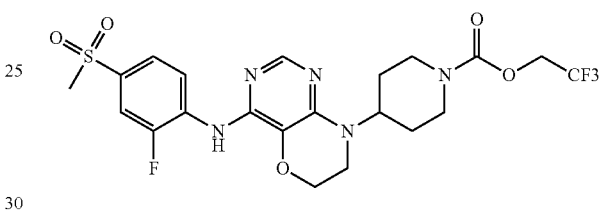

Example 145 was prepared according to procedures described in Example 142 with substitution of 2,2,2-trifluoroethanol for 1,1,1-trifluoro-2-propanol. $^1$H NMR (500 MHz, CDCl$_3$). δ 1H NMR (500 MHz, CDCl$_3$) δ 8.95 (brs, 1 H), 8.19-8.29 (m, 1 H), 8.15 (s, 1 H), 7.63-7.75 (m, 2 H), 4.81-4.96 (m, 1 H), 4.51-4.62 (m, 1 H), 4.41-4.51 (m, 1 H), 4.33-4.41 (m, 1 H), 4.24-4.33 (m, 1 H), 4.21 (t, J=4.40 Hz, 2 H), 3.52 (t, J=4.40 Hz, 2 H), 3.07 (s, 1 H), 2.82-3.11 (m, 2 H), 1.78-1.86 (m, 2 H), 1.70 (s, 2 H). LRMS (ESI) 534 (M+H)+.

Example 146

(±)-sec-Butyl 4-(4-(2-fluoro-4-(methylsulfonyl)phenylamino)-6H-pyrimido[5,4-b][1,4]oxazin-8(7H)-yl)piperidine-1-carboxylate, TFA salt

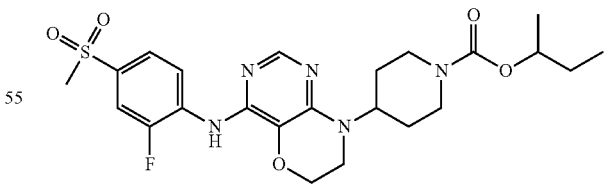

Example 146 was prepared according to procedures described in Example 142 with substitution of (±)-2-butanol for 1,1,1-trifluoro-2-propanol. $^1$H NMR (500 MHz, CDCl$_3$). δ 9.05 (brs, 1 H), 8.19 (t, J=7.97 Hz, 1 H), 8.14 (s, 1 H), 7.64-7.74 (m, 2 H), 4.81-4.92 (m, 1 H), 4.71-4.81 (m, 1 H), 4.33 (app brs, 2 H), 4.19 (t, J=4.40 Hz, 2 H), 3.52 (t, J=4.40 Hz, 2 H), 3.07 (s, 3 H), 2.85-2.99 (m, 2 H), 1.72-1.83 (m, 2 H), 1.50-1.72 (m, 4 H), 1.24 (d, J=6.60 Hz, 3 H), 0.92 (t, J=7.42 Hz, 3H). LRMS (ESI) 508 (M+H)+.

Example 147

1-Methyl-5-(trifluoromethyl)-1H-pyrazol-3-yl 4-(4-(2-fluoro-4-(methylsulfonyl)phenylamino)-6H-pyrimido[5,4-b][1,4]oxazin-8(7H)-yl)piperidine-1-carboxylate, TFA salt

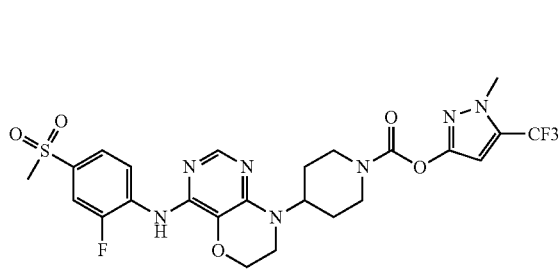 [SMILES: Cn1nc(OC(=O)N2CCC(N3CCOc4c(Nc5ccc(S(C)(=O)=O)cc5F)ncnc43)CC2)cc1C(F)(F)F]

Example 147 was prepared according to procedures described in Example 142 with substitution of 1-methyl-5-(trifluoromethyl)-1H-pyrazol-3-ol for 1,1,1-trifluoro-2-propanol. $^1$H NMR (500 MHz, CDCl$_3$). δ 9.13 (brs, 1 H), 8.11-8.22 (m, 2 H), 7.70 (dd, J=15.40, 9.35 Hz, 2 H), 6.49 (s, 1 H), 4.84-4.98 (m, 1 H), 4.37-4.52 (m, 2 H), 4.21 (t, J=4.40 Hz, 2 H), −3.92 (s, 3 H), 3.55 (t, J=4.40 Hz, 2 H), 3.17 (m, 1H), 3.07 (s, 3 H), 2.99-3.09 (m, 1 H), 1.73-1.89 (m, 4 H). LRMS (ESI) 600 (M+H)+.

Example 148

Isopropyl 4-(4-(4-cyano-2-fluorophenoxy)-6H-pyrimido[5,4-b][1,4]oxazin-8(7H)-yl)piperidine-1-carboxylate

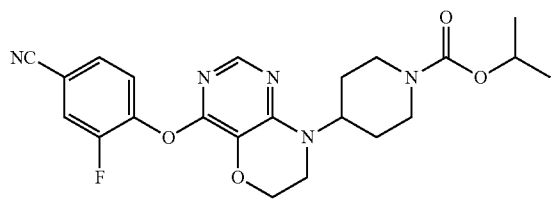 [SMILES: CC(C)OC(=O)N1CCC(N2CCOc3c(Oc4ccc(C#N)cc4F)ncnc32)CC1]

To a solution of isopropyl 4-(4-chloro-6H-pyrimido[5,4-b][1,4]oxazin-8(7H)-yl)piperidine-1-carboxylate from Example 20A (10.0 mg, 0.029 mmol) and 3-fluoro-4-hydroxybenzonitrile (12.07 mg, 0.088 mmol) in DMF (0.4 mL) was added K2CO3 (12.17 mg, 0.088 mmol). The reaction mixture was stirred in a sealed vial for 3 days at 120° C. The reaction mixture was cooled to RT. The reaction mixture was diluted with MeOH, filtered and purified by reverse phase HPLC (H$_2$O/CH$_3$CN) to give isopropyl 4-(4-(4-cyano-2-fluorophenoxy)-6H-pyrimido[5,4-b][1,4]oxazin-8(7 H)-yl)piperidine-1-carboxylate (1.0 mg, 2.265 μmol, 7.72% yield) as Example 148 as an off-white solid. 1H NMR (400 MHz, CDCl$_3$) δ ppm 1.27 (d, J=6.05 Hz, 6H) 1.55-1.79 (m, 4 H) 2.85-2.95 (m, 2 H) 3.44-3.54 (m, 2 H) 4.05-4.15 (m, 2 H) 4.24-4.35 (m, 2 H) 4.84-4.95 (m, 2 H) 7.29-7.40 (m, 1 H) 7.45-7.52 (m, 2 H) 7.88 (s, 1 H). LRMS (ESI): 442.5 [M+H]$^+$.

Example 149

3-Methoxyphenyl 4-(4-(2-fluoro-4-(methylsulfonyl)phenylamino)-6H-pyrimido[5,4-b][1,4]oxazin-8(7H)-yl)piperidine-1-carboxylate, TFA salt

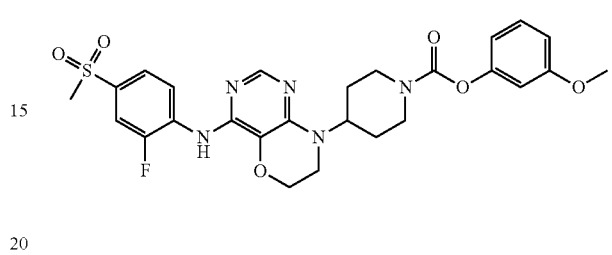

Example 149A

3-Methoxyphenyl 4-nitrophenyl carbonate

To a solution of 3-methoxyphenol (0.11 mL, 1.0 mmol) in CH$_2$Cl$_2$ (4.0 mL) was added DIEA (0.21 mL, 1.2 mmol) followed by addition of 4-nitrophenyl chloroformate (241.8 mg, 1.2 mmol). The reaction mixture was stirred at room temperature for 30 min, diluted with CH$_2$Cl$_2$ and washed with saturated NaHCO$_3$ solution, saturated NH$_4$Cl solution and brine. The organic layer was dried (MgSO$_4$) and evaporated under the reduced pressure to give the desired product (0.294 g) as a yellow solid which was used directly in the next step. MS (ESI) 290 (M+H)+.

Example 149

3-Methoxyphenyl 4-(4-(2-fluoro-4-(methylsulfonyl)phenylamino)-6H-pyrimido[5,4-b][1,4]oxazin-8(7H)-yl)piperidine-1-carboxylate, TFA salt

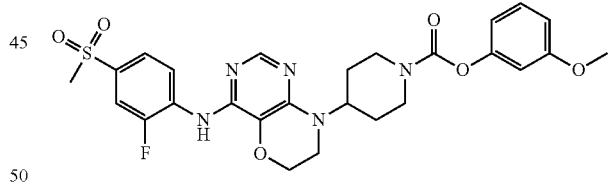

To a suspension of N-(2-fluoro-4-(methylsulfonyl)phenyl)-8-(piperidin-4-yl)-7,8-dihydro-6H-pyrimido[5,4-b][1,4]oxazin-4-amine hydrochloric acid salt from Example 8A (35.5 mg, 0.08 mmol) in CH$_2$Cl$_2$ (2.0 mL) was added DIEA (42 μL, 0.24 mmol, Aldrich) followed by addition of 3-methoxyphenyl 4-nitrophenyl carbonate from Example 149A (27.8 mg, 0.096 mmol). The reaction mixture was stirred for 2 hrs, diluted with CH$_2$Cl$_2$ and washed with 0.5N NaOH aqueous solution and brine. The organic layer was dried (Na$_2$SO$_4$) and evaporated under the reduced pressure to yield the crude product which was purified by preparative HPLC (C$_{18}$ column; 0-100% acetonitrile in water containing 0.05% trifluoroacetic acid) to give Example 149 (22.6 mg, off-white solid, 50%) upon lyophilization. $^1$H NMR (500 MHz, CDCl$_3$). δ ppm 8.75 (brs, 1 H), 8.27-8.41 (m, 1 H), 8.15 (s, 1 H), 7.61-7.80 (m, 2H), 7.19-7.37 (m, 1 H), 6.77 (dd, J=8.25, 2.20 Hz, 1 H), 6.71 (d, J=7.15 Hz, 1 H), 6.68 (d, J=2.20 Hz, 1 H), 4.87-4.98 (m, 1 H), 4.46 (app brs, 2 H), 4.24 (t, J=4.12 Hz, 2 H), 3.80 (s, 3 H), 3.56 (t, J=4.12 Hz, 2 H), 3.12-3.23 (m, 1 H), 3.07 (s, 3 H), 2.97-3.12 (m, 1 H), 1.71-1.92 (m, 4 H). LRMS (ESI) 558 (M+H)+.

Example 150 tert-Butyl 4-(4-(2,4-dichloropyridin-3-ylamino)-6H-pyrimido[5,4-b][1,4]oxazin-8(7H)-yl)piperidine-1-carboxylate

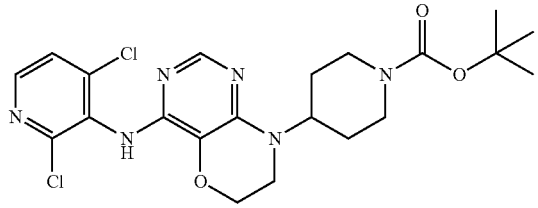 [SMILES: CC(C)(C)OC(=O)N1CCC(N2CCOc3c(Nc4c(Cl)ccnc4Cl)ncnc32)CC1]

To 2,4-dichloropyridin-3-amine (19.20 mg, 0.118 mmol) in DMF (1.5 mL) was added NaH (4.28 mg, 0.107 mmol), the reaction was stirred at room temperature for 30 minutes, then tert-butyl 4-(4-chloro-6H-pyrimido[5,4-b][1,4]oxazin-8(7H)-yl)piperidine-1-carboxylate from Example 3C (38 mg, 0.107 mmol) was added and the reaction mixture was heated under microwave irradiation at 140° C. for 60 minutes. No reaction. An additional 2 eq of NaH was added, and the reaction mixture was heated under microwave irradiation at 140° C. for 60 minutes. The reaction was filtered through a pad of silica gel, concentrated, and purified by a silica gel flash column, eluted by 0-50% EtOAc/Hexane to afford Example 150 (6 mg, 0.012 mmol, 11.06% yield) as a pale solid. 1H NMR (500 MHz, CDCl$_3$) δ ppm 1.47 (s, 9 H) 1.62 (d, J=15.95 Hz, 2 H) 1.69 (s, 2 H) 2.86 (s, 2 H) 3.42-3.51 (m, 2 H) 4.14-4.31 (m, 4H) 4.74-4.87 (m, 1 H) 6.28 (s, 1 H) 7.36 (d, J=4.95 Hz, 1 H) 7.92 (s, 1 H) 8.16 (d, J=5.50 Hz, 1 H). LRMS (ESI) 481.1 (M+H)+.

Example 151 tert-Butyl 4-(4-(2,6-dichloropyridin-3-ylamino)-6H-pyrimido[5,4-b][1,4]oxazin-8(7H)-yl)piperidine-1-carboxylate

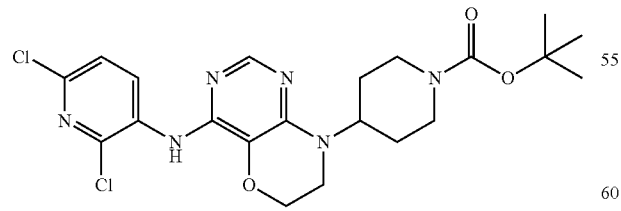

Example 151 was prepared from Example 3C by the procedure described in Example 150, with the exception that 2,4-dichloropyridin-3-amine was replaced by 2,6-dichloropyridin-3-amine 1H NMR (500 MHz, CDCl$_3$) δ ppm 1.47 (s, 9 H) 1.57-1.63 (m, 2 H) 1.68 (s, 2 H) 2.86 (s, 2 H) 3.42-3.49 (m, 2 H) 4.16-4.33 (m, 4 H) 4.75-4.87 (m, 1 H) 7.23-7.28 (m, 2 H) 8.03 (s, 1 H) 9.05 (d, J=8.80 Hz, 1 H). LRMS (ESI) 481.1 (M+H)+.

Example 152 tert-Butyl 4-(4-(2-fluoro-4-(methylsulfonyl)phenylamino)-2-methyl-6H-pyrimido[5,4-b][1,4]oxazin-8(7H)-yl)piperidine-1-carboxylate

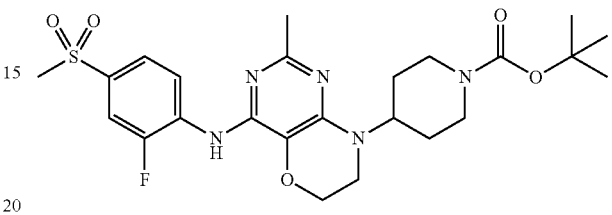

Example 152A

5-Methoxy-2-methylpyrimidine-4,6-diol

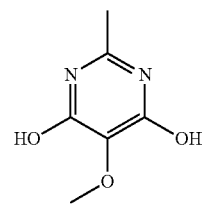

MeOH (100 mL) was added with ice bath cooling to Sodium tert-butoxide (12.22 g, 127 mmol). When the mixture had cooled to less than 20° C., dimethyl 2-methoxymalonate (8.25 g, 50.9 mmol) was added, and then solid acetamidamide, HCl (4.81 g, 50.9 mmol) was added, the mixture was stirred in the ice bath for 30 minutes and then refluxed for 1 hour. The mixture was cooled in a cold water bath and then concentrated HCl (about 35 ml) was added until the mixture was strongly acidic on pH test paper. The precipitate was filtered, suspended in cold water (about 50 ml), and then filtered again. The white powder was dried in vacuo and carried on without further purification (7.22 g, 46.2 mmol, 91% yield). $^1$H NMR (500 MHz, CD$_3$OD): δ 2.33 (s, 3 H), 3.72 (s, 3 H). LRMS (ESI): 157.1 [M+H]$^+$.

Example 152B 4,6-Dichloro-5-methoxy-2-methylpyrimidine

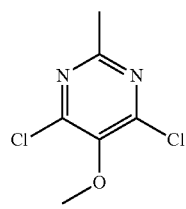

The mixture of Example 152A (3.80 g, 24.34 mmol) and N,N-Diethylaniline (1.5 mL, 24.34 mmol) in POCl$_3$ (20 ml, 215 mmol) was heated under microwave irradiation at 100° C. for 60 minutes. The reaction was filtered and the liquid was concentrated in vacuo. The residue was purified by a silica gel flash column and eluted by 0-30% EtOAc/Hexane to afford Example 152B (2.24 g, 11.60 mmol, 47.7% yield) as a needle-like crystal. $^1$H NMR (500 MHz, CD$_3$OD): δ 2.63 (s, 3 H), 3.92 (s, 3 H). LRMS (ESI): 193/195 [M+H]$^+$.

Example 152C tert-Butyl 4-(6-chloro-5-methoxy-2-methylpyrimidin-4-ylamino)piperidine-1-carboxylate

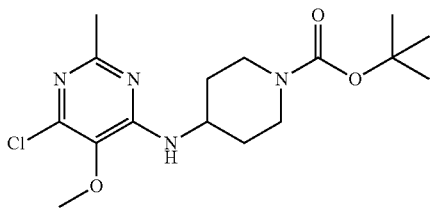 [SMILES: COc1c(Cl)nc(C)nc1NC1CCN(C(=O)OC(C)(C)C)CC1]

Example 152C was prepared using the same method described above for Example 3A, with the exception that 4,6-dichloro-5-methoxypyrimidine was replaced with Example 152B. $^1$H NMR (500 MHz, CDCl$_3$): δ 1.43 (s, 9 H) 1.90-2.04 (m, 2H) 2.41 (s, 3 H) 2.89 (s, 2 H) 3.77 (s, 3 H) 3.98-4.16 (m, 4 H) 5.15 (d, J=8.25 Hz, 1H). LRMS (ESI): 357.1 [M+H]$^+$.

Example 152D tert-Butyl 4-(6-chloro-5-hydroxy-2-methylpyrimidin-4-ylamino)piperidine-1-carboxylate

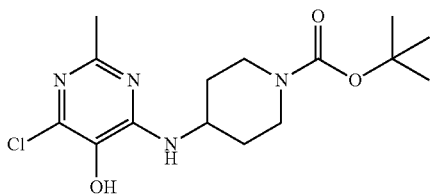 [SMILES: Cc1nc(Cl)c(O)c(NC2CCN(C(=O)OC(C)(C)C)CC2)n1]

Example 152D was prepared using the same method described above for Example 3B, with the exception that Example 3A was replaced with Example 152C. LRMS (ESI): 343.1 [M+H]$^+$.

Example 152E tert-Butyl 4-(4-chloro-2-methyl-6H-pyrimido[5,4-b][1,4]oxazin-8(7H)-yl)piperidine-1-carboxylate

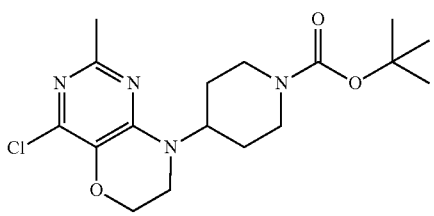 [SMILES: Cc1nc(Cl)c2c(n1)N(C1CCN(C(=O)OC(C)(C)C)CC1)CCO2]

Example 152E was prepared using the same method described above for Example 3C, with the exception that Example 3B was replaced with Example 152D. LRMS (ESI): 369.1 [M+H]$^+$.

Example 152 tert-Butyl 4-(4-(2-fluoro-4-(methylsulfonyl)phenylamino)-2-methyl-6H-pyrimido[5,4-b][1,4]oxazin-8(7 H)-yl)piperidine-1-carboxylate

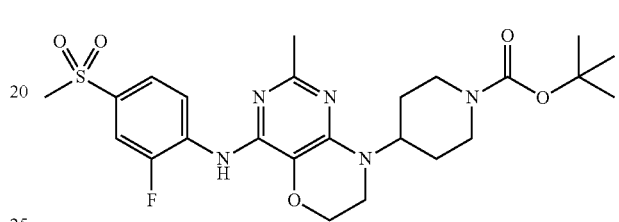

Example 152 was prepared using the same method described above for Example 3, with the exception that Example 3C was replaced with Example 152E. $^1$H NMR (500 MHz, CDCl$_3$): δ 1.46 (s, 9 H) 1.53-1.74 (m, 4 H) 2.43 (s, 3 H) 2.87 (d, J=11.55 Hz, 2 H) 3.02 (s, 3 H) 3.36-3.45 (m, 2 H) 4.12-4.31 (m, 4 H) 4.85 (t, J=4.12 Hz, 1 H) 7.16 (d, J=4.40 Hz, 1 H) 7.55-7.64 (m, 1 H) 7.68 (d, J=8.80 Hz, 1H) 8.94 (t, J=8.25 Hz, 1 H). LRMS (ESI): 522.2 [M+H]$^+$.

Example 153 iso-Propyl 4-(4-(2-fluoro-4-(methylsulfonyl)phenylamino)-2-methyl-6H-pyrimido[5,4-b][1,4]oxazin-8 (7H)-yl)piperidine-1-carboxylate

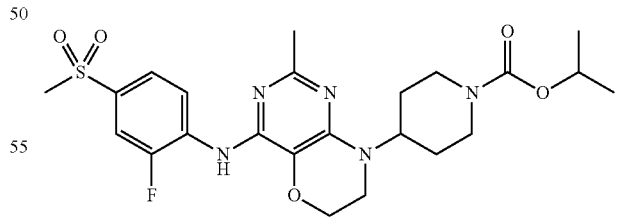

Example 153 was prepared from Example 152 using the methods described in Examples 8A and 8. $^1$H NMR (500 MHz, CDCl$_3$): δ 1.17-1.30 (m, 6H) 1.50-1.75 (m, 4 H) 2.44 (s, 3 H) 2.89 (s, 2 H) 3.02 (s, 3 H) 3.35-3.46 (m, 2 H) 4.12-4.38 (m, 4 H) 4.82-4.97 (m, 2 H) 7.16 (d, J=4.39 Hz, 1 H) 7.61 (dd, J=10.55, 2.20 Hz, 1 H) 7.68 (dd, J=8.79, 2.64 Hz, 1 H) 8.93 (t, J=8.35 Hz, 1 H). LRMS (ESI): 508.2 [M+H]⁺.

Example 154 tert-Butyl 4-(4-(2-chloro-4-(1H-imidazol-1-yl)phenylamino)-6H-pyrimido[5,4-b][1,4]oxazin-8(7H)-yl)piperidine-1-carboxylate

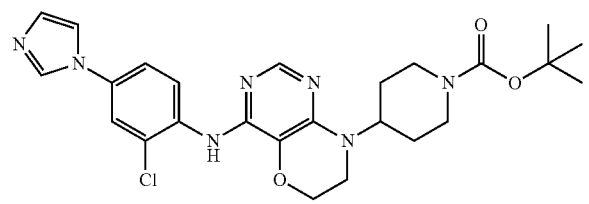 [SMILES: CC(C)(C)OC(=O)N1CCC(N2CCOc3c(Nc4ccc(-n5ccnc5)cc4Cl)ncnc32)CC1]

Example 154A

2-Chloro-4-(1H-imidazol-1-yl)aniline

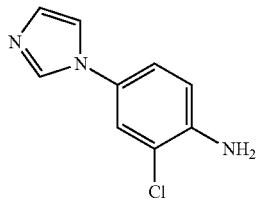 [SMILES: Nc1ccc(-n2ccnc2)cc1Cl]

To 4-(1H-imidazol-1-yl)aniline (800 mg, 5.03 mmol) in DMF (5 ml) was added NCS (671 mg, 5.03 mmol), the reaction mixture was stirred at room temperature for 1 hour and then at 50° C. overnight and then at 100° C. overnight. The reaction was diluted with EtOAc, washed with water and brine, dried over MgSO4 and concentrated in vacuo. The residue was purified by a silica gel flash column and eluted by 0-40% EtOAc/Heane to afford Example 154A (121 mg, 0.625 mmol, 12.43% yield) as a light yellow solid. ¹H NMR (500 MHz, CDCl₃): δ 4.31 (s, 2 H) 6.79 (d, J=8.80 Hz, 1 H) 7.04 (dd, J=8.52, 2.47 Hz, 1 H) 7.12 (d, J=3.85 Hz, 2 H) 7.25 (t, J=3.02 Hz, 1 H) 7.68 (s, 1 H). LRMS (ESI): 194.1 [M+H]⁺.

Example 154 tert-Butyl 4-(4-(2-chloro-4-(1H-imidazol-1-yl)phenylamino)-6H-pyrimido[5,4-b][1,4]oxazin-8(7H)-yl)piperidine-1-carboxylate

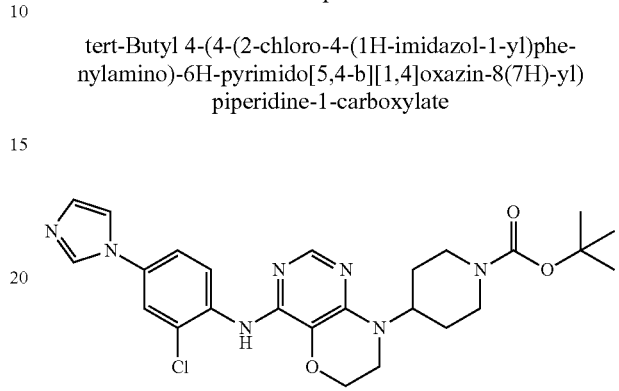

Example 154 was prepared from Example 3C using the same method described above for Example 3, with the exception that 2-fluoro-4-(methylsulfonyl)aniline was replaced with 2-chloro-4-(1H-imidazol-1-yl)aniline from Example 154A. ¹H NMR (400 MHz, CDCl₃): δ 1.39 (s, 9 H) 1.50-1.57 (m, 2 H) 1.58-1.66 (m, 2 H) 2.80 (s, 2 H) 3.35-3.42 (m, 2 H) 4.08-4.25 (m, 4 H) 4.68-4.82 (m, 1 H) 7.12 (d, J=8.79 Hz, 2 H) 7.17-7.21 (m, 1 H) 7.25 (s, 1 H) 7.33 (d, J=2.20 Hz, 1 H) 7.71 (s, 1 H) 7.98 (s, 1 H) 8.68 (d, J=8.79 Hz, 1 H). LRMS (ESI): 512.3 [M+H]⁺.

EXAMPLES OF DATA

Data relevant to the range of activity for compounds of the present invention includes the following data in Table 1.

TABLE 1

| Example No. | Structure | hEC₅₀ nM | IA |
|---|---|---|---|
| 7 | 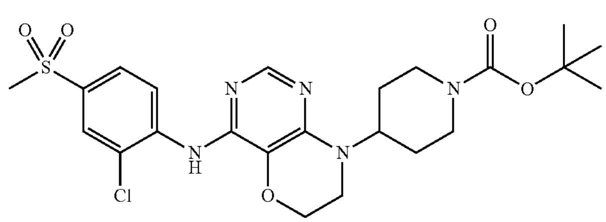 | 2.78 | 0.81 |
| 26 | 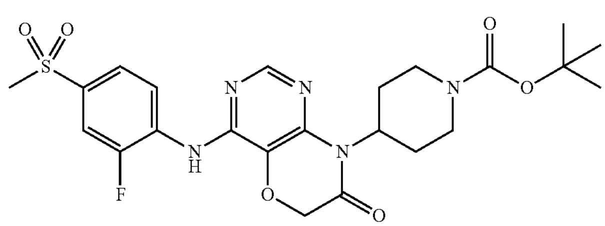 [SMILES: CC(C)(C)OC(=O)N1CCC(N2C(=O)COc3c(Nc4ccc(S(C)(=O)=O)cc4F)ncnc32)CC1] | 8.06 | 0.51 |

TABLE 1-continued
| Example No. | Structure | hEC50 nM | IA |
|---|---|---|---|
| 146 | 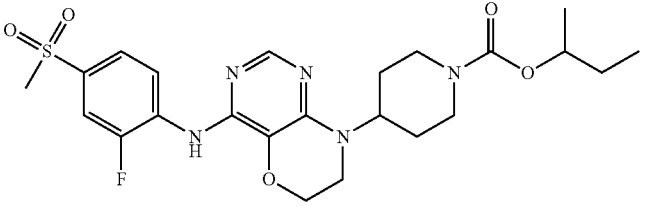 [SMILES: CCC(C)OC(=O)N1CCC(N2CCOc3c(Nc4ccc(S(C)(=O)=O)cc4F)ncnc32)CC1] | 8.52 | 0.88 |
| 143 | 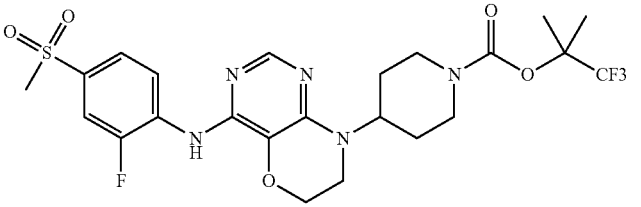 [SMILES: CC(C)(OC(=O)N1CCC(N2CCOc3c(Nc4ccc(S(C)(=O)=O)cc4F)ncnc32)CC1)C(F)(F)F] | 9.74 | 0.41 |
| 89 | 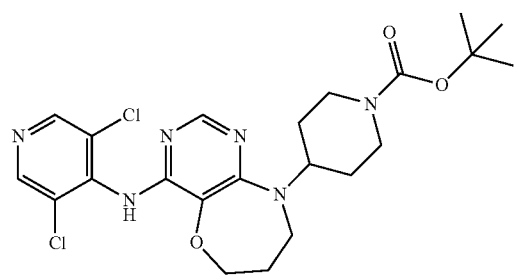 [SMILES: CC(C)(C)OC(=O)N1CCC(N2CCCOc3c(Nc4c(Cl)cncc4Cl)ncnc32)CC1] | 10.28 | 0.65 |
| 55 | 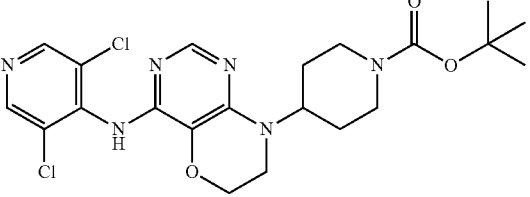 | 11.08 | 0.72 |
| 145 | 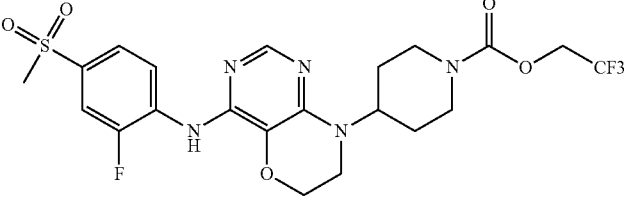 | 11.36 | 0.87 |
| 154 | 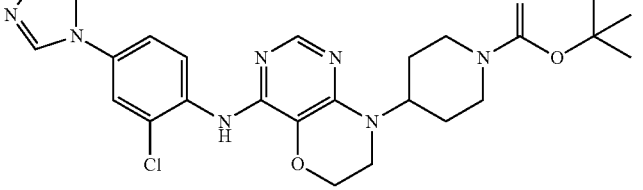 | 12.92 | 0.65 |

TABLE 1-continued

| Example No. | Structure | hEC$_{50}$ nM | IA |
|---|---|---|---|
| 45 | 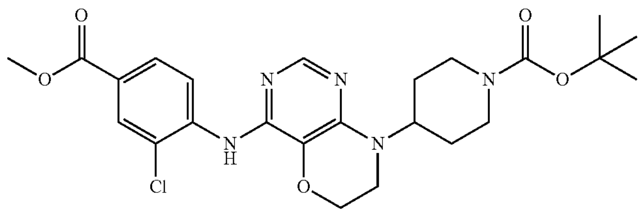 [SMILES: COC(=O)c1ccc(Nc2ncnc3c2OCCN3C2CCN(C(=O)OC(C)(C)C)CC2)c(Cl)c1] | 158.20 | 0.63 |
| 47 | 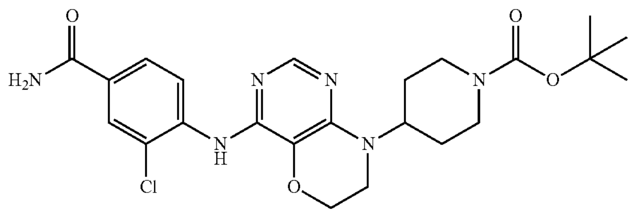 [SMILES: CC(C)(C)OC(=O)N1CCC(N2CCOc3c(Nc4ccc(C(N)=O)cc4Cl)ncnc32)CC1] | 162.70 | 0.78 |
| 134 | 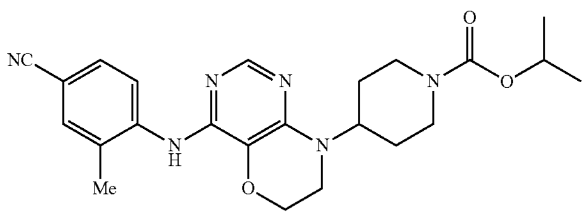 [SMILES: Cc1cc(C#N)ccc1Nc1ncnc2c1OCCN2C1CCN(C(=O)OC(C)C)CC1] | 163.50 | 0.59 |
| 118 | 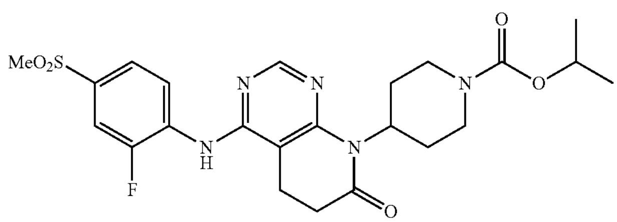 [SMILES: CC(C)OC(=O)N1CCC(N2C(=O)CCc3c(Nc4ccc(S(C)(=O)=O)cc4F)ncnc32)CC1] | 179.40 | 0.63 |
| 120 | 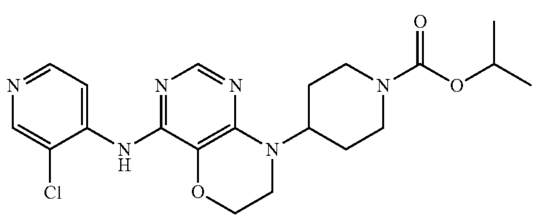 | 181.10 | 0.45 |
| 15 | 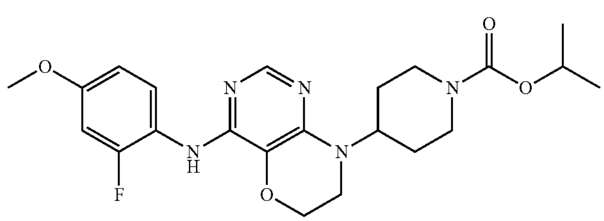 [SMILES: COc1ccc(Nc2ncnc3c2OCCN3C2CCN(C(=O)OC(C)C)CC2)c(F)c1] | 188.40 | 0.48 |
| 49 | 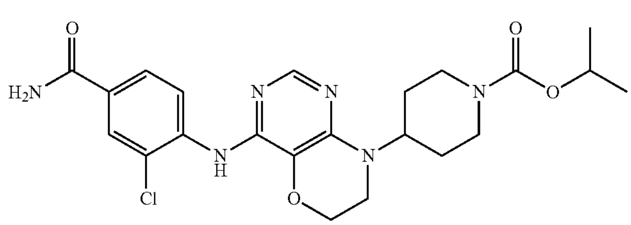 [SMILES: CC(C)OC(=O)N1CCC(N2CCOc3c(Nc4ccc(C(N)=O)cc4Cl)ncnc32)CC1] | 196.50 | 0.67 |

TABLE 1-continued

| Example No. | Structure | hEC$_{50}$ nM | IA |
|---|---|---|---|
| 18 | 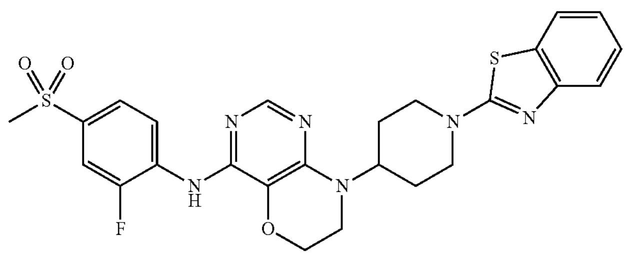 [SMILES: CS(=O)(=O)c1ccc(Nc2ncnc3c2OCCN3C2CCN(c3nc4ccccc4s3)CC2)c(F)c1] | 198.00 | 0.46 |
| 76 | 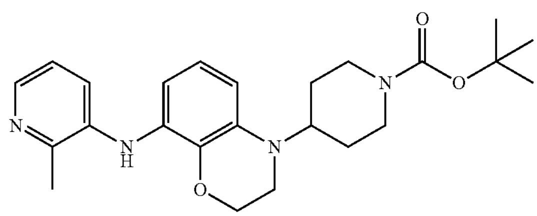 [SMILES: Cc1ncccc1Nc1cccc2c1OCCN2C1CCN(C(=O)OC(C)(C)C)CC1] | 3392.00 | 0.38 |
| 132 | 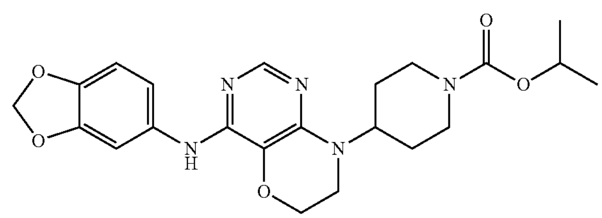 [SMILES: CC(C)OC(=O)N1CCC(N2CCOc3c(Nc4ccc5c(c4)OCO5)ncnc32)CC1] | 3401.00 | 0.37 |
| 100 | 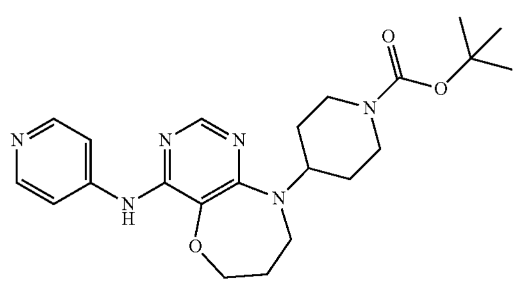 [SMILES: CC(C)(C)OC(=O)N1CCC(N2CCCOc3c(Nc4ccncc4)ncnc32)CC1] | 3454.00 | 0.53 |
| 128 | 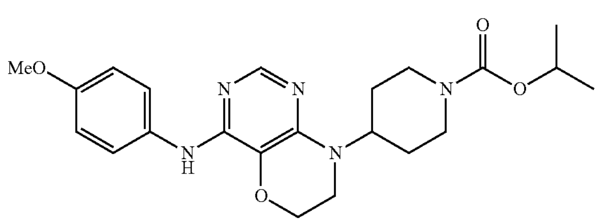 [SMILES: COc1ccc(Nc2ncnc3c2OCCN3C2CCN(C(=O)OC(C)C)CC2)cc1] | 3587.00 | 0.7 |
| 69 | 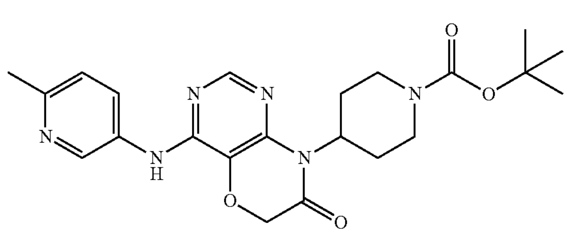 | 4308.00 | 0.35 |

TABLE 1-continued

| Example No. | Structure | hEC$_{50}$ nM | IA |
|---|---|---|---|
| 25 | 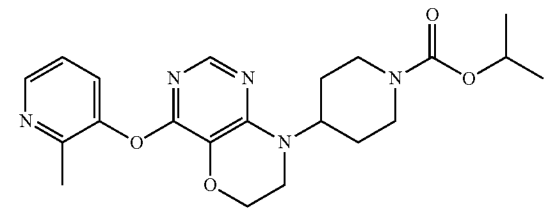 | 4518.00 | 0.27 |
| 127 | 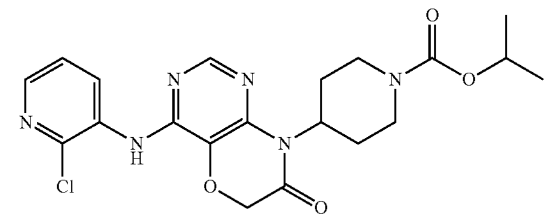 [SMILES: CC(C)OC(=O)N1CCC(N2C(=O)COc3c(Nc4cccnc4Cl)ncnc32)CC1] | 6176.00 | 0.52 |
| 72 | 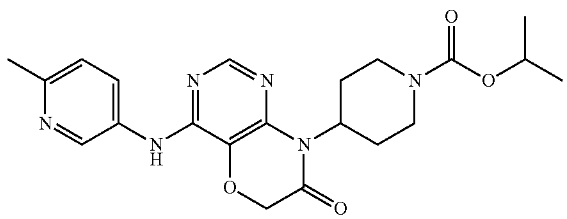 [SMILES: Cc1ccc(Nc2ncnc3c2OCC(=O)N3C2CCN(C(=O)OC(C)C)CC2)cn1] | 8581.00 | 0.34 |

What is claimed is:

1. A compound of Formula I

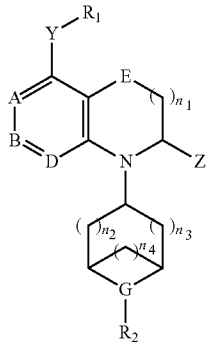

Formula I and enantiomers, diastereomers and pharmaceutically acceptable salts thereof wherein:

A and D are N;
B is CR$_{4b}$;
E is CH$_2$;
G is CH or N;
Y is —NR$_3$, O or S;
Z is absent or =O;
$n_1$ is 1;
$n_2$ and $n_3$ are each independently selected to be 0-2;
$n_4$ is 0-3;
R$_1$ is aryl or heteroaryl, each of which may optionally be substituted with one or more substituents selected from R$_4$;
R$_2$ is selected from the group consisting of cycloalkyl, aryl, heteroaryl, heterocyclyl, —C(=O)R$_5$ and —C(=O)OR$_5$, wherein the cycloalkyl, aryl, heteroaryl and heterocyclyl may each be optionally substituted with one or more R$_6$'s;

R$_3$ is selected from the group consisting of hydrogen, alkyl, alkoxy, cycloalkyl, aryl, arylalkyl, heteroaryl, heteroarylalkyl, heterocyclyl and heterocyclylalkyl;

R$_4$, at each occurrence, is independently selected from the group consisting of alkyl, aryl, alkenyl, alkynyl, cycloalkyl, heteroaryl, heterocyclyl, halo, —CN, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, alkenyl, alkynyl, cycloalkyl, heteroaryl and heterocyclyl may each be optionally substituted with one or more R$_6$'s;

R$_{4b}$, at each occurrence, is independently selected from the group consisting of hydrogen, alkyl, haloalkyl, aryl, alkenyl, alkynyl, cycloalkyl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, alkenyl, alkynyl, cycloalkyl, heteroaryl and heterocyclyl may each be optionally substituted with one or more $R_6$'s;

$R_5$ is selected from the group consisting of alkyl, aryl, cycloalkyl, heteroaryl and heterocyclyl, each of which may optionally be substituted with one or more $R_6$'s;

$R_6$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ and —$NR_9S(O_2)R_8$;

$R_8$, at each occurrence, is independently selected from the group consisting of alkyl, aryl, cycloalkyl, heteroaryl and heterocyclyl;

$R_9$, at each occurrence, is independently selected from the group consisting of hydrogen, alkyl, alkoxy, cycloalkyl, aryl, arylalkyl, heteroaryl, heteroarylalkyl, heterocyclyl and heterocyclylalkyl, wherein the aryl, arylalkyl, heteroaryl, heteroarylalkyl, heterocyclyl and heterocyclylalkyl may each be optionally substituted with 0-5 $R_{9a}$, and the heteroaryl, heteroarylalkyl, heterocyclyl and heterocyclylalkyl each contain 1-4 heteroatoms selected from N, O and S;

$R_{9a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C$(=O)$OR_{10}$, —$S(O)_2NR_{14}C$(=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C$(=O)$OR_8$, —$NR_{14}S(O_2)R_8$ and arylalkyl;

$R_{10}$, at each occurrence, is independently selected from the group consisting of alkyl, cycloalkyl, alkenyl, alkynyl, aryl, arylalkyl, heteroaryl, heteroarylalkyl, heterocyclyl and heterocyclylalkyl, wherein the aryl, arylalkyl, heteroaryl and heterocyclylalkyl may each be optionally substituted with 0-5 $R_{10a}$, and the heterocyclyl and heterocyclylalkyl each contain 1-4 heteroatoms selected from N, O and S;

$R_{10a}$, at each occurrence, is independently selected from the group consisting of alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C$(=O)$OR_9$, —$S(O)_2NR_{14}C$(=O)$NR_{14}R_{14}$, —C(=O)$NR_{14}S(O)_2CF_3$, —C(=O)$R_{14}$, —$NR_{14}C$(=O)H, —$NR_{14}C$(=O)$R_{14}$, —OC(=O)$R_{14}$, —C(=$NR_{14}$)$NR_{14}R_{14}$, —NHC(=$NR_{14}$) $NR_{14}R_{14}$, —S(=O)$R_{14}$, —$S(O)_2R_{14}$, —$NR_{14}C$(=O)$OR_8$, —$NR_{14}S(O_2)R_8$ and arylalkyl; and $R_{14}$, at each occurrence, is independently selected from the group consisting of hydrogen, alkyl, cycloalkyl and aryl.

2. A compound according to claim 1 wherein B is CH.

3. A compound according to claim 1 wherein:

Y is —$NR_3$, O or S;

Z is absent or =O;

$n_1$ is 1;

$n_2$ and $n_3$ are each independently 1 or 2;

$n_4$ is 0-3;

$R_1$ is aryl or heteroaryl, each of which may be optionally substituted with one or more substituents selected from $R_4$;

$R_2$ is selected from the group consisting of cycloalkyl, aryl, heteroaryl, heterocyclyl, —C(=O)$R_5$ and —C(=O) $OR_5$, wherein the cycloalkyl, aryl, heteroaryl and heterocyclyl may each be optionally substituted with one or more $R_6$'s;

$R_3$ is hydrogen, alkyl or cycloalkyl;

$R_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ and —$NR_9S(O_2)R_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, alkyl, haloalkyl, cycloalkyl, halo, CN, —OH, —$OR_{10}$, —$SR_{10}$, aryl, heteroaryl and heterocyclyl, wherein the alkyl, cycloalkyl, aryl, heteroaryl and heterocyclyl may each be optionally substituted with one or more $R_6$'s;

$R_5$ is alkyl, aryl, cycloalkyl, heteroaryl or heterocyclyl, each of which may be optionally substituted with one or more $R_6$'s;

$R_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C$(=O)$OR_9$, —$S(O)_2NR_9C$(=O)$NR_9R_9$, —C(=O)$NR_9S(O)_2CF_3$, —C(=O)$R_{10}$, —$NR_9C$(=O)H, —$NR_9C$(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C$(=O)$OR_8$ and —$NR_9S(O_2)R_8$;

$R_8$, at each occurrence, is independently selected from the group consisting of alkyl, aryl, cycloalkyl, heteroaryl and heterocyclyl;

$R_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may each be optionally substituted with 0-5 $R_{9a}$, and the heteroaryl and heterocyclyl each contain 1-4 heteroatoms selected from N, O and S;

$R_{9a}$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —C(═O)OH, —C(═O)OR$_{14}$, —OCF$_3$, —OR$_{14}$ and —OH;

R$_{10}$, at each occurrence, is independently selected from the group consisting of alkyl, cycloalkyl, aryl, heteroaryl and heterocyclyl, wherein the aryl, heteroaryl and heterocyclyl may be each optionally substituted with 0-5 R$_{10a}$, and the heteroaryl and heterocyclyl each contain 1-4 heteroatoms selected from N, O and S;

R$_{10a}$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —C(═O)OH, —C(═O)OR$_{14}$, —OCF$_3$, —OR$_{14}$ and —OH; and R$_{14}$, at each occurrence, is independently selected from the group consisting of hydrogen, C1-6 alkyl, C3-6 cycloalkyl and C6-10 aryl.

4. A compound according to claim 1 wherein:

Y is —NR$_3$, O or S;

Z is absent or ═O;

n$_1$ is 1;

n$_2$ and n$_3$ are each independently 1 or 2;

n$_4$ is 0-3;

R$_1$ is aryl or heteroaryl, each of which may be optionally substituted with one or more substituents selected from R$_4$;

R$_2$ is aryl, heteroaryl, heterocyclyl, —C(═O)R$_5$ or —C(═O)OR$_5$, wherein the aryl, heteroaryl and heterocyclyl may each be optionally substituted with one or more R$_6$'s;

R$_3$ is hydrogen or alkyl;

R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(═O)OH, —C(═O)OR$_{10}$, —OCF$_3$, —OR$_{10}$, —OH, —SR$_{10}$, —S(O)$_3$H, —P(O)$_3$H$_2$, —C(═O)NR$_9$R$_9$, —NR$_9$R$_9$, —S(O)$_2$NR$_9$R$_9$, —NR$_9$S(O)$_2$CF$_3$, —C(═O)NR$_9$S(O)$_2$R$_9$, —S(O)$_2$NR$_9$C(═O)OR$_9$, —S(O)$_2$NR$_9$C(═O)NR$_9$R$_9$, —C(═O)NR$_9$S(O)$_2$CF$_3$, —C(═O)R$_{10}$, —NR$_9$C(═O)H, —NR$_9$C(═O)R$_{10}$, —OC(═O)R$_{10}$, —OC(═O)NR$_9$R$_9$, —C(═NR$_{14}$)NR$_9$R$_9$, —NHC(═NR$_{14}$)NR$_{14}$R$_{14}$, —S(═O)R$_{10}$, —S(O)$_2$R$_{10}$, —NR$_9$C(═O)OR$_8$ and —NR$_9$S(O)$_2$R$_8$, wherein the alkyl, aryl, cycloalkyl, heteroaryl and heterocyclyl may each be optionally substituted with one or more R$_6$'s;

R$_{4b}$, at each occurrence, is independently selected from the group consisting of hydrogen, C1-6 alkyl, C1-4 haloalkyl, C6-10 aryl, C3-6 cycloalkyl, halo, CN, —OH, —OR$_{10}$ and —SR$_{10}$, wherein the alkyl, cycloalkyl and aryl may each be optionally substituted with one or more R$_6$'s;

R$_5$ is selected from the group consisting of C1-6 alkyl, C6-10 aryl, C3-6 cycloalkyl, heteroaryl and heterocyclyl, each of which may be optionally substituted with one or more R$_6$'s;

R$_6$, at each occurrence, is independently selected from the group consisting of C1-6 alkyl, C1-4 haloalkyl, C6-10 aryl, C3-6 cycloalkyl, heteroaryl, heterocyclyl, halo, —NH$_2$, —CN, —NO$_2$, —C(═O)OH, —C(═O)OR$_{10}$, —OCF$_3$, —OR$_{10}$, —OH, —SH, —SR$_{10}$, —S(O)$_3$H, —P(O)$_3$H$_2$, —C(═O)NR$_9$R$_9$, —NR$_9$R$_9$, —S(O)$_2$NR$_9$R$_9$, —NR$_9$S(O)$_2$CF$_3$, —C(═O)NR$_9$S(O)$_2$R$_9$, —S(O)$_2$NR$_9$C(═O)OR$_9$, —S(O)$_2$NR$_9$C(═O)NR$_9$R$_9$, —C(═O)NR$_9$S(O)$_2$CF$_3$, —C(═O)R$_{10}$, —NR$_9$C(═O)H, —NR$_9$C(═O)R$_{10}$, —OC(═O)R$_{10}$, —C(═NR$_{14}$)NR$_9$R$_9$, —NHC(═NR$_{14}$)NR$_{14}$R$_{14}$, —S(═O)R$_{10}$, —S(O)$_2$R$_{10}$, —NR$_9$C(═O)OR$_8$ and —NR$_9$S(O$_2$)R$_8$;

R$_8$, at each occurrence, is independently selected from the group consisting of C1-6 alkyl, C6-10 aryl, C3-6 cycloalkyl, heteroaryl and heterocyclyl;

R$_9$, at each occurrence, is independently selected from the group consisting of hydrogen, C1-6 alkyl, C6-10 aryl, C3-6 cycloalkyl, heteroaryl and heterocyclyl, wherein the aryl, heteroaryl and heterocyclyl may each be optionally substituted with 0-5 R$_{9a}$, and the heteroaryl and heterocyclyl each contain 1-4 heteroatoms selected from N, O and S;

R$_{9a}$, at each occurrence, is independently selected from the group consisting of C1-6 alkyl, halo, —NH$_2$, —CN, —C(═O)OH, —C(═O)OR$_{14}$, —OCF$_3$, —OR$_{14}$ and —OH;

R$_{10}$, at each occurrence, is independently selected from the group consisting of C1-6 alkyl, C3-6 cycloalkyl, C6-10 aryl, heteroaryl and heterocyclyl, wherein the aryl, heteroaryl and heterocyclyl may each be optionally substituted with 0-5 R$_{10a}$, and the heteroaryl and heterocyclyl each contains 1-4 heteroatoms selected from N, O and S;

R$_{10a}$, at each occurrence, is independently selected from the group consisting of C1-6 alkyl, halo, —NH$_2$, —CN, —C(═O)OH, —C(═O)OR$_{14}$, —OCF$_3$, —OR$_{14}$ and —OH; and R$_{14}$, at each occurrence, is independently selected from the group consisting of hydrogen, C1-6 alkyl and C6-10 aryl.

5. A compound according to claim 1 wherein:

Y is —NR$_3$, O or S;

Z is absent or ═O;

n$_1$ is 1;

n$_2$ and n$_3$ are independently 1 or 2;

n$_4$ is 0 or 2;

R$_1$ is C6-10 aryl or heteroaryl, each of which may be optionally substituted with one or more substituents selected from R$_4$;

R$_2$ is C6-10 aryl, heteroaryl, —C(═O)R$_5$ or —C(═O)OR$_5$, wherein the aryl and heteroaryl may each be optionally substituted with one or more R$_6$'s;

R$_3$ is hydrogen or C1-4 alkyl;

R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(═O)OH, —C(═O)OR$_{10}$, —OCF$_3$, —OR$_{10}$, —OH, —SR$_{10}$, —S(O)$_3$H, —P(O)$_3$H$_2$, —C(═O)NR$_9$R$_9$, —NR$_9$R$_9$, —S(O)$_2$NR$_9$R$_9$, —NR$_9$S(O)$_2$CF$_3$, —C(═O)NR$_9$S(O)$_2$R$_9$, —S(O)$_2$NR$_9$C(═O)OR$_9$, —S(O)$_2$NR$_9$C(═O)NR$_9$R$_9$, —C(═O)NR$_9$S(O)$_2$CF$_3$, —C(═O)R$_{10}$, —NR$_9$C(═O)H, —NR$_9$C(═O)R$_{10}$, —OC(═O)R$_{10}$, —OC(═O)NR$_9$R$_9$, —C(═NR$_{14}$)NR$_9$R$_9$, —NHC(═NR$_{14}$)NR$_{14}$R$_{14}$, —S(═O)R$_{10}$, —S(O)$_2$R$_{10}$, —NR$_9$C(═O)OR$_8$ and —NR$_9$S(O)$_2$R$_8$, wherein the alkyl, aryl, cycloalkyl, heteroaryl and heterocyclyl may each be optionally substituted with one or more R$_6$'s;

R$_{4b}$, at each occurrence, is independently selected from the group consisting of hydrogen, C1-6 alkyl, C1-4 haloalkyl, C6-10 aryl, C3-6 cycloalkyl, halo, CN, —OH, —OR$_{10}$ and —SR$_{10}$, wherein the alkyl, cycloalkyl and aryl may each be optionally substituted with one or more R$_6$'s;

R$_5$ is C1-6 alkyl, C6-10 aryl, C3-6 cycloalkyl or heteroaryl each of which may be optionally substituted with one or more R$_6$'s;

R$_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;

R$_8$, at each occurrence, is independently selected from the group consisting of C1-6 alkyl, C6-10 aryl, C3-6 cycloalkyl and heteroaryl;

R$_9$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 R$_{9a}$, and the heteroaryl contains 1-4 heteroatoms selected from N, O and S;

R$_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

R$_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 R$_{10a}$, and the heteroaryl contains 1-4 heteroatoms selected from N, O and S;

R$_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and R$_{14}$, at each occurrence, is independently selected from the group consisting of hydrogen, C1-6 alkyl and C6-10 aryl.

6. A compound according to claim 1 wherein:
Y is —NR$_3$, O or S;
Z is absent or =O;
n$_1$ is 1;
n$_2$ and n$_3$ are independently 1 or 2;
n$_4$ is 0 or 2;
R$_1$ is C6-10 aryl or heteroaryl, each of which may be optionally substituted with one or more substituents selected from R$_4$;
R$_2$ is heteroaryl, —C(=O)R$_5$ or —C(=O)OR$_5$, wherein the heteroaryl may be optionally substituted with one or more R$_6$'s;
R$_3$ is hydrogen;
R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more R$_6$'s;
R$_{4b}$, at each occurrence, is independently selected from the group consisting of hydrogen, C1-6 alkyl, C6-10 aryl and C3-6 cycloalkyl, wherein the alkyl, cycloalkyl, and aryl may each be optionally substituted with one or more R$_6$'s;

R$_5$ is C1-6 alkyl, C6-10 aryl or C3-6 cycloalkyl, each of which may be optionally substituted with one or more R$_6$'s;

R$_6$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$;

R$_8$, at each occurrence, is independently C1-6 alkyl or C6-10 aryl;

R$_9$, at each occurrence, is independently hydrogen, C1-6 alkyl, C3-6 cycloalkyl, C6-10 aryl or heteroaryl, wherein the aryl and heteroaryl may each be optionally substituted with 0-5 R$_{9a}$, and the heteroaryl contains 1-4 heteroatoms selected from N, O and S;

R$_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

R$_{10}$, at each occurrence, is independently selected from the group consisting of hydrogen, C1-6 alkyl, C3-6 cycloalkyl, C6-10 aryl and heteroaryl, wherein the aryl and heteroaryl may each be optionally substituted with 0-5 R$_{10a}$, and the heteroaryl contains 1-4 heteroatoms selected from N, O and S;

R$_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and R$_{14}$, at each occurrence, is independently selected from the group consisting of hydrogen, C1-6 alkyl and C6-10 aryl.

7. ently amended). A compound according to claim 1 wherein:
Y is —NR$_3$, O or S;
Z is absent or =O;
n$_1$ is 1;
n$_2$ and n$_3$ are independently 1 or 2;
n$_4$ is 0;
R$_1$ is C6-10 aryl or heteroaryl, each of which may be optionally substituted with one or more substituents selected from R$_4$;
R$_2$ is heteroaryl, —C(=O)R$_5$ or —C(=O)OR$_5$, wherein the heteroaryl may be optionally substituted with one or more R$_6$'s;
R$_3$ is hydrogen;
R$_4$, at each occurrence, is independently selected from the group consisting of C1-6 alkyl, C1-4 haloalkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, aryl, cycloalkyl, heteroaryl and heterocyclyl may each be optionally substituted with one or more $R_6$'s;

$R_{4b}$, at each occurrence, is independently selected from the group consisting of hydrogen, C1-6 alkyl and C3-6 cycloalkyl, wherein the alkyl and cycloalkyl may each be optionally substituted with one or more $R_6$'s;

$R_5$ is C1-6 alkyl, C6-10 aryl or C3-6 cycloalkyl, each of which may be optionally substituted with one or more $R_6$'s;

$R_6$, at each occurrence, is independently selected from the group consisting of C1-6 alkyl, C6-10 aryl, C3-6 cycloalkyl, heteroaryl, heterocyclyl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or C6-10 aryl;

$R_9$, at each occurrence, is independently hydrogen, C1-6 alkyl, C3-6 cycloalkyl or C6-10 aryl, wherein the aryl may be optionally substituted with 0-5 $R_{9a}$;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently hydrogen, C1-6 alkyl, C3-6 cycloalkyl or C6-10 aryl, wherein the aryl may be optionally substituted with 0-5 $R_{10a}$;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently selected from the group consisting of hydrogen, C1-6 alkyl and C6-10 aryl.

8. A compound according to claim 1 wherein:

A and D are N;

B is CH;

G is CH or N;

Y is —NR$_3$ or O;

Z is absent or =O;

$n_1$ is 1;

$n_2$ and $n_3$ are 1;

$n_4$ is 0;

$R_1$ is phenyl or heteroaryl, each of which may be optionally substituted with 1-5 of $R_4$;

$R_2$ is heteroaryl, —C(=O)R$_5$ or —C(=O)OR$_5$, wherein the heteroaryl may be optionally substituted with 1-5 of $R_6$'s;

$R_3$ is hydrogen;

$R_4$, at each occurrence, is independently selected from the group consisting of C1-6 alkyl, C1-4 haloalkyl, C3-6 cycloalkyl, phenyl, heteroaryl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, phenyl and heteroaryl may each be optionally substituted with 1-5 of $R_6$'s;

$R_{4b}$, at each occurrence, is independently selected from hydrogen and C1-6 alkyl;

$R_5$ is C1-6 alkyl, C3-6 cycloalkyl or phenyl, each of which may be optionally substituted with 1-5 of $R_6$'s;

$R_6$, at each occurrence, is independently selected from the group consisting of C1-6 alkyl, C1-4 haloalkyl, C3-6 cycloalkyl, phenyl, heteroaryl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$;

$R_8$, at each occurrence, is independently C1-6 alkyl or phenyl;

$R_9$, at each occurrence, is independently hydrogen, C1-6 alkyl, C3-6 cycloalkyl or phenyl, wherein the phenyl may be optionally substituted with 0-5 $R_{9a}$;

$R_{9a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH;

$R_{10}$, at each occurrence, is independently hydrogen, C1-6 alkyl, C3-6 cycloalkyl or phenyl, wherein the phenyl may be optionally substituted with 0-5 $R_{10a}$;

$R_{10a}$, at each occurrence, is independently selected from the group consisting of C1-6 alkyl, halo, —NH$_2$, —CN, —C(=O)OH, —C(=O)OR$_{14}$, —OCF$_3$, —OR$_{14}$ and —OH; and $R_{14}$, at each occurrence, is independently selected from the group consisting of hydrogen, C1-6 alkyl and phenyl.

9. A compound according to claim 1 wherein:

A and D are N;

B is CH;

G is N;

Y is —NR$_3$ or O;

Z is absent or =O;

$n_1$ is 1;

$n_2$ and $n_3$ are 1;

$n_4$ is 0;

$R_1$ is phenyl, pyridyl or pyrimidinyl, each of which may be optionally substituted with 1-5 of $R_4$;

$R_2$ is —C(=O)OR$_5$ or a heteroaryl selected from the group consisting of pyrimidinyl, pyridyl, oxadiazolyl and benzoxazole, wherein the heteroaryl may be optionally substituted with 1-5 of $R_6$'s;

$R_3$ is hydrogen;

$R_4$, at each occurrence, is independently selected from the group consisting of C1-6 alkyl, C1-4 haloalkyl, C3-6 cycloalkyl, phenyl, heteroaryl which has a single ring with 6 atoms of which 1-3 are selected from O, S and N, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, phenyl and heteroaryl may each be optionally substituted with 1-5 of $R_6$'s;

$R_{4b}$, at each occurrence, is hydrogen;

$R_5$ is C 1-6 alkyl, C3-6 cycloalkyl or phenyl, each of which may be optionally substituted with 1-5 of $R_6$'s;

$R_6$, at each occurrence, is independently selected from the group consisting of C1-6 alkyl, C1-4 haloalkyl, C3-6 cycloalkyl, phenyl, heteroaryl, halo, —CN, —C(=O)OH, —C(=O)OR$_{10}$, —OCF$_3$, —OR$_{10}$, —OH, —SR$_{10}$, —C(=O)NR$_9$R$_9$, —NR$_9$R$_9$, —S(O)$_2$NR$_9$R$_9$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)NR₉R₉, —S(=O)R₁₀, —S(O)₂R₁₀, —NR₉C(=O)OR₈ and —NR₉S(O₂)R₈;

R$_8$, at each occurrence, is independently C1-6 alkyl or phenyl;

R$_9$, at each occurrence, is independently hydrogen, C1-6 alkyl, C3-6 cycloalkyl or phenyl, wherein the phenyl may be optionally substituted with 0-5 R$_{9a}$;

R$_{9a}$, at each occurrence, is independently selected from the group consisting of C1-6 alkyl, halo, —NH₂, —CN, —C(=O)OH, —C(=O)OR₁₄, —OCF₃, —OR₁₄ and —OH;

R$_{10}$, at each occurrence, is independently selected from the group consisting of C1-6 alkyl, C3-6 cycloalkyl and phenyl, wherein the phenyl may be optionally substituted with 0-5 R$_{10a}$;

R$_{10a}$, at each occurrence, is independently selected from the group consisting of C1-6 alkyl, halo, —NH₂, —CN, —C(=O)OH, —C(=O)OR₁₄, —OCF₃, —OR₁₄ and —OH; and R$_{14}$, at each occurrence, is independently selected from the group consisting of hydrogen and C1-6 alkyl.

10. A compound according to claim 1 having the structure:

11. A pharmaceutical composition comprising a therapeutically effective amount of a compound of claim 1 and a pharmaceutically acceptable carrier.

12. The pharmaceutical composition of claim 11 further comprising at least one additional therapeutically active agent selected from the group consisting of anti-Type II diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

13. The pharmaceutical composition of claim 12, wherein the additional therapeutically active agent is a glucagon-like peptide-1 receptor agonist or a dipeptidyl peptidase-IV inhibitor.

14. A method of modulating the activity of the GPR119 G protein-coupled receptor to treat diseases or disorders associated therewith, comprising administering to a mammalian patient in need thereof a therapeutically effective amount of at least one compound of claim 1 and, optionally, at least one other therapeutic agent, wherein said diseases or disorders associated with modulating the activity of the GPR119 G protein-coupled receptor that are treated is selected from the group consisting of Type II diabetes, hyperglycemia, impaired glucose tolerance, insulin resistance, hyperinsulinemia, retinopathy associated with diabetes, neuropathy associated with diabetes, nephropathy associated with diabetes, delayed wound healing, atherosclerosis and its sequelae, abnormal heart function, myocardial ischemia, stroke associated with diabetes, Metabolic Syndrome, hypertension, obesity, dyslipidemia, hyperlipidemia, hypertriglyceridemia, hypercholesterolemia, low HDL, high LDL, non-cardiac ischemia, vascular restenosis, pancreatitis, cognitive impairment and dementia, HIV protease associated lipodystrophy and glaucoma, and said other therapeutic agent is selected from the group consisting of anti-Type II diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

15. The method as defined in claim 14 wherein the disease or disorder is selected from the group consisting of Type II diabetes, hyperglycemia, obesity, dyslipidemia, hypertension and cognitive impairment.

\* \* \* \* \*

UNITED STATES PATENT AND TRADEMARK OFFICE
CERTIFICATE OF CORRECTION

PATENT NO. : 8,513,265 B2  
APPLICATION NO. : 13/648436  
DATED : August 20, 2013  
INVENTOR(S) : John M. Fevig et al.

Page 1 of 1

It is certified that error appears in the above-identified patent and that said Letters Patent is hereby corrected as shown below:

On the Title Page:

Related U.S. Application Data:

Item (62), after "8,314,095", insert

-- , which is a division of application No. 13/022,819, filed on Feb. 8, 2011, now Pat. No. 8,076,322, which is a division of application No. 12/112,080, filed on Apr. 30, 2008, now Pat. No. 7,910,583.

(60) Provisional application No. 60/915,944, filed on May 4, 2007. --.

In the Claims:

Claim 1:

Column 139, line 10, change "heterocyclyl" to -- heterocyclyl, --.

Claim 7:

Column 144, line 45, before "A", delete "ently amended).".

Claim 8:

Column 145, line 65, change "substituted 1-5" to -- substituted with 1-5 --.

Claim 9:

Column 146, line 59, change "C 1-6" to -- C1-6 --.

Signed and Sealed this  
First Day of April, 2014

Michelle K. Lee  
*Deputy Director of the United States Patent and Trademark Office*